US012766184B2

(12) United States Patent
Demonbreun et al.

(10) Patent No.: US 12,766,184 B2
(45) Date of Patent: Oct. 20, 2026

(54) USE OF ANNEXINS IN PREVENTING AND TREATING MUSCLE MEMBRANE INJURY

(71) Applicant: NORTHWESTERN UNIVERSITY, Evanston, IL (US)

(72) Inventors: Alexis R. Demonbreun, Mokena, IL (US); Elizabeth M. McNally, Oak Park, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 1431 days.

(21) Appl. No.: 17/416,018

(22) PCT Filed: Dec. 20, 2019

(86) PCT No.: PCT/US2019/068168
§ 371 (c)(1),
(2) Date: Jun. 18, 2021

(87) PCT Pub. No.: WO2020/132647
PCT Pub. Date: Jun. 25, 2020

(65) Prior Publication Data
US 2022/0143136 A1 May 12, 2022

Related U.S. Application Data

(60) Provisional application No. 62/903,525, filed on Sep. 20, 2019, provisional application No. 62/783,619, filed on Dec. 21, 2018.

(51) Int. Cl.
*A61K 38/00* (2006.01)
*A61K 31/573* (2006.01)
*A61K 38/17* (2006.01)
*A61K 45/06* (2006.01)
*A61K 48/00* (2006.01)
*A61P 21/00* (2006.01)
*C12N 15/86* (2006.01)

(52) U.S. Cl.
CPC ........ *A61K 38/1709* (2013.01); *A61K 31/573* (2013.01); *A61K 45/06* (2013.01); *A61K 48/00* (2013.01); *A61P 21/00* (2018.01); *C12N 15/86* (2013.01)

(58) Field of Classification Search
CPC .. A61K 38/1709; A61K 31/573; A61K 45/06; A61K 48/00; A61K 2300/00; A61P 21/00; C12N 15/86
See application file for complete search history.

(56) References Cited

U.S. PATENT DOCUMENTS 3,687,808 A 8/1972 Merigan et al.
4,845,205 A 7/1989 Huynh et al.
5,130,302 A 7/1992 Spielvogel et al.
5,134,066 A 7/1992 Rogers et al.
5,175,273 A 12/1992 Bischofberger et al.
5,367,066 A 11/1994 Urdea et al.
5,399,363 A 3/1995 Liversidge et al.
5,432,272 A 7/1995 Benner
5,457,187 A 10/1995 Gmeiner et al.
5,459,255 A 10/1995 Cook et al.
5,466,468 A 11/1995 Schneider et al.
5,484,908 A 1/1996 Froehler et al.
5,502,177 A 3/1996 Matteucci et al.
5,525,711 A 6/1996 Hawkins et al.
5,552,540 A 9/1996 Haralambidis
5,587,469 A 12/1996 Cook et al.
5,594,121 A 1/1997 Froehler et al.
5,596,091 A 1/1997 Switzer
5,614,617 A 3/1997 Cook et al.
5,645,985 A 7/1997 Froehler et al.
5,681,941 A 10/1997 Cook et al.
5,720,950 A 2/1998 Poiani et al.
5,750,692 A 5/1998 Cook et al.
5,763,588 A 6/1998 Matteucci et al.
5,830,653 A 11/1998 Froehler et al.
6,004,937 A 12/1999 Wood et al.
6,005,096 A 12/1999 Matteucci et al.
6,096,506 A 8/2000 Lee et al.
6,369,201 B1 4/2002 Barker et al.
6,465,493 B1 10/2002 Burgess et al.
6,468,535 B1 10/2002 Lee et al.
6,906,089 B2 6/2005 Gaster et al.
7,192,717 B2 3/2007 Hill et al.
7,202,210 B2 4/2007 Wolfman et al.
7,223,833 B1 5/2007 Nielsen et al.
7,261,893 B2 8/2007 Veldman et al.
7,320,789 B2 1/2008 Dunham et al.
7,572,763 B2 8/2009 Hill et al.
9,499,817 B2 11/2016 Mcnally
9,873,739 B2 1/2018 Mcnally et al.
(Continued)

FOREIGN PATENT DOCUMENTS

EP 1072679 A2 1/2001
JP 2016-537340 A 12/2016
(Continued)

OTHER PUBLICATIONS

Ishii et al. Circ Res. 2001;89:1240-1245.*
Harper and Speicher, Methods Mol Biol. 2011 ; 681: 259-280.*
Peterzoli-Ribeil, Blood, Nov. 18, 2010, vol. 116, No. 20.*
Yeung et al., Contribution of phosphatidylserine to membrane surface charge and protein targeting during phagosome maturation, The Journal of Cell Biology, 185(5):917-28 (2009).
(Continued)

*Primary Examiner* — Jeanette M Lieb

(57) ABSTRACT

The present disclosure provides compositions and methods for increasing the activity of an annexin protein to treat a cellular membrane injury in a patient in need thereof.

36 Claims, 35 Drawing Sheets

Specification includes a Sequence Listing.

(56) References Cited

U.S. PATENT DOCUMENTS

| | | | |
|---|---|---|---|
| 2003/0166633 | A1 | 9/2003 | Gaster et al. |
| 2004/0039198 | A1 | 2/2004 | Bender et al. |
| 2004/0063745 | A1 | 4/2004 | Gellibert et al. |
| 2004/0138118 | A1 | 7/2004 | Wolfman et al. |
| 2004/0181033 | A1 | 9/2004 | Han et al. |
| 2004/0223966 | A1 | 11/2004 | Wolfman et al. |
| 2012/0039806 | A1 | 2/2012 | Lahoud et al. |
| 2012/0046345 | A1 | 2/2012 | Collard et al. |
| 2012/0058955 | A1 | 3/2012 | Kichler et al. |
| 2014/0037637 | A1 | 2/2014 | Mcnally et al. |
| 2016/0130608 | A1 | 5/2016 | Doudna et al. |
| 2016/0243196 | A1 | 8/2016 | Mumm et al. |
| 2017/0128528 | A1 | 5/2017 | Samulski |
| 2017/0226490 | A1 | 8/2017 | Ma et al. |
| 2018/0244763 | A1 | 8/2018 | Shapiro et al. |
| 2019/0070261 | A1 | 3/2019 | Nayer |
| 2019/0091282 | A1 | 3/2019 | Khaldi et al. |

FOREIGN PATENT DOCUMENTS

| | | | | |
|---|---|---|---|---|
| JP | 2017-522895 A | 8/2017 | | |
| JP | 2018-531609 A | 11/2018 | | |
| TW | 201833135 A | 9/2018 | | |
| WO | 1997/12896 A1 | 4/1997 | | |
| WO | 2000/43781 A2 | 7/2000 | | |
| WO | 2001/05820 A2 | 1/2001 | | |
| WO | 2001/53350 A1 | 7/2001 | | |
| WO | 2002/68650 A2 | 9/2002 | | |
| WO | 2002/85306 A2 | 10/2002 | | |
| WO | 2005/084699 A1 | 9/2005 | | |
| WO | 2005/094446 A2 | 10/2005 | | |
| WO | 2006/012627 A2 | 2/2006 | | |
| WO | 2006/025988 A1 | 3/2006 | | |
| WO | 2006/116269 A2 | 11/2006 | | |
| WO | WO-2011069090 A1 * | 6/2011 | ............. | A61K 38/39 |
| WO | 2016/059146 A1 | 4/2016 | | |
| WO | WO-2017/180587 A2 | 10/2017 | | |
| WO | 2018/046772 A1 | 3/2018 | | |

OTHER PUBLICATIONS

Zaks et al., Ca(2+)-dependent annexin self-association on membrane surfaces, Biochemistry, 30:9607-9615 (1991).

Zhang et al., An extremely stable and orthogonal DNA base pair with a simplified three-carbon backbone, J. Am. Chem. Soc., 127(1):74-75 (2005).

Zhang et al., Myoediting: Toward Prevention of Muscular Dystrophy by Therapeutic Genome Editing, Physiol. Rev., 98(3):1205-1240 (2018).

Zhang et al., NAD(+) repletion improves mitochondrial and stem cell function and enhances life span in mice, Science, 352:1436-1443 (2016).

Zimmermann et al., A novel silver(i)-mediated DNA base pair, J. Am. Chem. Soc., 124(46):13684-13685 (2002).

Zou et al., 2-NBDG as a fluorescent indicator for direct glucose uptake measurement, J. Biochem. Biophys Methods, 64:207-215 (2005).

Zweifach, FM1-43 reports plasma membrane phospholipid scrambling in T-lymphocytes, The Biochemical Journal, 349(Pt 1):255-60 (2000).

Ahn et al., MondoA coordinately regulates skeletal myocyte lipid homeostasis and insulin signaling, J. Clin. Invest., 126(9):3567-3579 (2016).

Akerboom et al., Optimization of a GCaMP calcium indicator for neural activity imaging, J. Neurosci., 32(40):13819-40 (2012).

Anders et al., HTSeq—a Python framework to work with high-throughput sequencing data, Bioinformatics, 31:166-169 (2015).

Ashburner et al., Gene ontology: tool for the unification of biology. The Gene Ontology Consortium, Nat. Genet., 25(1):25-29 (2000).

Avila-Sakar et al., Crystal structure of bovine annexin VI in a calcium-bound state, Biochimica Biophysica Acta., 1387(1-2):103-16 (1998).

Babbin et al., Annexin A1 regulates intestinal mucosal injury, inflammation, and repair, J. Immunol., 181(7):5035-44 (2008).

Babiychuk et al., Blebbing confers resistance against cell lysis, Cell Death Differ., 18(1):80-9 (2011).

Bansal et al., Defective membrane repair in dysferlin-deficient muscular dystrophy, Nature, 423(6936):168-72 (2003).

Bashir et al., A gene related to Caenorhabditis elegans spermatogenesis factor fer-1 is mutated in limb-girdle muscular dystrophy type 2B, Nat. Genet., 20(1):37-42 (1998).

Bement et al., Wound-induced assembly and closure of an actomyosin purse string in Xenopus oocytes, Curr. Biol., 9(11):579-87 (1999).

Bentzinger et al., Skeletal muscle-specific ablation of raptor, but not of rictor, causes metabolic changes and results in muscle dystrophy, Cell Metab., 8(5):411-424 (2008).

Benz et al., The structure of recombinant human annexin VI in crystals and membrane-bound, J. Mol. Biol., 260(5):638-43 (1996).

Berkner, Expression of Heterologous Sequences in Adenoviral Vectors, Curr. Top. Micro. Immunol., 158:39-66 (1992).

Bi et al., Calcium-regulated exocytosis is required for cell membrane resealing, The Journal of Cell Biology, 131(6 Pt 2):1747-58 (1995).

Bizzarro et al., Annexin A1: novel roles in skeletal muscle biology, J. Cell. Physiol., 227(8):3007-15 (2012).

Blackwood et al., Characterization of Ca2(+)-dependent phospholipid binding, vesicle aggregation and membrane fusion by annexins, The Biochemical Journal, 266(1):195-200 (1990).

Bodine et al., Identification of ubiquitin ligases required for skeletal muscle atrophy, Science, 294:1704-1708 (2001).

Boye et al., Annexin A4 and A6 induce membrane curvature and constriction during cell membrane repair, Nat. Comm., 8(1):1-11 (2017).

Boye et al., Annexins induce curvature on free-edge membranes displaying distinct morphologies, Sci. Rep., 8(1):10309 (2018).

Bruno et al., The combination of four analytical methods to explore skeletal muscle metabolomics: Better coverage of metabolic pathways or a marketing argument?, J. Pharm. Biomed. Anal., 148:273-279 (2018).

Bullard et al., Gadd45a Protein Promotes Skeletal Muscle Atrophy by Forming a Complex with the Protein Kinase MEKK4, J. Biol. Chem., 291(34):17496-17509 (2016).

Buzhynskyy et al., Annexin-A6 presents two modes of association with phospholipid membranes. A combined QCM-D, AFM and cryo-TEM study, Journal of Structural Biology, 168(1):107-16 (2009).

Cagliani et al., Mutation finding in patients with dysferlin deficiency and role of the dysferlin interacting proteins annexin A 1 and A2 in muscular dystrophies, Human Mutation, 26:283 (2005).

Cai et al., MG53 nucleates assembly of cell membrane repair machinery, Nat. Cell. Biol., 11(1):56-64 (2009).

Carey et al., Chromatin immunoprecipitation (ChIP), Cold Spring Harb Protoc, 2009:pdb.prot5279 (2009).

Carmeille et al., Annexin-A5 promotes membrane resealing in human trophoblasts, Biochimica et Biophysica Acta., 1853(9):2033-2044 (2015).

Ceco et al., Targeting latent TGFß release in muscular dystrophy, Science Translational Medicine, 6(259):259ra144 (2014).

Choi et al., Targeting Glutamine Metabolism for Cancer Treatment, Biomol. Ther. (Seoul), 26(1):19-28 (2018).

Chong et al., MetaboAnalyst 4.0: towards more transparent and integrative metabolomics analysis. Nucleic Acids Res., 46(W1):W486-W494 (2018).

Christmas et al., Selective secretion of annexin 1, a protein without a signal sequence, by the human prostate gland, The Journal of Biological Chemistry, 266:2499-2507 (1991).

Connolly et al., High dose weekly oral prednisone improves strength in boys with Duchenne muscular dystrophy, Neuromuscul. Disord., 12(10):917-925 (2002).

Cook, Medicinal chemistry of antisense oligonucleotides—future opportunities, Anti-Cancer Drug Design, 6(6):585-607 (1991).

D'Antona et al., Branched-chain amino acid supplementation promotes survival and supports cardiac and skeletal muscle mitochondrial biogenesis in middle-aged mice, Cell Metab., 12(4):362-372 (2010).

(56) References Cited

OTHER PUBLICATIONS

Davenport et al., Membrane dynamics during cellular wound repair, Mol. Biol. Cell., 27(14):2272-85 (2016).
Demonbreun et al., An actin-dependent annexin complex mediates plasma membrane repair in muscle, J. Cell Biol., 213(6): 705-718 (2016).
Demonbreun et al., DNA Electroporation, Isolation and Imaging of Myofibers, J. Vis. Exp., 106(106):e53551 (2015).
Demonbreun et al., Dysferlin and myoferlin regulate transverse tubule formation and glycerol sensitivity, Am. J. Pathol., 184(1):248-59 (2014).
Demonbreun et al., Dysferlin and myoferlin regulate transverse tubule formation and glycerol sensitivity, Am. J. Pathol., 184:248-259 (2014).
Demonbreun et al., Enhanced Muscular Dystrophy from Loss of Dysferlin Is Accompanied by Impaired Annexin A6 Translocation after Sarcolemmal Disruption, Am. J. Pathol., 186(6):1610-22 (2016).
Demonbreun et al., Eps 15 Homology Domain (EHD)-1 Remodels Transverse Tubules in Skeletal Muscle, PLoS One, 10(9):e0136679 (2015).
Demonbreun et al., Impaired muscle growth and response to insulin-like growth factor 1 in dysferlin-mediated muscular dystrophy, Hum. Mol. Genet., 20:779-789 (2011).
Demonbreun et al., Plasma Membrane Repair in Health and Disease, Curr. Top. Membr., 77:67-96 (2016).
Demonbreun et al., Recombinant annexin A6 promotes membrane repair and protects against muscle injury, J. Clin. Invest., 129(11):4657-4670 (2019).
Deora et al., An annexin 2 phosphorylation switch mediates p11-dependent translocation of annexin 2 to the cell surface, The Journal of Biological Chemistry, 279:43411-43418 (2004).
Detour et al., Annexin A2 links poor myofiber repair with inflammation and adipogenic replacement of the injured muscle, Human Molecular Genetics., 26(11):1979-91 (2017).
Difranco et al., DNA transfection of mammalian skeletal muscles using in vivo electroporation, J. Vis. Exp., 1520 (2009).
Duann et al., MG53-mediated cell membrane repair protects against acute kidney injury, Science Translational Medicine, 7(279):279ra36 (2015).
Echigoya et al., Multiple Exon Skipping in the Duchenne Muscular Dystrophy Hot Spots: Prospects and Challenges, J. Pers. Med., 8(4):41 (2018).
Englisch et al., Angewandte Chemie, International Edition, 30:613-722 (1991).
Fardet et al., Systemic glucocorticoid therapy: a review of its metabolic and cardiovascular adverse events, Drugs, 74(15):1731-1745 (2014).
Day et al., Determining the Role of Annexin A6 in Cell Membrane Repair, Faseb J., 32(1):542.29 (2018).
Kearby et al., Selective Androgen Receptor Modulator (SARM) Treatment Prevents Bone Loss and Reduces Body Fat in Ovariectomized Rats, Pharm Res., 24(2): 328-335 (2007).
Ramazi et al., Post-translational modifications in proteins: resources, tools and prediction methods, Database, 2021, (Apr. 2021).
Meng et al., Annexin A3 gene silencing promotes myocardial cell repair through activation of the PI3K/Akt signaling pathway in rats with acute myocardial infarction, J. Cell. Physiol., 234(7):10535-46 (2019).
Metsalu et al., ClustVis: a web tool for visualizing clustering of multivariate data using Principal Component Analysis and heatmap, Nucleic Acids Res., 43:W566-570 (2015).
Millay et al., Calcium influx is sufficient to induce muscular dystrophy through a TRPC-dependent mechanism, Proc. Natl. Acad. Sci. USA, 106(45):19023-8 (2009).
Min et al., CRISPR Correction of Duchenne Muscular Dystrophy, Annu. Rev. Med., 70:239-255 (2019).
Morrison-Nozik et al., Glucocorticoids enhance muscle endurance and ameliorate Duchenne muscular dystrophy through a defined metabolic program, Proc. Natl. Acad. Sci. USA, 112(49):E6780-6789 (2015).
Murphy et al., Proteomic analysis of the sarcolemma-enriched fraction from dystrophic mdx-4cv skeletal muscle, J. Proteomics., 191:212-227 (2019).
Nadal et al., Endocrine-disrupting chemicals and the regulation of energy balance, Nat. Rev. Endocrinol., 13(9):536-546 (2017).
Perez-Llamas et al., Gitools: analysis and visualisation of genomic data using interactive heat-maps, PLoS One, 6:e19541 (2011).
Petrof et al., Dystrophin protects the sarcolemma from stresses developed during muscle contraction. Proc. Natl. Acad. Sci. USA, 90(8):3710-4 (1993).
Pharmaceutics and Pharmacy Practice, J. B. Lippincott Co., Philadelphia. Pa., Banker and Chalmers. eds., 238-250 (1982).
Pickar-Oliver et al., The next generation of CRISPR-Cas technologies and applications, Nat. Rev. Mol. Cell. Biol., 20(8):490-507 (2019).
Quattrocelli et al., Genetic modifiers of muscular dystrophy act on sarcolemmal resealing and recovery from injury, PLoS Genet., 13(10):e1007070 (2017).
Quattrocelli et al., Intermittent Glucocorticoid Dosing Improves Muscle Repair and Function in Mice with Limb-Girdle Muscular Dystrophy, Am. J. Pathol., 187(11):2520-2535 (2017).
Quattrocelli et al., Intermittent glucocorticoid steroid dosing enhances muscle repair without eliciting muscle atrophy, J. Clin. Invest., 127(6):2418-2432 (2017).
Quattrocelli et al., Mesodermal iPSCderived progenitor cells functionally regenerate cardiac and skeletal muscle, J. Clin. Invest., 125:4463-4482 (2015).
Quattrocelli et al., Pulsed glucocorticoids enhance dystrophic muscle performance through epigenetic-metabolic reprogramming, JCI Insight., 4(24):e132402 (2019).
Ramsey et al., Circadian clock feedback cycle through NAMPT-mediated NAO+ biosynthesis, Science, 324:651-654 (2009).
Reddy et al., Plasma membrane repair is mediated by Ca(2+)-regulated exocytosis of lysosomes, Cell., 106(2):157-69 (2001).
Rivera et al., Mapping human epigenomes, Cell, 155(1):39-55 (2013).
Robinson et al., edgeR: a Bioconductor package for differential expression analysis of digital gene expression data, Bioinformatics, 26:139-140 (2010).
Rodriguez et al., Lysosomes behave as Ca2+-regulated exocytic vesicles in fibroblasts and epithelial cells, J. Cell. Biol., 137(1):93-104 (1997).
Roostalu et al., In vivo imaging of molecular interactions at damaged sarcolemma, Dev. Cell., 22(3):515-29 (2012).
Rosenfeld et al., In vivo transfer of the human cystic fibrosis transmembrane conductance regulator gene to the airway epithelium, Cell, 8: 143-144 (1992).
Ryu et al., NAD+ repletion improves muscle function in muscular dystrophy and counters global PARylation, Sci. Transl. Med., 8:361ra139 (2016).
Sali et al., Glucocorticoid-treated mice are an inappropriate positive control for long-term preclinical studies in the mdx mouse, PLoS One, 7:e34204 (2012).
Sancak et al., The Rag GTPases bind raptor and mediate amino acid signaling to mTORC1, Science, 320:1496-1501 (2008).
Sandri et al., Foxo transcription factors induce the atrophy-related ubiquitin ligase atrogin-1 and cause skeletal muscle atrophy, Cell, 117(3):399-412 (2004).
Sandri et al., PGC-1alpha protects skeletal muscle from atrophy by suppressing Fox03 action and atrophy-specific gene transcription, Proc. Natl. Acad. Sci. USA, 103(44):16260-16265 (2006).
Sanghvi, Antisense research and applications, Chapter 15, CRC Press, Inc., 289-302 (1999).
Schakman et al., Mechanisms of muscle atrophy induced by glucocorticoids, Horm. Res., 72 Suppl 1:36-41 (2009).
Schiaffino et al., Fiber types in mammalian skeletal muscles, Physiol. Rev., 91:1447-1531 (2011).
Schneider et al., NIH Image to ImageJ: 25 years of image analysis, Nat. Methods, 9:671-675 (2012).
Shintaku et al., Analysis of Aerobic Respiration in Intact Skeletal Muscle Tissue by Microplate-Based Respirometry, Methods Mol. Biol., 1460:337-343 (2016).

(56) References Cited

OTHER PUBLICATIONS

Shintaku et al., MyoD Regulates Skeletal Muscle Oxidative Metabolism Cooperatively with Alternative NF-kappaB, Cell. Rep., 17:514-526 (2016).
Stratford-Perricaudet et al., Evaluation of the transfer and expression in mice of an enzyme-encoding gene using a human adenovirus vector, Hum. Gene Ther., 1(3):241-256 (1990).
Stratford-Perricaudet et al., Widespread long-term gene transfer to mouse skeletal muscles and heart, J. Clin. Invest., 90(2):626-630 (1992).
Sun et al., Catabolic Defect of Branched-Chain Amino Acids Promotes Heart Failure, Circulation, 133:2038-2049 (2016).
Swaggart et al., Annexin A6 modifies muscular dystrophy by mediating sarcolemmal repair, Proc. Nat. Acad. Scien., 111(16):6004-6009 (2014).
Thomas, The Interaction of HgCl2 with Sodium Thymonucleate, J. Am. Chem. Soc., 76(23):6032-6034 (1954).
Toissel, ASHP Handbook on Injectable Drugs, 4th ed., pp. 622-630 (1986).
Trapnell et al., TopHat: discovering splice junctions with RNA-Seq, Bioinformatics, 25:1105-1111 (2009).
Vockley et al., Direct GR Binding Sites Potentiate Clusters of TF Binding across the Human Genome, Cell, 166(5):1269-1281.e1219 (2016).
Waddell et al., Dysferlin, annexin A1, and mitsugumin 53 are upregulated in muscular dystrophy and localize to longitudinal tubules of the T-system with stretch, J. Neur. Exp. Neur., 70(4):302-313 (2011).
Wallner et al., Cloning and expression of human lipocortin, a phospholipase A2 inhibitor with potential anti-inflammatory activity, Nature, 320:77-81 (1986).
Walter et al., Interventions Targeting Glucocorticoid-Kruppel-like Factor 15-Branched-Chain Amino Acid Signaling Improve Disease Phenotypes in Spinal Muscular Atrophy Mice, EBioMedicine, 31:226-242 (2018).
Walter et al., Treatment of dysferlinopathy with deflazacort: a double-blind, placebo-controlled clinical trial, Orphanet. J. Rare Dis., 8:26 (2013).
Weisleder et al., Recombinant MG53 protein modulates therapeutic cell membrane repair in treatment of muscular dystrophy, Science Translational Medicine, 4(139):139ra85 (2012).
White et al., The BCKDH Kinase and Phosphatase Integrate BCAA and Lipid Metabolism via Regulation of ATP-Citrate Lyase, Cell Metab., 27:1281-1293.e1287 (2018).
Xian et al., Inhibition of LDHA suppresses tumor progression in prostate cancer, Tumour Biol., 36:8093-8100 (2015).
Yamane et al., On the Complexing of Desoxyribonucleic Acid (DNA) by Mercuric IonJ. Am. Chem. Soc., 83(12):2599-2607 (1961).
Fiehn et al., Lipids and fatty acids of sarcolemma, sarcoplasmic reticulum, and mitochondria from rat skeletal muscle, The Journal of Biological Chemistry, 246(18):5617-20 (1971).
Flanigan et al., LTBP4 genotype predicts age of ambulatory loss in Duchenne muscular dystrophy, Ann. Neurol., 73(4):481-488 (2013).
Freier et al., The ups and downs of nucleic acid duplex stability: structure-stability studies on chemically-modified DNA:RNA duplexes, Nucleic Acids Research, 25(22):4429-4443 (1997).
Gerke et al., Annexins: from structure to function, Physiol. Rev., 82:331-371 (2002).
Gerke et al., Annexins: linking Ca2+ signalling to membrane dynamics, Nat. Rev. Mol. Cell. Biol., 6:449-461 (2005).
Godfrey et al., Fukutin gene mutations in steroid-responsive limb girdle muscular dystrophy, Ann. Neural., 60(5):603-610 (2006).
Goonasekera et al., Mitigation of muscular dystrophy in mice by SERCA overexpression in skeletal muscle, J. Clin. Invest., 121(3):1044-52 (2011).
Goulet et al., Glycosylation of annexin I and annexin II, Biochemical and Biophysical Research Communications, 188:554-558 (1992).
Grewal et al., Annexin A6—A multifunctional scaffold in cell motility, Cell. Adh. Migr., 11(3):288-304 (2017).
Hack et al., Gamma-sarcoglycan deficiency leads to muscle membrane defects and apoptosis independent of dystrophin, J. Cell. Biol., 142(5):1279-1287 (1998).
Hack et al., Muscle degeneration without mechanical injury in sarcoglycan deficiency, Proc. Natl. Acad. Sci. USA, 96(19):10723-8 (1999).
Hammers et al., Dual inhibition of complement factor 5 and leukotriene B4 synergistically suppresses murine pemphigoid disease, JCI Insight in press, https://doi.org/10.1172/id.insight i 33276 (2019).
Hannon et al., Aberrant inflammation and resistance to glucocorticoids in annexin 1-/-mouse, Faseb J., 17:253-255 (2003).
Hayes et al., Annexin-actin interactions, Traffic., 5(8):571-576 (2004).
He et al., Enhancing muscle membrane repair by gene delivery of MG53 ameliorates muscular dystrophy and heart failure in d-Sarcoglycan-deficient hamsters, Molecular Therapy, 20(4):727-35 (2012).
Heinz et al., Simple combinations of lineage-determining transcription factors prime cis-regulatory elements required for macrophage and B cell identities, Mol. Cell., 38:576-589 (2010).
Hill et al., Estimating abdominal adipose tissue with DXA and anthropometry, Obesity (Silver Spring), 15:504-510 (2007).
Hoffman et al., Dystrophin: the protein product of the Duchenne muscular dystrophy locus, Cell., 51(6):919-928 (1987).
International Application No. PCT/US19/68168, International Preliminary Report on Patentability, mailed Jul. 1, 2021.
International Application No. PCT/US19/68168, International Search Report and Written Opinion, mailed Apr. 6, 2020.
Ishii et al., Recombinant annexin II modulates impaired fibrinolytic activity in vitro and in rat carotid artery, Circ Res., 89(12):1240-1245 (2001).
Jennische et al., Postischemic skeletal muscle injury: patterns of injury in relation to adequacy of reperfusion, Exp. Mol. Pathol., 44(3):272-80 (1986).
Jia et al., Treatment of acute lung injury by targeting MG53-mediated cell membrane repair, Nat. Commun., 5:4387 (2014).
Jimenez et al., Plasma membrane repair: the adaptable cell life-insurance, Curr. Opin. Cell. Biol., 47:99-107 (2017).
Jost et al., Mapping of three unique Ca(2+)-binding sites in human annexin II, Eur. J. Biochem., 207(3):923-30 (1992).
Kaetzel et al., Phosphorylation mutants elucidate the mechanism of annexin IV-mediated membrane aggregation, Biochemistry, 40(13):4192-4199 (2001).
Kambo et al., Nitric oxide inhibits mammalian methylmalonyl-CoA mutase, J. Biol. Chem., 280:10073-10082 (2005).
Katz, The reversible reaction of sodium thymonucleate and mercuric chloride, J. Am. Chem. Soc., 74:2238 (1951).
Kerr et al., Dysferlin stabilizes stress-induced Ca2+ signaling in the transverse tubule membrane, Proc. Natl. Acad. Sci. USA, 110:20831-20836 (2013).
Koerdt et al., Annexin A2 is involved in Ca 2+-dependent plasma membrane repair in primary human endothelial cells, Biochim. Biophys. Acta. Mol. Cell Res., 1864(6):1046-1053 (2016).
Kosturko et al., The crystal and molecular structure of a 2:1 complex of 1-methylthymine-mercury (II), Biochemistry, 13(19):3949-3952 (1974).
Kozhemyakina et al., Parathyroid hormone-related peptide represses chondrocyte hypertrophy through a protein phosphatase 2A/histone deacetylase 4/MEF2 pathway, Mol. Cell Biol., 29:5751-5762 (2009).
Kroschwitz, Concise Encyclopedia of Polymer Science and Engineering, John Wiley & Sons, 858-859 (1990).
La et al., Annexin 1 peptides protect against experimental myocardial ischemia-reperfusion: analysis of their mechanism of action, Faseb J., 15(12):2247-2256 (2001).
Laat et al., Annexin A5 polymorphism (-1C-→T) and the presence of anti-annexin A5 antibodies in the antiphospholipid syndrome, Annals of the Rheumatic Diseases, 65:1468-1472 (2006).
Langmead et al., Fast gapped-read alignment with Bowtie 2, Nat. Methods, 9:357-359 (2012).
Lauritzen et al., Annexins are instrumental for efficient plasma membrane repair in cancer cells, Semin Cell. Dev. Biol., 45:32-38 (2015).

(56) References Cited

OTHER PUBLICATIONS

Lennon et al., Dysferlin interacts with annexins A1 and A2 and mediates sarcolemmal wound-healing, The Journal of Biological Chemistry, 278(50):50466-73 (2003).
Li et al., Defective Branched-Chain Amino Acid Catabolismisrupts Glucose Metabolism and Sensitizes the Heart to Ischemia-Reperfusion Injury, Cell Metab., 25(2):374-385 (2017).
Li et al., Precision Medicine through Antisense Oligonucleotide-Mediated Exon Skipping, Trends Pharmacol. Sci., 39(11):982-994 (2018).
Lin et al., Control of mouse cardiac morphogenesis and myogenesis by transcription factor MEF2C, Science, 276:1404-1407 (1997).
Ling et al., Annexin II regulates fibrin homeostasis and neoangiogenesis in vivo, The Journal of Clinical Investigation, 113:38-48 (2004).
Liu et al., Cardioprotection of recombinant human MG53 protein in a porcine model of ischemia and reperfusion injury, Journal of Molecular and Cellular Cardiology, 80:10-9 (2015).
Lynch et al., Branched-chain amino acids in metabolic signalling and insulin resistance., Nat. Rev. Endocrinol., 10(12):723-736 (2014).
Maeder et al., Genome-editing Technologies for Gene and Cell Therapy, Mol. Ther., 24(3):430-46 (2016).
Mcdade et al., Rapid actin-cytoskeleton-dependent recruitment of plasma membrane-derived dysferlin at wounds is critical for muscle membrane repair, Faseb J., 28(8):3660-70 (2014).
Mcdonald et al., Long-term effects of glucocorticoids on function, quality of life, and survival in patients with Duchenne muscular dystrophy: a prospective cohort study, Lancet, 391:451-461 (2018).
Mcneil et al., An emergency response team for membrane repair, Nat. Rev. Mol. Cell. Biol., 6(6):499-505 (2005).
Mcneil et al., Disruptions of muscle fiber plasma membranes. Role in exercise-induced damage, Am. J. Pathol., 140(5):1097-109 (1992).
Mcneil et al., Requirement for annexin A 1 in plasma membrane repair, The Journal of Biological Chemistry, 281(46):35202-7 (2006).
Braun et al., EHD proteins associate with syndapin I and II and such interactions play a crucial role in endosomal recycling, Molecular biology of the cell, 16(8):3642-3658 (Aug. 2005).
Brendza et al., PDAPP; YFP double transgenic mice: A tool to study amyloid-ß associated changes in axonal, dendritic, and synaptic structures, Journal of Comparative Neurology, 456(4):375-383 (Feb. 2003).
Buggia-Prevot et al., A function for EHD family proteins in unidirectional retrograde dendritic transport of BACE1 and Alzheimer's disease Aß production, Cell Reports, 5(6):1552-1563 (Dec. 2013).
Buikema et al., Wnt Activation and Reduced Cell-Cell Contact Synergistically Induce Massive Expansion of Functional Human iPSC-Derived Cardiomyocytes, Cell Stem Cell, 27(1):50-63 (Jul. 2020).
Condello et al., Microglia constitute a barrier that prevents neurotoxic protofibrillar Aß42 hotspots around plaques, Nature communications, 6(6176):1-14 (Jan. 2015).
Cook P.O., Medicinal chemistry of antisense oligonucleotides—future opportunities, Anti-Cancer Drug Design, 6(6):585-607 (Dec. 1991).
Dana et al., Sensitive red protein calcium indicators for imaging neural activity, elife, 5(1):e12727(1-24) (Mar. 2016).
Dralle et al., Changes in lipid membranes may trigger amyloid toxicity in Alzheimer's disease, PLoS One, 12(8):e0182194(1-16) (Aug. 2017).
Eimer et al., Neuron loss in the 5XFAD mouse model of Alzheimer's disease correlates with intraneuronal Aß42 accumulation and Caspase-3 activation, Molecular neurodegeneration, 8(2):1-12 (Jan. 2013).
Grathwohl et al., Replacement of Osmotic Minipumps to Extend the Intracerebral Infusion time of Compounds into the Mouse Brain, BioTechniques, 55(2):75-78 (Apr. 2018).
Gratuze et al., Activated microglia mitigate Aß-associated tau seeding and spreading, Journal of Experimental Medicine, 218(8):e20210542(1-14) (Aug. 2021).
Gratuze et al., APOE Antibody Inhibits Aß-Associated Tau Seeding and Spreading in a Mouse Model, Annals of Neurology, 91(6):847-852 (Jun. 2022).
He et al., Amyloid-ß plaques enhance Alzheimer's brain tau-seeded pathologies by facilitating neuritic plaque tau aggregation, Nature Medicine, 24(1):29-36 (Jan. 2018).
High blood triglycerides. National Heart, Lung, and Blood Institute. https://www.nhlbi.nih.gov/health-topics/high-blood-triglycerides. Accessed Aug. 7, 2018 (Year: 2018).
Ibraghimov-Beskrovnaya et al., Primary structure of dystrophin-associated glycoproteins linking dystrophin to the extracellular matrix, Nature, 355(6362):696-702 (Feb. 1992).
International Application No. PCT/US2019/068618, International Preliminary Report on Patentability, mailed Jul. 8, 2021.
International Application No. PCT/US2019/068618, International Search Report and Written Opinion, mailed Jun. 10, 2020.
Kandalepas et al., The Alzheimer's ß-secretase BACE1 localizes to normal presynaptic terminals and to dystrophic presynaptic terminals surrounding amyloid plaques, Acta Neuropathologica, 126(1):329-352 (Jul. 2013).
Kuchibhotla et al., Aß Plaques Lead to Aberrant Regulation of Calcium Homeostasis In Vivo Resulting in Structural and Functional Disruption of Neuronal Networks, Neuron, 59(2):214-225 (Jul. 2008).
Lambert et al., Evidence of the association of BIN1 and PICALM with the AD risk in contrasting European populations, Neurobiology of aging, 32(4):756.e11-756.e15 (Apr. 2011).
Levites et al., Intracranial adeno-associated virus-mediated delivery of anti-pan amyloid beta, amyloid beta40, and amyloid beta42 single-chain variable fragments attenuates plaque pathology in amyloid precursor protein mice, Journal of Neuroscience, 26(46):11923-11928 (Nov. 2006).
Malid et al. Increased plasma lipid levels exacerbate muscle pathology in the mdx mouse model of Duchenne muscular dystrophy, Skeletal Muscle, 2017, pp. 1-14. (Year: 2017).
Mastrella et al., Targeting APLN/APLNR Improves Antiangiogenic Efficiency and Blunts Proinvasive Side Effects of VEGFA/VEGFR2 Blockade in Glioblastoma, Cancer Research, 79(9):2298-2313 (May 2019).
Mattsson-Carlgren et al., Aß deposition is associated with increases in soluble and phosphorylated tau that precede a positive Tau PET in Alzheimer's disease, Science advances, 6(16):1-13 (Apr. 2020).
Oakley et al., Intraneuronal ß-Amyloid Aggregates, Neurodegeneration, and Neuron Loss in Transgenic Mice with Five Familial Alzheimer's Disease Mutations: Potential Factors in Amyloid Plaque Formation, Journal of Neuroscience, 26(40):10129-10140 (Oct. 2006).
Palmqvist et al., Cerebrospinal fluid and plasma biomarker trajectories with increasing amyloid deposition in Alzheimer's disease, EMBO Mol. Med., 11(1):e11170(1-13) (Nov. 2019).
Park et al., Annexin A1 restores Aß1-42-induced blood-brain barrier disruption through the inhibition of RhoA-ROCK signaling pathway, Aging cell, 16(1): 149-161 (Feb. 2017).
Peters et al., BACE1 inhibition more effectively suppresses initiation than progression of ß-amyloid pathology, Acta Neuropathologica, 135(1):695-710 (Jan. 2018).
Quattrocelli et al. Intermittent glucocorticoid steroid dosing enhances muscle repair without eliciting muscle atrophy, JCI, May 2017, pp. 2418-2432 (Year: 2017).
Rise et al., Annexin A1 restores cerebrovascular integrity concomitant with reduced amyloid-ß and tau pathology, Brain, 144(5):1526-1541 (May 2021).
Roy et al., Concerted type I interferon signaling in microglia and neural cells promotes memory impairment associated with amyloid ß plaques, Immunity, 55(5):879-894 (May 2022).
Sadleir et al., Cdk5 Protein Inhibition and Aß42 Increase BACE1 Protein Level in Primary Neurons by a Post-transcriptional Mechanism Implications of CDK5 as a Therapeutic Target for Alzheimer Disease, Journal of Biological Chemistry, 287(10):7224-7235 (Mar. 2012).
Sadleir et al., Genetic inhibition of phosphorylation of the translation initiation factor elF2a does not block Aß-dependent elevation of

(56) References Cited

OTHER PUBLICATIONS

BACE1 and APP levels or reduce amyloid pathology in a mouse model of Alzheimer's disease, PLoS One, 9(7):e101643(1-16) (Jul. 2014).
Sadleir et al., Presynaptic dystrophic neurites surrounding amyloid plaques are sites of microtubule disruption, BACE1 elevation, and increased Aß generation in Alzheimer's disease, Acta Neuropathologica, 132(1):235-256 (Mar. 2016).
Sheikh et al., Pharmacology and toxicology of eteplirsen and SRP-5051 for DMD exon 51 skipping: an update, Archives of Toxicology, 96(1):1-9 (Nov. 2021).
Srivastava et al. Abnormal lipid metabolism in skeletal muscle tissue of patients with muscular dystrophy: In vitro, high-resolution NMR spectroscopy based observation in early phase of the disease, MRI, Jan. 2017, pp. 163-173. (Year: 2017).
Stauffer et al., Receptor-induced transient reduction in plasma membrane PtdIns(4,5)P2 concentration monitored in living cells, Current Biology, 8(6):343-346 (Mar. 1998).
Suarez-Calvet et al., Novel tau biomarkers phosphorylated at T181, T217 or T231 rise in the initial stages of the preclinical Alzheimer's continuum when only subtle changes in Aß pathology are detected, EMBO Mol. Med., 12(1):e12921(1-19) (Nov. 2020).
Volovitz et al., Normal diurnal variation in serum cortisol concentration in asthmatic children treated with inhaled budesonide, Journal of Allergy and Clinical Immunology, 96(6):874-878 (Dec. 1995).
Zhao et al., ß-Site Amyloid Precursor Protein Cleaving Enzyme 1 Levels Become Elevated in Neurons Amyloid Plaques: Implications for Alzheimer's Disease Pathogenesis, Journal of Neuroscience,(Apr. 2007).
NCBI Reference Sequence: NP_001146.2, annexin VI isoform 1 [*Homo sapiens*], National Institutes of Health, 4 pages (Aug. 3, 2005).
NCBI Reference Sequence: NP_001180473.1, annexin A6 isoform 2 [*Homo sapiens*], National Institutes of Health, 3 pages (Aug. 3, 2010).

* cited by examiner (to be continued)

(continuation)

(to be continued)

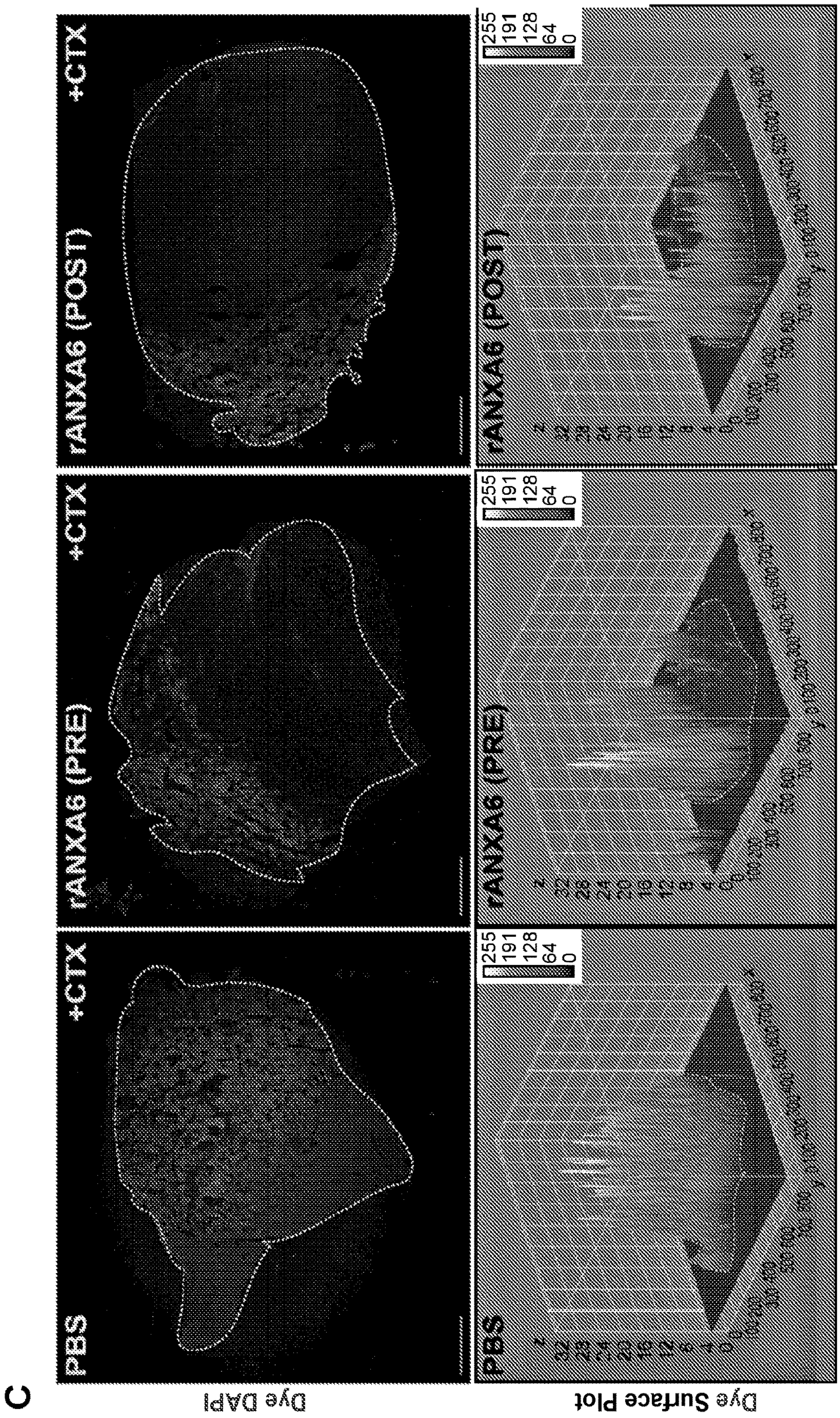
Figure 13 (continuation)

Annexin A6 Clustal protein alignment

```
Homo            MAKPAQGAKYRGSIHDFPGFDPNQDAEALYTAMKGFGSDKEAILDIITSRSNRQRQEVCQ      60
Macaca          MAKPAQGAKYRGSIHDFPGFDPNQDAEALYTAMKGFGSDKEAILDIITSRSNRQRQEICQ      60
Canis           -MAKPQGVKYRGSIHDFPNFDPNQDAEALYTAMKGFGSDKEAILELITSRSNRQRQEISQ      59
Rattus          MAKIAQGAMYRGSVHDFADFDANQDAEALYTAMKGFGSDKESILELITSRSNRQRQEICQ      60
Mus             MAKIAQGAMYRGSVHDFPEFDANQDAEALYTAMKGFGSDKESILELITSRSNKQRQEICQ      60
                     **. ****:***  ** *******************:**::******:****:.*

Homo            SYKSLYGKDLIADLKYELTGKFERLIVGLMRPPAYCDAKEIKDAISGIGTDEKCLIEILA      120
Macaca          SYKSLYGKDLIADLKYELTGKFERLIVGLMRPPAYCDAKEIKDAISGIGTDEKCLIEILA      120
Canis           SYKSLYGKDLIADLKYELTGKFERLIVGLMRPLAYCDAKEIKDAISGIGTDEKCLIEILA      119
Rattus          SYKSLYGKDLIADLKYELTGKFERLIVNLMRPLAYCDAKEIKDAISGIGTDEKCLIEILA      120
Mus             NYKSLYGKDLIEDLKYELTGKFERLIVNLMRPLAYCDAKEIKDAISGVGTDEKCLIEILA      120
                .********** ***************.**** **************:************

Homo            SRTNEQMHQLVAAYKDAYERDLEADIIGDTSGHFQKMLVVLLQGTREEDDVVSEDLVQQD      180
Macaca          SRTNEQMHQLVAAYKDAYERDLEADIIGDTSGHFQKMLVVLLQGTREEDDVVSEDLVQQD      180
Canis           SRTNEQIHQLVAAYKDAYERDLEADIIGDTSGHFQKMLVVLLQGTREQDDVVSEDLVQQD      179
Rattus          SRTNEQIHQLVAAYKDAYERDLESDIIGDTSGHFQKMLVVLLQGTRENDDVVSEDLVQQD      180
Mus             SRTNEQMHQLVAAYKDAYERDLESDIIGDTSGHFQKMLVVLLQGTRENDDVVSEDLVQQD      180
                ******:****************:***********************:************

Homo            VQDLYEAGELKWGTDEAQFIYILGNRSKQHLRLVFDEYLKTTGKPIEASIRGELSGDFEK      240
Macaca          VQDLYEAGELKWGTDEAQFIYILGNRSKQHLRLVFDEYLKTTGKPIEASIRGELSGDFEK      240
Canis           VQDLYEAGELKWGTDEAQFIYILGNRSKQHLRLVFDEYLRTTGKPIEASIRGELSGDFEK      239
Rattus          VQDLYEAGELKWGTDEAQFIYILGNRSKQHLRLVFDEYLKTTGKPIEASIRGELSGDFEK      240
Mus             VQDLYEAGELKWGTDEAQFIYILGNRSKQHLRLVFDEYLKTTGKPIEASIRGELSGDFEK      240
                ***************************************:********************

Homo            LMLAVVKCIRSTPEYFAERLFKAMKGLGTRDNTLIRIMVSRSELDMLDIREIFRTKYEKS      300
Macaca          LMLAVVKCIRSTPEYFAERLFKAMKGLGTRDNTLIRIMVSRSELDMLDIREIFRTKYEKS      300
Canis           LMLAVVKCIRSTPEYFAERLFKAMKGLGTRDNTLIRIMVSRSELDMLDIREIFRTKYEKS      299
Rattus          LMLAVVKCIRSTPEYFAERLFKAMKGLGTRDNTLIRIMVSRSELDMLDIREIFRTKYEKS      300
Mus             LMLAVVKCIRSTPEYFAERLFKAMKGLGTRDNTLIRIMVSRSELDMLDIREIFRTKYEKS      300
                ************************************************************

Homo            LYSMIKNDTSGEYKKTLLKLSGGDDDAAGQFFPEAAQVAYQMWELSAVARVELKGTVRPA      360
Macaca          LYSMIKNDTSGEYKKSLLKLCGGDDDAAGQFFPEAAQVAYQMWELSAVARVELKGTVRPA      360
Canis           LYSMIKNDTSGEYKKALLKLCGGDDDAAGQFFPEAAQVAYQMWELSAVARVELKGTVRPV      359
Rattus          LYSMIKNDTSGEYKKALLKLCGGDDDAAGQFFPEAAQVAYQMWELSAVSRVELKGTVRAA      360
Mus             LYSMIKNDTSGEYKKALLKLCGGDDDAAGQFFPEAAQVAYQMWELSAVSRVELKGTVCAA      360
                ***************:****.***************************:********  .

Homo            NDFNPDADAKALRKAMKGLGTDEDTIIDIITHRSNVQRQQIRQTFKSHFGRDLMTDLKSE      420
Macaca          NDFNPDADAKALRKAMKGLGTDEDTIIDIITHRSNAQRQQIRQTFKSHFGRDLMSDLKSE      420
Canis           DNFNPDADAKALRKAMKGLGTDEDTIIDIITHRSNAQRQQIRQTFKSHFGRDLMADLKSE      419
Rattus          NDFNPDADAKALRKAMKGIGTDEATIIDIITQRSNAQRQQIRQTFKSHFGRDLMADLKSE      420
Mus             NDFNPDADAKALRKAMKGIGTDEATIIDIVTHRSNAQRQQIRQTFKSHFGRDLMADLKSE      420
                ::****************:**** *****:*:***.******************:*****
```

Figure 21
(to be continued)

```
Homo            ISGDLARLILGLMMPPAHYDAKQLKKAMEGAGTDEKALIEILATRTNAEIRAINEAYKED      480
Macaca          ISGDLARLILGLMMPPAHYDAKQLKKAMEGAGTDEKALIEILATRTNAEIRAINEAYKED      480
Canis           ISGDLARLILGLMMPPAHYDAKQLKKAMEGAGTDEKALIEILATRTNAEIRAICEAYKED      479
Rattus          ISGDLARLILGLMMPPAHYDAKQLKKAMEGAGTDEKALIEILATRTNAEIRAINEAYKED      480
Mus             ISGDLARLILGLMMPPAHYDAKQLKKAMEGAGTDEKTLIEILATRTNAEIRAINEAYKED      480
                ************************************:**************** ******

Homo            YHKSLEDALSSDTSGHFRRILISLATGHREEGGENLDQAREDAQVAAEILEIADTPSGDK      540
Macaca          YHKSLEDALSSDTSGHFRRILISLATGNREEGGENLDQAREDAQVAAEILEIADTPSGDK      540
Canis           YHKSLEDALSSDTSGHFRRILISLATGNREEGGEDRNQAREDAQVAAEILEIADTPSGDK      539
Rattus          YHKSLEDALSSDTSGNFRRILISLATGNREEGGENRDQAQEDAQVAAEILEIADTPSGDK      540
Mus             YHKSLEDALSSDTSGHFRRILISLATGNREEGGENRDQAQEDAQVAAEILEIADTPSGDK      540
                ***************:***********:******: :**:********************

Homo            TSLETRFMTILCTRSYPHLRRVFQEFIKMTNYDVENTIKKEMSGDVRDAFVAIVQSVKNK      600
Macaca          ASLETRFMTILCTRSYPHLRRVFQEFIKMTNYDVENTIKKEMSGDVRDAFVAIVQSVKNK      600
Canis           TSLETRFMTILCTRSYPHLRRVFQEFVKMTNYDVENTIKKEMSGDVRDVFVAIVQSVKNK      599
Rattus          TSLETRFMTVLCTRSYPHLRRVFQEFIKKTNYDIENVIKKEMSGDVKDAFVAIVQSVKNK      600
Mus             TSLETRFMTVLCTRSYPHLRRVFQEFIKKTNYDIENVIKKEMSGDVKDAFVAIVQSVKNK      600
                :********:****************:* ****:**.*********:*.***********

Homo            PLFFADKLYKSNKGAGTDEKTLTRINVSRSEIDLLNIRREFIEKYDKSLHQAIEGDTSGD      660
Macaca          PLFFADKLYKSNKGAGTDEKTLTRINVSRSEIDLLNIRREFIEKYDKSLHQAIEGDTSGD      660
Canis           PLFFADKLYKSNKGAGTDDKTLTRINVSRSEIDLLNIRREFIEKYDKSLHQAIEGDTSGD      659
Rattus          PLFFADKLYKSNKGAGTDEKTLTRVNVSRSEIDLLNIRREFIEKYDKSLHQAIEGDTSGD      660
Mus             PLFFADKLYKSNKGAGTDEKTLTRVNVSRSEIDLLNIRREFIEKYDKSLHQAIEGDTSGD      660
                ******************:*****:***********************************

Homo            FLKALLALCGGED 673
Macaca          FLKALLALCGGED 673
Canis           FLKALLAICGGED 672
Rattus          FMKALLALCGGED 673
Mus             FMKALLALCGGED 673
                *:*****:*****
```

Percent Identity Matrix - created by Clustal2.1

| | | | | | |
|---|---|---|---|---|---|
| 1: Homo Sapien (AAH17846.1) | 100.00 | 98.96 | 95.54 | 94.65 | 94.35 |
| 2: Macaca mulatta (AFE65315.1) | 98.96 | 100.00 | 95.98 | 95.10 | 94.80 |
| 3: Canis lupus familiaris (XP_00519331.1) | 95.54 | 95.98 | 100.00 | 93.90 | 93.30 |
| 4: Rattus norvegicus (NP_07707.2) | 94.65 | 95.10 | 93.90 | 100.00 | 98.37 |
| 5: Mus musculus (NP_038500.2) | 94.35 | 94.80 | 93.30 | 98.37 | 100.00 |

Figure 21
(continuation)

USE OF ANNEXINS IN PREVENTING AND TREATING MUSCLE MEMBRANE INJURY

CROSS-REFERENCE TO RELATED APPLICATIONS

This application is a U.S. National Phase of International Application No. PCT/US2019/068168, filed Dec. 20, 2019, which claims the priority benefit under 35 U.S.C. § 119 (e) of U.S. Provisional Patent Application No. 62/783,619, filed Dec. 21, 2018 and U.S. Provisional Patent Application No. 62/903,525, filed Sep. 20, 2019, which are incorporated herein by reference in their entirety.

STATEMENT OF GOVERNMENT INTEREST

This invention was made with government support under grant numbers U54 AR052646 and R01 NS047726 awarded by the National Institutes of Health. The government has certain rights in the invention.

INCORPORATION BY REFERENCE OF MATERIALS SUBMITTED ELECTRONICALLY

This application contains, as a separate part of the disclosure, a Sequence Listing in computer readable form (Filename: 2018-119R_Seqlisting.txt; Size: 168,826 bytes; Created: Dec. 20, 2019), which is incorporated by reference in its entirety.

BACKGROUND

Plasma membrane repair occurs after membrane disruption and is a highly conserved process. The active process required for resealing membrane disruptions is thought to rely on $Ca^{2+}$-dependent vesicle fusion and local cytoskeletal remodeling (McNeil and Khakee, 1992; McNeil and Kirchhausen, 2005). Other models suggest that membrane repair is mediated through the fusion of lysosomal vesicles and/or lateral diffusion of membrane to the site of injury (Demonbreun et al., 2016b; McDade et al., 2014; Reddy et al., 2001; Rodriguez et al., 1997). These models are not mutually exclusive and may depend on the type and extent of damage. Skeletal muscle is highly dependent on plasma membrane repair as mutation in genes encoding repair proteins lead to muscle disease (Bansal et al., 2003; Bashir et al., 1998; Cai et al., 2009; Defour et al., 2017; Demonbreun and McNally, 2016; Demonbreun et al., 2015).

Annexins are $Ca^{2+}$-binding proteins that regulate lipid binding, cytoskeletal reorganization, and bleb formation, steps necessary for membrane repair (Bizzarro et al., 2012; Boye et al., 2018; Boye et al., 2017; Grewal et al., 2017; Jimenez and Perez, 2017; Lauritzen et al., 2015). Individual annexin repeat domains coordinate $Ca^{2+}$ binding with unique annexin-specific type II or type III binding sites. Differential $Ca^{2+}$ affinity of the type II and type III binding sites provides each annexin a unique ability to respond to a range of intracellular $Ca^{2+}$ levels and phospholipid binding (Blackwood and Ernst, 1990). Annexins have the ability to self- and hetero-oligomerize (Zaks and Creutz, 1991). Typical annexins like A1 and A2 contain one annexin core composed of four annexin repeat domains. In contrast, annexin A6 contains two annexin cores and thus eight annexin repeat domains (Benz et al., 1996). Annexin A6's duplicated structure makes it possible for the amino- and carboxyl-terminal annexin core domains to bind one or two distinct membranes making annexin A6 a prime target for facilitating membrane coalescence and folding required during membrane repair (Boye et al., 2018; Boye et al., 2017; Buzhynskyy et al., 2009).

Annexins have a high affinity for phosphatidylserine, phosphatidylinositol, and cholesterol, which are highly enriched in the sarcolemma (Fiehn et al., 1971; Gerke et al., 2005). Multiple annexins have been implicated in membrane repair in skeletal muscle, as well as *Xenopus oocytes*, human trophoblasts, and HeLa cancer cells, suggesting a conserved mechanism (Babbin et al., 2008; Bement et al., 1999; Carmeille et al., 2015; Davenport et al., 2016; Demonbreun et al., 2016b; Lennon et al., 2003; McNeil et al., 2006; Roostalu and Strahle, 2012). Annexins are recruited to the injured membrane in a sequential manner forming a macromolecular repair complex at the membrane lesion (Boye et al., 2017; Demonbreun et al., 2016b; Roostalu and Strahle, 2012).

SUMMARY

Defects in the ability of a cell to repair the plasma membrane lead to numerous diseases, including muscular dystrophy and other pathological conditions that result in cellular death. Membrane injury can result from events such as overuse, trauma, burn, chemical exposure and chronic disease. Currently, there is a lack of agents that prevent or treat membrane damage (Demonbreun and McNally, 2016). Annexins are calcium-binding proteins that have a high affinity for membrane lipids. Annexins have been implicated in membrane repair in many cell types including muscle, trophoblasts, HeLa cells, and oocytes, suggesting a widespread role for annexins (Babbin et al., 2008; Bement et al., 1999; Carmeille et al., 2015; Davenport et al., 2016; Demonbreun et al., 2016b; McNeil et al., 2006; Roostalu and Strahle, 2012). Annexin A1 ("A1"), annexin A2 ("A2"), annexin A5 ("A5"), and annexin A6 ("A6") are sequentially recruited to the injury site forming a large repair complex (Demonbreun et al., 2016b; Roostalu and Strahle, 2012). A polymorphism in Anxa6 was identified that created a truncated form of annexin A6 (Swaggart et al., 2014). Expression of truncated annexin A6 acted in a dominant-negative fashion, decreasing annexin repair complex formation. This correlated with impaired membrane repair and more severe muscle disease (Demonbreun et al., 2016a; Demonbreun et al., 2016b; Quattrocelli et al., 2017b; Swaggart et al., 2014). Conversely, overexpression of annexin A6 was sufficient to improve repair and decrease susceptibility to membrane injury (Quattrocelli et al., 2017a). Moreover, treatment with recombinant annexin A6 was sufficient to reduce muscle damage in cell based and whole animal studies.

An aspect of the disclosure is drawn to a method of treating a cellular membrane injury comprising administering to a patient in need thereof a therapeutically effective amount of a composition comprising an agent that increases the activity of an annexin protein. Another aspect of the disclosure is directed to a method of delaying onset, enhancing recovery from cellular membrane injury, or preventing a cellular membrane injury comprising administering to a patient in need thereof a therapeutically effective amount of a composition comprising an agent that increases the activity of an annexin protein. Embodiments of each of these aspects are contemplated wherein the agent is selected from the group consisting of a recombinant protein, a steroid, and a polynucleotide capable of expressing an annexin protein. In some embodiments, the steroid is a corticosteroid or a glucocorticoid. In some embodiments, the recombinant protein is an annexin protein. In some embodiments, the annexin protein is annexin A6 (SEQ ID NO: 7, SEQ ID NO: 8, SEQ ID NO: 45, or a combination thereof). In some embodiments, the recombinant protein is a wild type annexin protein, a modified annexin protein, an annexin-like protein, or a fragment of a wild type annexin protein or annexin-like protein. In some embodiments, the modified annexin protein is annexin A6 (SEQ ID NO: 7, SEQ ID NO: 8, SEQ ID NO: 45, or a combination thereof). In some embodiments, the patient suffers from an acute injury. In some embodiments, the acute injury results from surgery, a burn, a toxin, a chemical, radiation-induced injury, acute myocardial injury, acute muscle injury, acute lung injury, acute epithelial injury, acute epidermal injury, acute kidney injury, acute liver injury, vascular injury, an excessive mechanical force, or trauma. In some embodiments, the patient suffers from a chronic disorder. In some embodiments, the patient suffers from a chronic disorder, such as Becker Muscular Dystrophy (BMD), Duchenne Muscular Dystrophy (DMD), Limb Girdle Muscular Dystrophy, congenital Muscular Dystrophy, Emery-Dreifuss Muscular Dystrophy (EDMD), Myotonic Dystrophy, Fascioscapulohumeral Dystrophy (FSHD), Oculopharyngeal Muscular Dystrophy, Distal Muscular Dystrophy, cystic fibrosis, pulmonary fibrosis, muscle atrophy, cerebral palsy, an epithelial disorder, an epidermal disorder, a kidney disorder, a liver disorder, sarcopenia, or cardiomyopathy (hypertrophic, dilated, congenital, arrhythmogenic, restrictive, ischemic, heart failure). In some embodiments, the cardiomyopathy is hypertrophic, dilated, congenital, arrhythmogenic, restrictive, ischemic, or heart failure.

In some embodiments, the methods disclosed herein further comprise administering an effective amount of a second agent, wherein the second agent is selected from the group consisting of mitsugumin 53 (MG53), a modulator of latent TGF-β binding protein 4 (LTBP4), a modulator of transforming growth factor β (TGF-β) activity, a modulator of androgen response, a modulator of an inflammatory response, a promoter of muscle growth, a chemotherapeutic agent, a modulator of fibrosis, and a combination thereof.

In some embodiments of the methods disclosed herein, the polynucleotide is associated with a nanoparticle. In some embodiments, the polynucleotide is contained in a vector. In some embodiments, the vector is within a chloroplast. In some embodiments, the vector is a viral vector. In some embodiments, the viral vector is selected from the group consisting of a herpes virus vector, an adeno-associated virus (AAV) vector, an adeno virus vector, and a lentiviral vector. In some embodiments, the AAV vector is recombinant AAV5, AAV6, AAV8, AAV9, or AAV74, including embodiments wherein the AAV74 vector is AAVrh74.

In some embodiments of the methods disclosed herein, the composition increases the activity of annexin A1 (SEQ ID NO: 1), annexin A2 (SEQ ID NO: 2 or SEQ ID NO: 3), annexin A3 (SEQ ID NO: 4), annexin A4 (SEQ ID NO: 5), annexin A5 (SEQ ID NO: 6), annexin A6 (SEQ ID NO: 7, SEQ ID NO: 8, SEQ ID NO: 45, or a combination thereof), annexin A7 (SEQ ID NO: 9 or SEQ ID NO: 10), annexin A8 (SEQ ID NO: 11 or SEQ ID NO: 12), annexin A9 (SEQ ID NO: 13), annexin A10 (SEQ ID NO: 14), annexin A11 (SEQ ID NO: 15 or SEQ ID NO: 16), annexin A13 (SEQ ID NO: 17 or SEQ ID NO: 18), or a combination thereof. In some embodiments, the composition increases the activity of annexin A1 (SEQ ID NO: 1), annexin A2 (SEQ ID NO: 2 or SEQ ID NO: 3), and annexin A6 (SEQ ID NO: 7, SEQ ID NO: 8, SEQ ID NO: 45, or a combination thereof). In some embodiments, the composition increases the activity of annexin A2 (SEQ ID NO: 2 or SEQ ID NO: 3) and annexin A6 (SEQ ID NO: 7, SEQ ID NO: 8, SEQ ID NO: 45, or a combination thereof). In some embodiments, the composition increases the activity of annexin A1 (SEQ ID NO: 1) and annexin A6 (SEQ ID NO: 7, SEQ ID NO: 8, SEQ ID NO: 45, or a combination thereof). In some embodiments, the composition increases the activity of annexin A6 (SEQ ID NO: 7, SEQ ID NO: 8, SEQ ID NO: 45, or a combination thereof). In any of the aspects or embodiments of the disclosure, the composition for use in any of the methods described herein is a pharmaceutical composition as disclosed herein.

In some aspects, the disclosure provides a pharmaceutical composition comprising a modified annexin protein and a pharmaceutically acceptable carrier, buffer, and/or diluent. In some aspects, the disclosure provides a pharmaceutical composition comprising an annexin protein and a pharmaceutically acceptable carrier, buffer, and/or diluent. In some embodiments, the annexin protein or modified annexin protein is annexin A1 (SEQ ID NO: 1), annexin A2 (SEQ ID NO: 2 or SEQ ID NO: 3), annexin A3 (SEQ ID NO: 4), annexin A4 (SEQ ID NO: 5), annexin A5 (SEQ ID NO: 6), annexin A6 (SEQ ID NO: 7, SEQ ID NO: 8, SEQ ID NO: 45, or a combination thereof), annexin A7 (SEQ ID NO: 9 or SEQ ID NO: 10), annexin A8 (SEQ ID NO: 11 or SEQ ID NO: 12), annexin A9 (SEQ ID NO: 13), annexin A10 (SEQ ID NO: 14), annexin A11 (SEQ ID NO: 15 or SEQ ID NO: 16), annexin A13 (SEQ ID NO: 17 or SEQ ID NO: 18), or a combination thereof. In some embodiments, the annexin protein or modified annexin protein is annexin A6 (SEQ ID NO: 7, SEQ ID NO: 8, SEQ ID NO: 45, or a combination thereof). In further embodiments, the pharmaceutical composition comprises annexin A1 (SEQ ID NO: 1), annexin A2 (SEQ ID NO: 2 or SEQ ID NO: 3), and annexin A6 (SEQ ID NO: 7, SEQ ID NO: 8, SEQ ID NO: 45, or a combination thereof). In some embodiments, the pharmaceutical composition comprises annexin A2 (SEQ ID NO: 2 or SEQ ID NO: 3) and annexin A6 (SEQ ID NO: 7, SEQ ID NO: 8, SEQ ID NO: 45; or a combination thereof). In further embodiments, the pharmaceutical composition comprises annexin A1 (SEQ ID NO: 1) and annexin A6 (SEQ ID NO: 7, SEQ ID NO: 8, SEQ ID NO: 45, or a combination thereof). In some embodiments, the pharmaceutical composition further comprises a steroid. In further embodiments, the steroid is a corticosteroid or a glucocorticoid. In some embodiments, the pharmaceutical composition further comprises an effective amount of a second agent, wherein the second agent is selected from the group consisting of mitsugumin 53 (MG53), a modulator of latent TGF-β binding protein 4 (LTBP4), a modulator of transforming growth factor β (TGF-β) activity, a modulator of androgen response, a modulator of an inflammatory response, a promoter of muscle growth, a chemotherapeutic agent, a modulator of fibrosis, and a combination thereof. In further embodiments, purity of the annexin protein in the composition is about 90% or higher as measured by standard release assay, including but not limited to SDS-PAGE, SEC-HPLC, and immunoblot analysis. In some embodiments, the composition has an endotoxin level that is less than about 0.50000 endotoxin units per milligram (EU/mg) A280 annexin protein. In some embodiments, the modified annexin protein is produced in a prokaryotic cell.

In some aspects, the disclosure provides a pharmaceutical composition comprising modified annexin A6 (SEQ ID NO: 7, SEQ ID NO: 8, SEQ ID NO: 45, or a combination thereof) and a pharmaceutically acceptable carrier, buffer, and/or diluent. In some aspects, the disclosure provides a pharmaceutical composition comprising annexin A6 (SEQ ID NO:

7, SEQ ID NO: 8, SEQ ID NO: 45, or a combination thereof) and a pharmaceutically acceptable carrier, buffer, and/or diluent. In some embodiments, the pharmaceutical composition further comprises annexin A1 (SEQ ID NO: 1) and annexin A2 (SEQ ID NO: 2 or SEQ ID NO: 3). In some embodiments, the pharmaceutical composition further comprises annexin A2 (SEQ ID NO: 2 or SEQ ID NO: 3). In some embodiments, the pharmaceutical composition further comprises annexin A1 (SEQ ID NO: 1). In some embodiments, the pharmaceutical composition further comprises a steroid. In further embodiments, the steroid is a corticosteroid or a glucocorticoid. In some embodiments, the pharmaceutical composition further comprises an effective amount of a second agent, wherein the second agent is selected from the group consisting of mitsugumin 53 (MG53), a modulator of latent TGF-β binding protein 4 (LTBP4), a modulator of transforming growth factor β (TGF-β) activity, a modulator of androgen response, a modulator of an inflammatory response, a promoter of muscle growth, a chemotherapeutic agent, a modulator of fibrosis, and a combination thereof. In some embodiments, purity of the annexin protein in the composition is about 90% or higher as measured by standard release assay. In some embodiments, the composition has an endotoxin level that is less than about 0.50000 endotoxin units per milligram (EU/mg). In some embodiments, the modified annexin A6 (SEQ ID NO: 7, SEQ ID NO: 8, SEQ ID NO: 45, or a combination thereof) is produced in a prokaryotic cell.

Other features and advantages of the disclosure will be better understood by reference to the following detailed description, including the figures and the examples.

BRIEF DESCRIPTION OF THE FIGURES

FIG. 21 depicts the amino acid conservation of annexin A6.

DETAILED DESCRIPTION

Figure 1:
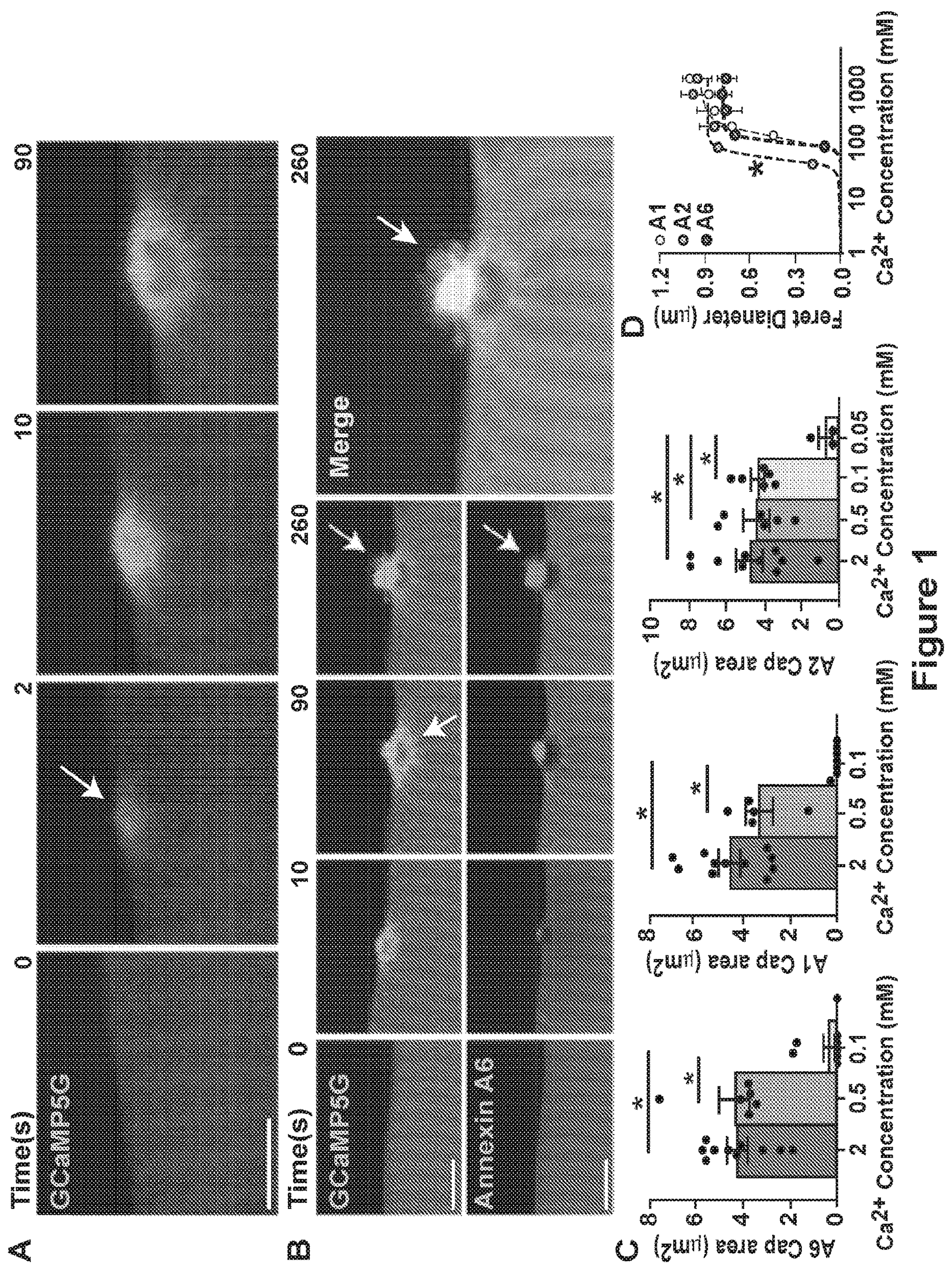
FIG. 1 shows that $Ca^{2+}$ dynamics influenced annexin repair cap recruitment at the site of injury. Myofibers were generated to express the $Ca^{2+}$ indicator GCaMP5G, and time-lapse single slice images were assessed at time points after membrane disruption. A) GCaMP5G fluorescence was present at the site of injury, at 2 seconds, indicating the presence of $Ca^{2+}$ immediately after damage at the site of injury. B) Time-lapse images of myofibers co-electroporated with GCaMP5G and annexin A6-tdTomato. GCaMP5G fluorescence was present at the site of injury localized around the annexin A6-free zone (arrowhead) and at the annexin A6 cap (arrow). GCaMP5G colocalized (merge, arrow) with the annexin A6 repair cap. Scale bar 5 μm. C) Myofibers expressing fluorescently tagged annexin A1, A2 or A6 were injured at multiple $Ca^{2+}$ concentrations. Annexin A1 and A6 repair cap size was reduced at 0.1 mM $Ca^{2+}$ compared to 2 mM and 0.5 mM. Annexin A2 repair cap area was significantly reduced at 0.05 mM $Ca^{2+}$ compared to 2 mM, 0.5 mM, and 0.1 mM $Ca^{2+}$. D) Cap kinetics were plotted as cap feret diameter over a range of $Ca^{2+}$ concentrations. Annexin A2 had a statistically significant leftward shift in $Km_{1/2}$ followed by annexin A6 then A1. Scale 5 μm.

Membrane repair is essential to cell survival and requires a quick and efficient process to limit cellular injury. Muscle is prone to membrane disruption due to the elongated shape of muscle cells and the continuous stress brought on by muscle contractions. Mutations in genes encoding membrane-associated proteins produce fragile membranes, reduce membrane repair capacity and result in progressive muscular dystrophy. Therapeutics and methods disclosed herein to enhance membrane repair and reduce susceptibility to membrane injury are contemplated to benefit muscle in both acute and chronic injury settings.

As used herein, an agent that "increases the activity of an annexin protein" is one that increases a property of an annexin protein as a calcium-binding membrane associated repair protein that enhances restoration of membrane integrity. The enhancement to restoring membrane integrity may be through facilitating the formation of a macromolecular repair complex at the membrane lesion including proteins such as, without limitation, annexin A1 (SEQ ID NO: 1), annexin A2 (SEQ ID NO: 2 or SEQ ID NO: 3), EHD2, dysferlin, and MG53.

As used herein, the term "treating" or "treatment" refers to an intervention performed with the intention of preventing the further development of or altering the pathology of a disease or infection. Accordingly, "treatment" refers to both therapeutic treatment and prophylactic or preventative measures. Of course, when "treatment" is used in conjunction with a form of the separate term "prophylaxis," it is understood that "treatment" refers to the narrower meaning of altering the pathology of a disease or condition. "Preventing" refers to a preventative measure taken with a subject not having a condition or disease. A therapeutic agent may directly decrease the pathology of a disease, or render the disease more susceptible to treatment by another therapeutic agent(s) or, for example, the host's own cellular membrane repair system. Treatment of patients suffering from clinical, biochemical, or subjective symptoms of a disease may include alleviating one or more of such symptoms or reducing the predisposition to the disease. Improvement after treatment may be manifested as a decrease or elimination of one or more of such symptoms.

Annexin Proteins

The annexin protein family is characterized by the ability to bind phospholipids and actin in a $Ca^{2+}$-dependent manner. Annexins preferentially bind phosphatidylserine, phosphatidylinositols, and cholesterol (Gerke et al., 2005). In humans, dominant or recessive mutations in annexin genes have not been associated with muscle disease. However, annexin A5 genetic variants are associated with pregnancy loss (de Laat et al., 2006). The annexin family is known to comprise over 160 distinct proteins that are present in more than 65 unique species (Gerke and Moss, 2002). Humans have 12 different annexin genes, characterized by distinct tissue expression and localization. Annexins are involved in a variety of cellular processes including membrane permeability, mobility, vesicle fusion, and membrane bending. These properties are $Ca^{2+}$-dependent. Although annexins do not contain EF hand domains, calcium ions bind to the individual annexin repeat domains. Differential $Ca^{2+}$ affinity allows each annexin protein to respond to changes in intracellular calcium levels under unique spatiotemporal conditions (Blackwood and Ernst, 1990).

Structurally, the annexin family of proteins contains a conserved carboxy-terminal core domain composed of multiple annexin repeats and a variable amino-terminal head. The amino-terminus differs in length and amino acid sequence amongst the annexin family members. Additionally, post-translational modifications alter protein function and protein localization (Goulet et al., 1992; Kaetzel et al., 2001). Annexin proteins have the potential to self-oligomerize and interact with membrane surfaces and actin in the presence of $Ca^{2+}$ (Zaks and Creutz, 1991, Hayes et al., 2006), Jaiswal et al., 2014)). The amino-terminal region is thought to bind actin or one lipid membrane in a $Ca^{2+}$-dependent manner, while the annexin core region binds an additional lipid membrane.

Annexins do not contain a predicted hydrophobic signal sequence targeting the annexins for classical secretion through the endoplasmic reticulum, yet annexins are found both on the interior and exterior of the cell (Christmas et al., 1991; Deora et al., 2004; Wallner et al., 1986). The process by which the annexins are externalized remains unknown. It is hypothesized that annexins may be released through exocytosis or cell lysis, although the method of externalization may vary by cell type. Functionally, localization both inside and outside the cell adds to the complexity of the roles annexins play within tissues and cell types. Annexin A5 is used commonly as a marker for apoptosis due to its high affinity to phosphatidylserine (PS). During cell death and injury, PS reverses membrane orientation from the inner to outer membrane, providing access for annexin binding from the cell exterior. Annexins have been shown to have anti-inflammatory, pro-fibrinolytic, and anti-thrombotic effects. The annexin A1-deleted mouse model exhibits an exacerbated inflammatory response when challenged and is resistant to the anti-inflammatory effects of glucocorticoids (Hannon et al., 2003). The annexin A2 null-mouse develops fibrin accumulation in the microvasculature and is defective in clearance of arterial thrombi (Ling et al., 2004). Although little is known about the precise function of extracellular annexins, the expression level of annexin proteins may function as a diagnostic marker for a number of diseases due to the strong correlation between high expression levels of annexins and the clinical severity of disease (Cagliani et al., 2005).

Agents

In some aspects, the disclosure provides methods of the disclosure contemplate treating a cellular membrane injury comprising administering to a patient in need thereof a therapeutically effective amount of a composition comprising an agent that increases the activity of an annexin protein. In further aspects, methods of delaying onset, preventing a cellular membrane injury, or enhancing recovery from cellular membrane injury are provided, comprising administering to a patient in need thereof a therapeutically effective amount of a composition comprising an agent that increases the activity of an annexin protein. "Increase the activity of an annexin protein" means that administration of the agent results in an overall increase in the activity (i.e., the increase in activity derived from administration of the agent plus any endogenous activity) of one or more annexin proteins as disclosed herein.

The term "agent" as used herein refers to a recombinant protein (e.g., a recombinant annexin protein), a steroid, an annexin peptide, and a polynucleotide capable of expressing an annexin protein.

Proteins/Recombinant Proteins

Methods of the disclosure include those in which a recombinant protein (e.g., one or more annexin proteins) is administered to a patient in need thereof in a therapeutically effective amount. Thus, in any of the aspects or embodiments of the disclosure, the agent that increases the activity of an annexin protein is a recombinant protein (e.g., an annexin protein). As used herein a "protein" refers to a polymer comprised of amino acid residues. "Annexin protein" as used herein includes without limitation a wild type annexin protein, a modified annexin protein, an annexin-like protein, or a fragment, analog, variant, fusion or mimetic, each as described herein. An "annexin peptide" is a shorter version (e.g., about 50 amino acids or less) of a wild type annexin protein, an annexin-like protein, or a fragment, analog, variant, fusion or mimetic that is sufficient to increase the overall activity of the annexin protein to which the annexin peptide is related.

Proteins of the present disclosure may be either naturally occurring or non-naturally occurring. Naturally occurring proteins include without limitation biologically active proteins that exist in nature or can be produced in a form that is found in nature by, for example, chemical synthesis or recombinant expression techniques. Naturally occurring proteins also include post-translationally modified proteins, such as, for example and without limitation, glycosylated proteins. Non-naturally occurring proteins contemplated by the present disclosure include but are not limited to synthetic proteins, as well as fragments, analogs and variants of naturally occurring or non-naturally occurring proteins as defined herein. Non-naturally occurring proteins also include proteins or protein substances that have D-amino acids, modified, derivatized, or non-naturally occurring amino acids in the D- or L-configuration and/or peptidomimetic units as part of their structure. The term "protein" typically refers to large polypeptides. The term "peptide" generally refers to short (e.g., about 50 amino acids or less) polypeptides.

Non-naturally occurring proteins are prepared, for example, using an automated protein synthesizer or, alternatively, using recombinant expression techniques using a modified oligonucleotide which encodes the desired protein.

As used herein a "fragment" of a protein is meant to refer to any portion of a protein smaller than the full-length protein expression product.

As used herein an "analog" refers to any of two or more proteins substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it.

As used herein a "variant" refers to a protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, polypeptides are modified by biotinylation, glycosylation, PEGylation, and/or polysialylation.

Fusion proteins, including fusion proteins wherein one fusion component is a fragment or a mimetic, are also contemplated. A "mimetic" as used herein means a peptide or protein having a biological activity that is comparable to the protein of which it is a mimetic.

In any of the aspects or embodiments of the disclosure, the recombinant protein is an annexin protein (e.g., a recombinant wild type annexin protein, a modified annexin protein, an annexin-like protein, or a fragment of a wild type annexin protein or annexin-like protein that exhibits one or more biological activities of an annexin protein). By "annexin-like protein" is meant a protein having sufficient amino acid sequence identity to a referent wild type annexin protein to exhibit the activity of an annexin protein, for example and without limitation, activity as a calcium-binding membrane associated repair protein that enhances restoration of membrane integrity through facilitating the formation of a macromolecular repair complex at the membrane lesion including proteins such as annexin A1 (SEQ ID NO: 1), annexin A2 (SEQ ID NO: 2 or SEQ ID NO: 3), EHD2, dysferlin, and MG53. In some embodiments, the annexin-like protein is a protein having about or at least about 75% amino acid sequence identity with a referent wild type human annexin protein (e.g., annexin A1 (SEQ ID NO: 1), annexin A2 (SEQ ID NO: 2 or SEQ ID NO: 3), annexin A3 (SEQ ID NO: 4), annexin A4 (SEQ ID NO: 5), annexin A5 (SEQ ID NO: 6), annexin A6 (SEQ ID NO: 7, SEQ ID NO: 8, SEQ ID NO: 45, or a combination thereof), annexin A7 (SEQ ID NO: 9 or SEQ ID NO: 10), annexin A8 (SEQ ID NO: 11 or SEQ ID NO: 12), annexin A9 (SEQ ID NO: 13), annexin A10 (SEQ ID NO: 14), annexin A11 (SEQ ID NO: 15 or SEQ ID NO: 16), or annexin A13 (SEQ ID NO: 17 or SEQ ID NO: 18)). In further embodiments, the annexin-like protein is a protein having about or at least about 80%, about or at least about 85%, about or at least about 90%, about or at least about 95%, or about 99% amino acid sequence identity with a wild type human annexin protein.

In some embodiments, an agent of the disclosure is an annexin protein that comprises a post-translational modification. In various embodiments, the post-translational modification increases production of an annexin or annexin-like protein, increases solubility of an annexin or annexin-like protein, decreases aggregation of an annexin or annexin-like protein, increases the half-life of an annexin or annexin-like protein, increases the stability of an annexin or annexin-like protein, enhances target membrane engagement of an annexin or annexin-like protein, or is a codon-optimized version of an annexin or annexin-like protein.

Polynucleotides

In some embodiments, an agent of the disclosure is a polynucleotide capable of expressing an annexin protein as described herein. The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases A, G, C, T, and U. Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polynucleotides and polyribonucleotides can also be prepared enzymatically via, e.g., polymerase chain reaction (PCR). Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am: Chem. Soc., 76:6032 (1954); Zhang, et al., J. Am. Chem. Soc., 127:74-75 (2005); and Zimmermann, et al., J. Am. Chem. Soc., 124:13684-13685 (2002).

Steroids

In some embodiments, the agent that increases the activity of an annexin protein is a steroid. In further embodiments, the steroid is a corticosteroid, a glucocorticoid, or a mineralocorticoid. In still further embodiments, the corticosteroid is Betamethasone, Budesonide, Cortisone, Dexamethasone, Hydrocortisone, Methylprednisolone, Prednisolone, or Prednisone. In some embodiments, the corticosteroid is salmeterol, fluticasone, or budesonide.

In some embodiments, the steroid is an anabolic steroid. In further embodiments anabolic steroids, include, but are not limited to, testosterone or related steroid compounds with muscle growth inducing properties, such as cyclostanazol or methadrostenol, prohomones or derivatives thereof, modulators of estrogen, and selective androgen receptor modulators (SARMS).

Vectors

An appropriate expression vector may be used to deliver exogenous nucleic acid to a recipient muscle cell in the methods of the disclosure. In order to achieve effective gene therapy, the expression vector must be designed for efficient cell uptake and gene product expression. In some embodiments, the vector is within a chloroplast. In some embodiments, the vector is a viral vector. In some embodiments, the viral vector is selected from the group consisting of a herpes virus vector, an adeno-associated virus (AAV) vector, an adeno virus vector, and a lentiviral vector.

Use of adenovirus or adeno-associated virus (AAV) based vectors for gene delivery have been described [Berkner, Current Topics in Microbiol, and Imunol. 158: 39-66 (1992); Stratford-Perricaudet et al., Hum. Gene Ther. 1: 241-256 (1990); Rosenfeld et al., Cell 8: 143-144 (1992); Stratford-Perricaudet et al., J. Clin. Invest. 90: 626-630 (1992)]. In various embodiments, the adeno-associated virus vector is AAV5, AAV6, AAV8, AAV9, or AAV74. In some embodiments, the adeno-associated virus vector is AAV9. In further embodiments, the adeno-associated virus vector is AAVrh74.

Specific methods for gene therapy useful in the context of the present disclosure depend largely upon the expression system employed; however, most methods involve insertion of coding sequence at an appropriate position within the expression vector, and subsequent delivery of the expression vector to the target muscle tissue for expression.

Additional delivery systems useful in the practice of the methods of the disclosure are discussed in U.S. Patent Publication Numbers 2012/0046345 and 2012/0039806, each of which is incorporated herein by reference in its entirety.

Disorders/Injuries

In various aspects, the disclosure provides compositions for treating, delaying onset, enhancing recovery from, or preventing a cellular membrane injury, comprising administering an agent and optionally an additional agent to a patient in need thereof.

Such a patient is one that is suffering from, for example, Duchenne Muscular Dystrophy, Limb Girdle Muscular Dystrophy, Becker Muscular Dystrophy, Emery-Dreifuss Muscular Dystrophy (EDMD), Myotonic Dystrophy, Fascioscapulohumeral Dystrophy (FSHD), Oculopharyngeal Muscular Dystrophy, Distal Muscular Dystrophy, cystic fibrosis, pulmonary fibrosis, muscle atrophy, cerebral palsy, an epithelial disorder, an epidermal disorder, a kidney disorder, a liver disorder, sarcopenia, cardiomyopathy, myopathy, cystic fibrosis, pulmonary fibrosis, cardiomyopathy (including hypertrophic, dilated, congenital, arrhythmogenic, restrictive, ischemic, or heart failure), acute lung injury, acute muscle injury, acute myocardial injury, radiation-induced injury, colon cancer, idiopathic pulmonary fibrosis, idiopathic interstitial pneumonia, autoimmune lung diseases, benign prostate hypertrophy, cerebral infarction, musculoskeletal fibrosis, post-surgical adhesions, liver cirrhosis, renal fibrotic disease, fibrotic vascular disease, neurofibromatosis, Alzheimer's disease, diabetic retinopathy, skin lesions, lymph node fibrosis associated with HIV, chronic obstructive pulmonary disease (COPD), inflammatory pulmonary fibrosis, rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; renal fibrosis, irritable bowel syndrome; pyresis; restenosis; cerebral malaria; stroke and ischemic injury; neural trauma; Huntington's disease; Parkinson's disease; allergies, including allergic rhinitis and allergic conjunctivitis; cachexia; Reiter's syndrome; acute synoviitis; muscle degeneration, bursitis; tendonitis; tenosynovitis; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and auto-immune diseases, such as multiple sclerosis, lupus and fibromyalgia; viral diseases such as Herpes Zoster, Herpes Simplex I or II, influenza virus, Severe Acute Respiratory Syndrome (SARS) and cytomegalovirus.

As used herein, "cardiomyopathy" refers to any disease or dysfunction of the myocardium (heart muscle) in which the heart is abnormally enlarged, thickened and/or stiffened. As a result, the heart muscle's ability to pump blood is usually weakened, often leading to congestive heart failure. The disease or disorder can be, for example, inflammatory, metabolic, toxic, infiltrative, fibrotic, hematological, genetic, or unknown in origin. Such cardiomyopathies may result from a lack of oxygen. Other diseases include those that result from myocardial injury which involves damage to the muscle or the myocardium in the wall of the heart as a result of disease or trauma. Myocardial injury can be attributed to many things such as, but not limited to, cardiomyopathy, myocardial infarction, or congenital heart disease. The cardiac disorder may be pediatric in origin. Cardiomyopathy includes, but is not limited to, cardiomyopathy (dilated, hypertrophic, restrictive, arrhythmogenic, genetic, idiopathic and unclassified cardiomyopathy), sporadic dilated cardiomyopathy, X-linked Dilated Cardiomyopathy (XLDC), acute and chronic heart failure, right heart failure, left heart failure, biventricular heart failure, congenital heart defects, myocardiac fibrosis, mitral valve stenosis, mitral valve insufficiency, aortic valve stenosis, aortic valve insufficiency, tricuspidal valve stenosis, tricuspidal valve insufficiency, pulmonal valve stenosis, pulmonal valve insufficiency, combined valve defects, myocarditis, acute myocarditis, chronic myocarditis, viral myocarditis, diastolic heart failure, systolic heart failure, diabetic heart failure and accumulation diseases.

Additional (Second) Agents

In various embodiments of the disclosure it is contemplated that a second agent is administered with the agent that increases the activity of an annexin protein. Nonlimiting examples of the second agent are mitsugumin 53 (MG53), micro-dystrophin, a modulator of latent TGF-β binding protein 4 (LTBP4), a modulator of transforming growth factor β (TGF-β) activity, a modulator of androgen response, a modulator of an inflammatory response, a promoter of muscle growth, a chemotherapeutic agent, a modulator of fibrosis, and a combination thereof. Further, the methods disclosed herein can, in various embodiments, encompass one or more of such agents, or one or more of such agents in composition with any other active agent(s).

Modulators of LTBP4

LTBP4 is located on human chromosome 19q13.1-q13.2, and is an extracellular matrix protein that binds and sequesters TGFβ. LTBP4 modifies murine muscular dystrophy through a polymorphism in the Ltbp4 gene. See U.S. Pat. No. 9,873,739, which is incorporated by reference herein in its entirety. There are two common variants of the Ltbp4 gene in mice. Most strains of mice, including the mdx mouse, have the Ltbp4 insertion allele (Ltbp41/l). Insertion of 36 base pairs (12 amino acids) into the proline-rich region of LTBP4 encoded by Ltbp41/leads to milder disease. Deletion of 36 bp/12aa in the proline-rich region is associated with more severe disease (Ltbp4D/D). It was found that the Ltbp4 genotype correlated strongly with two different aspects of muscular dystrophy pathology, i.e., membrane leakage and fibrosis, and these features define DMD pathology.

Modulators of LTBP4 are described in U.S. Pat. No. 9,873,739, which is incorporated by reference herein in its entirety.

Modulators of TGF-β Activity

Transforming Growth Factor-β (TGF-β) superfamily is a family of secreted proteins that is comprised of over 30 members including activins, nodals, bone morphogenic proteins (BMPs) and growth and differentiation factors (GDFs). Superfamily members are generally ubiquitously expressed and regulate numerous cellular processes including growth, development, and regeneration. Mutations in TGF-β superfamily members result in a multitude of diseases including autoimmune disease, cardiac disease, fibrosis and cancer.

TGF-β ligand family includes TGF-β1, TGF-β2, and TGF-β3. TGF-β is secreted into the extracellular matrix in an inactive form bound to latency associated peptide (LAP). Latent TGF-β proteins (LTBPs) binding the TGF-β/LAP complex provide yet another level of regulation. Extracellular proteases cleave LTBP/LAP/TGF-β releasing TGF-β. As a result, TGF-β is free to bind its receptors TGFBRI or TGFBRII. TGF-β/receptor binding, activates downstream canonical and non-canonical SMAD pathways, including activation of SMAD factors, leading to gene transcription. TGF-β signaling has emerged as a prominent mediator of the fibrotic response and disease progression in muscle disease and its expression is upregulated in dystrophy in both mouse and human. Blockade of TGF-β signaling in mice through expression of a dominant negative receptor (TGFBRII) expression, improved the dystrophic pathology, enhanced regeneration, and reduced muscle injury of 0-sarcoglycan-null mice, a mouse model of muscular dystrophy (Accornero, McNally et al Hum Mol Genet 2014). Additionally, antibody-mediated blockade of TGF-β signaling with a pan anti-TGF-β antibody, 1d11 monocloncal antibody, improved respiratory outcome measures in a mouse model of Duchenne muscular dystrophy (Nelson, Wentworth et al Am J Pathol 2011). Thus, therapeutic approaches against TGF-β signaling are contemplated herein to improve repair and delay disease progression.

Therapeutics contemplated as effective against TGF-β signaling include galunisertib (LY2157299 monohydrate), TEW-7917, monoclonal antibodies against TGF-β ligands (TGF-1, 2, 3 alone or pan 1,2,3), Fresolimemub (GC-1008), TGF-β peptide P144, LY2382770, small molecule, SB-525334, and GW788388.

Modulators of an Androgen Response

Selective androgen receptor modulators (SARMs) are a class of androgen receptor ligands that activate androgenic signaling and exist in nonsteroidal and steroidal forms. Studies have shown that SARMs have the potential to increase both muscle and bone mass. Testosterone is one of the most well-known SARMs, which promotes skeletal muscle growth in healthy and diseased tissue. Testosterone and dihydrotestosterone (DHT) promote myocyte differentiation and upregulate follistatin, while also downregulates TGF-β signaling, resulting in muscle growth (Singh et al 2003, Singh et al 2009, Gupta et al 2008). It is conceivable that SARM-mediated inhibition of TGF-β protects against muscle injury and improves repair. SARMS may include, testosterone, estrogen, dihydrotestosterone, estradiol, include dihydronandrolone, nandrolone, nandrolone decanoate, Ostarine, Ligandrol, LGD-3303, andarine, cardarine, 7-alpha methyl, 19-nortestosterone aryl-propionamide, bicyclic hydantoin, quinolinones, tetrahydroquinoline analog, benizimidazole, imidazolopyrazole, indole, and pyrazoline derivatives, azasteroidal derivatives, and aniline, diaryl aniline, and bezoxazepinones derivatives.

Modulators of an Inflammatory Response

A modulator of an inflammatory response includes the following agents. In one embodiment of the disclosure, the modulator of an inflammatory response is a beta2-adrenergic receptor agonist (e.g., albuterol). The term beta2-adrenergic receptor agonist is used herein to define a class of drugs which act on the β2-adrenergic receptor, thereby causing smooth muscle relaxation resulting in dilation of bronchial passages, vasodilation in muscle and liver, relaxation of uterine muscle and release of insulin. In one embodiment, the beta2-adrenergic receptor agonist for use according to the disclosure is albuterol, an immunosuppressant drug that is widely used in inhalant form for asthmatics. Albuterol is thought to slow disease progression by suppressing the infiltration of macrophages and other immune cells that contribute to inflammatory tissue loss. Albuterol also appears to have some anabolic effects and promotes the growth of muscle tissue. Albuterol may also suppress protein degradation (possibly via calpain inhibition).

In DMD, the loss of dystrophin leads to breaks in muscle cell membrane, and destabilizes neuronal nitric oxide synthase (nNOS), a protein that normally generates nitric oxide (NO). It is thought that at least part of the muscle degeneration observed in DMD patients may result from the reduced production of muscle membrane-associated neuronal nitric oxide synthase. This reduction may lead to impaired regulation of the vasoconstrictor response and eventual muscle damage.

In one embodiment, modulators of an inflammatory response suitable for use in compositions of the disclosure are Nuclear Factor Kappa-B (NF-κB) inhibitors. NF-κB is a major transcription factor modulating cellular immune, inflammatory and proliferative responses. NF-κB functions in activated macrophages to promote inflammation and muscle necrosis and in skeletal muscle fibers to limit regeneration through the inhibition of muscle progenitor cells. The activation of this factor in DMD contributes to diseases pathology. Thus, NF-κB plays an important role in the progression of muscular dystrophy and the IKK/NF-κB signaling pathway is a potential therapeutic target for the treatment of a TGFβ-related disease. Inhibitors of NF-κB (for example and without limitation, IRFI 042, a vitamin E analog) enhance muscle function, decrease serum creatine kinase (CK) level and muscle necrosis and enhance muscle regeneration. Edasalonexent is a small molecule inhibitor NF-κB. Edasalonexent administered orally as 100 mg/kg delayed muscle disease progression in Duchenne muscular dystrophy boys. Furthermore, specific inhibition of NF-κB-mediated signaling by IKK has similar benefits.

In a further embodiment, the modulator of an inflammatory response is a tumor necrosis factor alpha antagonist. TNF-α is one of the key cytokines that triggers and sustains the inflammation response. In one specific embodiment of the disclosure, the modulator of an inflammatory response is the TNF-α antagonist infliximab.

TNF-α antagonists for use according to the disclosure include, in addition to infliximab (Remicade™), a chimeric monoclonal antibody comprising murine VK and VH domains and human constant Fc domains. The drug blocks the action of TNF-α by binding to it and preventing it from signaling the receptors for TNF-α on the surface of cells. Another TNF-α antagonist for use according to the disclosure is adalimumab (Humira™). Adalimumab is a fully human monoclonal antibody. Another TNF-α antagonist for use according to the disclosure is etanercept (Enbrel™). Etanercept is a dimeric fusion protein comprising soluble human TNF receptor linked to an Fc portion of an IgG1. It is a large molecule that binds to TNF-α and thereby blocks its action. Etanercept mimics the inhibitory effects of naturally occurring soluble TNF receptors, but as a fusion protein it has a greatly extended half-life in the bloodstream and therefore a more profound and long-lasting inhibitory effect.

Another TNF-α antagonist for use according to the disclosure is pentoxifylline (Trental™), chemical name 1-(5-oxohexyl)-3,7-dimethylxanthine. The usual dosage in controlled-release tablet form is one tablet (400 mg) three times a day with meals.

Dosing: Remicade is administered by intravenous infusion, typically at 2-month intervals. The recommended dose is 3 mg/kg given as an intravenous infusion followed with additional similar doses at 2 and 6 weeks after the first infusion, then every 8 weeks thereafter. For patients who have an incomplete response, consideration may be given to adjusting the dose up to 10 mg/kg or treating as often as every 4 weeks. Humira is marketed in both preloaded 0.8 ml (40 mg) syringes and also in preloaded pen devices, both injected subcutaneously, typically by the patient at home. Etanercept can be administered at a dose of 25 mg (twice weekly) or 50 mg (once weekly).

In another embodiment of the disclosure, the modulator of an inflammatory response is cyclosporin. Cyclosporin A, the main form of the drug, is a cyclic nonribosomal peptide of 11 amino acids produced by the fungus *Tolypocladium inflatum*. Cyclosporin is thought to bind to the cytosolic protein cyclophilin (immunophilin) of immunocompetent lymphocytes (especially T-lymphocytes). This complex of cyclosporin and cyclophylin inhibits calcineurin, which under normal circumstances is responsible for activating the transcription of interleukin-2. It also inhibits lymphokine production and interleukin release and therefore leads to a reduced function of effector T-cells. It does not affect cytostatic activity. It has also an effect on mitochondria, preventing the mitochondrial PT pore from opening, thus inhibiting cytochrome c release (a potent apoptotic stimulation factor). Cyclosporin may be administered at a dose of 1-10 mg/kg/day.

Promoters of Muscle Growth

In some embodiments of the disclosure, a therapeutically effective amount of a promoter of muscle growth is administered to a patient. Promoters of muscle growth contemplated by the disclosure include, but are not limited to, insulin-like growth factor-1 (IGF-1), Akt/protein kinase B, clenbuterol, creatine, decorin (see U.S. Patent Publication Number 20120058955), a steroid (for example and without limitation, a corticosteroid or a glucocorticoid steroid), testosterone and a myostatin antagonist.

Myostatin Antagonists

Another class of promoters of muscle growth suitable for use in the combinations of the disclosure is myostatin antagonists. Myostatin, also known as growth/differentiation factor 8 (GDF-8) is a transforming growth factor-β (TGFβ) superfamily member involved in the regulation of skeletal muscle mass. Most members of the TGF-β-GDF family are widely expressed and are pleiotropic; however, myostatin is primarily expressed in skeletal muscle tissue where it negatively controls skeletal muscle growth. Myostatin is synthesized as an inactive preproprotein which is activated by proteolyic cleavage. The precursor protein is cleaved to produce an approximately 109-amino-acid COOH-terminal protein which, in the form of a homodimer of about 25 kDa, is the mature, active form. The mature dimer appears to circulate in the blood as an inactive latent complex bound to the propeptide. As used herein the term "myostatin antagonist" defines a class of agents that inhibits or blocks at least one activity of myostatin, or alternatively, blocks or reduces the expression of myostatin or its receptor (for example, by interference with the binding of myostatin to its receptor and/or blocking signal transduction resulting from the binding of myostatin to its receptor). Such agents therefore include agents which bind to myostatin itself or to its receptor.

Myostatin antagonists for use according to the disclosure include antibodies to GDF-8; antibodies to GDF-8 receptors; soluble GDF-8 receptors and fragments thereof (e.g., the ActRIIB fusion polypeptides as described in U.S. Patent Publication Number 2004/0223966, which is incorporated herein by reference in its entirety, including soluble ActRIIB receptors in which ActRIIB is joined to the Fc portion of an immunoglobulin); GDF-8 propeptide and modified forms thereof (e.g., as described in WO 2002/068650 or U.S. Pat. No. 7,202,210, including forms in which GDF-8 propeptide is joined to the Fc portion of an immunoglobulin and/or form in which GDF-8 is mutated at an aspartate (asp) residue, e.g., asp-99 in murine GDF-8 propeptide and asp-100 in human GDF-8 propeptide); a small molecule inhibitor of GDF-8; follistatin (e.g., as described in U.S. Pat. No. 6,004,937, incorporated herein by reference) or follistatin-domain-containing proteins (e.g., GASP-1 or other proteins as described in U.S. Pat. Nos. 7,192,717 and 7,572,763, each incorporated herein by reference); and modulators of metalloprotease activity that affect GDF-8 activation, as described in U.S. Patent Publication Number 2004/0138118, incorporated herein by reference.

Additional myostatin antagonists include myostatin antibodies which bind to and inhibit or neutralize myostatin (including the myostatin proprotein and/or mature protein, in monomeric or dimeric form). Myostatin antibodies are mammalian or non-mammalian derived antibodies, for example an IgNAR antibody derived from sharks, or humanized antibodies, or comprise a functional fragment derived from antibodies. Such antibodies are described, for example, in WO 2005/094446 and WO 2006/116269, the content of which is incorporated herein by reference. Myostatin antibodies also include those antibodies that bind to the myostatin proprotein and prevent cleavage into the mature active form. Additional antibody antagonists include the antibodies described in U.S. Pat. Nos. 6,096,506 and 6,468,535 (each of which is incorporated herein by reference). In some embodiments, the GDF-8 inhibitor is a monoclonal antibody or a fragment thereof that blocks GDF-8 binding to its receptor. Further embodiments include murine monoclonal antibody JA-16 (as described in U.S. Pat. No. 7,320,789 (ATCC Deposit No. PTA-4236); humanized derivatives thereof and fully human monoclonal anti-GDF-8 antibodies (e.g., Myo29, Myo28 and Myo22, ATCC Deposit Nos. PTA-4741, PTA-4740, and PTA-4739, respectively, or derivatives thereof) as described in U.S. Pat. No. 7,261,893 and incorporated herein by reference.

In still further embodiments, myostatin antagonists include soluble receptors which bind to myostatin and inhibit at least one activity thereof. The term "soluble receptor" herein includes truncated versions or fragments of the myostatin receptor that specifically bind myostatin thereby blocking or inhibiting myostatin signal transduction. Truncated versions of the myostatin receptor, for example, include the naturally occurring soluble domains, as well as variations produced by proteolysis of the N- or C-termini. The soluble domain includes all or part of the extracellular domain of the receptor, either alone or attached to additional peptides or other moieties. Because myostatin binds activin receptors (including the activin type IEB receptor (ActRHB) and activin type HA receptor (ActRHA)), activin receptors can form the basis of soluble receptor antagonists. Soluble receptor fusion proteins can also be used, including soluble receptor Fc (see U.S. Patent Publication Number 2004/0223966 and WO 2006/012627, both of which are incorporated herein by reference in their entireties).

Other myostatin antagonists based on the myostatin receptors are ALK-5 and/or ALK-7 inhibitors (see for example WO 2006/025988 and WO 2005/084699, each incorporated herein by reference). As a TGF-β cytokine, myostatin signals through a family of single transmembrane serine/threonine kinase receptors. These receptors can be divided in two classes, the type I or activin-like kinase (ALK) receptors and type II receptors. The ALK receptors are distinguished from the Type II receptors in that the ALK receptors (a) lack the serine/threonine-rich intracellular tail, (b) possess serine/threonine kinase domains that are highly homologous among Type I receptors, and (c) share a common sequence motif called the GS domain, consisting of a region rich in glycine and serine residues. The GS domain is at the amino terminal end of the intracellular kinase domain and is believed to be critical for activation by the Type II receptor. Several studies have shown that TGF-β signaling requires both the ALK (Type I) and Type II receptors. Specifically, the Type II receptor phosphorylates the GS domain of the Type 1 receptor for TGFβ ALK5, in the presence of TGFβ. The ALK5, in turn, phosphorylates the cytoplasmic proteins smad2 and smad3 at two carboxy terminal serines. Generally, it is believed that in many species, the Type II receptors regulate cell proliferation and the Type I receptors regulate matrix production. Various ALK5 receptor inhibitors have been described (see, for example, U.S. Pat. Nos. 6,465,493, 6,906,089, U.S. Patent Publication Numbers 2003/0166633, 2004/0063745 and 2004/0039198, the disclosures of which are incorporated herein by reference). Thus, the myostatin antagonists for use according to the disclosure may comprise the myostatin binding domain of an ALK5 and/or ALK7 receptor.

Other myostatin antagonists include soluble ligand antagonists that compete with myostatin for binding to myostatin receptors. The term "soluble ligand antagonist" herein refers to soluble peptides, polypeptides or peptidomimetics capable of non-productively binding the myostatin receptor(s) (e.g., the activin type HB receptor (ActRHA)) and thereby competitively blocking myostatin-receptor signal transduction. Soluble ligand antagonists include variants of myostatin, also referred to as "myostatin analogs" that have homology to, but not the activity of, myostatin. Such analogs include truncates (such as N- or C-terminal truncations, substitutions, deletions, and other alterations in the amino acid sequence, such as variants having non-amino acid substitutions).

Additional myostatin antagonists contemplated by the disclosure include inhibitory nucleic acids as described herein. These antagonists include antisense or sense polynucleotides comprising a single-stranded polynucleotide sequence (either RNA or DNA) capable of binding to target mRNA (sense) or DNA (antisense) sequences. Thus, RNA interference (RNAi) produced by the introduction of specific small interfering RNA (siRNA), may also be used to inhibit or eliminate the activity of myostatin.

In specific embodiments, myostatin antagonists include, but are not limited to, follistatin, the myostatin prodomain, growth and differentiation factor 11 (GDF-11) prodomain, prodomain fusion proteins, antagonistic antibodies or antibody fragments that bind to myostatin, antagonistic antibodies or antibody fragments that bind to the activin type IEB receptor, soluble activin type IHB receptor, soluble activin type IEB receptor fusion proteins, soluble myostatin analogs (soluble ligands), polynucleotides, small molecules, peptidomimetics, and myostatin binding agents. Other antagonists include the peptide immunogens described in U.S. Pat. No. 6,369,201 and WO 2001/05820 (each of which is incorporated herein by reference) and myostatin multimers and immunoconjugates capable of eliciting an immune response and thereby blocking myostatin activity. Other antagonists include the protein inhibitors of myostatin described in WO 2002/085306 (incorporated herein by reference), which include the truncated Activin type II receptor, the myostatin pro-domain, and follistatin. Other myostatin inhibitors include those released into culture from cells overexpressing myostatin (see WO 2000/43781), dominant negative myostatin proteins (see WO 2001/53350) including the protein encoded by the Piedmontese allele, and mature myostatin peptides having a C-terminal truncation at a position either at or between amino acid positions 335 to 375. The small peptides described in U.S. Patent Publication Number 2004/0181033 (incorporated herein by reference) that comprise the amino acid sequence WMCPP, are also suitable for use in the compositions of the disclosure.

Chemotherapeutic Agents

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Modulators of Fibrosis

A "modulator of fibrosis" as used herein is synonymous with antifibrotic agent. The term "antifibrotic agent" refers to a chemical compound that has antifibrotic activity (i.e., prevents or reduces fibrosis) in mammals. This takes into account the abnormal formation of fibrous connective tissue, which is typically comprised of collagen. These compounds may have different mechanisms of action, some reducing the formation of collagen or another protein, others enhancing the catabolismor removal of collagen in the affected area of the body. All such compounds having activity in the reduction of the presence of fibrotic tissue are included herein, without regard to the particular mechanism of action by which each such drug functions. Antifibrotic agents useful in the methods and compositions of the disclosure include those described in U.S. Pat. No. 5,720,950, incorporated herein by reference. Additional antifibrotic agents contemplated by the disclosure include, but are not limited to, Type II interferon receptor agonists (e.g., interferon-gamma); pirfenidone and pirfenidone analogs; anti-angiogenic agents, such as VEGF antagonists, VEGF receptor antagonists, bFGF antagonists, bFGF receptor antagonists, TGFβ antagonists, TGFβ receptor antagonists; anti-inflammatory agents, IL-1 antagonists, such as IL-1Ra, angiotensin-converting-enzyme (ACE) inhibitors, angiotensin receptor blockers and aldosterone antagonists.

Gene Correction Approaches

Gene correction approaches are contemplated by the disclosure to be used in conjunction with the methods and compositions as described herein. As used herein, "gene correction" approaches include, without limitation, technologies related to gene editing (i.e., CRISPR technology), exon skipping, and other technologies known in the art for modifying mRNA). Thus, in some embodiments, methods are provided in which an agent of the disclosure is used to increase the activity of an annexin protein in an individual suffering from Becker muscular dystrophy (BMD), Duchenne muscular dystrophy (DMD), all Limb Girdle muscular dystrophy (LGMD) type 1 subtypes, all LGMD type 2 subtypes, congenital muscular dystrophy, Emery-Dreifuss muscular dystrophy (EDMD), myotonic dystrophy, Fascioscapulohumeral dystrophy (FSHD), Oculopharyngeal muscular dystrophy, and Distal muscular dystrophy, wherein the patient will be, is concurrently being, or has previously been, administered a composition that results in correction of a gene involved in any one of the foregoing disorders. In further embodiments, methods are provided in which an agent of the disclosure is used to increase the activity of an annexin protein in an individual suffering from Becker muscular dystrophy (BMD), Duchenne muscular dystrophy (DMD), all Limb Girdle muscular dystrophy (LGMD) type 1 subtypes, all LGMD type 2 subtypes, congenital muscular dystrophy, Emery-Dreifuss muscular dystrophy (EDMD), myotonic dystrophy, Fascioscapulohumeral dystrophy (FSHD), Oculopharyngeal muscular dystrophy, and Distal muscular dystrophy, wherein the patient will be, is concurrently being, or has previously been, administered a viral-based or non-viral-based composition that results in correction of a gene involved in any one of the foregoing disorders.

Gene correction approaches are known in the art (see, e.g., U.S. Patent Application Publication No. 2016/0130608 and U.S. Pat. No. 9,499,817, respectively, each incorporated by reference herein in their entirety). Further discussion of such methods can be found in Echigoya et al., J Pers Med 8, 2018; Li et al., Trends Pharmacol Sci 39: 982-994, 2018; Min et al., Annu Rev Med, 2018; and Zhang et al., Physiol Rev 98: 1205-1240, 2018.

Compositions

Any of the agents and/or additional agents described herein (or nucleic acids encoding any of the agents and/or additional agents described herein) also is provided in a composition. In this regard, the agent and/or additional agent is formulated with a physiologically-acceptable (i.e., pharmacologically acceptable) carrier, buffer, or diluent, as described further herein. Optionally, the protein/recombinant protein is in the form of a physiologically acceptable salt, which is encompassed by the disclosure. "Physiologically acceptable salts" means any salts that are pharmaceutically acceptable. Some examples of appropriate salts include acetate, trifluoroacetate, hydrochloride, hydrobromide, sulfate, citrate, tartrate, glycolate, and oxalate. Accordingly, in some aspects the disclosure provides pharmaceutical compositions comprising one or more annexin proteins and a pharmaceutically acceptable carrier, buffer, and/or diluent. In any of the aspects or embodiments of the disclosure, one or more (or all) annexin proteins in a composition is a modified annexin protein. In any of the aspects or embodiments of the disclosure, one or more (or all) annexin proteins in a composition is a naturally-occurring mammalian annexin protein. In some embodiments, the modified annexin protein is expressed in a prokaryotic cell (for example and without limitation, an *E. coli* cell). In general, a modified protein is a protein that is altered relative to the version of the protein that normally exists in nature. In some embodiments, a modified protein is one in which at least one amino acid of the modified protein has an altered posttranslational modification relative to the naturally-occurring mammalian protein. By way of example, a naturally-occurring mammalian protein may comprise an amino acid that is phosphorylated while the same amino acid in the modified protein has either a different posttranslational modification or has no posttranslational modification. In some embodiments, the annexin protein is annexin A1 (SEQ ID NO: 1), annexin A2 (SEQ ID NO: 2 or SEQ ID NO: 3), annexin A3 (SEQ ID NO: 4), annexin A4 (SEQ ID NO: 5), annexin A5 (SEQ ID NO: 6), annexin A6 (SEQ ID NO: 7, SEQ ID NO: 8, SEQ ID NO: 45, or a combination thereof), annexin A7 (SEQ ID NO: 9 or SEQ ID NO: 10), annexin A8 (SEQ ID NO: 11 or SEQ ID NO: 12), annexin A9 (SEQ ID NO: 13), annexin A10 (SEQ ID NO: 14), annexin A11 (SEQ ID NO: 15 or SEQ ID NO: 16), annexin A13 (SEQ ID NO: 17 or SEQ ID NO: 18), or a combination thereof. In some embodiments, the annexin protein is annexin A6 (SEQ ID NO: 7, SEQ ID NO: 8, SEQ ID NO: 45, or a combination thereof). In some embodiments, and as described herein, the pharmaceutical composition comprises a combination of annexin proteins wherein one or more of the annexin proteins is a modified annexin protein. In some embodiments, the pharmaceutical composition comprises a combination of annexin proteins and each annexin protein is a naturally-occurring mammalian annexin protein. Pharmaceutical compositions of the disclosure comprising one or more annexin proteins are formulated such that the one or more annexin proteins are present in the composition at a high level of purity. By "purity" it is meant that a protein (e.g., an annexin protein) used in a pharmaceutical composition is largely composed of the full-length protein (e.g., annexin protein) that was expressed and is largely free of truncated or degraded protein products. In various embodiments, the one or more annexin proteins that is/are present in a pharmaceutical composition is/are at least 90%, at least 95%, or at least 99% pure as measured by standard release assay including but not limited to one or more of SDS-PAGE, SEC-HPLC, and immunoblot analysis. A pharmaceutical composition of the disclosure is also relatively free of endotoxin. In various embodiments, a pharmaceutical composition of the disclosure has an endotoxin level that is or is less than about 10, is or is less than about 5, is or is less than about 1, is or is less than about 0.50000, is or is less than about 0.40000, is or is less than about 0.30000 endotoxin units per milligram (EU/mg) A280 annexin protein as determined by standard methods.

As disclosed herein, the disclosure provides compositions comprising one or more agents and/or additional agents that increase the activity of an annexin protein. In various embodiments, the annexin protein is annexin A1 (SEQ ID NO: 1), annexin A2 (SEQ ID NO: 2 and/or SEQ ID NO: 3), annexin A3 (SEQ ID NO: 4), annexin A4 (SEQ ID NO: 5), annexin A5 (SEQ ID NO: 6), annexin A6 (SEQ ID NO: 7 and/or SEQ ID NO: 8), annexin A7 (SEQ ID NO: 9 and/or SEQ ID NO: 10), annexin A8 (SEQ ID NO: 11 and/or SEQ ID NO: 12), annexin A9 (SEQ ID NO: 13), annexin A10 (SEQ ID NO: 14), annexin A11 (SEQ ID NO: 15 and/or SEQ ID NO: 16), annexin A13 (SEQ ID NO: 17 and/or SEQ ID NO: 18), or a combination thereof. In some embodiments, the composition increases the activity of annexin A1 (SEQ ID NO: 1), annexin A2 (SEQ ID NO: 2 and/or SEQ ID NO: 3), and annexin A6 (SEQ ID NO: 7 and/or SEQ ID NO: 8). In further embodiments, the composition increases the activity of annexin A2 (SEQ ID NO: 2 and/or SEQ ID NO: 3) and annexin A6 (SEQ ID NO: 7 and/or SEQ ID NO: 8). In still further embodiments, the composition increases the activity of annexin A1 (SEQ ID NO: 1) and annexin A6 (SEQ ID NO: 7 and/or SEQ ID NO: 8).

The disclosure also contemplates, in various embodiments, compositions that increase the activity of annexin A1 (SEQ ID NO: 1), annexin A2 (SEQ ID NO: 2 and/or SEQ ID NO: 3), annexin A3 (SEQ ID NO: 4), annexin A4 (SEQ ID NO: 5), annexin A5 (SEQ ID NO: 6), annexin A6 (SEQ ID NO: 7 and/or SEQ ID NO: 8), annexin A7 (SEQ ID NO: 9 and/or SEQ ID NO: 10), annexin A8 (SEQ ID NO: 11 and/or SEQ ID NO: 12), annexin A9 (SEQ ID NO: 13), annexin A10 (SEQ ID NO: 14), annexin A11 (SEQ ID NO: 15 and/or SEQ ID NO: 16), and annexin A13 (SEQ ID NO: 17 and/or SEQ ID NO: 18) in any combination. Note that when more than one sequence identifier is used to identify an annexin protein herein (e.g., annexin A2 is identified herein by SEQ ID NO: 2 and/or SEQ ID NO: 3) it will be understood that the different sequence identifiers serve to identify isoforms of the particular annexin protein, and that the isoforms may be used interchangeably or in combination in methods and compositions of the disclosure.

Refseq Accession Number NP_000691.1 annexin A1 [*Homo sapiens*]
(SEQ ID NO: 1):
MAMVSEFLKQAWFIENEEQEYVQTVKSSKGGPGSAVSPYPTFNPSSDVAALHKAIMVKGV

DEATIIDILTKRNNAQRQQIKAAYLQETGKPLDETLKKALTGHLEEVVLALLKTPAQFDADELR

AAMKGLGTDEDTLIEILASRTNKEIRDINRVYREELKRDLAKDITSDTSGDFRNALLSLAKGD

RSEDFGVNEDLADSDARALYEAGERRKGTDVNVFNTILTTRSYPQLRRVFQKYTKYSKHD

MNKVLDLELKGDIEKCLTAIVKCATSKPAFFAEKLHQAMKGVGTRHKALIRIMVSRSEIDMND

IKAFYQKMYGISLCQAILDETKGDYEKILVALCGGN

Refseq Accession Number NP_001002858.1 annexin A2 isoform 1 [*Homo sapiens*] (SEQ ID NO: 2):
MGRQLAGCGDAGKKASFKMSTVHEILCKLSLEGDHSTPPSAYGSVKAYTNFDAERDALNIE

TAIKTKGVDEVTIVNILTNRSNAQRQDIAFAYQRRTKKELASALKSALSGHLETVILGLLKTPA

QYDASELKASMKGLGTDEDSLIEIICSRTNQELQEINRVYKEMYKTDLEKDIISDTSGDFRKL

MVALAKGRRAEDGSVIDYELIDQDARDLYDAGVKRKGTDVPKWISIMTERSVPHLQKVFDR

YKSYSPYDMLESIRKEVKGDLENAFLNLVQCIQNKPLYFADRLYDSMKGKGTRDKVLIRIMV

SRSEVDMLKIRSEFKRKYGKSLYYYIQQDTKGDYQKALLYLCGGDD

Refseq Accession Number NP_001129487.1 annexin A2 isoform 2 [*Homo sapiens*] (SEQ ID NO: 3):
MSTVHEILCKLSLEGDHSTPPSAYGSVKAYTNFDAERDALNIETAIKTKGVDEVTIVNILTNRS

NAQRQDIAFAYQRRTKKELASALKSALSGHLETVILGLLKTPAQYDASELKASMKGLGTDED

SLIEIICSRTNQELQEINRVYKEMYKTDLEKDIISDTSGDFRKLMVALAKGRRAEDGSVIDYELI

DQDARDLYDAGVKRKGTDVPKWISIMTERSVPHLQKVFDRYKSYSPYDMLESIRKEVKGDL

ENAFLNLVQCIQNKPLYFADRLYDSMKGKGTRDKVLIRIMVSRSEVDMLKIRSEFKRKYGKS

LYYYIQQDTKGDYQKALLYLCGGDD

Refseq Accession Number NP_005130.1 annexin A3 [*Homo sapiens*]
(SEQ ID NO: 4):
MASIWVGHRGTVRDYPDFSPSVDAEAIQKAIRGIGTDEKMLISILTERSNAQRQLIVKEYQAA

YGKELKDDLKGDLSGHFEHLMVALVTPPAVFDAKQLKKSMKGAGTNEDALIEILTTRTSRQ

MKDISQAYYTVYKKSLGDDISSETSGDFRKALLTLADGRRDESLKVDEHLAKQDAQILYKAG

ENRWGTDEDKFTEILCLRSFPQLKLTFDEYRNISQKDIVDSIKGELSGHFEDLLLAIVNCVRN

-continued

TPAFLAERLHRALKGIGTDEFTLNRIMVSRSEIDLLDIRTEFKKHYGYSLYSAIKSDTSGDYEI

TLLKICGGDD

Refseq Accession Number NP_001144.1 annexin A4 isoform a [*Homo sapiens*] (SEQ ID NO: 5):
MAMATKGGTVKAASGFNAMEDAQTLRKAMKGLGTDEDAIISVLAYRNTAQRQEIRTAYKST

IGRDLIDDLKSELSGNFEQVIVGMMTPTVLYDVQELRRAMKGAGTDEGCLIEILASRTPEEIR

RISQTYQQQYGRSLEDDIRSDTSFMFQRVLVSLSAGGRDEGNYLDDALVRQDAQDLYEAG

EKKWGTDEVKFLTVLCSRNRNHLLHVFDEYKRISQKDIEQSIKSETSGSFEDALLAIVKCMR

NKSAYFAEKLYKSMKGLGTDDNTLIRVMVSRAEIDMLDIRAHFKRLYGKSLYSFIKGDTSGD

YRKVLLVLCGGDD

Refseq Accession Number NP_001145.1 annexin A5 [*Homo sapiens*] (SEQ ID NO: 6):
MAQVLRGTVTDFPGFDERADAETLRKAMKGLGTDEESILTLLTSRSNAQRQEISAAFKTLFG

RDLLDDLKSELTGKFEKLIVALMKPSRLYDAYELKHALKGAGTNEKVLTEIIASRTPEELRAIK

QVYEEEYGSSLEDDVVGDTSGYYQRMLVVLLQANRDPDAGIDEAQVEQDAQALFQAGELK

WGTDEEKFITIFGTRSVSHLRKVFDKYMTISGFQIEETIDRETSGNLEQLLLAVVKSIRSIPAYL

AETLYYAMKGAGTDDHTLIRVMVSRSEIDLFNIRKEFRKNFATSLYSMIKGDTSGDYKKALLL

LCGEDD

Refseq Accession Number NP_001146.2 annexin A6 isoform 1 [*Homo sapiens*] (SEQ ID NO: 7):
MAKPAQGAKYRGSIHDFPGFDPNQDAEALYTAMKGFGSDKEAILDIITSRSNRQRQEVCQS

YKSLYGKDLIADLKYELTGKFERLIVGLMRPPAYCDAKEIKDAISGIGTDEKCLIEILASRTNEQ

MHQLVAAYKDAYERDLEADIIGDTSGHFQKMLVVLLQGTREEDDVVSEDLVQQDVQDLYEA

GELKWGTDEAQFIYILGNRSKQHLRLVFDEYLKTTGKPIEASIRGELSGDFEKLMLAVVKCIR

STPEYFAERLFKAMKGLGTRDNTLIRIMVSRSELDMLDIREIFRTKYEKSLYSMIKNDTSGEY

KKTLLKLSGGDDDAAGQFFPEAAQVAYQMWELSAVARVELKGTVRPANDFNPDADAKALR

KAMKGLGTDEDTIIDIITHRSNVQRQQIRQTFKSHFGRDLMTDLKSEISGDLARLILGLMMPP

AHYDAKQLKKAMEGAGTDEKALIEILATRTNAEIRAINEAYKEDYHKSLEDALSSDTSGHFRR

ILISLATGHREEGGENLDQAREDAQVAAEILEIADTPSGDKTSLETRFMTILCTRSYPHLRRV

FQEFIKMTNYDVEHTIKKEMSGDVRDAFVAIVQSVKNKPLFFADKLYKSMKGAGTDEKTLTR

IMVSRSEIDLLNIRREFIEKYDKSLHQAIEGDTSGDFLKALLALCGGED

Refseq Accession Number NP_001180473.1 annexin A6 isoform 2 [*Homo sapiens*] (SEQ ID NO: 8):
MKGFGSDKEAILDIITSRSNRQRQEVCQSYKSLYGKDLIADLKYELTGKFERLIVGLMRPPAY

CDAKEIKDAISGIGTDEKCLIEILASRTNEQMHQLVAAYKDAYERDLEADIIGDTSGHFQKML

VVLLQGTREEDDVVSEDLVQQDVQDLYEAGELKWGTDEAQFIYILGNRSKQHLRLVFDEYL

KTTGKPIEASIRGELSGDFEKLMLAVVKCIRSTPEYFAERLFKAMKGLGTRDNTLIRIMVSRS

ELDMLDIREIFRTKYEKSLYSMIKNDTSGEYKKTLLKLSGGDDDAAGQFFPEAAQVAYQMW

ELSAVARVELKGTVRPANDFNPDADAKALRKAMKGLGTDEDTIIDIITHRSNVQRQQIRQTF

KSHFGRDLMTDLKSEISGDLARLILGLMMPPAHYDAKQLKKAMEGAGTDEKALIEILATRTN

AEIRAINEAYKEDYHKSLEDALSSDTSGHFRRILISLATGHREEGGENLDQAREDAQVAAEIL

EIADTPSGDKTSLETRFMTILCTRSYPHLRRVFQEFIKMTNYDVEHTIKKEMSGDVRDAFVAI

VQSVKNKPLFFADKLYKSMKGAGTDEKTLTRIMVSRSEIDLLNIRREFIEKYDKSLHQAIEGD

TSGDFLKALLALCGGED

-continued

Refseq Accession Number NP_001147.1 annexin A7 isoform 1 [*Homo sapiens*] (SEQ ID NO: 9):
MSYPGYPPTGYPPFPGYPPAGQESSFPPSGQYPYPSGFPPMGGGAYPQVPSSGYPGAG

GYPAPGGYPAPGGYPGAPQPGGAPSYPGVPPGQGFGVPPGGAGFSGYPQPPSQSYGG

GPAQVPLPGGFPGGQMPSQYPGGQPTYPSQPATVTQVTQGTIRPAANFDAIRDAEILRKA

MKGFGTDEQAIVDVVANRSNDQRQKIKAAFKTSYGKDLIKDLKSELSGNMEELILALFMPPT

YYDAWSLRKAMQGAGTQERVLIEILCTRTNQEIREIVRCYQSEFGRDLEKDIRSDTSGHFER

LLVSMCQGNRDENQSINHQMAQEDAQRLYQAGEGRLGTDESCFNMILATRSFPQLRATME

AYSRMANRDLLSSVSREFSGYVESGLKTILQCALNRPAFFAERLYYAMKGAGTDDSTLVRIV

VIRSEIDLVQIKQMFAQMYQKTLGTMIAGDTSGDYRRLLLAIVGQ

Refseq Accession Number NP_004025.1 annexin A7 isoform 2 [*Homo sapiens*] (SEQ ID NO: 10):
MSYPGYPPTGYPPFPGYPPAGQESSFPPSGQYPYPSGFPPMGGGAYPQVPSSGYPGAG

GYPAPGGYPAPGGYPGAPQPGGAPSYPGVPPGQGFGVPPGGAGFSGYPQPPSQSYGG

GPAQVPLPGGFPGGQMPSQYPGGQPTYPSQINTDSFSSYPVFSPVSLDYSSEPATVTQVT

QGTIRPAANFDAIRDAEILRKAMKGFGTDEQAIVDVVANRSNDQRQKIKAAFKTSYGKDLIKD

LKSELSGNMEELILALFMPPTYYDAWSLRKAMQGAGTQERVLIEILCTRTNQEIREIVRCYQS

EFGRDLEKDIRSDTSGHFERLLVSMCQGNRDENQSINHQMAQEDAQRLYQAGEGRLGTD

ESCFNMILATRSFPQLRATMEAYSRMANRDLLSSVSREFSGYVESGLKTILQCALNRPAFFA

ERLYYAMKGAGTDDSTLVRIVVIRSEIDLVQIKQMFAQMYQKTLGTMIAGDTSGDYRRLLLA

IVGQ

Refseq Accession Number NP_001258631.1 annexin A8 isoform 1 [*Homo sapiens*] (SEQ ID NO: 11):
MAWWKSWIEQEGVTVKSSSHFNPDPDAETLYKAMKGIGVGSQLLSHQAAAFAFPSSALTS

VSPWGQQGHLCCNPAGTNEQAIIDVLIKRSNTQRQQIAKSFKAQFGKDLTETLKSELSGKF

ERLIVALMYPPYRYEAKELHDAMKGLGTKEGVIIEILASRTKNQLREIMKAYEEDYGSSLEEDI

QADTSGYLERILVCLLQGSRDDVSSFVDPGLALQDAQDLYAAGEKIRGTDEMKFITILCTRS

ATHLLRVFEEYEKIANKSIEDSIKSETHGSLEEAMLTVVKCTQNLHSYFAERLYYAMKGAGT

RDGTLIRNIVSRSEIDLNLIKCHFKKMYGKTLSSMIMEDTSGDYKNALLSLVGSDP

Refseq Accession Number NP_001035173.1 annexin A8 isoform 2 [*Homo sapiens*] (SEQ ID NO: 12):
MAWWKSWIEQEGVTVKSSSHFNPDPDAETLYKAMKGIGTNEQAIIDVLIKRSNTQRQQIAK

SFKAQFGKDLTETLKSELSGKFERLIVALMYPPYRYEAKELHDAMKGLGTKEGVIIEILASRT

KNQLREIMKAYEEDYGSSLEEDIQADTSGYLERILVCLLQGSRDDVSSFVDPGLALQDAQDL

YAAGEKIRGTDEMKFITILCTRSATHLLRVFEEYEKIANKSIEDSIKSETHGSLEEAMLTVVKC

TQNLHSYFAERLYYAMKGAGTRDGTLIRNIVSRSEIDLNLIKCHFKKMYGKTLSSMIMEDTS

GDYKNALLSLVGSDP

Refseq Accession Number NP_003559.2 annexin A9 [*Homo sapiens*] (SEQ ID NO: 13):
MSVTGGKMAPSLTQEILSHLGLASKTAAWGTLGTLRTFLNFSVDKDAQRLLRAITGQGVDR

SAIVDVLTNRSREQRQLISRNFQERTQQDLMKSLQAALSGNLERIVMALLQPTAQFDAQEL

RTALKASDSAVDVAIEILATRTPPQLQECLAVYKHNFQVEAVDDITSETSGILQDLLLALAKG

GRDSYSGIIDYNLAEQDVQALQRAEGPSREETWVPVFTQRNPEHLIRVFDQYQRSTGQELE

EAVQNRFHGDAQVALLGLASVIKNTPLYFADKLHQALQETEPNYQVLIRILISRCETDLLSIRA

EFRKKFGKSLYSSLQDAVKGDCQSALLALCRAEDM

-continued

Refseq Accession Number NP_009124.2 annexin A10 [*Homo sapiens*] (SEQ ID NO: 14):
MFCGDYVQGTIFPAPNFNPIMDAQMLGGALQGFDCDKDMLINILTQRCNAQRMMIAEAYQS

MYGRDLIGDMREQLSDHFKDVMAGLMYPPPLYDAHELWHAMKGVGTDENCLIEILASRTN

GEIFQMREAYCLQYSNNLQEDIYSETSGHFRDTLMNLVQGTREEGYTDPAMAAQDAMVLW

EACQQKTGEHKTMLQMILCNKSYQQLRLVFQEFQNISGQDMVDAINECYDGYFQELLVAIV

LCVRDKPAYFAYRLYSAIHDFGFHNKTVIRILIARSEIDLLTIRKRYKERYGKSLFHDIRNFASG

HYKKALLAICAGDAEDY

Refseq Accession Number NP_665875.1 annexin A11 isoform 1 [*Homo sapiens*] (SEQ ID NO: 15):
MSYPGYPPPPGGYPPAAPGGGPWGGAAYPPPPSMPPIGLDNVATYAGQFNQDYLSGMA

ANMSGTFGGANMPNLYPGAPGAGYPPVPPGGFGQPPSAQQPVPPYGMYPPPGGNPPSR

MPSYPPYPGAPVPGQPMPPPGQQPPGAYPGQPPVTYPGQPPVPLPGQQQPVPSYPGYP

GSGTVTPAVPPTQFGSRGTITDAPGFDPLRDAEVLRKAMKGFGTDEQAIIDCLGSRSNKQR

QQILLSFKTAYGKDLIKDLKSELSGNFEKTILALMKTPVLFDIYEIKEAIKGVGTDEACLIEILAS

RSNEHIRELNRAYKAEFKKTLEEAIRSDTSGHFQRLLISLSQGNRDESTNVDMSLAQRDAQE

LYAAGENRLGTDESKFNAVLCSRSRAHLVAVFNEYQRMTGRDIEKSICREMSGDLEEGMLA

VVKCLKNTPAFFAERLNKAMRGAGTKDRTLIRIMVSRSETDLLDIRSEYKRMYGKSLYHDIS

GDTSGDYRKILLKICGGND

Refseq Accession Number NP_001265338.1 annexin A11 isoform 2 [*Homo sapiens*] (SEQ ID NO: 16):
MPPIGLDNVATYAGQFNQDYLSGMAANMSGTFGGANMPNLYPGAPGAGYPPVPPGGFG

QPPSAQQPVPPYGMYPPPGGNPPSRMPSYPPYPGAPVPGQPMPPPGQQPPGAYPGQPP

VTYPGQPPVPLPGQQQPVPSYPGYPGSGTVTPAVPPTQFGSRGTITDAPGFDPLRDAEVL

RKAMKGFGTDEQAIIDCLGSRSNKQRQQILLSFKTAYGKDLIKDLKSELSGNFEKTILALMKT

PVLFDIYEIKEAIKGVGTDEACLIEILASRSNEHIRELNRAYKAEFKKTLEEAIRSDTSGHFQRL

LISLSQGNRDESTNVDMSLAQRDAQELYAAGENRLGTDESKFNAVLCSRSRAHLVAVFNEY

QRMTGRDIEKSICREMSGDLEEGMLAVVKCLKNTPAFFAERLNKAMRGAGTKDRTLIRIMV

SRSETDLLDIRSEYKRMYGKSLYHDISGDTSGDYRKILLKICGGND

Refseq Accession Number NP_004297.2 annexin A13 isoform a [*Homo sapiens*] (SEQ ID NO: 17):
MGNRHAKASSPQGFDVDRDAKKLNKACKGMGTNEAAIIEILSGRTSDERQQIKQKYKATYG

KELEEVLKSELSGNFEKTALALLDRPSEYAARQLQKAMKGLGTDESVLIEVLCTRTNKEIIAIK

EAYQRLFDRSLESDVKGDTSGNLKKILVSLLQANRNEGDDVDKDLAGQDAKDLYDAGEGR

WGTDELAFNEVLAKRSYKQLRATFQAYQILIGKDIEEAIEEETSGDLQKAYLTLVRCAQDCE

DYFAERLYKSMKGAGTDEETLIRIVVTRAEVDLQGIKAKFQEKYQKSLSDMVRSDTSGDFR

KLLVALLH

Refseq Accession Number NP_001003954.1 annexin A13 isoform b [*Homo sapiens*] (SEQ ID NO: 18):
MGNRHSQSYTLSEGSQQLPKGDSQPSTVVQPLSHPSRNGEPEAPQPAKASSPQGFDVDR

DAKKLNKACKGMGTNEAAIIEILSGRTSDERQQIKQKYKATYGKELEEVLKSELSGNFEKTAL

ALLDRPSEYAARQLQKAMKGLGTDESVLIEVLCTRTNKEIIAIKEAYQRLFDRSLESDVKGDT

SGNLKKILVSLLQANRNEGDDVDKDLAGQDAKDLYDAGEGRWGTDELAFNEVLAKRSYKQ

LRATFQAYQILIGKDIEEAIEEETSGDLQKAYLTLVRCAQDCEDYFAERLYKSMKGAGTDEET

LIRIVVTRAEVDLQGIKAKFQEKYQKSLSDMVRSDTSGDFRKLLVALLH

-continued

Refseq Accession Number NP_001350043.1 annexin A6 isoform 3 [*Homo sapiens*] (SEQ ID NO: 45):

MAKPAQGAKYRGSIHDFPGFDPNQDAEALYTAMKGFGSDKEAILDIITSRSNRQRQEVCQS

YKSLYGKDLIADLKYELTGKFERLIVGLMRPPAYCDAKEIKDAISGIGTDEKCLIEILASRTNEQ

MHQLVAAYKDAYERDLEADIIGDTSGHFQKMLVVLLQGTREEDDVVSEDLVQQDVQDLYEA

GELKWGTDEAQFIYILGNRSKQHLRLVFDEYLKTTGKPIEASIRGELSGDFEKLMLAVVKCIR

STPEYFAERLFKAMKGLGTRDNTLIRIMVSRSELDMLDIREIFRTKYEKSLYSMIKNDTSGEY

KKTLLKLSGGDDDAAGQFFPEAAQVAYQMWELSAVARVELKGTVRPANDFNPDADAKALR

KAMKGLGTDEDTIIDIITHRSNVQRQQIRQTFKSHFGRDLMTDLKSEISGDLARLILGLMMPP

AHYDAKQLKKAMEGAGTDEKALIEILATRTNAEIRAINEAYKEDYHKSLEDALSSDTSGHFRR

ILISLATGHREEGGENLDQAREDAQEIADTPSGDKTSLETRFMTILCTRSYPHLRRVFQEFIK

MTNYDVEHTIKKEMSGDVRDAFVAIVQSVKNKPLFFADKLYKSMKGAGTDEKTLTRIMVSR

SEIDLLNIRREFIEKYDKSLHQAIEGDTSGDFLKALLALCGGED

The disclosure also contemplates corresponding polynucleotides that encode each of the foregoing annexin proteins. The following polynucleotides are contemplated for use according to the disclosure. Specifically, the following polynucleotides are messenger RNA (mRNA) sequences contemplated for use with a vector of the disclosure to increase activity of an annexin protein. As discussed above, when more than one sequence identifier is used to identify an mRNA sequence in relation to the same annexin species herein (e.g., mRNA sequences relating to annexin A2 are identified herein by SEQ ID NO: 20 and SEQ ID NO: 21) it will be understood that the different sequence identifiers serve to identify transcript variants that may be utilized with a vector of the disclosure to be translated into the particular annexin protein, and that the transcript variants may be used interchangeably or in combination in the methods and compositions of the disclosure.

NM_000700.3 *Homo sapiens* annexin A1 (ANXA1), mRNA (SEQ ID NO: 19)

AGTGTGAAATCTTCAGAGAAGAATTTCTCTTTAGTTCTTTGCAAGAAGGTAGA

GATAAAGACACTTTTTCAAAAATGGCAATGGTATCAGAATTCCTCAAGCAGGCCTGGTTT

ATTGAAAATGAAGAGCAGGAATATGTTCAAACTGTGAAGTCATCCAAAGGTGGTCCCGG

ATCAGCGGTGAGCCCCTATCCTACCTTCAATCCATCCTCGGATGTCGCTGCCTTGCATA

AGGCCATAATGGTTAAAGGTGTGGATGAAGCAACCATCATTGACATTCTAACTAAGCGA

AACAATGCACAGCGTCAACAGATCAAAGCAGCATATCTCCAGGAAACAGGAAAGCCCC

TGGATGAAACACTGAAGAAAGCCCTTACAGGTCACCTTGAGGAGGTTGTTTTAGCTCTG

CTAAAAACTCCAGCGCAATTTGATGCTGATGAACTTCGTGCTGCCATGAAGGGCCTTGG

AACTGATGAAGATACTCTAATTGAGATTTTGGCATCAAGAACTAACAAAGAAATCAGAGA

CATTAACAGGGTCTACAGAGAGGAACTGAAGAGAGATCTGGCCAAAGACATAACCTCA

GACACATCTGGAGATTTTCGGAACGCTTTGCTTTCTCTTGCTAAGGGTGACCGATCTGA

GGACTTTGGTGTGAATGAAGACTTGGCTGATTCAGATGCCAGGGCCTTGTATGAAGCA

GGAGAAAGGAGAAAGGGGACAGACGTAAACGTGTTCAATACCATCCTTACCACCAGAA

GCTATCCACAACTTCGCAGAGTGTTTCAGAAATACACCAAGTACAGTAAGCATGACATG

AACAAAGTTCTGGACCTGGAGTTGAAAGGTGACATTGAGAAATGCCTCACAGCTATCGT

GAAGTGCGCCACAAGCAAACCAGCTTTCTTTGCAGAGAAGCTTCATCAAGCCATGAAAG

GTGTTGGAACTCGCCATAAGGCATTGATCAGGATTATGGTTTCCCGTTCTGAAATTGAC

ATGAATGATATCAAAGCATTCTATCAGAAGATGTATGGTATCTCCCTTTGCCAAGCCATC

CTGGATGAAACCAAAGGAGATTATGAGAAAATCCTGGTGGCTCTTTGTGGAGGAAACTA

AACATTCCCTTGATGGTCTCAAGCTATGATCAGAAGACTTTAATTATATATTTTCATCCTA

TAAGCTTAAATAGGAAAGTTTCTTCAACAGGATTACAGTGTAGCTACCTACATGCTGAAA

-continued

AATATAGCCTTTAAATCATTTTTATATTATAACTCTGTATAATAGAGATAAGTCCATTTTTT

AAAAATGTTTTCCCCAAACCATAAAACCCTATACAAGTTGTTCTAGTAACAATACATGAG

AAAGATGTCTATGTAGCTGAAAATAAAATGACGTCACAAGACAA

NM_001002858.2 *Homo sapiens* annexin A2 (ANXA2), transcript variant 1, mRNA (SEQ ID NO: 20)

GCTCAGCATTTGGGGACGCTCTCAGCTCTCGGCGCACGGCCCAGGTAAGCG

GGGCGCGCCCTGCCCGCCCGCGATGGGCCGCCAGCTAGCGGGGTGTGGAGACGCTG

GGAAGAAGGCTTCCTTCAAAATGTCTACTGTTCACGAAATCCTGTGCAAGCTCAGCTTG

GAGGGTGATCACTCTACACCCCCAAGTGCATATGGGTCTGTCAAAGCCTATACTAACTT

TGATGCTGAGCGGGATGCTTTGAACATTGAAACAGCCATCAAGACCAAAGGTGTGGAT

GAGGTCACCATTGTCAACATTTTGACCAACCGCAGCAATGCACAGAGACAGGATATTGC

CTTCGCCTACCAGAGAAGGACCAAAAAGGAACTTGCATCAGCACTGAAGTCAGCCTTAT

CTGGCCACCTGGAGACGGTGATTTTGGGCCTATTGAAGACACCTGCTCAGTATGACGC

TTCTGAGCTAAAAGCTTCCATGAAGGGGCTGGGAACCGACGAGGACTCTCTCATTGAG

ATCATCTGCTCCAGAACCAACCAGGAGCTGCAGGAAATTAACAGAGTCTACAAGGAAAT

GTACAAGACTGATCTGGAGAAGGACATTATTTCGGACACATCTGGTGACTTCCGCAAGC

TGATGGTTGCCCTGGCAAAGGGTAGAAGAGCAGAGGATGGCTCTGTCATTGATTATGA

ACTGATTGACCAAGATGCTCGGGATCTCTATGACGCTGGAGTGAAGAGGAAAGGAACT

GATGTTCCCAAGTGGATCAGCATCATGACCGAGCGGAGCGTGCCCCACCTCCAGAAAG

TATTTGATAGGTACAAGAGTTACAGCCCTTATGACATGTTGGAAAGCATCAGGAAAGAG

GTTAAAGGAGACCTGGAAAATGCTTTCCTGAACCTGGTTCAGTGCATTCAGAACAAGCC

CCTGTATTTTGCTGATCGGCTGTATGACTCCATGAAGGGCAAGGGGACGCGAGATAAG

GTCCTGATCAGAATCATGGTCTCCCGCAGTGAAGTGGACATGTTGAAAATTAGGTCTGA

ATTCAAGAGAAAGTACGGCAAGTCCCTGTACTATTATATCCAGCAAGACACTAAGGGCG

ACTACCAGAAAGCGCTGCTGTACCTGTGTGGTGGAGATGACTGAAGCCCGACACGGCC

TGAGCGTCCAGAAATGGTGCTCACCATGCTTCCAGCTAACAGGTCTAGAAAACCAGCTT

GCGAATAACAGTCCCCGTGGCCATCCCTGTGAGGGTGACGTTAGCATTACCCCCAACC

TCATTTTAGTTGCCTAAGCATTGCCTGGCCTTCCTGTCTAGTCTCTCCTGTAAGCCAAAG

AAATGAACATTCCAAGGAGTTGGAAGTGAAGTCTATGATGTGAAACACTTTGCCTCCTG

TGTACTGTGTCATAAACAGATGAATAAACTGAATTTGTACTTTAGAAACACGTACTTTGT

GGCCCTGCTTTCAACTGAATTGTTTGAAAATTAAACGTGCTTGGGGTTCAGCTGGTGAG

GCTGTCCCTGTAGGAAGAAAGCTCTGGGACTGAGCTGTACAGTATGGTTGCCCCTATC

CAAGTGTCGCTATTTAAGTTAAATTTAAATGAAATAAAATAAAATAAAATCAAAAAAA

NM_001136015.2 *Homo sapiens* annexin A2 (ANXA2), transcript variant 4, mRNA (SEQ ID NO: 21)

GCTCAGCATTTGGGGACGCTCTCAGCTCTCGGCGCACGGCCCAGGGTGAAA

ATGTTTGCCATTAAACTCACATGAAGTAGGAAATATTTATATGGATACAAAAGGCACCTG

CATGGGATAATGTCAAATTTCATAGATACTGCTTTGTGCTTCCTTCAAAATGTCTACTGT

TCACGAAATCCTGTGCAAGCTCAGCTTGGAGGGTGATCACTCTACACCCCCAAGTGCA

TATGGGTCTGTCAAAGCCTATACTAACTTTGATGCTGAGCGGGATGCTTTGAACATTGA

AACAGCCATCAAGACCAAAGGTGTGGATGAGGTCACCATTGTCAACATTTTGACCAACC

GCAGCAATGCACAGAGACAGGATATTGCCTTCGCCTACCAGAGAAGGACCAAAAAGGA

ACTTGCATCAGCACTGAAGTCAGCCTTATCTGGCCACCTGGAGACGGTGATTTTGGGC

-continued

CTATTGAAGACACCTGCTCAGTATGACGCTTCTGAGCTAAAAGCTTCCATGAAGGGGCT

GGGAACCGACGAGGACTCTCTCATTGAGATCATCTGCTCCAGAACCAACCAGGAGCTG

CAGGAAATTAACAGAGTCTACAAGGAAATGTACAAGACTGATCTGGAGAAGGACATTAT

TTCGGACACATCTGGTGACTTCCGCAAGCTGATGGTTGCCCTGGCAAAGGGTAGAAGA

GCAGAGGATGGCTCTGTCATTGATTATGAACTGATTGACCAAGATGCTCGGGATCTCTA

TGACGCTGGAGTGAAGAGGAAAGGAACTGATGTTCCCAAGTGGATCAGCATCATGACC

GAGCGGAGCGTGCCCCACCTCCAGAAAGTATTTGATAGGTACAAGAGTTACAGCCCTT

ATGACATGTTGGAAAGCATCAGGAAAGAGGTTAAAGGAGACCTGGAAAATGCTTTCCTG

AACCTGGTTCAGTGCATTCAGAACAAGCCCCTGTATTTTGCTGATCGGCTGTATGACTC

CATGAAGGGCAAGGGGACGCGAGATAAGGTCCTGATCAGAATCATGGTCTCCCGCAGT

GAAGTGGACATGTTGAAAATTAGGTCTGAATTCAAGAGAAAGTACGGCAAGTCCCTGTA

CTATTATATCCAGCAAGACACTAAGGGCGACTACCAGAAAGCGCTGCTGTACCTGTGTG

GTGGAGATGACTGAAGCCCGACACGGCCTGAGCGTCCAGAAATGGTGCTCACCATGCT

TCCAGCTAACAGGTCTAGAAAACCAGCTTGCGAATAACAGTCCCCGTGGCCATCCCTG

TGAGGGTGACGTTAGCATTACCCCCAACCTCATTTTAGTTGCCTAAGCATTGCCTGGCC

TTCCTGTCTAGTCTCTCCTGTAAGCCAAAGAAATGAACATTCCAAGGAGTTGGAAGTGA

AGTCTATGATGTGAAACACTTTGCCTCCTGTGTACTGTGTCATAAACAGATGAATAAACT

GAATTTGTACTTTAGAAACACGTACTTTGTGGCCCTGCTTTCAACTGAATTGTTTGAAAA

TTAAACGTGCTTGGGGTTCAGCTGGTGAGGCTGTCCCTGTAGGAAGAAAGCTCTGGGA

CTGAGCTGTACAGTATGGTTGCCCCTATCCAAGTGTCGCTATTTAAGTTAAATTTAAATG

AAATAAAATAAAATAAAATCAAAAAAA

NM_005139.3 *Homo sapiens* annexin A3 (ANXA3), mRNA (SEQ ID NO: 22)
AGCGCGGAGCACCTGCGCCCGCGGCTGACACCTTCGCTCGCAGTTTGTTCG

CAGTTTACTCGCACACCAGTTTCCCCCACCGCGCTTTGGATTAGTGTGATCTCAGCTCA

AGGCAAAGGTGGGATATCATGGCATCTATCTGGGTTGGACACCGAGGAACAGTAAGAG

ATTATCCAGACTTTAGCCCATCAGTGGATGCTGAAGCTATTCAGAAAGCAATCAGAGGA

ATTGGAACTGATGAGAAAATGCTCATCAGCATTCTGACTGAGAGGTCAAATGCACAGCG

GCAGCTGATTGTTAAGGAATATCAAGCAGCATATGGAAAGGAGCTGAAAGATGACTTGA

AGGGTGATCTCTCTGGCCACTTTGAGCATCTCATGGTGGCCCTAGTGACTCCACCAGC

AGTCTTTGATGCAAAGCAGCTAAAGAAATCCATGAAGGGCGCGGGAACAAACGAAGAT

GCCTTGATTGAAATCTTAACTACCAGGACAAGCAGGCAAATGAAGGATATCTCTCAAGC

CTATTATACAGTATACAAGAAGAGTCTTGGAGATGACATTAGTTCCGAAACATCTGGTGA

CTTCCGGAAAGCTCTGTTGACTTTGGCAGATGGCAGAAGAGATGAAAGTCTGAAAGTG

GATGAGCATCTGGCCAAACAAGATGCCCAGATTCTCTATAAAGCTGGTGAGAACAGATG

GGGCACGGATGAAGACAAATTCACTGAGATCCTGTGTTTAAGGAGCTTTCCTCAATTAA

AACTAACATTTGATGAATACAGAAATATCAGCCAAAAGGACATTGTGGACAGCATAAAA

GGAGAATTATCTGGGCATTTTGAAGACTTACTGTTGGCCATAGTTAATTGTGTGAGGAA

CACGCCGGCCTTTTTAGCCGAAAGACTGCATCGAGCCTTGAAGGGTATTGGAACTGAT

GAGTTTACTCTGAACCGAATAATGGTGTCCAGATCAGAAATTGACCTTTTGGACATTCG

AACAGAGTTCAAGAAGCATTATGGCTATTCCCTATATTCAGCAATTAAATCGGATACTTC

TGGAGACTATGAAATCACACTCTTAAAAATCTGTGGTGGAGATGACTGAACCAAGAAGA

-continued

TAATCTCCAAAGGTCCACGATGGGCTTTCCCAACAGCTCCACCTTACTTCTTCTCATACT

ATTTAAGAGAACAAGCAAATATAAACAGCAACTTGTGTTCCTAACAGGAATTTTCATTGT

TCTATAACAACAACAACAAAAGCGATTATTATTTTAGAGCATCTCATTTATAATGTAGCAG

CTCATAAATGAAATTGAAAATGGTATTAAAGATCTGCAACTACTATCCAACTTATATTTCT

GCTTTCAAAGTTAAGAATCTTTATAGTTCTACTCCATTAAATATAAAGCAAGATAATAAAA

ATTGTTGCTTTTGTTAAAA

NM_001153.5 *Homo sapiens* annexin A4 (ANXA4), transcript variant 2, mRNA (SEQ ID NO: 23)

GTGACCTCCGCAGCCGCAGAGGAGGAGCGCAGCCCGGCCTCGAAGAACTTC

TGCTTGGGTGGCTGAACTCTGATCTTGACCTAGAGTCATGGCCATGGCAACCAAAGGA

GGTACTGTCAAAGCTGCTTCAGGATTCAATGCCATGGAAGATGCCCAGACCCTGAGGA

AGGCCATGAAAGGGCTCGGCACCGATGAAGACGCCATTATTAGCGTCCTTGCCTACCG

CAACACCGCCCAGCGCCAGGAGATCAGGACAGCCTACAAGAGCACCATCGGCAGGGA

CTTGATAGACGACCTGAAGTCAGAACTGAGTGGCAACTTCGAGCAGGTGATTGTGGGG

ATGATGACGCCCACGGTGCTGTATGACGTGCAAGAGCTGCGAAGGGCCATGAAGGGA

GCCGGCACTGATGAGGGCTGCCTAATTGAGATCCTGGCCTCCCGGACCCCTGAGGAG

ATCCGGCGCATAAGCCAAACCTACCAGCAGCAATATGGACGGAGCCTTGAAGATGACA

TTCGCTCTGACACATCGTTCATGTTCCAGCGAGTGCTGGTGTCTCTGTCAGCTGGTGG

GAGGGATGAAGGAAATTATCTGGACGATGCTCTCGTGAGACAGGATGCCCAGGACCTG

TATGAGGCTGGAGAGAAGAAATGGGGGACAGATGAGGTGAAATTTCTAACTGTTCTCT

GTTCCCGGAACCGAAATCACCTGTTGCATGTGTTTGATGAATACAAAAGGATATCACAG

AAGGATATTGAACAGAGTATTAAATCTGAAACATCTGGTAGCTTTGAAGATGCTCTGCTG

GCTATAGTAAAGTGCATGAGGAACAAATCTGCATATTTTGCTGAAAAGCTCTATAAATCG

ATGAAGGGCTTGGGCACCGATGATAACACCCTCATCAGAGTGATGGTTTCTCGAGCAG

AAATTGACATGTTGGATATCCGGGCACACTTCAAGAGACTCTATGGAAAGTCTCTGTAC

TCGTTCATCAAGGGTGACACATCTGGAGACTACAGGAAAGTACTGCTTGTTCTCTGTGG

AGGAGATGATTAAAATAAAAATCCCAGAAGGACAGGAGGATTCTCAACACTTTGAATTTT

TTTAACTTCATTTTTCTACACTGCTATTATCATTATCTCAGAATGCTTATTTCCAATTAAAA

CGCCTACAGCTGCCTCCTAGAATATAGACTGTCTGTATTATTATTCACCTATAATTAGTC

ATTATGATGCTTTAAAGCTGTACTTGCATTTCAAAGCTTATAAGATATAAATGGAGATTTT

AAAGTAGAAATAAATATGTATTCCATGTTTTTAAAAGATTACTTTCTACTTTGTGTTTCAC

AGACATTGAATATATTAAATTATTCCATATTTTCTTTTCAGTGAAAAATTTTTTAAATGGAA

GACTGTTCTAAAATCACTTTTTTCCCTAATCCAATTTTTAGAGTGGCTAGTAGTTTCTTCA

TTTGAAATTGTAAGCATCCGGTCAGTAAGAATGCCCATCCAGTTTTCTATATTTCATAGT

CAAAGCCTTGAAAGCATCTACAAATCTCTTTTTTAGGTTTTGTCCATAGCATCAGTTGA

TCCTTACTAAGTTTTTCATGGGAGACTTCCTTCATCACATCTTATGTTGAAATCACTTTCT

GTAGTCAAAGTATACCAAAACCAATTTATCTGAACTAAATTCTAAAGTATGGTTATACAAA

CCATATACATCTGGTTACCAAACATAAATGCTGAACATTCCATATTATTATAGTTAATGTC

TTAATCCAGCTTGCAAGTGAATGGAAAAAAAAAATAAGCTTCAAACTAGGTATTCTGGGAA

TGATGTAATGCTCTGAATTTAGTATGATATAAAGAAAACTTTTTTGTGCTAAAAATACTTT

TTAAAATCAATTTTGTTGATTGTAGTAATTTCTATTTGCACTGTGCCTTTCAACTCCAGAA

-continued

ACATTCTGAAGATGTACTTGGATTTAATTAAAAAGTTCACTTTGTAAGAACGTGGAAAAA

TAATTTTAATTTAAAAATGGTGTTTTTAGGCCGGGGGCGGGGGCTCACGCCAGTAATCC

CAACACTTTGGGAGGCCAAGGCGGGTGGATCACCTAAGGTCAGGAGTTCAAGACTAGC

CTGGCCAACATGGAGAAACTGCATCTCTACTAAAAATATAAAAATTAGCCGGGTGTGGT

GGCTGGTGCCTGTAATCCCAGCCACTCGGAGGCTGAGTCAGGGAGAACTGCTTGAAC

CCAGGAGGCAGGAGGCAAAGGTTGCAGTGAGCCGAGATCACGCCAGCCTGGGCGACA

GAGCGAGAATCCATCTAAAAAAAAAAAAAAAAAAAAGTGTCTTTAAAGTGAGGTATAGTCT

TTCTCTGATCCACTTTTCACCTTCTGAGGTTTTTCATCTTGGCCCCTGAAAGGAGCTATT

TTTGAAGGACTTGTGTTACTCAGTTTCTACAGGAATTACAAGATAAGAAAAAAAAAAATCA

TATTTAGTCTTATGCGTGCCTACTGGCTAATGTTCACATATGCCAAACACTACTCAATAA

CATAAAATAATGTATGAACTTATTCTCTGGAAATGAGTGATGCCCTCTGCTCTAAGTAGA

CCATTTATATTAAATATCATAAATGTATAAAGGACATTCATATTCTTA

NM_001154.4 *Homo sapiens* annexin A5 (ANXA5), mRNA (SEQ ID NO: 24)
AGTCTAGGTGCAGCTGCCGGATCCTTCAGCGTCTGCATCTCGGCGTCGCCCC

GCGTACCGTCGCCCGGCTCTCCGCCGCTCTCCCGGGGTTTCGGGGCACTTGGGTCCC

ACAGTCTGGTCCTGCTTCACCTTCCCCTGACCTGAGTAGTCGCCATGGCACAGGTTCT

CAGAGGCACTGTGACTGACTTCCCTGGATTTGATGAGCGGGCTGATGCAGAAACTCTT

CGGAAGGCTATGAAAGGCTTGGGCACAGATGAGGAGAGCATCCTGACTCTGTTGACAT

CCCGAAGTAATGCTCAGCGCCAGGAAATCTCTGCAGCTTTTAAGACTCTGTTTGGCAGG

GATCTTCTGGATGACCTGAAATCAGAACTAACTGGAAAATTTGAAAAATTAATTGTGGCT

CTGATGAAACCCTCTCGGCTTTATGATGCTTATGAACTGAAACATGCCTTGAAGGGAGC

TGGAACAAATGAAAAAGTACTGACAGAAATTATTGCTTCAAGGACACCTGAAGAACTGA

GAGCCATCAAACAAGTTTATGAAGAAGAATATGGCTCAAGCCTGGAAGATGACGTGGT

GGGGGACACTTCAGGGTACTACCAGCGGATGTTGGTGGTTCTCCTTCAGGCTAACAGA

GACCCTGATGCTGGAATTGATGAAGCTCAAGTTGAACAAGATGCTCAGGCTTTATTTCA

GGCTGGAGAACTTAAATGGGGGACAGATGAAGAAAAGTTTATCACCATCTTTGGAACAC

GAAGTGTGTCTCATTTGAGAAAGGTGTTTGACAAGTACATGACTATATCAGGATTTCAAA

TTGAGGAAACCATTGACCGCGAGACTTCTGGCAATTTAGAGCAACTACTCCTTGCTGTT

GTGAAATCTATTCGAAGTATACCTGCCTACCTTGCAGAGACCCTCTATTATGCTATGAAG

GGAGCTGGGACAGATGATCATACCCTCATCAGAGTCATGGTTTCCAGGAGTGAGATTG

ATCTGTTTAACATCAGGAAGGAGTTTAGGAAGAATTTTGCCACCTCTCTTTATTCCATGA

TTAAGGGAGATACATCTGGGGACTATAAGAAAGCTCTTCTGCTGCTCTGTGGAGAAGAT

GACTAACGTGTCACGGGGAAGAGCTCCCTGCTGTGTGCCTGCACCACCCCACTGCCTT

CCTTCAGCACCTTTAGCTGCATTTGTATGCCAGTGCTTAACACATTGCCTTATTCATACT

AGCATGCTCATGACCAACACATACACGTCATAGAAGAAAATAGTGGTGCTTCTTTCTGA

TCTCTAGTGGAGATCTCTTTGACTGCTGTAGTACTAAAGTGTACTTAATGTTACTAAGTT

TAATGCCTGGCCATTTTCCATTTATATATATTTTTTAAGAGGCTAGAGTGCTTTTAGCCTT

TTTTAAAAACTCCATTTATATTACATTTGTAACCATGATACTTTAATCAGAAGCTTAGCCT

TGAAATTGTGAACTCTTGGAAATGTTATTAGTGAAGTTCGCAACTAAACTAAACCTGTAA

AATTATGATGATTGTATTCAAAAGATTAATGAAAAATAAACATTTCTGTCCCCCTGAATTA

TGTGTACATGTGTGTTTAGATTTATTATTAAATTTATTTAACAATGTT

-continued

NM_001155.5 *Homo sapiens* annexin A6 (ANXA6), transcript variant 1, mRNA (SEQ ID NO: 25)

GCGGTTGCTGCTGGGCTAACGGGCTCCGATCCAGCGAGCGCTGCGTCCTCG

AGTCCCTGCGCCCGTGCGTCCGTCTGCGACCCGAGGCCTCCGCTGCGCGTGGATTCT

GCTGCGAACCGGAGACCATGGCCAAACCAGCACAGGGTGCCAAGTACCGGGGCTCCA

TCCATGACTTCCCAGGCTTTGACCCCAACCAGGATGCCGAGGCTCTGTACACTGCCAT

GAAGGGCTTTGGCAGTGACAAGGAGGCCATACTGGACATAATCACCTCACGGAGCAAC

AGGCAGAGGCAGGAGGTCTGCCAGAGCTACAAGTCCCTCTACGGCAAGGACCTCATT

GCTGATTTAAAGTATGAATTGACGGGCAAGTTTGAACGGTTGATTGTGGGCCTGATGAG

GCCACCTGCCTATTGTGATGCCAAAGAAATTAAAGATGCCATCTCGGGCATTGGCACTG

ATGAGAAGTGCCTCATTGAGATCTTGGCTTCCCGGACCAATGAGCAGATGCACCAGCT

GGTGGCAGCATACAAAGATGCCTACGAGCGGGACCTGGAGGCTGACATCATCGGCGA

CACCTCTGGCCACTTCCAGAAGATGCTTGTGGTCCTGCTCCAGGGAACCAGGGAGGAG

GATGACGTAGTGAGCGAGGACCTGGTACAACAGGATGTCCAGGACCTATACGAGGCA

GGGGAACTGAAATGGGGAACAGATGAAGCCCAGTTCATTTACATCTTGGGAAATCGCA

GCAAGCAGCATCTTCGGTTGGTGTTCGATGAGTATCTGAAGACCACAGGGAAGCCGAT

TGAAGCCAGCATCCGAGGGGAGCTGTCTGGGGACTTTGAGAAGCTAATGCTGGCCGTA

GTGAAGTGTATCCGGAGCACCCCGGAATATTTTGCTGAAAGGCTCTTCAAGGCTATGAA

GGGCCTGGGGACTCGGGACAACACCCTGATCCGCATCATGGTCTCCCGTAGTGAGTT

GGACATGCTCGACATTCGGGAGATCTTCCGGACCAAGTATGAGAAGTCCCTCTACAGC

ATGATCAAGAATGACACCTCTGGCGAGTACAAGAAGACTCTGCTGAAGCTGTCTGGGG

GAGATGATGATGCTGCTGGCCAGTTCTTCCCGGAGGCAGCGCAGGTGGCCTATCAGAT

GTGGGAACTTAGTGCAGTGGCCCGAGTAGAGCTGAAGGGAACTGTGCGCCCAGCCAA

TGACTTCAACCCTGACGCAGATGCCAAAGCGCTGCGGAAAGCCATGAAGGGACTCGG

GACTGACGAAGACACAATCATCGATATCATCACGCACCGCAGCAATGTCCAGCGGCAG

CAGATCCGGCAGACCTTCAAGTCTCACTTTGGCCGGGACTTAATGACTGACCTGAAGT

CTGAGATCTCTGGAGACCTGGCAAGGCTGATTCTGGGGCTCATGATGCCACCGGCCCA

TTACGATGCCAAGCAGTTGAAGAAGGCCATGGAGGGAGCCGGCACAGATGAAAAGGC

TCTTATTGAAATCCTGGCCACTCGGACCAATGCTGAAATCCGGGCCATCAATGAGGCCT

ATAAGGAGGACTATCACAAGTCCCTGGAGGATGCTCTGAGCTCAGACACATCTGGCCA

CTTCAGGAGGATCCTCATTTCTCTGGCCACGGGGCATCGTGAGGAGGGAGGAGAAAAC

CTGGACCAGGCACGGGAAGATGCCCAGGTGGCTGCTGAGATCTTGGAAATAGCAGAC

ACACCTAGTGGAGACAAAACTTCCTTGGAGACACGTTTCATGACGATCCTGTGTACCCG

GAGCTATCCGCACCTCCGGAGAGTCTTCCAGGAGTTCATCAAGATGACCAACTATGAC

GTGGAGCACACCATCAAGAAGGAGATGTCTGGGGATGTCAGGGATGCATTTGTGGCCA

TTGTTCAAAGTGTCAAGAACAAGCCTCTCTTCTTTGCCGACAAACTTTACAAATCCATGA

AGGGTGCTGGCACAGATGAGAAGACTCTGACCAGGATCATGGTATCCCGCAGTGAGAT

TGACCTGCTCAACATCCGGAGGGAATTCATTGAGAAATATGACAAGTCTCTCCACCAAG

CCATTGAGGGTGACACCTCCGGAGACTTCCTGAAGGCCTTGCTGGCTCTCTGTGGTGG

TGAGGACTAGGGCCACAGCTTTGGCGGGCACTTCTGCCAAGAAATGGTTATCAGCACC

AGCCGCCATGGCCAAGCCTGATTGTTCCAGCTCCAGAGACTAAGGAAGGGGCAGGGG

TGGGGGGAGGGGTTGGGTTGGGCTCTTATCTTCAGTGGAGCTTAGGAAACGCTCCCAC

-continued

TCCCACGGGCCATCGAGGGCCCAGCACGGCTGAGCGGCTGAAAAACCGTAGCCATAG

ATCCTGTCCACCTCCACTCCCCTCTGACCCTCAGGCTTTCCCAGCTTCCTCCCCTTGCT

ACAGCCTCTGCCCTGGTTTGGGCTATGTCAGATCCAAAAACATCCTGAACCTCTGTCTG

TAAAATGAGTAGTGTCTGTACTTTGAATGAGGGGGTTGGTGGCAGGGGCCAGTTGAAT

GTGCTGGGCGGGGTGGTGGGAAGGATAGTAAATGTGCTGGGGCAAACTGACAAATCTT

CCCATCCATTTCACCACCCATCTCCATCCAGGCCGCGCTAGAGTACTGGACCAGGAAT

TTGGATGCCTGGGTTCAAATCTGCATCTGCCATGCACTTGTTTCTGACCTTAGGCCAGC

CCCTTTCCCTCCCTGAGTCTCTATTTTCTTATCTACAATGAGACAGTTGGACAAAAAAAT

CTTGGCTTCCCTTCTAACATTAACTTCCTAAAGTATGCCTCCGATTCATTCCCTTGACAC

TTTTTATTTCTAAGGAAGAAATAAAAAGAGATACACAAACACATAAACACA

NM_001193544.1 *Homo sapiens* annexin A6 (ANXA6), transcript variant 2, mRNA (SEQ ID NO: 26)

AGAGACCAGAGAGCATCCAGAGGCCTGGCCGGGGTCCTGCAGTGCAGACGT

TGGGAGGCACGGAGACGGGGAGAGGGGGAGGCGGTCCAGGACTCACTCTGCTCCAC

CTCTGACTCCTTGAAGGGTGCCAAGTACCGGGGCTCCATCCATGACTTCCCAGGCTTT

GACCCCAACCAGGATGCCGAGGCTCTGTACACTGCCATGAAGGGCTTTGGCAGTGACA

AGGAGGCCATACTGGACATAATCACCTCACGGAGCAACAGGCAGAGGCAGGAGGTCT

GCCAGAGCTACAAGTCCCTCTACGGCAAGGACCTCATTGCTGATTTAAAGTATGAATTG

ACGGGCAAGTTTGAACGGTTGATTGTGGGCCTGATGAGGCCACCTGCCTATTGTGATG

CCAAAGAAATTAAAGATGCCATCTCGGGCATTGGCACTGATGAGAAGTGCCTCATTGAG

ATCTTGGCTTCCCGGACCAATGAGCAGATGCACCAGCTGGTGGCAGCATACAAAGATG

CCTACGAGCGGGACCTGGAGGCTGACATCATCGGCGACACCTCTGGCCACTTCCAGA

AGATGCTTGTGGTCCTGCTCCAGGGAACCAGGGAGGAGGATGACGTAGTGAGCGAGG

ACCTGGTACAACAGGATGTCCAGGACCTATACGAGGCAGGGGAACTGAAATGGGGAAC

AGATGAAGCCCAGTTCATTTACATCTTGGGAAATCGCAGCAAGCAGCATCTTCGGTTGG

TGTTCGATGAGTATCTGAAGACCACAGGGAAGCCGATTGAAGCCAGCATCCGAGGGGA

GCTGTCTGGGGACTTTGAGAAGCTAATGCTGGCCGTAGTGAAGTGTATCCGGAGCACC

CCGGAATATTTTGCTGAAAGGCTCTTCAAGGCTATGAAGGGCCTGGGGACTCGGGACA

ACACCCTGATCCGCATCATGGTCTCCCGTAGTGAGTTGGACATGCTCGACATTCGGGA

GATCTTCCGGACCAAGTATGAGAAGTCCCTCTACAGCATGATCAAGAATGACACCTCTG

GCGAGTACAAGAAGACTCTGCTGAAGCTGTCTGGGGGAGATGATGATGCTGCTGGCCA

GTTCTTCCCGGAGGCAGCGCAGGTGGCCTATCAGATGTGGGAACTTAGTGCAGTGGC

CCGAGTAGAGCTGAAGGGAACTGTGCGCCCAGCCAATGACTTCAACCCTGACGCAGAT

GCCAAAGCGCTGCGGAAAGCCATGAAGGGACTCGGGACTGACGAAGACACAATCATC

GATATCATCACGCACCGCAGCAATGTCCAGCGGCAGCAGATCCGGCAGACCTTCAAGT

CTCACTTTGGCCGGGACTTAATGACTGACCTGAAGTCTGAGATCTCTGGAGACCTGGC

AAGGCTGATTCTGGGGCTCATGATGCCACCGGCCCATTACGATGCCAAGCAGTTGAAG

AAGGCCATGGAGGGAGCCGGCACAGATGAAAAGGCTCTTATTGAAATCCTGGCCACTC

GGACCAATGCTGAAATCCGGGCCATCAATGAGGCCTATAAGGAGGACTATCACAAGTC

CCTGGAGGATGCTCTGAGCTCAGACACATCTGGCCACTTCAGGAGGATCCTCATTTCT

CTGGCCACGGGGCATCGTGAGGAGGGAGGAGAAAACCTGGACCAGGCACGGGAAGA

-continued

TGCCCAGGTGGCTGCTGAGATCTTGGAAATAGCAGACACACCTAGTGGAGACAAAACT

TCCTTGGAGACACGTTTCATGACGATCCTGTGTACCCGGAGCTATCCGCACCTCCGGA

GAGTCTTCCAGGAGTTCATCAAGATGACCAACTATGACGTGGAGCACACCATCAAGAA

GGAGATGTCTGGGGATGTCAGGGATGCATTTGTGGCCATTGTTCAAAGTGTCAAGAAC

AAGCCTCTCTTCTTTGCCGACAAACTTTACAAATCCATGAAGGGTGCTGGCACAGATGA

GAAGACTCTGACCAGGATCATGGTATCCCGCAGTGAGATTGACCTGCTCAACATCCGG

AGGGAATTCATTGAGAAATATGACAAGTCTCTCCACCAAGCCATTGAGGGTGACACCTC

CGGAGACTTCCTGAAGGCCTTGCTGGCTCTCTGTGGTGGTGAGGACTAGGGCCACAG

CTTTGGCGGGCACTTCTGCCAAGAAATGGTTATCAGCACCAGCCGCCATGGCCAAGCC

TGATTGTTCCAGCTCCAGAGACTAAGGAAGGGGCAGGGGTGGGGGGAGGGGTTGGGT

TGGGCTCTTATCTTCAGTGGAGCTTAGGAAACGCTCCCACTCCCACGGGCCATCGAGG

GCCCAGCACGGCTGAGCGGCTGAAAAACCGTAGCCATAGATCCTGTCCACCTCCACTC

CCCTCTGACCCTCAGGCTTTCCCAGCTTCCTCCCCTTGCTACAGCCTCTGCCCTGGTTT

GGGCTATGTCAGATCCAAAAACATCCTGAACCTCTGTCTGTAAAATGAGTAGTGTCTGT

ACTTTGAATGAGGGGGTTGGTGGCAGGGGCCAGTTGAATGTGCTGGGCGGGGTGGTG

GGAAGGATAGTAAATGTGCTGGGGCAAACTGACAAATCTTCCCATCCATTTCACCACCC

ATCTCCATCCAGGCCGCGCTAGAGTACTGGACCAGGAATTTGGATGCCTGGGTTCAAA

TCTGCATCTGCCATGCACTTGTTTCTGACCTTAGGCCAGCCCCTTTCCCTCCCTGAGTC

TCTATTTTCTTATCTACAATGAGACAGTTGGACAAAAAAATCTTGGCTTCCCTTCTAACAT

TAACTTCCTAAAGTATGCCTCCGATTCATTCCCTTGACACTTTTTATTTCTAAGGAAGAAA

TAAAAAGAGATACACAAACACATAAACACAAAAAAAAAAA

NM_001156.5 *Homo sapiens* annexin A7 (ANXA7), transcript variant 1, mRNA (SEQ ID NO: 27)

ATCTTGCGGGAGACCGGGTTGGGCTGTGACGCTGCTGCTGGGGTCAGAATG

TCATACCCAGGCTATCCCCCAACAGGCTACCCACCTTTCCCTGGATATCCTCCTGCAGG

TCAGGAGTCATCTTTTCCCCCTTCTGGTCAGTATCCTTATCCTAGTGGCTTTCCTCCAAT

GGGAGGAGGTGCCTACCCACAAGTGCCAAGTAGTGGCTACCCAGGAGCTGGAGGCTA

CCCTGCGCCTGGAGGTTATCCAGCCCCTGGAGGCTATCCTGGTGCCCCACAGCCAGG

GGGAGCTCCATCCTATCCCGGAGTTCCTCCAGGCCAAGGATTTGGAGTCCCACCAGGT

GGAGCAGGCTTTTCTGGGTATCCACAGCCACCTTCACAGTCTTATGGAGGTGGTCCAG

CACAGGTTCCACTACCTGGTGGCTTTCCTGGAGGACAGATGCCTTCTCAGTATCCTGG

AGGACAACCTACTTACCCTAGTCAGCCTGCCACAGTGACTCAGGTCACTCAAGGAACTA

TCCGACCAGCTGCCAACTTCGATGCTATAAGAGATGCAGAAATTCTTCGTAAGGCAATG

AAGGGTTTTGGGACAGATGAGCAGGCAATTGTGGATGTGGTGGCCAACCGTTCCAATG

ATCAGAGGCAAAAAATTAAAGCAGCATTTAAGACCTCCTATGGCAAGGATTTAATCAAA

GATCTCAAATCAGAGTTAAGTGGAAATATGGAAGAACTGATCCTGGCCCTCTTCATGCC

TCCTACGTATTACGATGCCTGGAGCTTACGGAAAGCAATGCAGGGAGCAGGAACTCAG

GAACGTGTATTGATTGAGATTTTGTGCACAAGAACAAATCAGGAAATCCGAGAAATTGT

CAGATGTTATCAGTCAGAATTTGGACGAGACCTTGAAAAGGACATTAGGTCAGATACAT

CAGGACATTTTGAACGTTTACTTGTGTCCATGTGCCAGGGAAATCGTGATGAGAACCAG

AGTATAAACCACCAAATGGCTCAGGAAGATGCTCAGCGTCTCTATCAAGCTGGTGAGG

-continued

GGAGACTAGGGACCGATGAATCTTGCTTTAACATGATCCTTGCCACAAGAAGCTTTCCT

CAGCTGAGAGCTACCATGGAGGCTTATTCTAGGATGGCTAATCGAGACTTGTTAAGCAG

TGTGAGCCGTGAGTTTTCCGGATATGTAGAAAGTGGTTTGAAGACCATCTTGCAGTGTG

CCCTGAACCGCCCTGCCTTCTTTGCTGAGAGGCTCTACTATGCTATGAAAGGTGCTGG

CACAGATGACTCCACCCTGGTCCGGATTGTGGTCACTCGAAGTGAGATTGACCTTGTA

CAAATAAAACAGATGTTCGCTCAGATGTATCAGAAGACTCTGGGCACAATGATTGCAGG

TGACACGAGTGGAGATTACCGAAGACTTCTTCTGGCTATTGTGGGCCAGTAGGAGGGA

TTTTTTTTTTTTTAATGAAAAAAAATTTCTATTCATAGCTTATCCTTCAGAGCAATGACCTG

CATGCAGCAATATCAAACATCAGCTAACCGAAAGAGCTTTCTGTCAAGGACCGTATCAG

GGTAATGTGCTTGGTTTGCACATGTTGTTATTGCCTTAATTCTAATTTTATTTTGTTCTCT

ACATACAATCAATGTAAAGCCATATCACAATGATACAGTAATATTGCAATGTTTGTAAAC

CTTCATTCTTACTAGTTTCATTCTAATCAAGATGTCAAATTGAATAAAAATCACAGCAATC

TCTGATTCTGTGTAATAATATTGAATAATTTTTTAGAAGGTTACTGAAAGCTCTGCCTTCC

GGAATCCCTCTAAGTCTGCTTGATAGAGTGGATAGTGTGTTAAAACTGTGTACTTTAAAA

AAAAATTCAACCTTTACATCTAGAATAATTTGCATCTCATTTTGCCTAAATTGGTTCTGTA

TTCATAAACACTTTCCACATAGAAAATAGATTAGTATTACCTGTGGCACCTTTTAAGAAA

GGGTCAAATGTTTATATGCTTAAGATACATAGCCTACTTTTTTTTCGCAGTTGTTTTCTTT

TTTTAAATTGAGTTATGACAAATAAAAAATTGCATATATTTAAGGTGTACAATATGGTGTT

TTGATATCAGCATTCCTTGTGTAATGATTCCACAATTAAGGTCAGGCTAATTACGTATCT

GTCACCTTGACATAGTTACCATTTTTTCATGTGTGGTGAAAACACTTAAGATCTACTACC

TTAGCAAATTTTAAGTGTTCAGTACATTATTAACTATAGATACTGTGCTCTACATTAAACC

TCTAGCATTTATTCGTTTTATAACTGAAAGTTTATACCCTTTGACCAACATCTCCCCATTT

TCCCCACCTCTCACCTGGACAACCACCACTGTGTTTAAGTTCAGCTATTTTAGATTCCAC

GTATAAATGGTATACAATA

NM_004034.3 *Homo sapiens* annexin A7 (ANXA7), transcript variant 2, mRNA (SEQ ID NO: 28)

GCCCACCCTGGGCCCGCCCCCGGCTCCATCTTGCGGGAGACCGGGTTGGG

CTGTGACGCTGCTGCTGGGGTCAGAATGTCATACCCAGGCTATCCCCCAACAGGCTAC

CCACCTTTCCCTGGATATCCTCCTGCAGGTCAGGAGTCATCTTTTCCCCCTTCTGGTCA

GTATCCTTATCCTAGTGGCTTTCCTCCAATGGGAGGAGGTGCCTACCCACAAGTGCCAA

GTAGTGGCTACCCAGGAGCTGGAGGCTACCCTGCGCCTGGAGGTTATCCAGCCCCTG

GAGGCTATCCTGGTGCCCCACAGCCAGGGGGAGCTCCATCCTATCCCGGAGTTCCTC

CAGGCCAAGGATTTGGAGTCCCACCAGGTGGAGCAGGCTTTTCTGGGTATCCACAGCC

ACCTTCACAGTCTTATGGAGGTGGTCCAGCACAGGTTCCACTACCTGGTGGCTTTCCTG

GAGGACAGATGCCTTCTCAGTATCCTGGAGGACAACCTACTTACCCTAGTCAGATCAAT

ACAGATTCTTTTTCTTCCTATCCTGTTTTCTCTCCTGTTTCTTTGGATTATAGCAGTGAAC

CTGCCACAGTGACTCAGGTCACTCAAGGAACTATCCGACCAGCTGCCAACTTCGATGC

TATAAGAGATGCAGAAATTCTTCGTAAGGCAATGAAGGGTTTTGGGACAGATGAGCAGG

CAATTGTGGATGTGGTGGCCAACCGTTCCAATGATCAGAGGCAAAAAATTAAAGCAGCA

TTTAAGACCTCCTATGGCAAGGATTTAATCAAAGATCTCAAATCAGAGTTAAGTGGAAAT

ATGGAAGAACTGATCCTGGCCCTCTTCATGCCTCCTACGTATTACGATGCCTGGAGCTT

ACGGAAAGCAATGCAGGGAGCAGGAACTCAGGAACGTGTATTGATTGAGATTTTGTGC

-continued

ACAAGAACAAATCAGGAAATCCGAGAAATTGTCAGATGTTATCAGTCAGAATTTGGACG

AGACCTTGAAAAGGACATTAGGTCAGATACATCAGGACATTTTGAACGTTTACTTGTGTC

CATGTGCCAGGGAAATCGTGATGAGAACCAGAGTATAAACCACCAAATGGCTCAGGAA

GATGCTCAGCGTCTCTATCAAGCTGGTGAGGGGAGACTAGGGACCGATGAATCTTGCT

TTAACATGATCCTTGCCACAAGAAGCTTTCCTCAGCTGAGAGCTACCATGGAGGCTTAT

TCTAGGATGGCTAATCGAGACTTGTTAAGCAGTGTGAGCCGTGAGTTTTCCGGATATGT

AGAAAGTGGTTTGAAGACCATCTTGCAGTGTGCCCTGAACCGCCCTGCCTTCTTTGCTG

AGAGGCTCTACTATGCTATGAAAGGTGCTGGCACAGATGACTCCACCCTGGTCCGGAT

TGTGGTCACTCGAAGTGAGATTGACCTTGTACAAATAAAACAGATGTTCGCTCAGATGT

ATCAGAAGACTCTGGGCACAATGATTGCAGGTGACACGAGTGGAGATTACCGAAGACT

TCTTCTGGCTATTGTGGGCCAGTAGGAGGGATTTTTTTTTTTTAATGAAAAAAAATTTCT

ATTCATAGCTTATCCTTCAGAGCAATGACCTGCATGCAGCAATATCAAACATCAGCTAAC

CGAAAGAGCTTTCTGTCAAGGACCGTATCAGGGTAATGTGCTTGGTTTGCACATGTTGT

TATTGCCTTAATTCTAATTTTATTTTGTTCTCTACATACAATCAATGTAAAGCCATATCACA

ATGATACAGTAATATTGCAATGTTTGTAAACCTTCATTCTTACTAGTTTCATTCTAATCAA

GATGTCAAATTGAATAAAAATCACAGCAATCTCTGATTCTGTGTAATAATATTGAATAATT

TTTTAGAAGGTTACTGAAAGCTCTGCCTTCCGGAATCCCTCTAAGTCTGCTTGATAGAG

TGGATAGTGTGTTAAAACTGTGTACTTTAAAAAAAAATTCAACCTTTACATCTAGAATAAT

TTGCATCTCATTTTGCCTAAATTGGTTCTGTATTCATAAACACTTTCCACATAGAAAATAG

ATTAGTATTACCTGTGGCACCTTTTAAGAAAGGGTCAAATGTTTATATGCTTAAGATACA

TAGCCTACTTTTTTTTCGCAGTTGTTTTCTTTTTTTAAATTGAGTTATGACAAATAAAAAAT

TGCATATATTTAAGGTGTACAATATGGTGTTTTGATATCAGCATTCCTTGTGTAATGATTC

CACAATTAAGGTCAGGCTAATTACGTATCTGTCACCTTGACATAGTTACCATTTTTTCAT

GTGTGGTGAAAACACTTAAGATCTACTACCTTAGCAAATTTTAAGTGTTCAGTACATTAT

TAACTATAGATACTGTGCTCTACATTAAACCTCTAGCATTTATTCGTTTTATAACTGAAAG

TTTATACCCTTTGACCAACATCTCCCCATTTTCCCCACCTCTCACCTGGACAACCACCAC

TGTGTTTAAGTTCAGCTATTTTAGATTCCACGTATAAATGGTATACAATAAAAAAAAAAAA

AAA

NM_001271702.1 *Homo sapiens* annexin A8 (ANXA8), transcript variant 1, mRNA (SEQ ID NO: 29)

CTGGGTGGGGCCTGGGAGCCACAGGAGATGCCCAAAGCCAGGCAGAGCCC

GGGGGCGAGGGGACGGCAGGCAGGTGTGGCGCTGCCCTGGGCGGGCTTGCACCCC

CACACCCAAGTGAGCGGCCTGCTCACTCCTCAGCTGCAGGAGCCAGACGTGTGGAGT

CCCAGCAGAGGCCAACCTGTGTCTCTTCATCTCCCTGGGAAAGGTGCCCCCGAGGTGA

AAGAGATGGCCTGGTGGAAATCCTGGATTGAACAGGAGGGTGTCACAGTGAAGAGCAG

CTCCCACTTCAACCCAGACCCTGATGCAGAGACCCTCTACAAAGCCATGAAGGGGATC

GGTGTCGGGTCCCAACTGCTCAGCCACCAAGCAGCTGCCTTCGCCTTCCCCTCCTCCG

CCCTCACCAGTGTGTCACCCTGGGGGCAGCAGGGTCACTTGTGCTGTAACCCTGCAG

GGACCAACGAGCAGGCTATCATCGATGTGCTCACCAAGAGAAGCAACACGCAGCGGC

AGCAGATCGCCAAGTCCTTCAAGGCTCAGTTCGGCAAGGACCTCACTGAGACCTTGAA

GTCTGAGCTCAGTGGCAAGTTTGAGAGGCTCATTGTGGCCCTTATGTACCCGCCATAC

-continued

AGATACGAAGCCAAGGAGCTGCATGACGCCATGAAGGGCTTAGGAACCAAGGAGGGT

GTCATCATTGAGATCCTGGCCTCTCGGACCAAGAACCAGCTGCGGGAGATAATGAAGG

CGTATGAGGAAGACTATGGGTCCAGCCTGGAGGAGGACATCCAAGCAGACACAAGTG

GCTACCTGGAGAGGATCCTGGTGTGCCTCCTGCAGGGCAGCAGGGATGATGTGAGCA

GCTTTGTGGACCCAGGACTGGCCCTCCAAGACGCACAGGATCTGTATGCGGCAGGCG

AGAAGATTCGTGGGACTGATGAGATGAAATTCATCACCATCCTGTGCACGCGCAGTGC

CACTCACCTGCTGAGAGTGTTTGAAGAGTATGAGAAAATTGCCAACAAGAGCATTGAGG

ACAGCATCAAGAGTGAGACCCATGGCTCACTGGAGGAGGCCATGCTCACTGTGGTGAA

ATGCACCCAAAACCTCCACAGCTACTTTGCAGAGAGACTCTACTATGCCATGAAGGGAG

CAGGGACGCGTGATGGGACCCTGATAAGAAACATCGTTTCAAGGAGCGAGATTGACTT

AAATCTTATCAAATGTCACTTCAAGAAGATGTACGGCAAGACCCTCAGCAGCATGATCA

TGGAAGACACCAGCGGTGACTACAAGAACGCCCTGCTGAGCCTGGTGGGCAGCGACC

CCTGAGGCACAGAAGAACAAGAGCAAAGACCATGAAGCCAGAGTCTCCAGGACTCCTC

ACTCAACCTCGGCCATGGACGCAGGTTGGGTGTGAGGGGGGTCCCAGCCTTTCGGTC

TTCTATTTCCCTATTTCCAGTGCTTTCCAGCCGGGTTTCTGACCCAGAGGGTGGAACCG

GCCTGGACTCCTCTTCCCAACTTCCTCCAGGTCATTTCCCAGTGTGAGCACAATGCCAA

CCTTAGTGTTTCTCCAGCCAGACAGATGCCTCAGCATGAAGGGCTTGGGGACTTGTGG

ATCATTCCTTCCTCCCTGCAGGAGCTTCCCAAGCTGGTCACAGAGTCTCCTGGGCACA

GGTTATACAGACCCCAGCCCCATTCCCATCTACTGAAACAGGGTCTCCACAAGAGGGG

CCAGGGAATATGGGTTTTTAACAAGCGTCTTACAAAACACTTCTCTATCATGCAGCCGG

AGAGCTGGCTGGGAGCCCTTTTGTTTTAGAACACACATCCTTCAGCAGCTGAGAAACGA

ACACGAATCCATCCCAACCGAGATGCCATTAACATTCATCTAAAAATGTTAGGCTCTAAA

TGGACGAAAAATTCTCTCGCCATCTTAATAACAAAATAAACTACAAATTCCTGACCCAAG

GACACTGTGTTATAAGAGGCGTGGGCTCCCCTGGTGGCTGACCAGGTCAGCTGCCCT

GGCCTTGCACCCCTCTGCATGCAGCACAGAAGGGTGTGACCATGCCCTCAGCACCACT

CTTGTCCCCACTGAACGGCAACTGAGACTGGGTACCTGGAGATTCTGAAGTGCCTTTG

CTGTGGTTTTCAAAATAATAAAGATTTGTATTCAACTCAAAAAAAAAAAAAAAAAAAAAA

AAAAAAAA

NM_001040084.2 *Homo sapiens* annexin A8 (ANXA8), transcript variant 2, mRNA (SEQ ID NO: 30)

CTGGGTGGGGCCTGGGAGCCACAGGAGATGCCCAAAGCCAGGCAGAGCCC

GGGGGCGAGGGGACGGCAGGCAGGTGTGGCGCTGCCCTGGGCGGGCTTGCACCCC

CACACCCAAGTGAGCGGCCTGCTCACTCCTCAGCTGCAGGAGCCAGACGTGTGGAGT

CCCAGCAGAGGCCAACCTGTGTCTCTTCATCTCCCTGGGAAAGGTGCCCCCGAGGTGA

AAGAGATGGCCTGGTGGAAATCCTGGATTGAACAGGAGGGTGTCACAGTGAAGAGCAG

CTCCCACTTCAACCCAGACCCTGATGCAGAGACCCTCTACAAAGCCATGAAGGGGATC

GGGACCAACGAGCAGGCTATCATCGATGTGCTCACCAAGAGAAGCAACACGCAGCGG

CAGCAGATCGCCAAGTCCTTCAAGGCTCAGTTCGGCAAGGACCTCACTGAGACCTTGA

AGTCTGAGCTCAGTGGCAAGTTTGAGAGGCTCATTGTGGCCCTTATGTACCCGCCATA

CAGATACGAAGCCAAGGAGCTGCATGACGCCATGAAGGGCTTAGGAACCAAGGAGGG

TGTCATCATTGAGATCCTGGCCTCTCGGACCAAGAACCAGCTGCGGGAGATAATGAAG

GCGTATGAGGAAGACTATGGGTCCAGCCTGGAGGAGGACATCCAAGCAGACACAAGT

-continued

GGCTACCTGGAGAGGATCCTGGTGTGCCTCCTGCAGGGCAGCAGGGATGATGTGAGC

AGCTTTGTGGACCCAGGACTGGCCCTCCAAGACGCACAGGATCTGTATGCGGCAGGC

GAGAAGATTCGTGGGACTGATGAGATGAAATTCATCACCATCCTGTGCACGCGCAGTG

CCACTCACCTGCTGAGAGTGTTTGAAGAGTATGAGAAAATTGCCAACAAGAGCATTGAG

GACAGCATCAAGAGTGAGACCCATGGCTCACTGGAGGAGGCCATGCTCACTGTGGTGA

AATGCACCCAAAACCTCCACAGCTACTTTGCAGAGAGACTCTACTATGCCATGAAGGGA

GCAGGGACGCGTGATGGGACCCTGATAAGAAACATCGTTTCAAGGAGCGAGATTGACT

TAAATCTTATCAAATGTCACTTCAAGAAGATGTACGGCAAGACCCTCAGCAGCATGATC

ATGGAAGACACCAGCGGTGACTACAAGAACGCCCTGCTGAGCCTGGTGGGCAGCGAC

CCCTGAGGCACAGAAGAACAAGAGCAAAGACCATGAAGCCAGAGTCTCCAGGACTCCT

CACTCAACCTCGGCCATGGACGCAGGTTGGGTGTGAGGGGGGTCCCAGCCTTTCGGT

CTTCTATTTCCCTATTTCCAGTGCTTTCCAGCCGGGTTTCTGACCCAGAGGGTGGAACC

GGCCTGGACTCCTCTTCCCAACTTCCTCCAGGTCATTTCCCAGTGTGAGCACAATGCCA

ACCTTAGTGTTTCTCCAGCCAGACAGATGCCTCAGCATGAAGGGCTTGGGGACTTGTG

GATCATTCCTTCCTCCCTGCAGGAGCTTCCCAAGCTGGTCACAGAGTCTCCTGGGCAC

AGGTTATACAGACCCCAGCCCCATTCCCATCTACTGAAACAGGGTCTCCACAAGAGGG

GCCAGGGAATATGGGTTTTTAACAAGCGTCTTACAAAACACTTCTCTATCATGCAGCCG

GAGAGCTGGCTGGGAGCCCTTTTGTTTTAGAACACACATCCTTCAGCAGCTGAGAAAC

GAACACGAATCCATCCCAACCGAGATGCCATTAACATTCATCTAAAAATGTTAGGCTCTA

AATGGACGAAAAATTCTCTCGCCATCTTAATAACAAAATAAACTACAAATTCCTGACCCA

AGGACACTGTGTTATAAGAGGCGTGGGCTCCCCTGGTGGCTGACCAGGTCAGCTGCC

CTGGCCTTGCACCCCTCTGCATGCAGCACAGAAGGGTGTGACCATGCCCTCAGCACCA

CTCTTGTCCCCACTGAACGGCAACTGAGACTGGGTACCTGGAGATTCTGAAGTGCCTTT

GCTGTGGTTTTCAAAATAATAAAGATTTGTATTCAACTCAAAAAAAAAA

NM_003568.3 *Homo sapiens* annexin A9 (ANXA9), mRNA (SEQ ID NO: 31)
CTCTACCAGGCCACACCGGAGGCAGTGCTCACACAGGCAAGCTACCAGGCC

ACAACAACGACACCCACCTCACCTCTGGCACCTCTGAGCATCCACGTACTTGCAAGAA

CTCTTGCTCACATCAGCTAAGAGATTGCACCTGCTGACCTAGAGATTCCGGCCTGTGCT

CCTGTGCTGCTGAGCAGGGCAACCAGTAGCACCATGTCTGTGACTGGCGGGAAGATG

GCACCGTCCCTCACCCAGGAGATCCTCAGCCACCTGGGCCTGGCCAGCAAGACTGCA

GCGTGGGGGACCCTGGGCACCCTCAGGACCTTCTTGAACTTCAGCGTGGACAAGGAT

GCGCAGAGGCTACTGAGGGCCATTACTGGCCAAGGCGTGGACCGCAGTGCCATTGTG

GACGTGCTGACCAACCGGAGCAGAGAGCAAAGGCAGCTCATCTCACGAAACTTCCAGG

AGCGCACCCAACAGGACCTGATGAAGTCTCTACAGGCAGCACTTTCCGGCAACCTGGA

GAGGATTGTGATGGCTCTGCTGCAGCCCACAGCCCAGTTTGACGCCCAGGAATTGAGG

ACAGCTCTGAAGGCCTCAGATTCTGCTGTGGACGTGGCCATTGAAATTCTTGCCACTCG

AACCCCACCCCAGCTGCAGGAGTGCCTGGCAGTCTACAAACACAATTTCCAGGTGGAG

GCTGTGGATGACATCACATCTGAGACCAGTGGCATCTTGCAGGACCTGCTGTTGGCCC

TGGCCAAGGGGGGCCGTGACAGCTACTCTGGAATCATTGACTATAATCTGGCAGAACA

AGATGTCCAGGCACTGCAGCGGGCAGAAGGACCTAGCAGAGAGGAAACATGGGTCCC

AGTCTTCACCCAGCGAAATCCTGAACACCTCATCCGAGTGTTTGATCAGTACCAGCGGA

-continued

GCACTGGGCAAGAGCTGGAGGAGGCTGTCCAGAACCGTTTCCATGGAGATGCTCAGG

TGGCTCTGCTCGGCCTAGCTTCGGTGATCAAGAACACACCGCTGTACTTTGCTGACAAA

CTTCATCAAGCCCTCCAGGAAACTGAGCCCAATTACCAAGTCCTGATTCGCATCCTTAT

CTCTCGATGTGAGACTGACCTTCTGAGTATCAGAGCTGAGTTCAGGAAGAAATTTGGGA

AGTCCCTCTACTCTTCTCTCCAGGATGCAGTGAAAGGGGATTGCCAGTCAGCCCTCCT

GGCCTTGTGCAGGGCTGAAGACATGTGAGACTTCCCTGCCCCACCCCACATGACATCC

GAGGATCTGAGATTTCCGTGTTTGGCTGAACCTGGGAGACCAGCTGGGCCTCCAAGTA

GGATAACCCCTCACTGAGCACCACATTCTCTAGCTTCTTGTTGAGGCTGGAACTGTTTC

TTTAAAATCCCTTAATTTTCCCATCTCAAAATTATATCTGTACCTGGGTCATCCAGCTCCT

TCTTGGGTGTGGGGAAATGAGTTTTCTTTGATAGTTTCTGCCTCACTCATCCCTCCTGTA

CCCTGGCCAGAACATCTCACTGATACTCGAATTCTTTTGGCAAA

NM_007193.4 *Homo sapiens* annexin A10 (ANXA10), mRNA
(SEQ ID NO: 32)
ATCCAGATTTGCTTTTACATTTTCTTGCCTGAGTCTGAGGTGAACAGTGAACAT

ATTTACATTTGATTTAACAGTGAACCTTAATTCTTTCTGGCTTCACAGTGAAACAAGTTTA

TGCAATCGATCAAATATTTTCATCCCTGAGGTTAACAATTACCATCAAAATGTTTTGTGG

AGACTATGTGCAAGGAACCATCTTCCCAGCTCCCAATTTCAATCCCATAATGGATGCCC

AAATGCTAGGAGGAGCACTCCAAGGATTTGACTGTGACAAAGACATGCTGATCAACATT

CTGACTCAGCGCTGCAATGCACAAAGGATGATGATTGCAGAGGCATACCAGAGCATGT

ATGGCCGGGACCTGATTGGGGATATGAGGGAGCAGCTTTCGGATCACTTCAAAGATGT

GATGGCTGGCCTCATGTACCCACCACCACTGTATGATGCTCATGAGCTCTGGCATGCC

ATGAAGGGAGTAGGCACTGATGAGAATTGCCTCATTGAAATACTAGCTTCAAGAACAAA

TGGAGAAATTTTCCAGATGCGAGAAGCCTACTGCTTGCAATACAGCAATAACCTCCAAG

AGGACATTTATTCAGAGACCTCAGGACACTTCAGAGATACTCTCATGAACTTGGTCCAG

GGGACCAGAGAGGAAGGATATACAGACCCTGCGATGGCTGCTCAGGATGCAATGGTC

CTATGGGAAGCCTGTCAGCAGAAGACGGGGGAGCACAAAACCATGCTGCAAATGATCC

TGTGCAACAAGAGCTACCAGCAGCTGCGGCTGGTTTTCCAGGAATTTCAAAATATTTCT

GGGCAAGATATGGTAGATGCCATTAATGAATGTTATGATGGATACTTTCAGGAGCTGCT

GGTTGCAATTGTTCTCTGTGTTCGAGACAAACCAGCCTATTTTGCTTATAGATTATATAG

TGCAATTCATGACTTTGGTTTCCATAATAAAACTGTAATCAGGATTCTCATTGCCAGAAG

TGAAATAGACCTGCTGACCATAAGGAAACGATACAAAGAGCGATATGGAAAATCCCTAT

TTCATGATATCAGAAATTTTGCTTCAGGGCATTATAAGAAAGCACTGCTTGCCATCTGTG

CTGGTGATGCTGAGGACTACTAAAATGAAGAGGACTTGGAGTACTGTGCACTCCTCTTT

CTAGACACTTCCAAATAGAGATTTTCTCACAAATTTGTACTGTTCATGGCACTATTAACA

AAACTATACAATCATATTTTCTCTTCTATCTTTGAAATTATTCTAAGCCAAAGAAAACTAT

GAATGAAAGTATATGATACTGAATTTGCCTACTATCCTGAATTTGCCTACTATCTAATCA

GCAATTAAATAAATTGTGCATGATGGAATAATAGAAAAATTGCATTGGAATAGATTTTATT

TAAATGTGAACCATCAACAACCTACAACAA

NM_145868.2 *Homo sapiens* annexin A11 (ANXA11), transcript
variant b, mRNA (SEQ ID NO: 33)
GGAGTTTTCCGCCCGGCGCTGACGGCTGCTGCGCCCGCGGCTCCCCAGTGC

CCCGAGTGCCCCGCGGGCCCCGCGAGCGGGAGTGGGACCCAGCCCCTAGGCAGAAC

-continued

CCAGGCGCCGCGCCCGGGACGCCCGCGGAGAGAGCCACTCCCGCCCACGTCCCATT

TCGCCCCTCGCGTCCGGAGTCCCCGTGGCCAGGTGTGTGTCTGGGGAAGAGACTTAC

AGAAGTGGAGTTGCTGAGTCAAAGATCTAACCATGAGCTACCCTGGCTATCCCCCGCC

CCCAGGTGGCTACCCACCAGCTGCACCAGGTGGTGGTCCCTGGGGAGGTGCTGCCTA

CCCTCCTCCGCCCAGCATGCCCCCCATCGGGCTGGATAACGTGGCCACCTATGCGGG

GCAGTTCAACCAGGACTATCTCTCGGGAATGGCGGCCAACATGTCTGGGACATTTGGA

GGAGCCAACATGCCCAACCTGTACCCTGGGGCCCCTGGGGCTGGCTACCCACCAGTG

CCCCCTGGCGGCTTTGGGCAGCCCCCCTCTGCCCAGCAGCCTGTTCCTCCCTATGGG

ATGTATCCACCCCCAGGAGGAAACCCACCCTCCAGGATGCCCTCATATCCGCCATACC

CAGGGGCCCCTGTGCCGGGCCAGCCCATGCCACCCCCCGGACAGCAGCCCCCAGGG

GCCTACCCTGGGCAGCCACCAGTGACCTACCCTGGTCAGCCTCCAGTGCCACTCCCTG

GGCAGCAGCAGCCAGTGCCGAGCTACCCAGGATACCCGGGGTCTGGGACTGTCACCC

CCGCTGTGCCCCCAACCCAGTTTGGAAGCCGAGGCACCATCACTGATGCTCCCGGCTT

TGACCCCCTGCGAGATGCCGAGGTCCTGCGGAAGGCCATGAAAGGCTTCGGGACGGA

TGAGCAGGCCATCATTGACTGCCTGGGGAGTCGCTCCAACAAGCAGCGGCAGCAGAT

CCTACTTTCCTTCAAGACGGCTTACGGCAAGGATTTGATCAAAGATCTGAAATCTGAAC

TGTCAGGAAACTTTGAGAAGACAATCTTGGCTCTGATGAAGACCCCAGTCCTCTTTGAC

ATTTATGAGATAAAGGAAGCCATCAAGGGGGTTGGCACTGATGAAGCCTGCCTGATTG

AGATCCTCGCTTCCCGCAGCAATGAGCACATCCGAGAATTAAACAGAGCCTACAAAGC

AGAATTCAAAAAGACCCTGGAAGAGGCCATTCGAAGCGACACATCAGGGCACTTCCAG

CGGCTCCTCATCTCTCTCTCTCAGGGAAACCGTGATGAAAGCACAAACGTGGACATGT

CACTCGCCCAGAGAGATGCCCAGGAGCTGTATGCGGCCGGGGAGAACCGCCTGGGAA

CAGACGAGTCCAAGTTCAATGCGGTTCTGTGCTCCCGGAGCCGGGCCCACCTGGTAG

CAGTTTTCAATGAGTACCAGAGAATGACAGGCCGGGACATTGAGAAGAGCATCTGCCG

GGAGATGTCCGGGGACCTGGAGGAGGGCATGCTGGCCGTGGTGAAATGTCTCAAGAA

TACCCCAGCCTTCTTTGCGGAGAGGCTCAACAAGGCCATGAGGGGGGCAGGAACAAA

GGACCGGACCCTGATTCGCATCATGGTGTCTCGCAGCGAGACCGACCTCCTGGACATC

AGATCAGAGTATAAGCGGATGTACGGCAAGTCGCTGTACCACGACATCTCGGGAGATA

CTTCAGGGGATTACCGGAAGATTCTGCTGAAGATCTGTGGTGGCAATGACTGAACAGT

GACTGGTGGCTCACTTCTGCCCACCTGCCGGCAACACCAGTGCCAGGAAAAGGCCAAA

AGAATGTCTGTTTCTAACAAATCCACAAATAGCCCCGAGATTCACCGTCCTAGAGCTTA

GGCCTGTCTTCCACCCCTCCTGACCCGTATAGTGTGCCACAGGACCTGGGTCGGTCTA

GAACTCTCTCAGGATGCCTTTTCTACCCCATCCCTCACAGCCTCTTGCTGCTAAAATAG

ATGTTTCATTTTTCTGACTCATGCAATCATTCCCCTTTGCCTGTGGCTAAGACTTGGCTT

CATTTCGTCATGTAATTGTATATTTTTATTTGGAGGCATATTTTCTTTTCTTACAGTCATTG

CCAGACAGAGGCATACAAGTCTGTTTGCTGCATACACATTTCTGGTGAGGGCGACTGG

GTGGGTGAAGCACCGTGTCCTCGCTGAGGAGAGAAAGGGAGGCGTGCCTGAGAAGGT

AGCCTGTGCATCTGGTGAGTGTGTCACGAGCTTTGTTACTGCCAAACTCACTCCTTTTT

AGAAAAAACAAAAAAAAAGGGCCAGAAAGTCATTCCTTCCATCTTCCTTGCAGAAACCA

CGAGAACAAAGCCAGTTCCCTGTCAGTGACAGGGCTTCTTGTAATTTGTGGTATGTGCC

TTAAACCTGAATGTCTGTAGCCAAAACTTGTTTCCACATTAAGAGTCAGCCAGCTCTGG

-continued

AATGGTCTGGAAATGTCTTCCTGGTACCAACTTGTTTTCTTCTGCTTGATTCTGCCCTGT
GGCTCAGAGGTCTGGCCTTATCAGCCAGTGAAAGTTCATGTAACCTTACGTAGAGATTT
GTGTGCAGGAAACCCTGAGCATACACTAGTTTGCAGGGACTCGTAAGGACATGGGAAG
GGAGGTTCCCGAAATCCAGGCAGGAGGCCCAGACACCTGAAAGGCAAAGGGATCTTG
GTTGGTTGCAGGTGCAGTGAAGTCCACTGAAGGTGTGGTGCGAAGAATGCAGTCCTTC
ACCCAGGTCCCAGGAGGGAAGAAGGGTGTGTGCTAATTCCTGGTGCCCCTCGGCGGG
GGCCAGAGAGAAGGATGGGGACAACCCAGAGAGTCACAAGACCAGTGCCTCCCCTCA
GGGTGCCTCCAGGCTGAAAGGGGCTCCTGGCTCTGGTCTCTGGGGACCCTGTGCCCG
TTGGTTGGTGGTGTGAGGGAAGAGAATCCATAAGAGAGTTTCTGAGAATTATGGTGTCA
TGTCCAGAAGCTAGAGCTTACCTTGCATCAGGGGTCTCCACCCACTCCTTTTCCAACCT
CCTGCGTTGAGGTTTAGAAAAGAGAGAATCGACTAGGCACTATGGCTCACGCCTGTAAT
CCAAGGACTTTGGGAAGCTGAGGTGAGAGGATCACTTGAGCTCAGGAGTTCAAGACTA
GCCTAGCCAACAGCGAGACCCCTGTCTCTACTAAAAAATTTGGCCAGGCGTGGTGGCT
CACGGCTGTAATCCCAGCACTTTGGGAGGTGAGGCGGGCAGATCACCTGAGGTCAGG
AGTTCGAGACCCAGCCTGGCCAACATGGTGAAACCCCATCTCTACTAAAAATACAAAAA
TTAGCCAGGCATGGTGGCACATTCCTGTAATCCCAGCTACACAGGATGCTGAGGCAGG
AGAATCACTTGAACCCAGGAGGCAGAGGTTGTAGTGAGCTGAGATCACACCATTGCAC
TTCAACCTGGGTGGACAGAGTGAGACTCTGTCTCAAAAAAAAAAAAAAATTTACCTGGC
ATTGTAGTGCATTCCCTATAGTCGGCTACTCTGGAGGCTGAGGCAGGAAGATCCTTAGA
GCCCAAGAAATTGAGGCCGTAGTAAGCTGTGATTACACCACTGCACTCCAGCCTGGAC
AACAGAGCGAGACCTTGTCTCAAATGAGAAAAAAACAAAAAGAAATGGGAGAATCCAGA
GAGACTAGGCTAGATCAAGCCTGCTGGGTCCTGGCAGGAGCCCCAGGGAGTAGCTCA
TCTGCAGACATTTGCTTGAGGACTACCCCCTAAACATAAAGGAAGAATGACATCCGAAG
GGTGTGGAGCAGCCATGAGCTGAGAACTAGCCTGGTCTACCTGAGATTGATGGCAGGT
CCTGGTCAACACGTCAGCTCTGCGTCAGAGTCCATGCCTCAAGCCCAAGCTGAAGCCC
CATCCCTGCTGCTCTCCCAAGAACTCCTCTGCTAGGGCAGGCCCCTTGCCCTTGGGTG
CCAGGTGGGACCTGCCTGATGGGATGGGGTGCTTGGCATATACAACTTGCCATGAACT
CAAGGTGACCCTGGGGGCCTCCTGAATTGTGATGGGGCCTAGAACCAATGTGCTCTGA
TGTGACCATATTCTGTGACATTACCTTGCCCTGTTTACTCCAAAGTTCCCAGCCTGGTG
CCCAGCAGGCAATATTGCACCTACAGACACATTTACTTTGGTTTCCAAAGTGTTTTTAGA
CATTTGAATTTGTTGCCAACATTTAAACATTGAGAGATTTCATATTTTTAAAAATCTGGAA
TTCTGGCTTCTCTTGAAAACTCAGAAATTCTGGCACTATGGGGCTTGCATTCCTGCATG
GCTGGAGCTGAGTTGCAGCTGCCCCTTTAGGCCTGTACTCCTTATTTGCTATAGGCTCC
GTCTTGTATTACACTAAGCCCATGTCACCCATTTGGCTCCTGCAGGCCTTTGGGTTTGA
GACCCTGGTCTACACACTTGGAGACCACCTGTTGTAAAGTACATGGATGTGCTTTGGTC
AAGGAATAGACCAAGGTGGATATCCAGGCCAGAGTGACTCAGCGAGTTTAGGTCACAG
GCGTATACTCCACTTGTTATATAACCTGCTTGTGTAAGTTCATACTTGGCTCAAAGCCAC
TATTGTTTGGAAAAGGTATAACTGCCCTGCTGACGCTGTACAGATGTTCTTGGGCTCGG
ATGGGCATGGCTCCACGTGGTGTGCACTAGCACCCAGAGAGAGTGAAGCTATTGACCC
CTGTAAGGGAGAGTGACCATCTGGCAGATAGATAGAGGGGAGCCAGGACATGGCTCA

-continued

GCTTGTGCCCAGAGGGAGAGTTAAGCCGCTGACCCTGTAGCCAGGGAGTGCACCTGC

AAGCATGGGGGTGGCAGGAGCCACAGAGCTGGCTGCTGAGAGGAGCTGCAGATCTGG

AGAAGACAGCCTAGGTAAAGGTGGACAGTGTGAGAGCTGCTGATGAGATAGCTGCTGA

ATAAAACTACATTTTACCTGCCTATGGCCCGCCAGGTTTTCTTTCAGCTATCGCCCATCC

ACCCAGTCCCCTCGAACCTCAGCATGGGCTGGAACCTGACCCTGGGCATGACATTTGG

CATAGTTGTGGACCTGACACCTGTGTTTGTCCTAGTCCTGTTTCTCCCTGCCTTCCTGTT

CCTCTCGCTGCCCTCATGGTCACTCCCAAGAGATCCAACCCATGTTAAGTATGGGCTG

GAGGACTGCATGAATGCCTCATGATCTTCCCAGAGGCAAAGGCACCTACTGCCTTCCA

AGGTCAGTGGGAGGTTGGGATCAACACTGTTTATTATGCTTAGGACAAAAAAGATAGGG

AGAAAGATGTGCAACCTTACAGGTCATCTTTCTGGGATAGAACACAATGGGTCTTCTCC

TGCCTCCTGGATATGTTAGTCAAGGCCAGTCCATGCTACACATCTAGTCTGACTTCTAA

AATAGAAGCACCAGATGAATTCAGCCCTGAGAGAATTTTCAGCAGCTGTGGGGGCGCT

GGAGGAAACACTATTAAATAGTTTTGCACCTGAGACAGATAGCCTCACTCGCCTCACCC

TAGTCCTGGTGGCATTTGTCTCAGGTGCAAAATTTAAGAAAGAAACCTTGGAGTGCTCA

CCCTGTGGCTGGGTAGATGGTCCTAAAGTGGTGGTTTTCAAGCCTGAGTGTGTATCAG

GATCATCAGGGGAGCTTGCTAAAGAGCAGTTCCTGCGGTCAGACCCTCATGCATTTTG

AGCAGGTGTGGGGACTGGGAAACTGCATCTGTAACCTGCTGTAATCTAACGCTTATCTA

AATACTACTGTGCTCACACAGAGAACACCGCAAAAGTAGAGGTGTTCCTCCAGAGGGC

AGGTGAGCAGATGGCACAGTCTGCTTGGAATTCAGTCAGGTGATGAGAGATGAGATGA

GGCACTCCTAGCTTTGGGAAGAGGGAGCTGAAAGATGAACCTTTGCAGGTGCCCACGG

TCAAAGTGGTGGTTTAATGCCATGCCATGCCCATTTTCTGTTGGCCTTGGCAGGGAGTT

ACAGCCCTACCTTAGGACCTGGCTCCTTATTTCTGCTGTAGGCTCTTTCCTGCCCTGGC

CGAGATGGAGTGGAATGAGACCTAGAAACATCAAGCTAAATACATGTCCTCAGAAAGAT

AAAGGTTTACATTTTCACCCCCATCAAATCTGAAAGCTCTCTGCCTGTGTTTTTCTAAGG

GATAGGGACATCATTACTCAGTCCACAACCTGGACTCATGTAGGGTCCCCTGTCAGTAA

AGGAGTCAGTCAAGCCCACCAGGTATACCAAGGACTCTTACCCTCAGCCCCTACTCCTT

GGAAAGCTGCCCCTTGGCCTAATATTGGTGTTTAGCTTGAGCCTGACTCCTTCTCAACA

CTAAGAGCTGATGAAGTCCTGAAGCAGAAAGAGCTCTGACCTGAGAGTCAAACATCCTT

ATTCTGATCTCAGCTCAGCCCCTGATTTGTTGTGTGACCCTGGATATGTCACTTCCTGT

CTTTTTGACTTTTTAAAATGAAGGGTAGACTAGAGGAGAGCTTCTAAAACTTTAATGTGG

TCAACGAAATGGAATAGGAAATTCCACAAGTCTGTCCTTCCACAAAAGCAGCAAATAAG

GTGGCAAAAACTCAAATTTATGGGAACTCTGGAAACGAATTGAAAGTTTACAGCAATCA

GGTGAATACCTAAGAATAAAAGCTGGATTTAGTAAGA

NM_001278409.1 *Homo sapiens* annexin A11 (ANXA11), transcript variant f, mRNA (SEQ ID NO: 34)

GCACTGCCTCTGGCACCTGGGGCAGCCGCGCCCGCGGAGTTTTCCGCCCGG

CGCTGACGGCTGCTGCGCCCGCGGCTCCCCAGTGCCCCGAGTGCCCCGCGGGCCCC

GCGAGCGGGAGTGGGACCCAGCCCCTAGGCAGAACCCAGGCGCCGCGCCCGGGACG

CCCGCGGAGAGAGCCACTCCCGCCCACGTCCCATTTCGCCCCTCGCGTCCGGAGTCC

CCGTGGCCAGGTGTGTGTCTGGGGAAGAGACTTACAGAAGTGGAGTTGCTGAGTCAAA

GATCTAACCATGAGCTACCCTGGCTATCCCCCGCCCCCAGGTGGCTACCCACCAGCTG

CACCAGGTTGGCTGGCACTGGCCTGGGTTCTCTCTCTATAGTAGAAATCCTGCCATCCA

-continued

GATCCTGCCACTGCCACCTTTGCTAGCACAGCTGAGCAGCCTCTGAGCAGCAAGAGAG

GAGGAGGCAGGAAATTTAGGGAAGGTTCTTCCTGGAGGGTCTGGAGCCCTGGAGATG

AAGAGCCGATCCGAAGCTGCCATGTAGAGGAAAGCATCTAACAGGCCAGAGGCCCCAT

GATGATGTCGAATGCCCATCGGGCACCCAGCTGAGCCCTGCAGGTGGTGGTCCCTGG

GGAGGTGCTGCCTACCCTCCTCCGCCCAGCATGCCCCCCATCGGGCTGGATAACGTG

GCCACCTATGCGGGGCAGTTCAACCAGGACTATCTCTCGGGAATGGCGGCCAACATGT

CTGGGACATTTGGAGGAGCCAACATGCCCAACCTGTACCCTGGGGCCCCTGGGGCTG

GCTACCCACCAGTGCCCCCTGGCGGCTTTGGGCAGCCCCCCTCTGCCCAGCAGCCTG

TTCCTCCCTATGGGATGTATCCACCCCCAGGAGGAAACCCACCCTCCAGGATGCCCTC

ATATCCGCCATACCCAGGGGCCCCTGTGCCGGGCCAGCCCATGCCACCCCCCGGACA

GCAGCCCCCAGGGGCCTACCCTGGGCAGCCACCAGTGACCTACCCTGGTCAGCCTCC

AGTGCCACTCCCTGGGCAGCAGCAGCCAGTGCCGAGCTACCCAGGATACCCGGGGTC

TGGGACTGTCACCCCCGCTGTGCCCCCAACCCAGTTTGGAAGCCGAGGCACCATCACT

GATGCTCCCGGCTTTGACCCCCTGCGAGATGCCGAGGTCCTGCGGAAGGCCATGAAA

GGCTTCGGGACGGATGAGCAGGCCATCATTGACTGCCTGGGGAGTCGCTCCAACAAG

CAGCGGCAGCAGATCCTACTTTCCTTCAAGACGGCTTACGGCAAGGATTTGATCAAAGA

TCTGAAATCTGAACTGTCAGGAAACTTTGAGAAGACAATCTTGGCTCTGATGAAGACCC

CAGTCCTCTTTGACATTTATGAGATAAAGGAAGCCATCAAGGGGGTTGGCACTGATGAA

GCCTGCCTGATTGAGATCCTCGCTTCCCGCAGCAATGAGCACATCCGAGAATTAAACA

GAGCCTACAAAGCAGAATTCAAAAAGACCCTGGAAGAGGCCATTCGAAGCGACACATC

AGGGCACTTCCAGCGGCTCCTCATCTCTCTCTCTCAGGGAAACCGTGATGAAAGCACA

AACGTGGACATGTCACTCGCCCAGAGAGATGCCCAGGAGCTGTATGCGGCCGGGGAG

AACCGCCTGGGAACAGACGAGTCCAAGTTCAATGCGGTTCTGTGCTCCCGGAGCCGG

GCCCACCTGGTAGCAGTTTTCAATGAGTACCAGAGAATGACAGGCCGGGACATTGAGA

AGAGCATCTGCCGGGAGATGTCCGGGGACCTGGAGGAGGGCATGCTGGCCGTGGTG

AAATGTCTCAAGAATACCCCAGCCTTCTTTGCGGAGAGGCTCAACAAGGCCATGAGGG

GGGCAGGAACAAAGGACCGGACCCTGATTCGCATCATGGTGTCTCGCAGCGAGACCG

ACCTCCTGGACATCAGATCAGAGTATAAGCGGATGTACGGCAAGTCGCTGTACCACGA

CATCTCGGGAGATACTTCAGGGGATTACCGGAAGATTCTGCTGAAGATCTGTGGTGGC

AATGACTGAACAGTGACTGGTGGCTCACTTCTGCCCACCTGCCGGCAACACCAGTGCC

AGGAAAAGGCCAAAAGAATGTCTGTTTCTAACAAATCCACAAATAGCCCCGAGATTCAC

CGTCCTAGAGCTTAGGCCTGTCTTCCACCCCTCCTGACCCGTATAGTGTGCCACAGGA

CCTGGGTCGGTCTAGAACTCTCTCAGGATGCCTTTTCTACCCCATCCCTCACAGCCTCT

TGCTGCTAAAATAGATGTTTCATTTTTCTGACTCATGCAATCATTCCCCTTTGCCTGTGG

CTAAGACTTGGCTTCATTTCGTCATGTAATTGTATATTTTTATTTGGAGGCATATTTTCTT

TTCTTACAGTCATTGCCAGACAGAGGCATACAAGTCTGTTTGCTGCATACACATTTCTG

GTGAGGGCGACTGGGTGGGTGAAGCACCGTGTCCTCGCTGAGGAGAGAAAGGGAGG

CGTGCCTGAGAAGGTAGCCTGTGCATCTGGTGAGTGTGTCACGAGCTTTGTTACTGCC

AAACTCACTCCTTTTTAGAAAAAACAAAAAAAAAGGGCCAGAAAGTCATTCCTTCCATCT

TCCTTGCAGAAACCACGAGAACAAAGCCAGTTCCCTGTCAGTGACAGGGCTTCTTGTAA

-continued

TTTGTGGTATGTGCCTTAAACCTGAATGTCTGTAGCCAAAACTTGTTTCCACATTAAGAG

TCAGCCAGCTCTGGAATGGTCTGGAAATGTCA

NM_004306.4 *Homo sapiens* annexin A13 (ANXA13), transcript variant 1, mRNA (SEQ ID NO: 35)

GCCTGTAGGAGGACTGATCTCTTGATGAAATACAGAAAAACCATCTCAGAAAA

AGGAAAATGGGCAATCGTCATGCTAAAGCGAGCAGTCCTCAGGGTTTTGATGTGGATC

GAGATGCCAAAAAGCTGAACAAAGCCTGCAAAGGAATGGGGACCAATGAAGCAGCCAT

CATTGAAATCTTATCGGGCAGGACATCAGATGAGAGGCAACAAATCAAGCAAAAGTACA

AGGCAACGTACGGCAAGGAGCTGGAGGAAGTACTCAAGAGTGAGCTGAGTGGAAACTT

CGAGAAGACAGCGTTGGCCCTTCTGGACCGTCCCAGCGAGTACGCCGCCCGGCAGCT

GCAGAAGGCTATGAAGGGTCTGGGCACAGATGAGTCCGTCCTCATTGAGGTCCTGTGC

ACGAGGACCAATAAGGAAATCATCGCCATTAAAGAGGCCTACCAAAGGCTATTTGATAG

GAGCCTCGAATCAGATGTCAAAGGTGATACAAGTGGAAACCTAAAAAAAATCCTGGTGT

CTCTGCTGCAGGCTAATCGCAATGAAGGAGATGACGTGGACAAAGATCTAGCTGGTCA

GGATGCCAAAGATCTGTATGATGCAGGGGAAGGCCGCTGGGGCACTGATGAGCTTGC

GTTCAATGAAGTCCTGGCCAAGAGGAGCTACAAGCAGTTACGAGCCACCTTTCAAGCC

TATCAAATTCTCATTGGCAAAGACATAGAAGAAGCCATTGAAGAAGAAACATCAGGCGA

CTTGCAGAAGGCCTATTTAACTCTCGTGAGATGTGCCCAGGATTGTGAGGACTATTTTG

CTGAACGTCTGTACAAGTCGATGAAGGGTGCGGGGACCGATGAGGAGACGTTGATTCG

CATAGTCGTGACCAGGGCCGAGGTGGACCTTCAGGGGATCAAAGCAAAGTTCCAAGAG

AAGTATCAGAAGTCTCTCTCTGACATGGTTCGCTCAGATACCTCCGGGGACTTCCGGAA

ACTGCTAGTAGCCCTCTTGCACTGAGCCAAGCCAGGGCAATAGGAACACAGGGTGGAA

CCGCCTTTGTCAAGAGCACATTCCAAATCAAACTTGCAAATGAGACTCCCGCACGAAAA

CCCTTAAGAGTCCCGGATTACTTTCTTGGCAGCTTAAGTGGCGCAGCCAGGCCAAGCT

GTGTAAGTTAAGGGCAGTAACGTTAAGATGCGTGGGCAGGGCACCTTGAACTCTGGCT

TAGCAAGCATCTAGGCTGCCTCTTCACTTTCTTTTAGCATGGTAACTGGATGTTTTCTAA

ACACTAATGAAATCAGCAGTTGATGAAAAAACTATGCATTTGTAATGGCACATTTAGAAG

GATATGCATCACACAAGTAAGGTACAGGAAAGACAAAATTAAACAATTTATTAATTTTCC

TTCTGTGTGTTCAATTTGAAAGCCTCATTGTTAATTAAAGTTGTGGATTATGCCTCTA

NM_001003954.2 *Homo sapiens* annexin A13 (ANXA13), transcript variant 2, mRNA (SEQ ID NO: 36)

ATTATGTCCGGGGGGAAAACTGTTGTAAACTTTGCCTGTAGGAGGACTGATCT

CTTAATGAAATACAGAAAAACCATCTCAGAAAAAGGAAAATGGGCAATCGTCATAGCCA

GTCGTACACCCTCTCAGAAGGCAGTCAACAGTTGCCTAAAGGGGACTCCCAACCCTCG

ACAGTCGTGCAGCCTCTCAGCCACCCATCACGGAATGGAGAGCCAGAGGCCCCACAG

CCTGCTAAAGCGAGCAGTCCTCAGGGTTTTGATGTGGATCGAGATGCCAAAAAGCTGA

ACAAAGCCTGCAAAGGAATGGGGACCAATGAAGCAGCCATCATTGAAATCTTATCGGG

CAGGACATCAGATGAGAGGCAACAAATCAAGCAAAAGTACAAGGCAACGTACGGCAAG

GAGCTGGAGGAAGTACTCAAGAGTGAGCTGAGTGGAAACTTCGAGAAGACAGCGTTGG

CCCTTCTGGACCGTCCCAGCGAGTACGCCGCCCGGCAGCTGCAGAAGGCTATGAAGG

GTCTGGGCACAGATGAGTCCGTCCTCATTGAGGTCCTGTGCACGAGGACCAATAAGGA

AATCATCGCCATTAAAGAGGCCTACCAAAGGCTATTTGATAGGAGCCTCGAATCAGATG

TCAAAGGTGATACAAGTGGAAACCTAAAAAAAATCCTGGTGTCTCTGCTGCAGGCTAAT

-continued

CGCAATGAAGGAGATGACGTGGACAAAGATCTAGCTGGTCAGGATGCCAAAGATCTGT

ATGATGCAGGGGAAGGCCGCTGGGGCACTGATGAGCTTGCGTTCAATGAAGTCCTGG

CCAAGAGGAGCTACAAGCAGTTACGAGCCACCTTTCAAGCCTATCAAATTCTCATTGGC

AAAGACATAGAAGAAGCCATTGAAGAAGAAACATCAGGCGACTTGCAGAAGGCCTATTT

AACTCTCGTGAGATGTGCCCAGGATTGTGAGGACTATTTTGCTGAACGTCTGTACAAGT

CGATGAAGGGTGCGGGGACCGATGAGGAGACGTTGATTCGCATAGTCGTGACCAGGG

CCGAGGTGGACCTTCAGGGGATCAAAGCAAAGTTCCAAGAGAAGTATCAGAAGTCTCT

CTCTGACATGGTTCGCTCAGATACCTCCGGGGACTTCCGGAAACTGCTAGTAGCCCTC

TTGCACTGAGCCAAGCCAGGGCAATAGGAACACAGGGTGGAACCGCCTTTGTCAAGAG

CACATTCCAAATCAAACTTGCAAATGAGACTCCCGCACGAAAACCCTTAAGAGTCCCGG

ATTACTTTCTTGGCAGCTTAAGTGGCGCAGCCAGGCCAAGCTGTGTAAGTTAAGGGCA

GTAACGTTAAGATGCGTGGGCAGGGCACCTTGAACTCTGGCTTAGCAAGCATCTAGGC

TGCCTCTTCACTTTCTTTTAGCATGGTAACTGGATGTTTTCTAAACACTAATGAAATCAG

CAGTTGATGAAAAAACTATGCATTTGTAATGGCACATTTAGAAGGATATGCATCACACAA

GTAAGGTACAGGAAAGACAAAATTAAACAATTTATTAATTTTCCTTCTGTGTGTTCAATTT

GAAAGCCTCATTGTTAATTAAAGTTGTGGATTATGCCTCTAAAAAAAAAAAAAAAAAAAA

AA

NM_001363114.2 *Homo sapiens* annexin A6 (ANXA6), transcript variant 3, mRNA (SEQ ID NO: 46):

GCGGTTGCTGCTGGGCTAACGGGCTCCGATCCAGCGAGCGCTGCGTCCTCGAGTCCC

TGCGCCCGTGCGTCCGTCTGCGACCCGAGGCCTCCGCTGCGCGTGGATTCTGCTGCG

AACCGGAGACCATGGCCAAACCAGCACAGGGTGCCAAGTACCGGGGCTCCATCCATG

ACTTCCCAGGCTTTGACCCCAACCAGGATGCCGAGGCTCTGTACACTGCCATGAAGGG

CTTTGGCAGTGACAAGGAGGCCATACTGGACATAATCACCTCACGGAGCAACAGGCAG

AGGCAGGAGGTCTGCCAGAGCTACAAGTCCCTCTACGGCAAGGACCTCATTGCTGATT

TAAAGTATGAATTGACGGGCAAGTTTGAACGGTTGATTGTGGGCCTGATGAGGCCACC

TGCCTATTGTGATGCCAAAGAAATTAAAGATGCCATCTCGGGCATTGGCACTGATGAGA

AGTGCCTCATTGAGATCTTGGCTTCCCGGACCAATGAGCAGATGCACCAGCTGGTGGC

AGCATACAAAGATGCCTACGAGCGGGACCTGGAGGCTGACATCATCGGCGACACCTCT

GGCCACTTCCAGAAGATGCTTGTGGTCCTGCTCCAGGGAACCAGGGAGGAGGATGAC

GTAGTGAGCGAGGACCTGGTACAACAGGATGTCCAGGACCTATACGAGGCAGGGGAA

CTGAAATGGGGAACAGATGAAGCCCAGTTCATTTACATCTTGGGAAATCGCAGCAAGCA

GCATCTTCGGTTGGTGTTCGATGAGTATCTGAAGACCACAGGGAAGCCGATTGAAGCC

AGCATCCGAGGGGAGCTGTCTGGGGACTTTGAGAAGCTAATGCTGGCCGTAGTGAAGT

GTATCCGGAGCACCCCGGAATATTTTGCTGAAAGGCTCTTCAAGGCTATGAAGGGCCT

GGGGACTCGGGACAACACCCTGATCCGCATCATGGTCTCCCGTAGTGAGTTGGACATG

CTCGACATTCGGGAGATCTTCCGGACCAAGTATGAGAAGTCCCTCTACAGCATGATCAA

GAATGACACCTCTGGCGAGTACAAGAAGACTCTGCTGAAGCTGTCTGGGGGAGATGAT

GATGCTGCTGGCCAGTTCTTCCCGGAGGCAGCGCAGGTGGCCTATCAGATGTGGGAA

CTTAGTGCAGTGGCCCGAGTAGAGCTGAAGGGAACTGTGCGCCCAGCCAATGACTTCA

ACCCTGACGCAGATGCCAAAGCGCTGCGGAAAGCCATGAAGGGACTCGGGACTGACG

-continued

```
AAGACACAATCATCGATATCATCACGCACCGCAGCAATGTCCAGCGGCAGCAGATCCG

GCAGACCTTCAAGTCTCACTTTGGCCGGGACTTAATGACTGACCTGAAGTCTGAGATCT

CTGGAGACCTGGCAAGGCTGATTCTGGGGCTCATGATGCCACCGGCCCATTACGATGC

CAAGCAGTTGAAGAAGGCCATGGAGGGAGCCGGCACAGATGAAAAGGCTCTTATTGAA

ATCCTGGCCACTCGGACCAATGCTGAAATCCGGGCCATCAATGAGGCCTATAAGGAGG

ACTATCACAAGTCCCTGGAGGATGCTCTGAGCTCAGACACATCTGGCCACTTCAGGAG

GATCCTCATTTCTCTGGCCACGGGGCATCGTGAGGAGGGAGGAGAAAACCTGGACCA

GGCACGGGAAGATGCCCAGGAAATAGCAGACACACCTAGTGGAGACAAAACTTCCTTG

GAGACACGTTTCATGACGATCCTGTGTACCCGGAGCTATCCGCACCTCCGGAGAGTCT

TCCAGGAGTTCATCAAGATGACCAACTATGACGTGGAGCACACCATCAAGAAGGAGAT

GTCTGGGGATGTCAGGGATGCATTTGTGGCCATTGTTCAAAGTGTCAAGAACAAGCCT

CTCTTCTTTGCCGACAAACTTTACAAATCCATGAAGGGTGCTGGCACAGATGAGAAGAC

TCTGACCAGGATCATGGTATCCCGCAGTGAGATTGACCTGCTCAACATCCGGAGGGAA

TTCATTGAGAAATATGACAAGTCTCTCCACCAAGCCATTGAGGGTGACACCTCCGGAGA

CTTCCTGAAGGCCTTGCTGGCTCTCTGTGGTGGTGAGGACTAGGGCCACAGCTTTGGC

GGGCACTTCTGCCAAGAAATGGTTATCAGCACCAGCCGCCATGGCCAAGCCTGATTGT

TCCAGCTCCAGAGACTAAGGAAGGGGCAGGGGTGGGGGGAGGGGTTGGGTTGGGCT

CTTATCTTCAGTGGAGCTTAGGAAACGCTCCCACTCCCACGGGCCATCGAGGGCCCAG

CACGGCTGAGCGGCTGAAAAACCGTAGCCATAGATCCTGTCCACCTCCACTCCCCTCT

GACCCTCAGGCTTTCCCAGCTTCCTCCCCTTGCTACAGCCTCTGCCCTGGTTTGGGCT

ATGTCAGATCCAAAAACATCCTGAACCTCTGTCTGTAAAATGAGTAGTGTCTGTACTTTG

AATGAGGGGGTTGGTGGCAGGGGCCAGTTGAATGTGCTGGGCGGGGTGGTGGGAAG

GATAGTAAATGTGCTGGGGCAAACTGACAAATCTTCCCATCCATTTCACCACCCATCTC

CATCCAGGCCGCGCTAGAGTACTGGACCAGGAATTTGGATGCCTGGGTTCAAATCTGC

ATCTGCCATGCACTTGTTTCTGACCTTAGGCCAGCCCCTTTCCCTCCCTGAGTCTCTAT

TTTCTTATCTACAATGAGACAGTTGGACAAAAAAATCTTGGCTTCCCTTCTAACATTAACT

TCCTAAAGTATGCCTCCGATTCATTCCCTTGACACTTTTTATTTCTAAGGAAGAAATAAAA

AGAGATACACAAACACATAAACACA
```

Therapeutic Endpoints

In various aspects of the disclosure, use of the agent(s) and optional additional agent(s) as described herein provide one or more benefits related to specific therapeutic endpoints relative to a patient not receiving the agent(s) and/or additional agent(s).

Creatine kinase (CK) is a clinically validated serum biomarker of skeletal muscle, cardiac, kidney, and brain injury. Lactate dehydrogenase (LDH) is a clinically validated serum biomarker of skeletal muscle, cardiac, kidney, liver, lung, and brain injury. Creatine kinase and lactate dehydrogenase levels in serum are elevated with both acute and chronic tissue injury. In theoretical or verified conditions of comparable muscle mass levels, a reduction in creatine kinase and/or lactate dehydrogenase may be indicative of enhanced repair or protection against injury. Aspartate aminotransferase (AST) is yet another clinically validated serum biomarker of skeletal muscle, cardiac, kidney, liver, and brain injury. Additionally, increased serum troponin is indicative of cardiac injury, while elevated alanine transaminase (ALT) is a biomarker of liver injury. Reduction in AST, ALT, or troponin in the acute period following injury may indicate enhanced repair or protection against injury. Evan's blue due is a vital dye that binds serum albumin and is normally excluded from healthy, intact muscle. Membrane disruption due to acute or chronic injury promotes the influx of dye into the damaged cell. Evan's blue dye is commonly used to quantify cellular damage in experimental settings, measuring inherent dye fluorescence and/or through measuring radiolabeled-dye uptake. Reduction in dye uptake after acute injury or in models of chronic damage would indicate protection against injury and/or enhanced repair. Indocyanine green (ICG) is a near-infrared dye that binds plasma proteins and is used clinically to evaluate blood flow and tissue damage (ischemia; necrosis) in organs including heart, liver, kidney, skin, vasculature, lung, muscle and eye. Improved blood flow and reduction in ischemic areas indicate protection from injury and/or improved repair.

It is contemplated that increasing membrane integrity and repair results in enhanced function measured through multiple modalities including plethysmography, echocardiography, muscle force, 6-min walk test. Additionally, histological benefits may be noted, including decreased necrosis, decreased inflammation, reduced fibrosis, reduced fatty infiltrate and reduced edema. These beneficial effects may also be visible through MR and PET imaging.

Dosing/Administration/Kits

A particular administration regimen for a particular subject will depend, in part, upon the agent and optional additional agent used, the amount of the agent and optional additional agent administered, the route of administration, the particular ailment being treated, and the cause and extent of any side effects. The amount of agent and optional additional agent administered to a subject (e.g., a mammal, such as a human) is sufficient to effect the desired response. Dosage typically depends upon a variety of factors, including the particular agent and/or additional agent employed, the age and body weight of the subject, as well as the existence and severity of any disease or disorder in the subject. The size of the dose also will be determined by the route, timing, and frequency of administration. Accordingly, the clinician may titer the dosage and modify the route of administration to obtain optimal therapeutic effect, and conventional range-finding techniques are known to those of ordinary skill in the art. Purely by way of illustration, in some embodiments, the method comprises administering an agent (e.g., a protein), e.g., from about 0.1 μg/kg up to about 100 mg/kg or more, depending on the factors mentioned above. In other embodiments, the dosage may range from 1 μg/kg up to about 75 mg/kg; or 5 μg/kg up to about 50 mg/kg; or 10 μg/kg up to about 20 mg/kg. In certain embodiments, the dose comprises about 0.5 mg/kg to about 20 mg/kg (e.g., about 1 mg/kg, 1.5 mg/kg, 2 mg/kg, 2.3 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 8 mg/kg, 9 mg/kg, or 10 mg/kg) of agent and optional additional agent. In embodiments in which an agent and additional agent are administered, the above dosages are contemplated to represent the amount of each agent administered, or in further embodiments the dosage represents the total dosage administered. In some embodiments wherein a chronic condition is treated, it is envisioned that a subject will receive the agent and/or additional agent over a treatment course lasting weeks, months, or years, and may require one or more doses daily or weekly. In any of the aspects or embodiments of the disclosure, the amount of an annexin protein in a pharmaceutical composition is from about 0.1 μg/kg up to about 100 mg/kg or more, depending on the factors mentioned above. In other embodiments, the dosage may range from 1 μg/kg up to about 75 mg/kg; or 5 μg/kg up to about 50 mg/kg; or 10 μg/kg up to about 20 mg/kg. In some embodiments, the dose comprises about 0.5 mg/kg to about 20 mg/kg (e.g., about 1 mg/kg, 1.5 mg/kg, 2 mg/kg, 2.3 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 8 mg/kg, 9 mg/kg, or 10 mg/kg) of annexin protein. Dosages are also contemplated for once daily, twice daily (BID) or three times daily (TID) dosing. A unit dose may be formulated in either capsule or tablet form. In other embodiments, the agent and optional additional agent is administered to treat an acute condition (e.g., acute muscle injury or acute myocardial injury) for a relatively short treatment period, e.g., one to 14 days.

Suitable methods of administering a physiologically-acceptable composition, such as a pharmaceutical composition comprising an agent (e.g., a recombinant protein) and optional additional agent described herein, are well known in the art. Although more than one route can be used to administer an agent and/or additional agent, a particular route can provide a more immediate and more effective avenue than another route. Depending on the circumstances, a pharmaceutical composition is applied or instilled into body cavities, absorbed through the skin or mucous membranes, ingested, inhaled, and/or introduced into circulation. In some embodiments, a composition comprising an agent and/or additional agent is administered intravenously, intraarterially, or intraperitoneally to introduce an agent and optional additional agent into circulation. Non-intravenous administration also is appropriate, particularly with respect to low molecular weight therapeutics. In certain circumstances, it is desirable to deliver a pharmaceutical composition comprising the agent and/or additional agent orally, topically, sublingually, vaginally, rectally; through injection by intracerebral (intra-parenchymal), intracerebroventricular, intramuscular, intra-ocular, intraportal, intralesional, intramedullary, intrathecal, intraventricular, transdermal, subcutaneous, intranasal, urethral, or enteral means; by sustained release systems; or by implantation devices. If desired, the agent and/or additional agent is administered regionally via intraarterial or intravenous administration to a region of interest, e.g., via the femoral artery for delivery to the leg. In one embodiment, the composition is administered via implantation of a membrane, sponge, or another appropriate material within or upon which the desired agent and optional additional agent has been absorbed or encapsulated. Where an implantation device is used, the device in one aspect is implanted into any suitable tissue, and delivery of the desired agent and/or additional agent is, in various embodiments, effected via diffusion, time-release bolus, or continuous administration. In other embodiments, the agent and optional additional agent is administered directly to exposed tissue during surgical procedures or treatment of injury, or is administered via transfusion of blood products. Therapeutic delivery approaches are well known to the skilled artisan, some of which are further described, for example, in U.S. Pat. No. 5,399,363.

In some embodiments facilitating administration, the agent and optional additional agent in one embodiment is formulated into a physiologically acceptable composition comprising a carrier (i.e., vehicle, adjuvant, buffer, or diluent). The particular carrier employed is limited only by chemico-physical considerations, such as solubility and lack of reactivity with the agent and/or additional agent, by the route of administration, and by the requirement of compatibility with the recipient organism. Physiologically acceptable carriers are well known in the art. Illustrative pharmaceutical forms suitable for injectable use include, without limitation, sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia. Pa., Banker and Chalmers. eds., pages 238-250 (1982), and ASHP Handbook on Injectable Drugs, Toissel, 4th ed., pages 622-630 (1986), incorporated herein by reference).

A pharmaceutical composition comprising an agent (e.g., a recombinant protein) and optional additional agent as provided herein is optionally placed within containers/kits, along with packaging material that provides instructions regarding the use of such pharmaceutical compositions. Generally, such instructions include a tangible expression describing the reagent concentration, as well as, in certain embodiments, relative amounts of excipient ingredients or diluents that may be necessary to reconstitute the pharmaceutical composition.

The disclosure thus includes administering to a subject one or more agent(s), in combination with one or more additional agent(s), each being administered according to a regimen suitable for that medicament. In some embodiments, the agent is a recombinant protein such as an annexin protein (e.g., annexin A6). Administration strategies include concurrent administration (i.e., substantially simultaneous administration) and non-concurrent administration (i.e., administration at different times, in any order, whether overlapping or not) of the agent and one or more additional agents(s). It will be appreciated that different components are optionally administered in the same or in separate compositions, and by the same or different routes of administration.

All publications, patents and patent applications cited in this specification are herein incorporated by reference as if each individual publication or patent application were specifically and individually indicated to be incorporated by reference. In addition, the entire document is intended to be related as a unified disclosure, and it should be understood that all combinations of features described herein are contemplated, even if the combination of features are not found together in the same sentence, or paragraph, or section of this document. For example, where protein therapy is described, embodiments involving polynucleotide therapy (using polynucleotides/vectors that encode the protein) are specifically contemplated, and the reverse also is true. With respect to elements described as one or more members of a set, it should be understood that all combinations within the set are contemplated.

EXAMPLES

The following examples show results from experiments in which muscle membrane repair was monitored with real-time high-resolution imaging to visualize annexin cap formation and $Ca^{2+}$ dynamics after laser-induced injury. It is demonstrated herein that overexpression of annexin proteins induced extracellular bleb formation at the site of membrane injury, which correlated with decreased intracellular $Ca^{2+}$ accumulation. Pretreatment with recombinant annexin A6 prevented muscle injury in vitro and in vivo. Post-treatment with recombinant annexin A6 enhanced muscle repair in vivo. Overexpression of annexin A6 enhanced myofiber membrane repair, while overexpression of a dominant-negative annexin A6 mutant protein decreased membrane repair capacity. In addition, treatment with extracellular recombinant annexin A6 protein reduced laser-induced muscle damage of both wildtype and dystrophic myofibers. Moreover, administration of recombinant annexin A6 protected against toxin-induced muscle injury in vivo using multiple routes of administration. Furthermore, in dystrophic mice administration of recombinant annexin A6 reduced circulating levels of creatine kinase and lactate dehydrogenase, indicating enhanced membrane repair. The data provided herein show that annexin proteins are important agonists of membrane repair and that recombinant annexin A6 is a therapeutic target to treat conditions resulting from membrane fragility like muscle injury and muscular dystrophies.

A polymorphism in Anxa6, the gene encoding annexin A6, was previously identified in several commonly used experimental mouse strains that correlated with impaired muscle repair (Demonbreun et al., 2016a; Quattrocelli et al., 2017b; Swaggart et al., 2014). This polymorphism produced a truncated annexin A6 protein that interferes with sarcolemmal repair. Additional studies in mice have shown that loss of annexin A2 results in poor myofiber repair (Defour et al., 2017).

Annexin $Ca^{2+}$ binding during muscle membrane repair was investigated and the kinetics of annexin A1, A2, and A6 repair cap formation after injury was assessed. Mutations in $Ca^{2+}$-coordinating residues in annexin A1, A2, and A6 interfered with normal annexin repair cap formation. Annexin overexpression promoted the formation of external blebs at the site of membrane injury, which were released from the repair cap. Overexpression of annexin A6 resulted in the formation of larger blebs being released from the repair cap. These vesicles were enriched in $Ca^{2+}$-binding protein GCaMP5G, which correlated with a reduction of intracellular $Ca^{2+}$ fluorescence at the site of injury. Overexpression of annexin A6 reduced membrane injury, while mutation of E233, a critical $Ca^{2+}$-coordinating residue in annexin A6 interfered with annexin repair complex formation, and correlated with decreased repair capacity. Local and systemic treatment with recombinant annexin A6 reduced muscle damage and promoted membrane repair in vivo. The data provided herein identify a new role for annexins in bleb release from muscle membrane lesions during membrane repair and identifies annexin A6 as a therapeutic target to enhance membrane repair capacity.

Example 1

Materials and Methods

Animals. Wildtype mice from the 129T2/SvEmsJ background were bred and housed in a specific pathogen free facility on a 12-hour light/dark cycle and fed ad libitum in accordance with the Northwestern University's Institutional Animal Care and Use Committee regulations. 129T2/SvEmsJ (129T2) mice were purchased from the Jackson Laboratory (Ben Harbor, ME; Stock #002065). mdx/hLTBP4 mice were generated as described in (Ceco et al., 2014; Quattrocelli et al., 2017b). sgcg-null mice were generated as described (Hack et al 1998). Two to three-month-old male and female were used for all experiments.

Plasmids. Plasmids encoding annexin A1, A2 and A6 with a carboxyl-terminal turboGFP tag were obtained from Origene (Rockville, MD). Subcloning of annexin A1, A2, and A6 to replace the GFP tag with tdTomato (Addgene) was performed by Mutagenix (Suwanee, GA). Site directed mutagenesis was performed by Mutagenix on annexin A1-GFP, A2-GFP and A6-GFP to create the $Ca^{2+}$-binding mutants A1-D171A-GFP, A2-D161A-GFP, A6-D149A-GFP, and A6-E233A-GFP. Constructs were sequenced to verify mutagenesis. Plasmid DNA was isolated using the Qiagen endo-free Maxi prep kit (Qiagen #12362). The $Ca^{2+}$ sensor GCaMP5G was purchased from (Addgene #31788).

Sequence comparison and protein schematics. Protein ribbon diagrams were generated using Swiss-PdbViewer using solved crystal structures of annexin A1 (1MCX), A2 (2HYW), and annexin A6 (1AVC) available on www.rcsb.org. Clustal Omega from the European Bioinformatics Institute (EMBL-EBI) was used to align annexin mouse sequences from www.ncbi.nlm.nih.gov annexin A1 (NM_010730; SEQ ID NO: 37), A2 (NM_007585; SEQ ID NO: 38) and A6 (NM_013472: SEQ ID NO:39).).

Electroporation, myofiber isolation, laser injury, cap and vesicle measurement. Flexor digitorum brevis (FDB) fibers were transfected with endo-free plasmid DNA by in vivo electroporation. Methods were described previously in (Demonbreun and McNally, 2015; Demonbreun et al., 2016b; DiFranco et al., 2009). Z-stack projections were acquired from consecutive acquisitions after the final time-lapse frame, approximately 4 minutes post damage, with a 0.125 μM step size between slices. Z-stack renderings were constructed in FIJI. Measurement of the cap area and feret diameter were conducted from a single slice near the middle of the z-stack using FIJI imaging tools. Fibers expressing similar levels of tagged or GCaMP5G protein were compared. GCaMP5G $Ca^{2+}$ fluorescence was measured from the acquired timelapse images, using a standard rectangular ROI, placed inside the myofiber below the site of damage using FIJI. Fluorescence was expressed as F/F0. External vesicle number and GCaMP5G area were measured from endpoint z-stacks and max projection images using FIJI. Vesicles were considered external if they were found outside the sarcolemma assessed in brightfield and fluorescent channels. All measurements were acquired from myofibers isolated from at least n≥3 mice, n≥3 myofibers per mouse.

For recombinant myofibers studies, myofibers were isolated from mdx/hLTBP4 mice as described above. Myofibers were incubated in Ringer's media with or without 25 μg/ml recombinant annexin A6 (5186-A6-050, R&D systems). FM 4-64 (2.5 μm) was added to the myofibers just prior to imaging. Images were acquired and quantitated as described above. FM 4-64 area was measured using FIJI at imaging endpoint from a single slice near the middle of the z-stack. Z-stack step size (0.125 μm) was acquired from cap end to end.

Myofiber quality control was based on a number of characteristics including using adherent myofibers with intact sarcomere structure detected through brightfield imaging. Myofibers appeared devoid of tears or ruptures induced during the isolation protocol. The region of the myofiber selected for damage was linear and not located on a nucleus or neuromuscular junction. Additionally, fluorescence intensity within both the red and green channels suggested similar expression levels prior to damage.

Multiphoton laser injury and imaging. Fibers were subjected to laser-induced damage at room temperature using the Nikon A1R-MP multiphoton microscope. Imaging was performed using a 25×1.1NA objective directed by the NIS-Elements AR imaging software. Green fluorescence protein (GFP) and FM 4-64 were excited using a 920 nm wavelength laser and emission wavelengths of 575 nm and 629 nm were collected respectively. To induce laser damage on isolated myofibers, a diffraction limited spot (diameter approximately 410 nm) was created on the lateral membrane of the myofiber using a 920 nm wavelength laser at 10-15% laser power for 1 second. Time lapse images were collected as follows: one image was collected prior to damage, one image upon damage, then every 8 seconds for 80 seconds (10 images) followed by every 30 seconds for 5 minutes (10 images). At the end of the time lapsed image series, z-stack images were collected at 250 nm intervals through the damaged site on the myofiber directed by the NIS-Elements AR imaging software.

Cardiotoxin Injury and analysis. Tibialis anterior muscle of wildtype mice were injected with 25 μg/ml recombinant annexin A6 (5186-A6-050, R&D systems) or Ringers in sedated mice (3% isoflurane, 0.8 l/min $O_2$). Additionally, mice were injected intraperitoneally with Evans' blue dye at 5 μl/g body weight (E-2129; Sigma-Aldrich, St. Louis, MO) dissolved in phosphate-buffered saline at 10 mg/mL. For systemic administration, wildtype mice were injected with 1 mg/kg recombinant annexin A6 (5186-A6-050, R&D systems) or PBS diluted in EBD (5 μl/g body weight) into the retro-orbital cavity of sedated mice (3% isoflurane, 0.8 l/min $O_2$). Cardiotoxin injury was performed injecting 20 μl of a 10 μM cardiotoxin (discontinued, Sigma-Aldrich) solution in PBS in tibialis muscles in sedated animals (3% isoflurane, 0.8 l/min $O_2$) 2 hours post pretreatment. Cardiotoxin was released down the midline of the muscle to induce a homogenous area of injury at the center of the muscle. 3 hours post cardiotoxin injection muscle was harvested and frozen in liquid nitrogen.

Chronic Injury and biomarker analysis. For systemic administration, sgcg-null mice or wildtype mice were injected with 1 mg/kg recombinant annexin A6 (5186-A6-050, R&D systems) or PBS into the retro-orbital cavity of sedated mice (3% isoflurane, 0.8 l/min $O_2$). Mice were injected once every 3 days for a period of 12 days. Serum was acquired as previously described (Demonbreun et al 2016a). Serum CK was analyzed for each mouse using the EnzyChrom Creatine Kinase Assay (catalog ECPK-100, BioAssay Systems) following the manufacturer's instructions. Lactate dehydrogenase was analyzed for each mouse using (LDH cytotoxicity kit MK401, Takara) following the manufacturer's instructions. Results were acquired with the Synergy HTX multi-mode plate reader (BioTeK).

Immunofluorescence microscopy. Sections (10 μm thick) from the center of frozen-embedded muscles were collected on the cryostat (chamber, −20° C.; sample, −15° C.; catalog number CM1950; Leica, Wetzlar, Germany) for immunostaining. Tissues were fixed with 4% paraformaldehyde for 10 minutes on ice. Block and permeabilization were with 0.1% Triton (catalog number X-100; Sigma-Aldrich), 10% fetal bovine serum, and PBS for 60 minutes. For dystrophin detection, anti-dystrophin (ab15277; Abcam, Cambridge, MA) was used at a dilution of 1:100 overnight at 4° C. Sections were PBS rinsed, incubated with secondary antibody goat anti rabbit (A11008, Invitrogen) for 1 hour, PBS rinsed, and mounted in vectashield with DAPI (H-1200, Vector Laboratories). Imaging was performed using a Zeiss Axio Observer A1 microscope (Zeiss, Oberkochen, Germany), using a 10× objective. ZEN software (Zeiss, Jena, Germany) was used for acquiring images. Fluorescence quantitation and muscle area were performed using FIJI (NIH). Surface plots were created in FIJI (NIH). Fluorescence volume was quantified using Imaris Software v9.1.2.

Calcium kinetics. FDB muscle was electroporated and isolated as described above. Myofibers were damaged in Ringers solution with $Ca^{2+}$ concentrations of 2 mM, 1 mM, 0.5 mM, 0.25 mM, 0.175 mM, 0.1 mM, 0.050 mM, and 0 mM. EDTA was added as a $Ca^{2+}$ chelating agent in only in the 0 mM $Ca^{2+}$ Ringers. Myofibers were isolated directly into 2 mM, 1 mM and 0.5 mM Ringers for those experiments respectively. For experiments using less than 0.5 mM $Ca^{2+}$ myofibers were isolated in 0.5 mM $Ca^{2+}$ Ringers and then diluted with 0 mM EDTA-free $Ca^{2+}$ Ringers. For 0 mM experiments, myofibers were isolated in 0.5 mM $Ca^{2+}$ Ringers and then replaced with 0 mM $Ca^{2+}$+EDTA Ringers just prior to imaging. Co-electroporation of wildtype annexin+wildtype annexin constructs was performed in one mouse foot, while the contralateral foot was co-electroporated with wildtype annexin+mutant annexin. All measurements were acquired from myofibers isolated from at least n≥2 mice, n≥3 myofibers per mouse at each $Ca^{2+}$ concentration. Area-$Ca^{2+}$ curves were fitted with a Hill Curve at $Ca^{2+}$ concentrations ranging from 0-2 mM. Kinetic parameters were calculated using Prism Graphpad.

Single cell $Ca^{2+}$ and shortening measurements. Isolated FDB fibers were plated on laminin coated glass-bottomed 35 mm dishes for one hour and then cultured overnight in DMEM with 10% FBS and 1% penicillin/streptomycin at 37° C. in a 10% $CO_2$ incubator. One hour prior to data acquisition, the medium was removed and cells were incubated in Tyrode buffer (119 mM NaCl, 5 mM KCl, 25 mM HEPES, 2 mM $CaCl_2$), 2 mM $MgCl_2$) with 10 μM Indo-1 AM (TefLabs) for 1 hour at 37° C. in a 10% $CO_2$ incubator. Dishes were then filled with Tyrode buffer, mounted on a custom stage and platinum pacing electrodes were inserted into the dish. Stimulation was elicited using a 701C high-powered stimulator controlled by the 950A software (Aurora Scientific). Stimulation was performed at 40 and 80 Hz, 5 ms pulse width, 100 ms duration. Ratiometric $Ca^{2+}$ signals were collected with two photomultiplier tubes and a FluoroDaq controller. Video sarcomere length was recorded with a high-speed camera and fast Fourier transform using the Aurora Scientific 900B-VSL system (Aurora, Ontario). Ten transients were collected over 20 seconds and averaged together per cell per frequency.

Statistical analysis. Statistical analyses were performed with Prism (Graphpad, La Jolla, CA). Comparisons relied on ANOVA ((1way ANOVA for 1 variable, 2way ANOVA for two variables (typically area and $Ca^{2+}$ concentration)). Otherwise, unpaired t-tests were performed. Error bars represent+/−standard error of the mean (SEM).

Example 2

$Ca^{2+}$ Localizes to the Repair Cap Upon Membrane Damage

Activation of muscle membrane repair requires the presence of external $Ca^{2+}$ (Bansal et al., 2003). It was previously shown that annexin proteins aggregate into repair caps at the site of injury bordered by annexin-free zone within the cytoplasm under the repair cap (Demonbreun et al., 2016a; Demonbreun et al., 2016b; Quattrocelli et al., 2017a; Swaggart et al., 2014). To visualize $Ca^{2+}$ dynamics at the site of injury in real-time, an in vivo fluorescent $Ca^{2+}$ indicator protein, GCaMP5G, was utilized. GCaMP5G is a fusion protein composed of green fluorescent protein (GFP), the calcium-binding protein calmodulin, and the calmodulin M13 binding peptide. GCaMP5G has minimal fluorescence when not bound to $Ca^{2+}$, and $Ca^{2+}$ binding results in a conformational change within the protein increasing the fluorescence intensity of GFP (Akerboom et al., 2012). Wildtype flexor digitorum brevis (FDB) muscle was electroporated with the GCaMP5G plasmid and then injured the plasma membrane using laser ablation (Demonbreun and McNally, 2015; Demonbreun et al., 2016b). Within two seconds of membrane injury, GCaMP5G fluorescence accumulated in the cytoplasm at the site of injury. GCaMP5G fluorescence intensity progressively increased through 90 seconds of imaging (FIG. 1A, arrow). In myofibers co-electroporated with plasmids expressing GCaMP5G and annexin A6 with a carboxyl-terminal tdTomato fluorescent tag, GCaMP5G fluorescence localized in a ring around the annexin A6-free zone (FIG. 1B, arrowhead) and co-localized with annexin A6 at the repair cap (FIG. 1B, arrow, merge). This temporal sequence is consistent with $Ca^{2+}$ increasing at the site of injury likely facilitating annexin translocation and assembly into repair caps.

Figure 2:
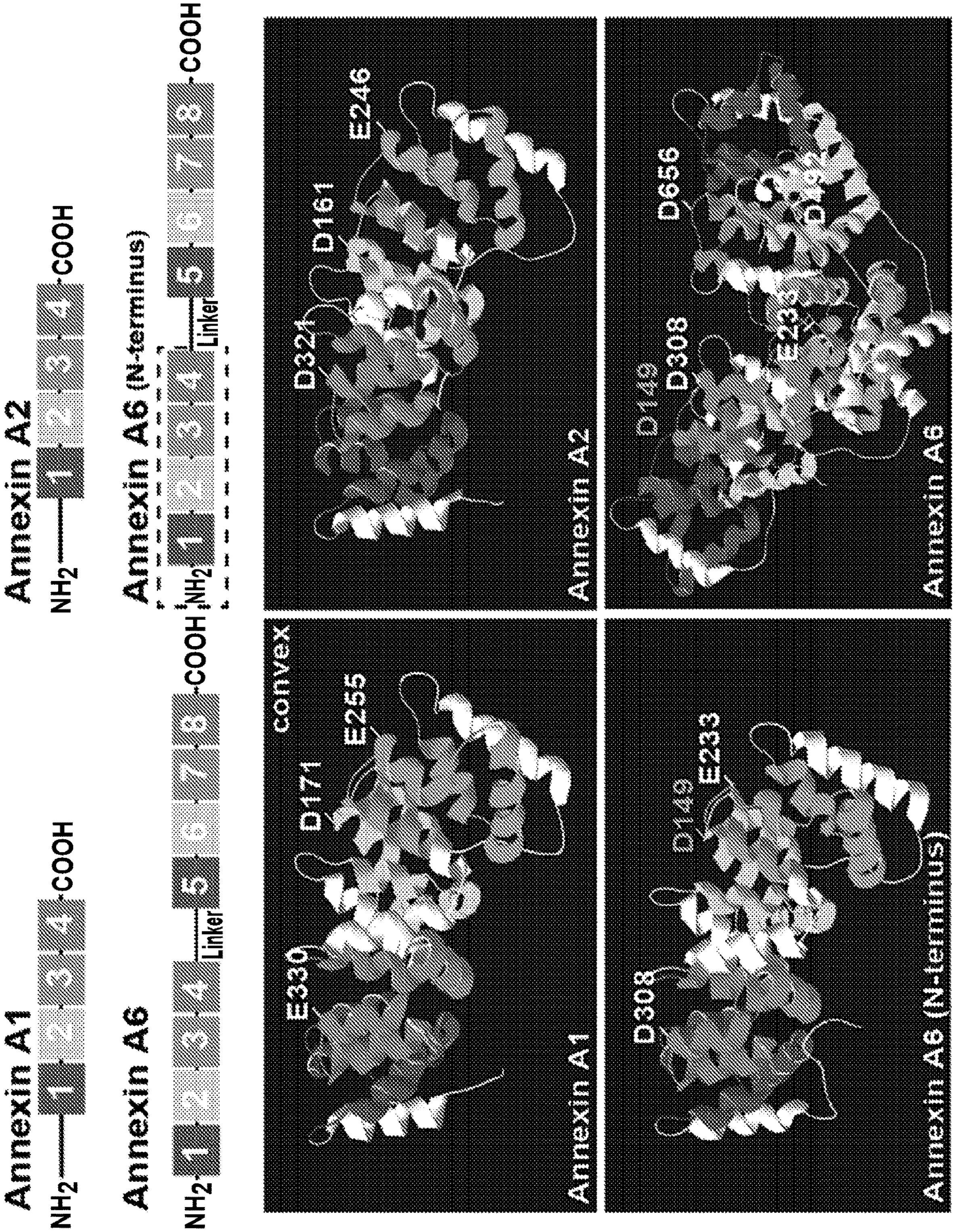
FIG. 2 shows domain modeling of annexin's multiple $Ca^{2+}$ binding sites. Annexins typically contain four annexin domains with the exception of annexin A6, which is duplicated to have 8 annexin domains. Annexin A1, A2, and A6 coordinate multiple $Ca^{2+}$ ions and bind membrane on the convex face, positioned facing the top of each ribbon diagram. The D171 residue in annexin A1 and the D161 residue in annexin A2 were previously described as necessary residues to coordinate $Ca^{2+}$ binding (Jost et al., 1992). Both D171 and D161 localize in the second (yellow) annexin domain in annexin A1 and A2, respectively. The orthologous residue in annexin A6, D149, which falls into the first half of annexin A6, was not observed to coordinate $Ca^{2+}$ in bovine A6 (Avila-Sakar et al., 1998). In this study, D149 was examined in annexin A6 as well as E233, which fall into the second and third annexin domains, respectively.
Figure 3:
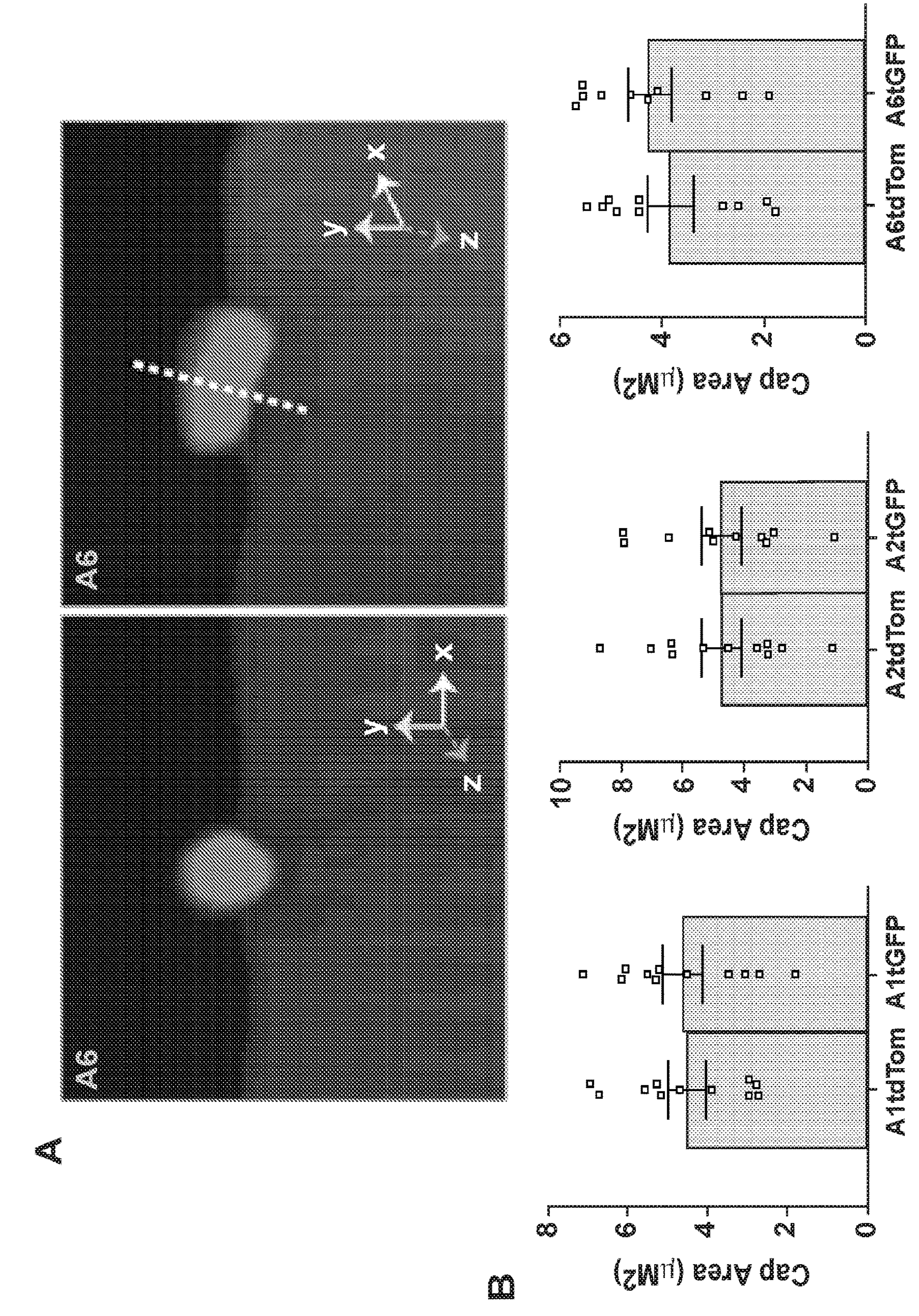
FIG. 3 shows A) Max projection of Z-stack imaging of repair cap (left). Rotated Z-stack projection (right). Cap size is measured from the center z-stack 2-D image represented by the white dotted line. B) Myofibers were co-electroporated with wildtype annexin-tdTomato and wildtype annexin-turboGFP. Cap size was assessed in both the red and green channels. The type of fluorescent tag did not influence cap size. Data are expressed as mean±SEM. Differences were tested by two-tailed t-test, (n≥10 fibers per condition).
Figure 4:
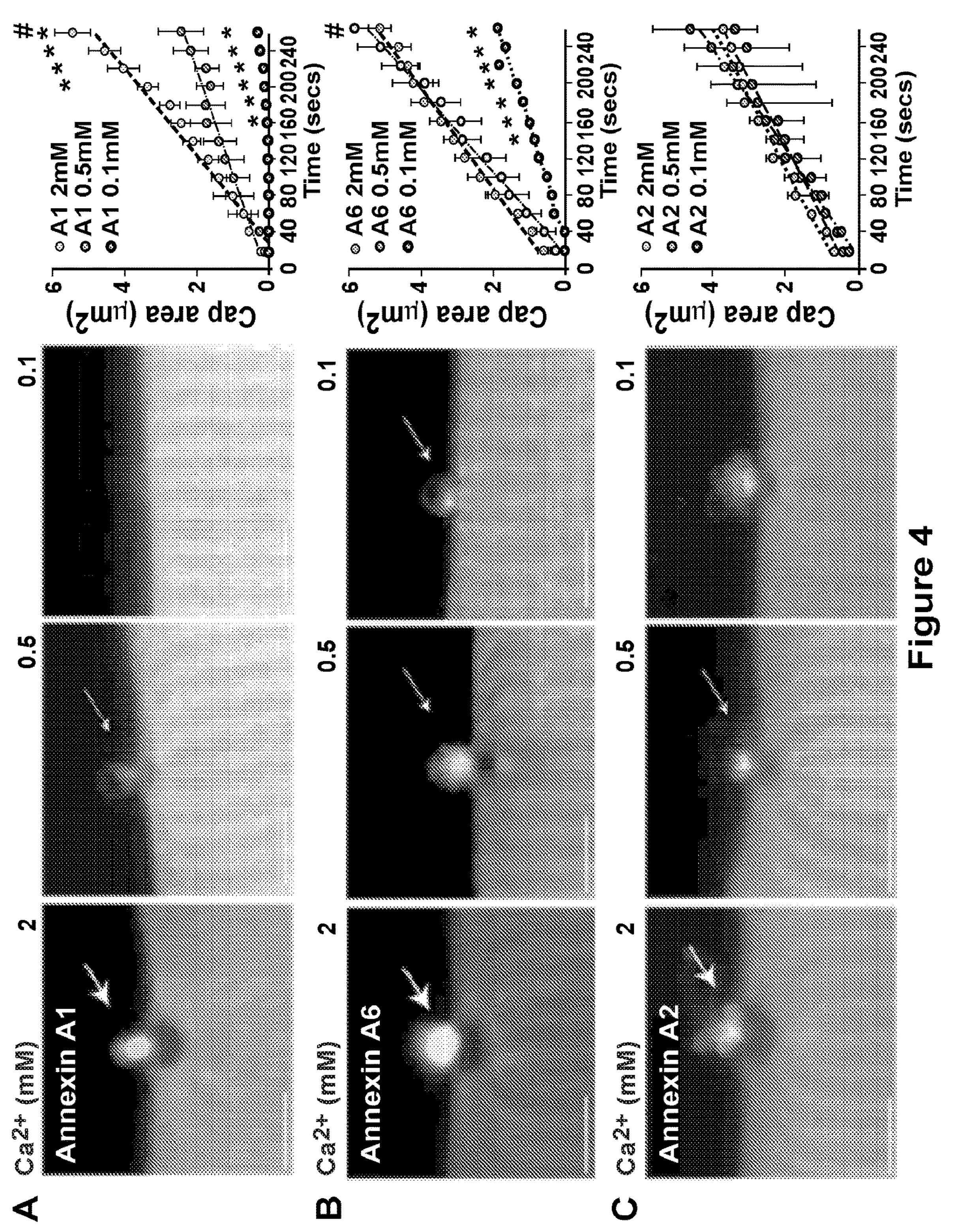
FIG. 4 shows differential $Ca^{2+}$ sensitivity of annexin A1, A2 and A6 in repair cap formation. Myofibers expressing fluorescently tagged annexin A1, A2 or A6 were injured at multiple $Ca^{2+}$ concentrations. A & B) Annexin A1 and A6 repair cap size was reduced with decreasing $Ca^{2+}$ concentrations. Annexin A1 and A6 repair cap area and rate of repair cap formation was reduced at 0.5 mM $Ca^{2+}$ and 0.1 mM compared to 2 mM. C) Annexin A2 repair cap area was significantly reduced at 0.05 mM $Ca^{2+}$ compared to 2 mM, 0.5 mμM, and 0.1 mM $Ca^{2+}$. The rate of annexin A2 repair cap formation was equivalent at the $Ca^{2+}$ concentrations tested. Data from the 0.05 mM concentration was not plotted as caps were too small to measure over time. Large arrow indicates large cap. Small arrow indicates small cap. * $p<0.05$ cap area or time, #$p<0.05$ statistically different slopes. Scale bar 5 μm. Data are expressed as mean±SEM. Differences were tested by 2-way ANOVA with Bonferroni's multiple comparisons test. * $p<0.05$ cap area or time, #$p<0.05$ statistically different slopes (n=4-7 myofibers per condition).
Figure 5:
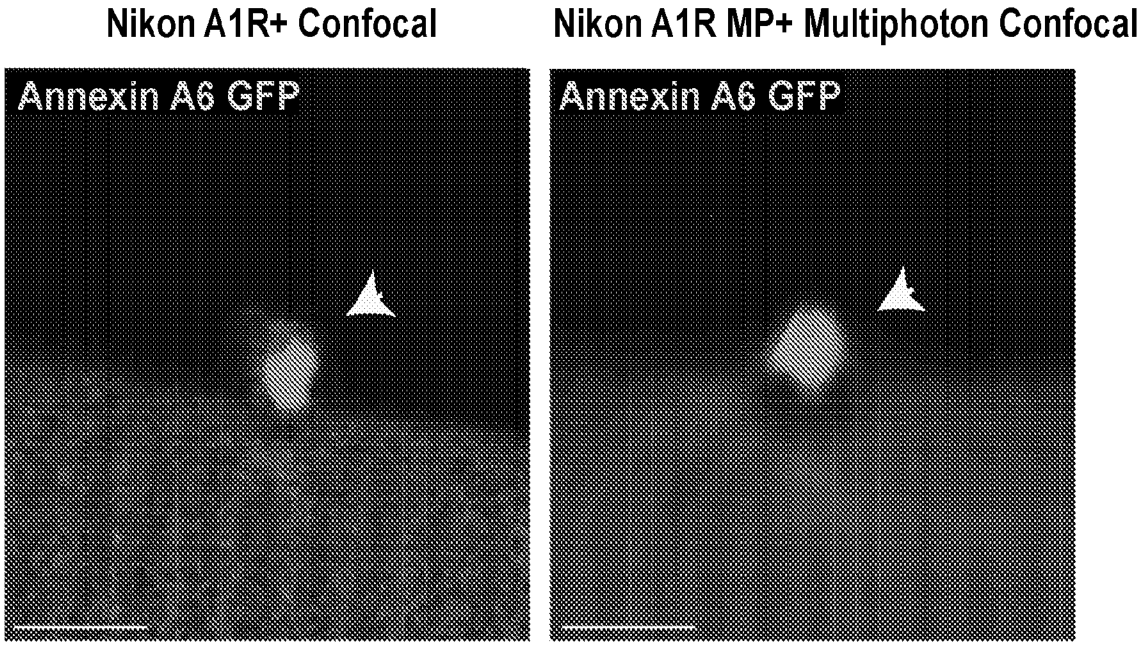
FIG. 5 shows myofiber laser injury on the Nikon A1R+ GaSP confocal and the Nikon A1R MP+ multiphoton confocal induced comparable annexin A6-GFP repair caps (arrowhead) at the site of membrane injury. Scale 5 μm. Myofibers from n≥3 mice per condition.

Annexin Repair Caps Exhibit Differential $Ca^{2+}$ Sensitivity During Repair Cap Recruitment Annexin proteins are $Ca^{2+}$-dependent phospholipid and actin binding proteins that contain four annexin repeat domains or eight in the case of annexin A6 (FIG. 2). Annexin repeat domains bind $Ca^{2+}$, but are distinct from the $Ca^{2+}$ binding of C2 domains and EF-hands seen in other classes of repair proteins (Gerke and Moss, 2002). Annexins coordinate $Ca^{2+}$ and bind membranes from their convex face (FIG. 2), and both type II and type III $Ca^{2+}$ binding sites have been described in annexin proteins. To further define the $Ca^{2+}$ requirements in annexin-mediated sarcolemmal repair in myofibers, annexins A1, A2, or A6 repair cap formation were examined over a range of $Ca^{2+}$ concentrations. Cap size was measured from the center of a z-stack, and the type of fluorescent tag, turboGFP or tdTomato, did not alter assessed parameters (FIGS. 3A and 3B). Annexin A1 and A6 repair cap size was $Ca^{2+}$-dependent, with the largest repair caps forming at 2 mM and smaller repair caps forming at 0.1 mM, while annexin A2 repair caps were not significantly reduced until 0.05 mM $Ca^{2+}$ (FIGS. 1C and 1D). Repair cap area was plotted as a function of $Ca^{2+}$ concentration using a modified Hill equation. Annexin A2 formed a repair cap at the lowest concentration of $Ca^{2+}$, 0.05 mM, while annexins A1 and A6 did not form a discernable cap at $Ca^{2+}$ concentrations lower than 0.1 mM $Ca^{2+}$, seen as the significant leftward annexin A2 curve with a $Km_{1/2}$ of 0.067 mM compared to A6 and A1, which showed $Km_{1/2}$ of 0.12 mM and 0.17 mM, respectively (FIG. 1D). Annexin A1 and A6 repair cap size and rate was highly dependent on $Ca^{2+}$ concentration (FIG. 4). The rate of annexin A2 cap formation and cap size was similar at 2 mM, 0.5 mM and 0.1 mM $Ca^{2+}$, while annexin A1 and A6 rates decreased with lower $Ca^{2+}$ concentrations, suggesting a high $Ca^{2+}$ affinity for annexin A2 (FIG. 4). To ensure that repair cap formation was not artifact due to the type of laser injury, we induced laser injury on both the Nikon A1R GaSP confocal and the Nikon A1R. MP+ multiphoton confocal. Injury induced by a multiphoton laser is more focused theoretically producing less collateral membrane damage. Annexin A6 repair caps appeared comparable with both types of lasers (FIG. 5). These data indicate that annexin A1, A2, and A6 repair cap formation is influenced by the level of $Ca^{2+}$ present during myofiber repair with annexin A2 being the most $Ca^{2+}$ sensitive of the three annexins studied.

Figure 6:
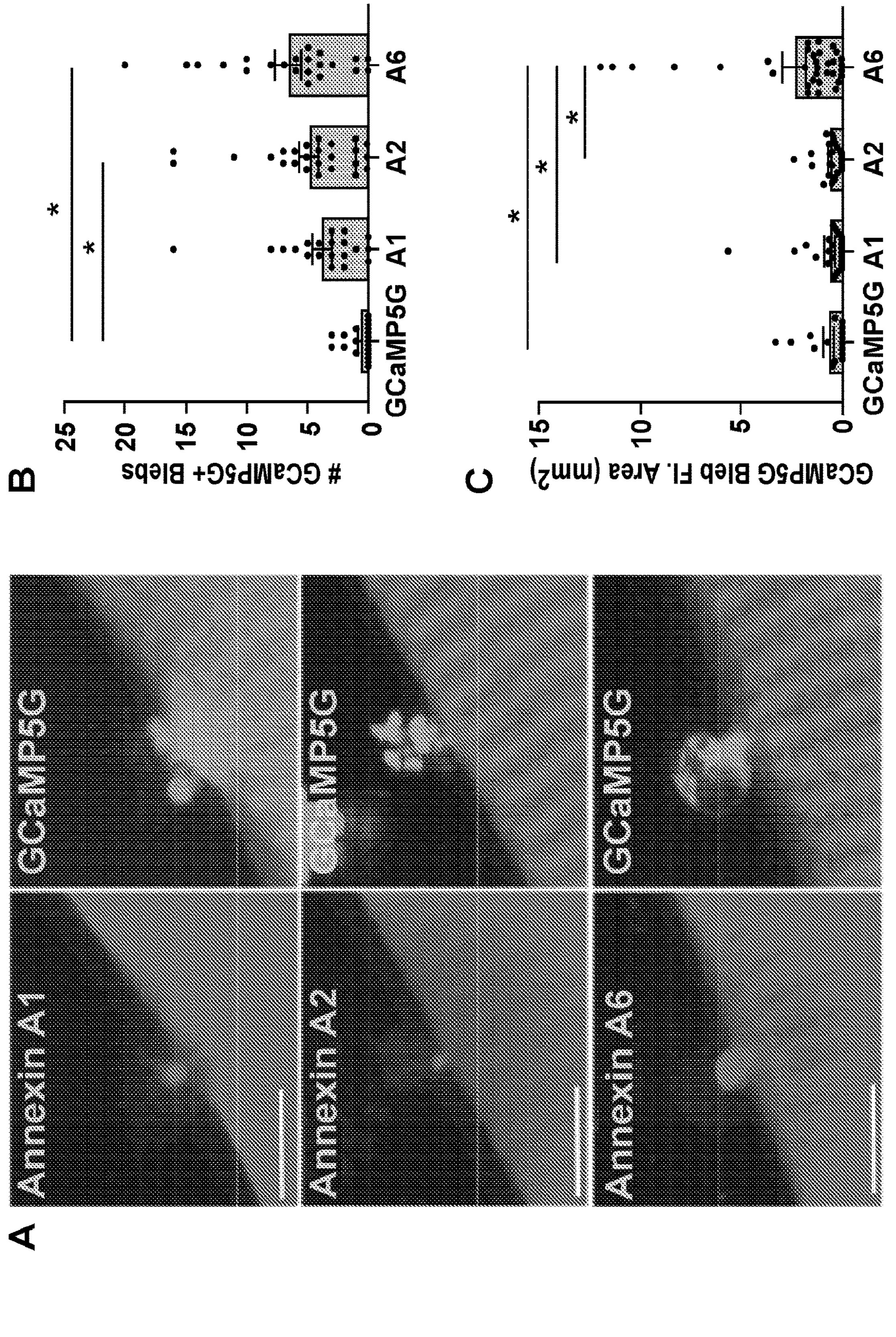
FIG. 6 shows that annexin expression promoted release of blebs from the site of myofiber repair. Myofibers were electroporated with the $Ca^{2+}$ indicator GCaMP5G with or without tdTomato-labeled annexin A1, annexin A2, or annexin A6. $Ca^{2+}$ area and fluorescence were assessed after membrane damage. A) High magnification z-projection images illustrate external blebs filled with the $Ca^{2+}$ indicator emanating from the lesion when annexin A1, A2, or A6 was co-expressed and a corresponding reduction of $Ca^{2+}$ indicator within the myofiber when compared to GCaMP5G alone. B) Expression of annexin A6 or A2 resulted in an increased number of GCaMP5G-positive blebs. C) Expression of annexin A6 resulted in the formation of the largest GCaMP5G-positive blebs. * $p<0.05$. (myofibers from n≥3 mice per condition).

Annexin Overexpression Promotes Bleb Formation at the Site of Membrane Injury Membrane repair assays in *Lytechinus pictus* and *Xenopus oocytes* suggested that membranous structures merge and erupt at the site of membrane repair (Bi et al., 1995; Davenport et al., 2016). Additionally, extracellular recombinant annexins promoted membrane folding and bleb formation of artificial membrane patches at sites of membrane imperfection in a $Ca^{2+}$ dependent manner (Boye et al., 2018; Boye et al., 2017). It was next investigated whether similar findings could be observed at the site of muscle membrane injury, which are sites of membrane imperfection, in live skeletal myofibers. GCaMP5G was expressed alone or in combination with annexin A1, A2 or A6 in skeletal myofibers. Overexpression of annexins was found to promote the formation of extracellular blebs emanating from annexin repair caps at the membrane lesion (FIG. 6A). These blebs appeared after the formation of annexin repair caps and were seen at the extracellular tip of the repair cap (FIG. 6A). Overexpression of annexin A6 and annexin A2 induced significantly more blebs than were observed after annexin A1 overexpression or GCaMP5G alone (FIGS. 6A and 6B). Furthermore, annexin-induced blebs contained significant GCaMP5G signal, and annexin A6 induced the formation of significantly larger GCaMP5G-containing blebs as compared to annexin A1, A2, or GCaMP5G alone (FIGS. 6A and 6C). These data indicated that annexins not only form a repair cap at the site of membrane disruption, but that these caps serve as sites for excretion of extracellular blebs enriched for $Ca^{2+}$-binding proteins.

Figure 7:
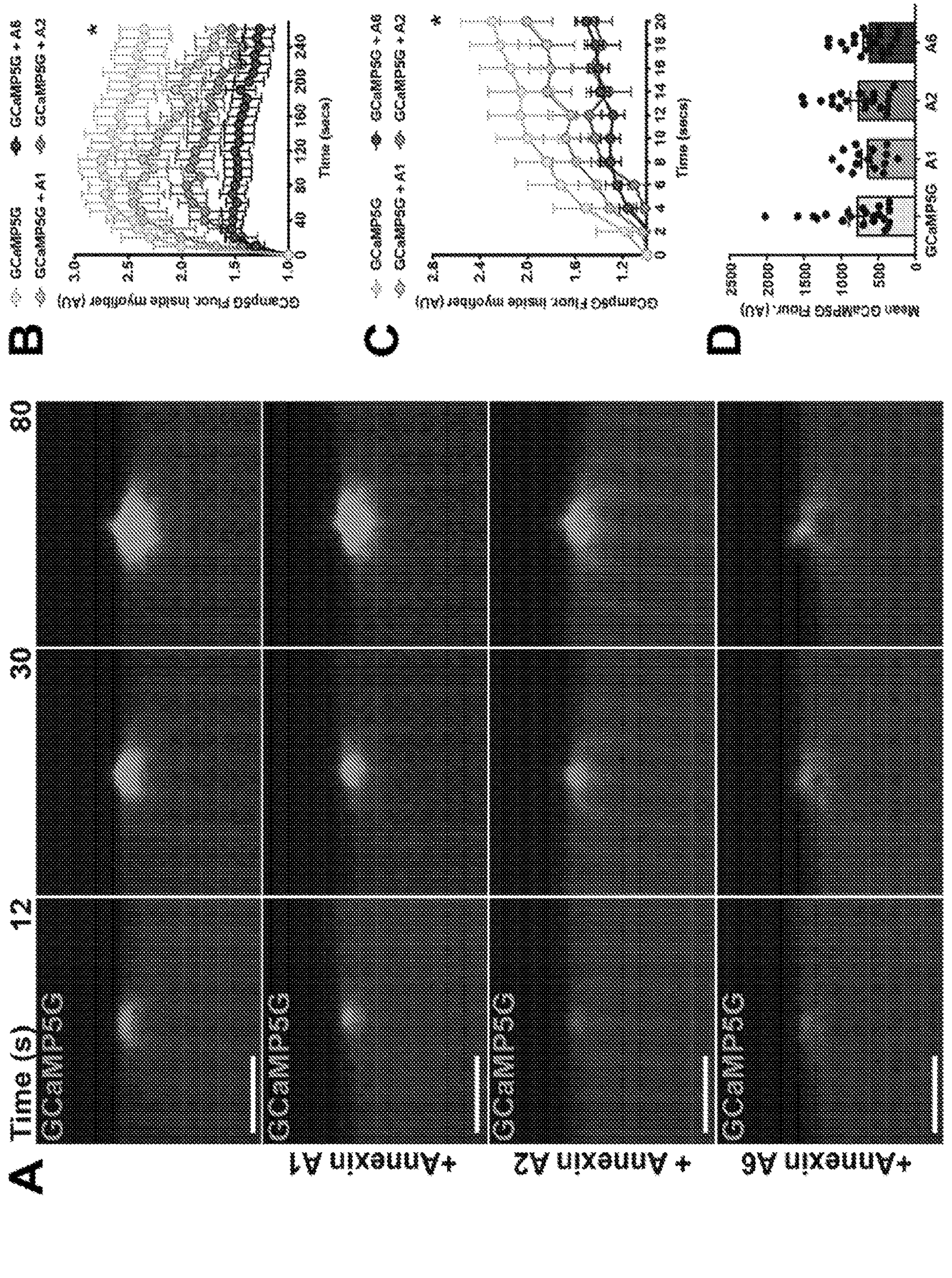
FIG. 7 shows that annexin expression reduced $Ca^{2+}$ within the myofiber. Myofibers were electroporated with the $Ca^{2+}$ indicator GCaMP5G with or without tdTomato-labeled annexin A1, annexin A2, or annexin A6 (annexin channel not shown). $Ca^{2+}$ area and fluorescence were assessed after membrane damage. A) Time-lapse single slice images illustrate co-expression of either annexin A1, A2 or A6 resulted in a significant reduction in GCaMP5G fluorescence measured inside the myofiber at the site of injury over time. B) Expression of either annexin A1, A2 or A6 resulted in a significant reduction in GCaMP5G fluorescence measured inside the myofiber at the site of injury over 240 seconds of imaging, with annexin A6 inducing the greatest reduction in GCaMP5G fluorescence. C) Both annexin A2 and A6 contributed to the early reduction in GCaMP5G fluorescence as seen by imaging during the first 20 seconds after injury. D) Initial GCaMP5G mean fluorescence is not significantly different between groups. Scale bar 5 μm. * $p<0.05$. Myofibers from n≥3 mice per condition. Data are expressed as mean±SEM. Differences were tested by 2-way-ANOVA test with Bonferroni's multiple comparisons test (B, C) or one-way ANOVA test with Tukey's multiple comparisons test (D). * $p<0.05$, (n=9 myofibers from n≥3 mice per condition).

Decreased Intracellular $Ca^{2+}$ Fluorescence at the Site of Injury with Annexin Overexpression Time lapse imaging of the $Ca^{2+}$ indicator GCaMP5G after laser injury suggested intracellular $Ca^{2+}$ was decreasing concomitant with extracellular bleb formation suggesting that these blebs serve to reduce intracellular $Ca^{2+}$ accumulation and/or excretion of cytoplasmic protein content emanating from the site of injury. The annexin-induced reduction in intracellular $Ca^{2+}$ fluorescence was seen for all three annexins A1, A2 and A6, but was most evident for annexin A2 and A6 (FIG. 7A). Over the 240 seconds of imaging, overexpression of annexin A6 induced the most significant reduction in intracellular $Ca^{2+}$, visualized as internal GCaMP5G $Ca^{2+}$ fluorescence (FIG. 7B). Detailed analysis of the first 20 seconds post injury showed a significant reduction in internal GCaMP5G $Ca^{2+}$ fluorescence with annexin A2 and A6, but not annexin A1, when compared to GCaMP5G alone (FIG. 7C). Baseline GCaMP5G fluorescence intensity prior to injury was not significantly different between groups (FIG. 7D). Thus, annexin expression induces a reduction of $Ca^{2+}$ signal within the injured myofiber concomitant with enhanced egress of $Ca^{2+}$-binding protein-filled blebs. Moreover, annexin A6 was the most effective of the three annexins tested at sustaining this response.

Figure 8:
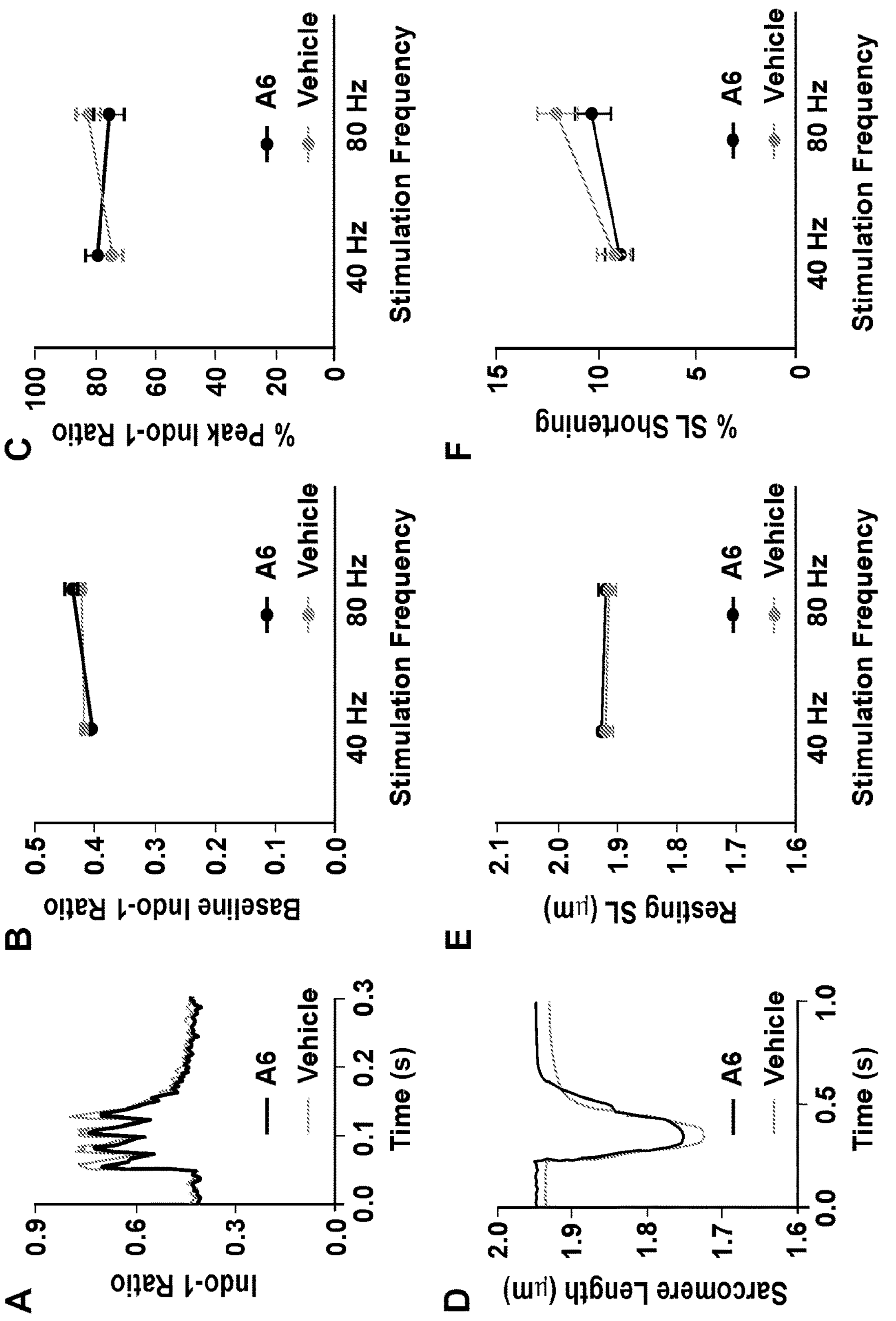
FIG. 8 shows that baseline $Ca^{2+}$ is not changed in myofibers overexpressing annexin A6. Myofibers electroporated with annexin A6-GFP or vehicle control. Isolated myofibers were loaded with Indo-1 AM dye and stimulated to measure $Ca^{2+}$ cycling and cell shortening. A) Representative $Ca^{2+}$ transient at 80 Hz. B & C) Resting $Ca^{2+}$ levels and peak $Ca^{2+}$ transient values were not changed between myofibers electroporated with annexin A6-GFP or vehicle control. D) Representative sarcomere length shortening traces. E & F). Resting sarcomere length and peak unloaded sarcomere length shortening did not differ between treatment groups. Myofibers from n≥3 mice per condition. Data are expressed as mean±SEM. Differences were tested by 2-way ANOVA (A, D) or two-tailed t-test (B, C, E, F), (n≥30 myofibers from n≥3 mice per condition).

Next, the $Ca^{2+}$ handling and contractile properties of isolated myofibers overexpressing annexin A6 compared to controls was evaluated. Isolated myofibers expressing annexin A6 were loaded with the ratiometric $Ca^{2+}$ indicator dye Indo-1, and no differences in $Ca^{2+}$ cycling at 40 or 80 Hz stimulation frequencies between annexin A6 or control fibers (FIGS. 8A, 8B, and 8C) were observed. Unloaded cell shortening was also unaffected by the presence of overexpressed annexin A6 (FIGS. 8D, 8E, and 8F). These results indicated that annexin A6 overexpression was well-tolerated by myofibers.

Figure 9:
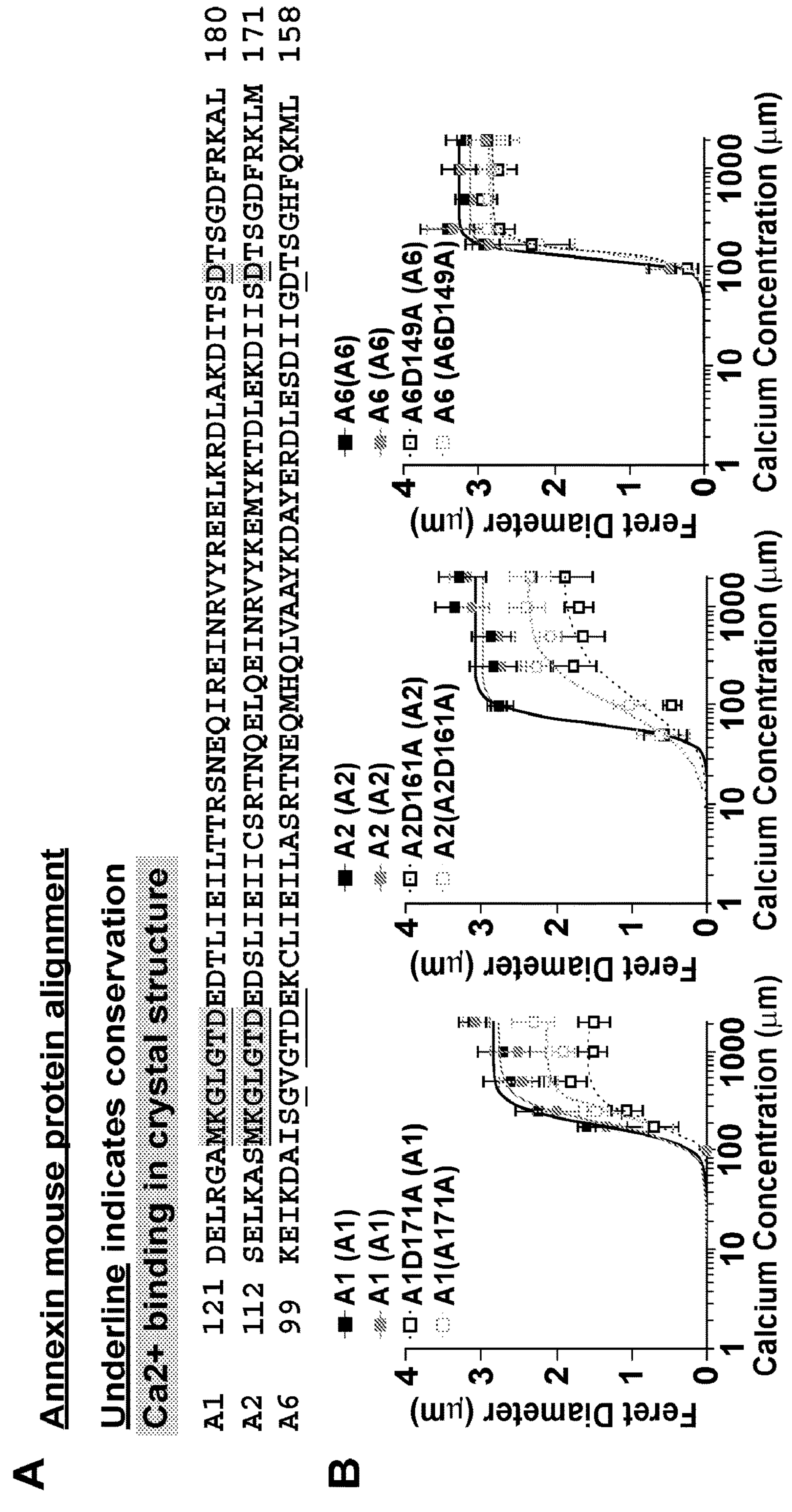
FIG. 9 shows A) The first type II $Ca^{2+}$-binding site in annexin A1 and A2 is conserved, while it is not conserved in annexin A6. B) Myofibers were co-electroporated with wildtype+wildtype or wildtype+mutant annexin constructs and cap size was assessed after sarcolemmal injury. Parentheses indicate protein that is co-expressed in the myofiber, but not visualized within the channel, to determine the effect on the co-expressed annexin. Cap kinetics were plotted as cap feret diameter over a range of $Ca^{2+}$ concentrations, from 0-2 mM. Expression of mutant annexin A1D171A and A2D161A, but not A6D149A was sufficient to significantly reduce the co-expressed wildtype annexin cap maximum diameter (DMAX). C) Expression of annexin A1D171A and A2D161A was not sufficient to significantly reduce the cap area of co-expressed annexin A6, although annexin A2D161A results were trending. #, * $p<0.05$ ns=non-significant. Myofibers from n≥3 mice per condition. Data are expressed as mean±SEM. Differences were tested by 2-way ANOVA with Bonferroni's multiple comparisons test (B) or two-tailed t-test (C). * $p<0.05$ #, ns=non-significant, (n≥5 myofibers from n≥3 mice per condition).
Figure 9:
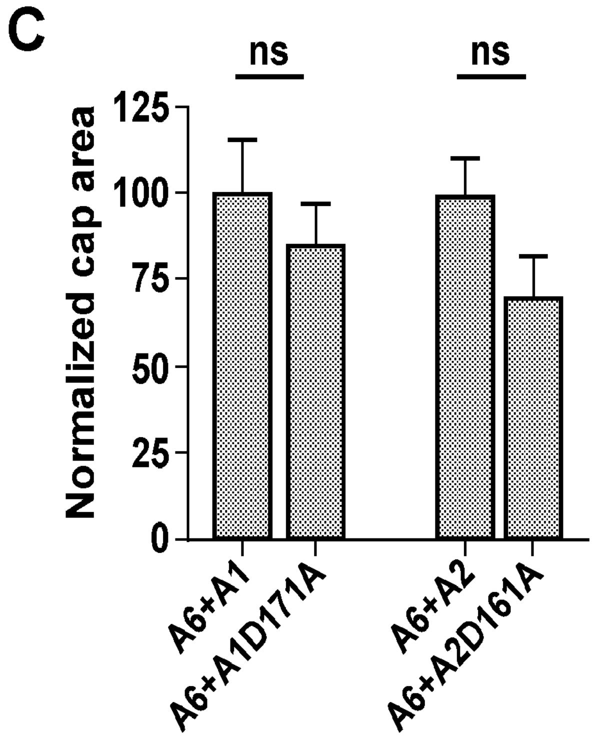
Figure 10:
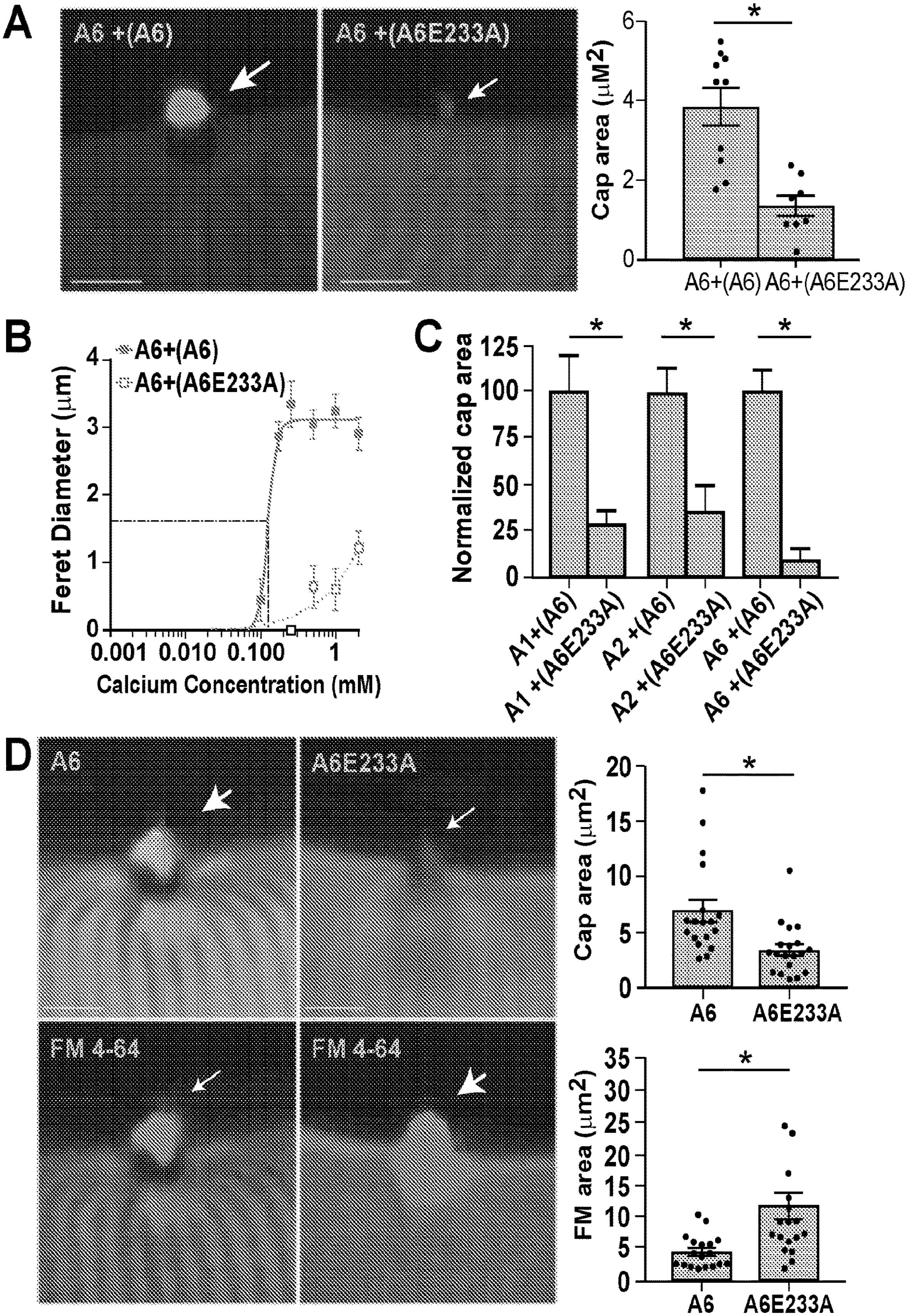
FIG. 10 shows annexin A6 $Ca^{2+}$ binding mutant reduced annexin repair cap recruitment and decreased myofiber membrane repair capacity. A) Myofibers were co-electroporated with wildtype-tdTomato and either wildtype-GFP or mutant-GFP annexin constructs. Cap size was assessed after membrane damage and only the red channel is shown to demonstrate the effect on wildtype annexin. B) Co-expression of mutant annexin A6E233A was sufficient to reduce wildtype annexin A6 cap assembly. Cap kinetics were plotted as cap feret diameter over a range of $Ca^{2+}$ concentrations, from 0-2 mM. C) Co-expression of annexin A6E233A was sufficient to significantly reduce the cap area of co-expressed annexin A1, A2 and A6. * $p<0.05$ WT (WT) vs. WT (MUT). D) Myofibers were electroporated with annexin A6-GFP or mutant A6E233A-GFP. Annexin A6E233A cap area was significantly smaller compared (small arrow) to annexin A6 (large arrowhead), correlating with increased FM 4-64 fluorescence area (large arrowhead). Scale bar 5 μm. * $p<0.05$. Myofibers from n≥3 mice per condition. Data are expressed as mean±SEM. Differences were tested by two-tailed t-test (A, C, D) * $p<0.05$, (n=4-18 myofibers from n≥3 mice per condition).

Annexin A6 $Ca^{2+}$ Binding is Required for Repair Cap Formation and Myofiber Repair Mutation of annexin A1D171 and A2D161 were previously shown to inhibit annexin membrane translocation in HEK cells (Jost et al., 1992; McNeil et al., 2006). It was queried whether these mutations would inhibit translocation and formation of the macromolecular annexin repair cap formed after muscle membrane injury. Alignment of annexins A1, A2 and A6 protein sequences identified conserved residues within the consensus sequence of type II $Ca^{2+}$ binding sites across all three annexin proteins (FIG. 2). In order to disrupt $Ca^{2+}$ binding in annexin A1, A2, and A6, site-directed mutagenesis was performed to convert the aspartic acid residue in the first type II $Ca^{2+}$ binding site into an alanine residue (A1D171A, A2D161A, A6D149A, respectively) (FIG. 9A). E233A was also generated in annexin A6 to create a similar change in the $Ca^{2+}$ binding site in the second annexin repeat domain of annexin A6. Each construct also contained turboGFP or tdTomato at the C-terminus. To assess the effect of homotypic annexin interactions during repair cap formation, myofibers were co-electroporated with wildtype+wildtype (A6+A6) or wildtype+mutant (A6+A6E233A) annexin combinations. Mutation of E233 in annexin A6 acted in a dominant-negative fashion, significantly decreasing cap size of the co-expressed wildtype annexin A6 protein (FIG. 10A). Prior structural studies suggested that D149 in the first annexin repeat domain of annexin A6 does not bind $Ca^{2+}$ (Avila-Sakar et al., 1998), and consistent with this, the D149A mutant in annexin A6 had little effect on cap size (FIG. 9B, right panel). The repair cap feret diameter was plotted as a function of $Ca^{2+}$ concentration using a modified Hill equation. Expression of mutant annexin A6E233A was sufficient to significantly reduce the cap diameter (DMAX) of the co-expressed wildtype annexin A6 protein (FIG. 10B). To assess the effect of heterotypic annexin interactions on repair cap formation, myofibers were co-electroporated with various combinations of wildtype and mutant annexin constructs. Co-expression of mutant annexin A6E233A resulted in a significant reduction in annexin A1, A2, and A6 cap size compared to A1+A6, A2+A6, A6+A6 controls, respectively (FIG. 10C). Together, these data showed that annexin proteins interact in a homotypic and heterotypic fashion influencing annexin repair complex-assembly and that the mutant annexin A6 protein is sufficient to negatively modulate annexin complex assembly during repair.

$Ca^{2+}$-binding of both annexin A1 and A2 was also required for repair cap formation. A1D171A and A2D161A mutant cap size was reduced compared to wildtype annexin A1 and A2 controls, respectively. Expression of mutant annexin A1D171A and A2D161A was sufficient to significantly reduce the repair cap diameter (DMAX) of the respective co-expressed wildtype annexin protein (FIG. 9B, left and middle panels). Despite the ability of mutant annexin A1D171A and A2D161A to significantly decrease co-expressed wildtype annexin A1 and A2 cap size, respectively, A1D171A or A2D171A had minimal effect of wildtype annexin A6 cap size (FIG. 9C). These data showed that annexin A1 and A2 interact in a homotypic fashion influencing self-cap assembly, while A6 localization to the repair cap is minimally modulated by annexin A1 and A2 localization.

To determine the effect of dominant negative annexin A6 on the assembly of annexins A1, A2, and A6 at the repair cap and membrane repair capacity, laser injury was similarly performed on isolated myofibers in the presence of FM 4-64. FM 4-64 is a membrane impermeable dye that is non-fluorescent in aqueous solution and increases fluorescence intensity as it binds membrane phospholipids exposed during injury, and is commonly used as a marker of membrane injury (Bansal et al., 2003; Cai et al., 2009; Demonbreun and McNally, 2015; Yeung et al., 2009; Zweifach, 2000). Myofibers expressing annexin A6E233A-GFP had increased FM 4-64 fluorescence area after laser injury compared to control myofibers expressing wildtype annexin A6-GFP (FIG. 10D). These results indicated that a functional annexin repair complex is required for proper membrane repair and annexin A6 participates in orchestrating complex formation.

Annexin A6 Protected Against Laser-Induced Myofiber Injury In Vitro

Figure 11:
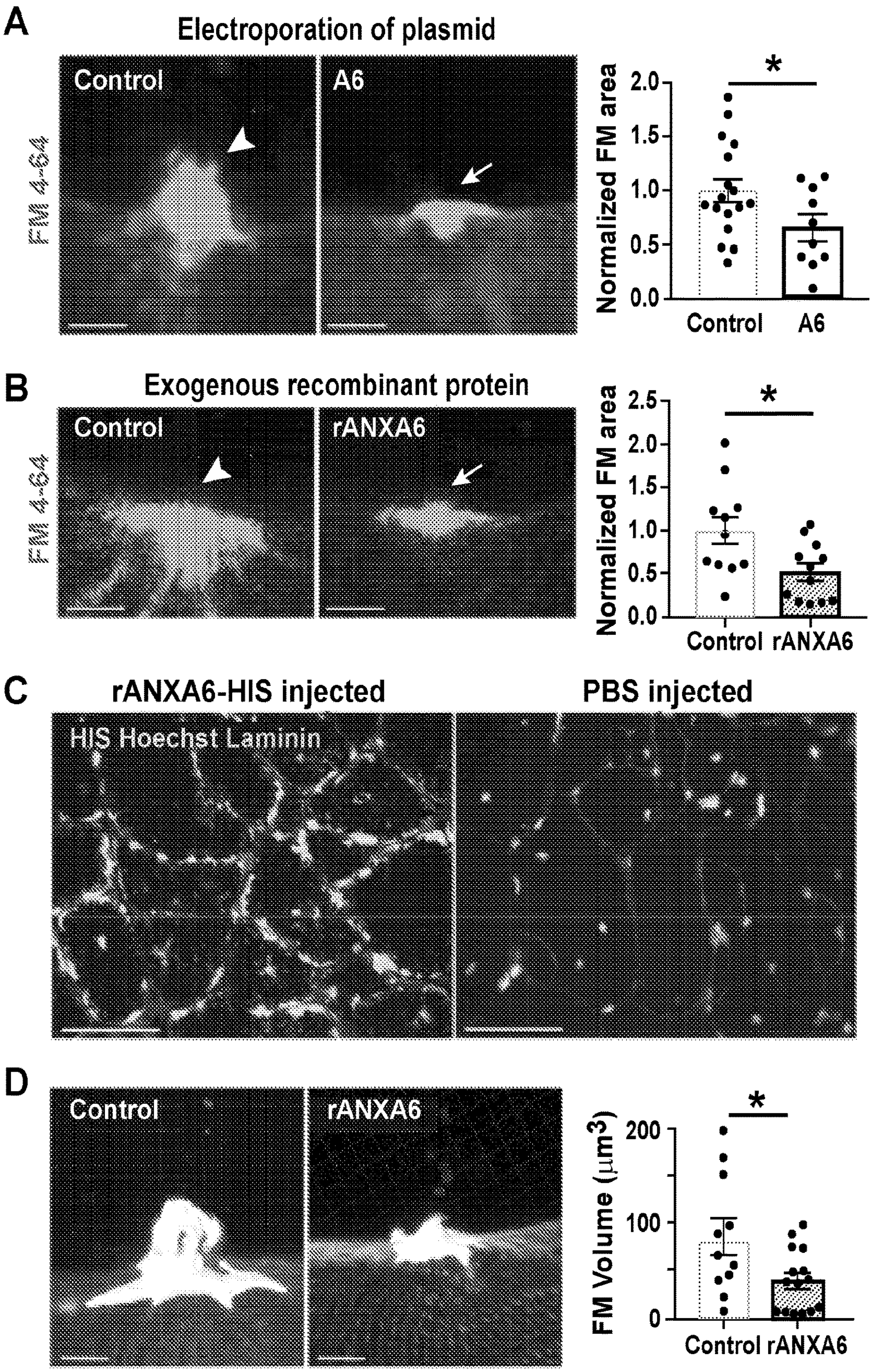
FIG. 11 shows annexin A6 enhanced myofiber membrane repair capacity. A) Overexpression of annexin A6 in wildtype myofibers reduced FM 4-64 dye uptake, a marker of membrane damage, after laser-induced injury as compared to control myofibers. B) Wildtype myofibers injured in the presence of extracellular recombinant annexin A6 (rANXA6) had significantly smaller FM 4-64 dye uptake than control myofibers. C) rANXA6 with a C-terminal HIS tag localized to the plasma membrane of mdx/hLTBP4 myofibers 6 hours post systemic injection, visualized by immunofluorescence microscopy. Anti-HIS staining was not visible in control muscle from mice injected with phosphate buffered saline (PBS). D) mdx/hLTBP4 myofibers injured in the presence of extracellular rANXA6 had significantly smaller FM 4-64 dye uptake (volume) than control myofibers depicted by the Imaris surface rendering of FM 4-64 fluorescence. Scale bar 5 μm (A, B, D). Scale bar 1 mm (C). * $p<0.05$. (myofibers from n≥3 mice per condition).

Since annexin A6 facilitates the formation of the macromolecular repair cap complex and was the most efficient at forming large, $Ca^{2+}$-filled blebs at the site of membrane injury, whether overexpression of annexin A6 would reduce membrane injury in wildtype myofibers was assessed. Wildtype myofibers were electroporated with annexin A6-GFP or mock electroporated and then laser damaged in the presence of FM 4-64, to mark the injury area. Wildtype myofibers overexpressing annexin A6 had decreased FM 4-64 dye uptake after laser-induced membrane injury compared to control myofibers (FIG. 11A). These results suggested that overexpression of annexin A6 is effective at improving membrane repair in isolated myofibers.

Next, it was tested whether extracellular recombinant annexin A6 could also protect against membrane injury in wildtype myofibers. Wildtype myofibers were isolated and incubated with recombinant annexin A6 (rANXA6) or vehicle control. Laser injury was conducted in the presence of FM 4-64. Pretreatment with extracellular recombinant annexin A6 reduced FM 4-64 fluorescence area compared to vehicle control treated myofibers (FIG. 11B). These data demonstrated that recombinant annexin A6 protects against membrane injury through extracellular exposure.

Recombinant Annexin A6 Protected Against Myofiber Injury in a Model of Chronic Muscle Disease Muscular dystrophy is a progressive muscle wasting disease, due to loss-of-function mutations in critical cytoskeletal or membrane associated proteins, that results in fragile membranes. mdx mice lack the integral membrane protein dystrophin and are a model of Duchenne muscular dystrophy (DMD) (Hoffman et al., 1987; Petrof et al., 1993). mdx mice expressing human Latent TGFβ binding protein 4 (mdx/hLTBP4) have a more severe form of muscular dystrophy, similar to what is seen in humans with DMD (Ceco et al., 2014; Flanigan et al., 2013; Quattrocelli et al., 2017b). Since recombinant annexin A6 protected against laser-induced membrane injury in wildtype muscle, it was next assessed whether exposure to recombinant annexin A6 would protect against membrane injury in the context of chronic muscle disease. anti-HIS (green) immunostaining revealed the presence of recombinant annexin A6-HIS at the sarcolemma of mdx/hLTBP4 dystrophic muscle after systemic injection, while vehicle control muscle lacked anti-HIS staining (FIG. 11C). Similar to isolated wildtype myofibers, pretreatment with extracellular recombinant annexin A6 reduced FM 4-64 fluorescence after laser-induced injury in mdx/hLTBP4 myofibers as compared to vehicle control treated myofibers (FIG. 11D). These combined data indicated that extracellular annexin A6 targets injured membrane, promotes more efficient repair and protects against injury of healthy and dystrophic myofibers.

Recombinant Annexin A6 Protected Against Myofiber Injury In Vivo

Figure 12:
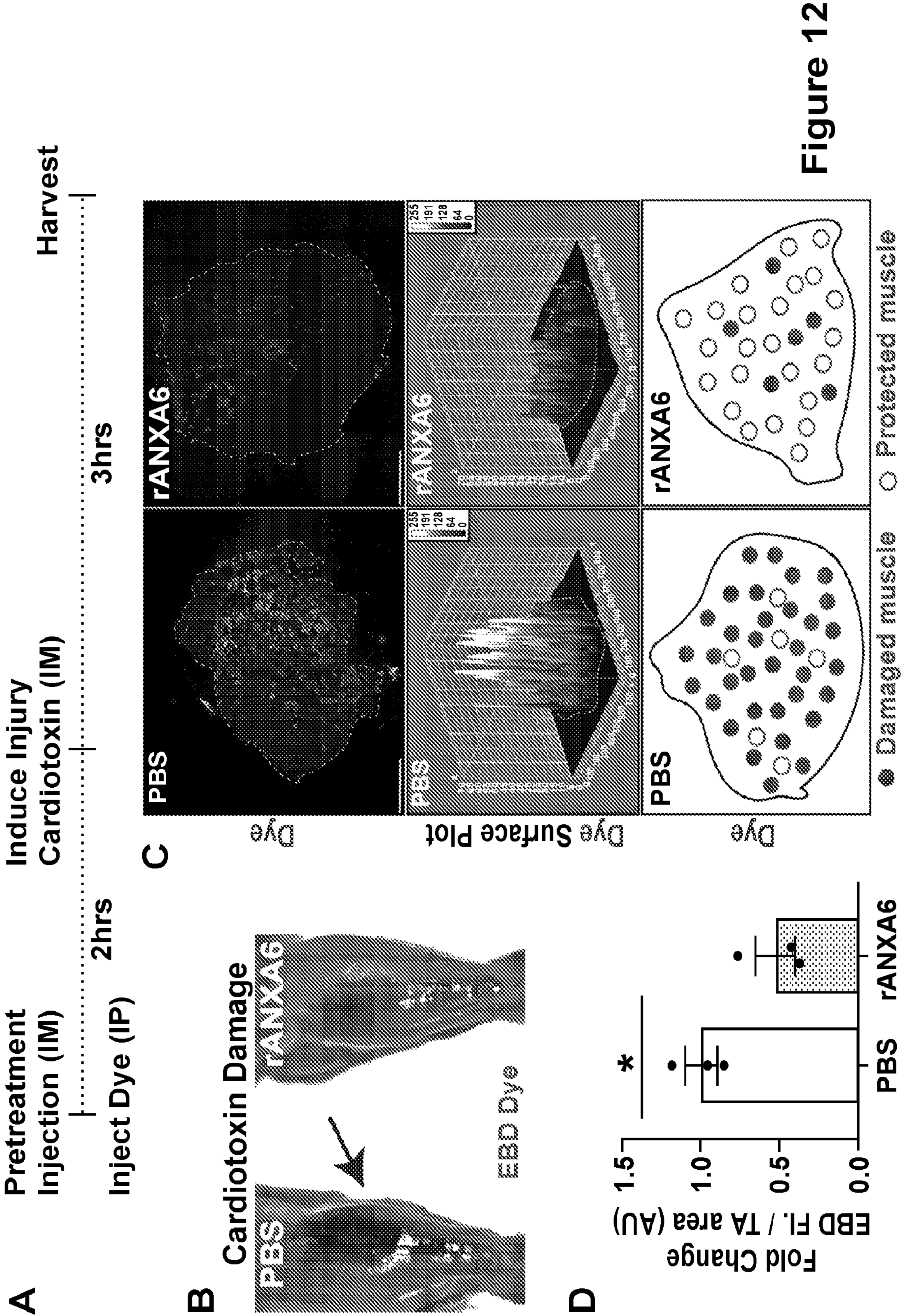
FIG. 12 shows that intramuscular injection of recombinant annexin A6 (rANXA6) protected against muscle damage in vivo. A) Tibialis anterior muscles of wildtype mice were pre-injected with rANXA6 or control solution and then damaged with cardiotoxin to induce muscle injury. B) Gross imaging revealed decreased dye uptake in rANXA6 pretreated muscle compared to the contralateral control muscle. C) Immunofluorescence imaging revealed decreased dye uptake in muscle pretreated with rANXA6. Surface plots of dye uptake depict reduced fluorescence in muscle pretreated with rANXA6. White dotted lines outline the muscle sections. D) Muscle pretreated with rANXA6 had a significant reduction, approximately 50%, of dye fluorescence over muscle area compared to control muscle. Scale 1 mm. * $p>0.05$ (from n=3 mice per condition). Data are expressed as mean±SEM. Differences were tested by two-tailed t-test * $p<0.05$, (n=3 mice per condition).

It was next assessed whether recombinant annexin A6 could protect against muscle injury in vivo. Recombinant annexin A6 or vehicle control was injected intramuscularly into the tibialis anterior (TA) muscles of wildtype mice. Mice were also injected intraperitoneally with Evan's blue dye, a vital tracer that is excluded by intact healthy myofibers but is readily taken up in injured permeable myofibers (Jennische and Hansson, 1986). Two hours post injection of recombinant annexin A6, the TA muscle was injured with cardiotoxin. Muscle was harvested 3 hours post-cardiotoxin injury and evaluated for Evan's blue dye uptake (FIG. 12A). Gross imaging showed that pretreatment with recombinant annexin A6 reduced cardiotoxin-induced muscle damage in vivo, as seen by reduced dye uptake compared to controls (FIG. 12B). Fluorescence imaging showed a 50% decrease in dye uptake with recombinant annexin A6 pretreatment compared to control muscle (FIGS. 12C and 12D). Surface plot profiles illustrate reduced dye fluorescence in tibialis anterior muscle pretreated with intramuscular recombinant annexin A6 (FIG. 12C). These results indicated that intramuscular recombinant annexin A6 can reduce membrane injury and promote membrane repair in vivo.

Figure 13:
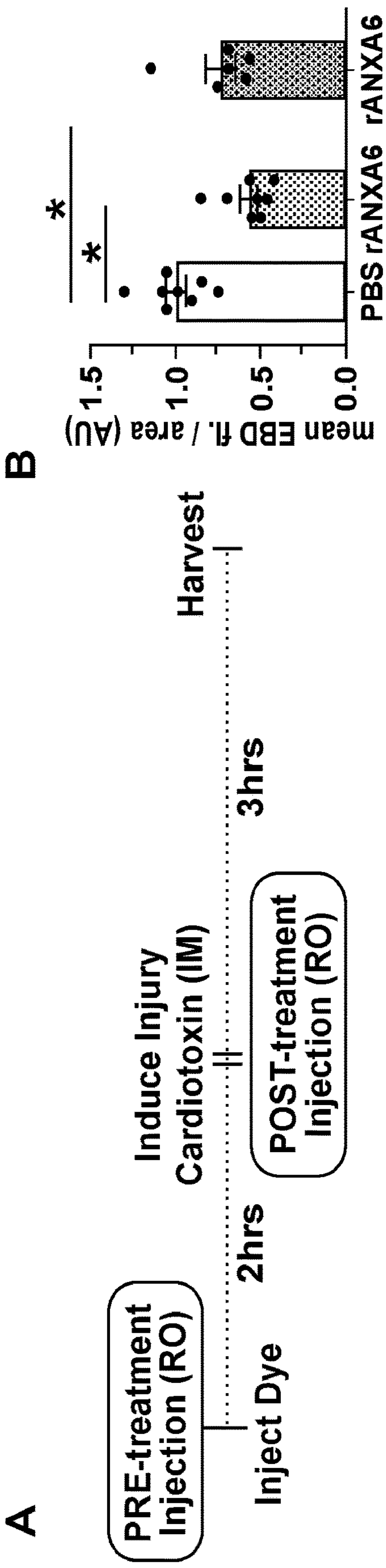
FIG. 13 shows that systemic injection of recombinant annexin A6 (rANXA6) protected against muscle damage in vivo. A) Wildtype mice were systemically injected with rANXA6 or control solution prior to cardiotoxin-induced muscle injury (pre-injected) or after cardiotoxin-induced muscle injury (post-injury). B-C) Immunofluorescence imaging revealed a significant decrease in dye uptake in Tibialis muscle pretreated or post-treated with rANXA6 compared to vehicle control. White dotted lines outline the muscle sections. Surface plots of dye uptake depict reduced fluorescence in muscle pretreated with rANXA6. Scale 1 mm. * $p>0.05$ (from n≥3 mice, n≥6 legs per condition).

Although intramuscular injection of annexin A6 was effective at reducing injury, this route of application is not optimal for large muscle groups, internal tissues, or treatment of chronic diseases. Therefore, the efficacy of recombinant annexin A6 administered via systemic retro-orbital (RO) injection was examined. Recombinant annexin A6 or control solution was injected 2 hours prior to cardiotoxin-induced tibialis anterior muscle injury (pretreatment). Alternatively, recombinant annexin A6 was administered immediately after tibialis anterior (TA) muscles were injured with cardiotoxin (post-treatment). Additionally, Evan's blue dye, was injected prior to injury. Muscle was harvested 3 hours post cardiotoxin injury and evaluated for dye uptake (FIG. 13A). Fluorescence imaging showed a significant decrease in dye uptake with recombinant annexin A6 pretreatment and post-treatment compared to vehicle control (FIGS. 13B and 13C). Surface plot profiles illustrate reduced dye fluorescence in tibialis anterior muscle pretreated and post-treated with systemic recombinant annexin A6 (FIG. 13C). These results demonstrated that recombinant annexin A6 reduces membrane injury and promotes membrane repair through intravenous systemic administration in vivo administered both before and after muscle injury.

Recombinant Annexin A6 Protected Against Chronic Muscle Injury In Vivo

Figure 14:
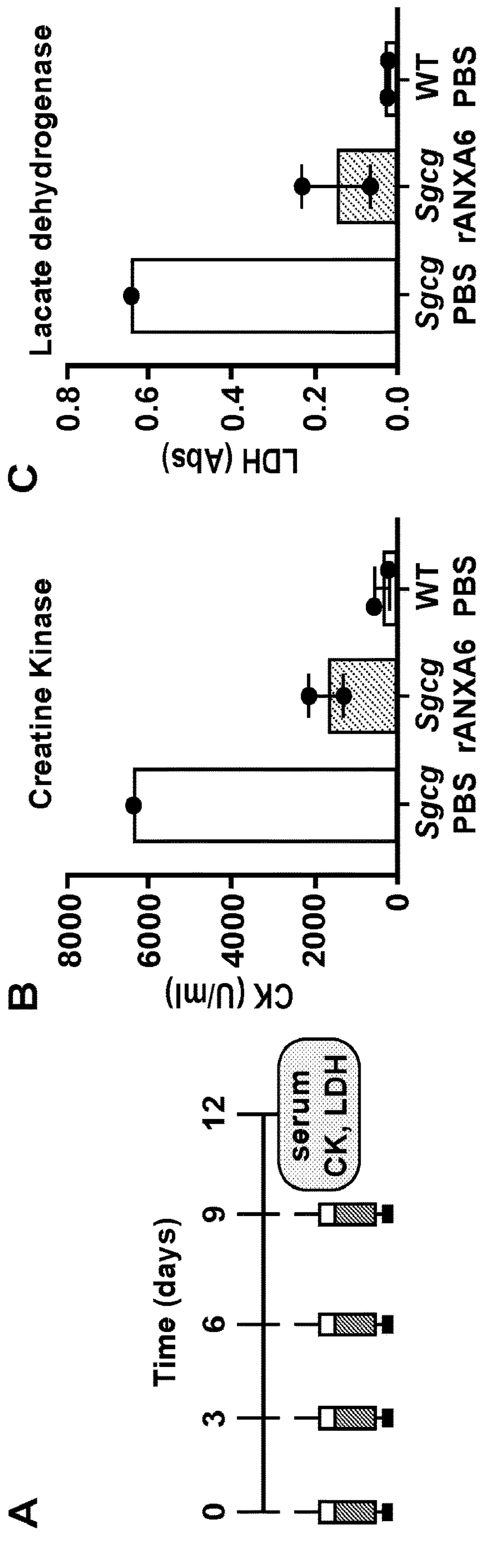
FIG. 14 shows that systemic injection of recombinant annexin A6 (rANXA6) protected against chronic muscle damage in vivo. A) Sgcg-null mice, a model of limb girdle muscular dystrophy 2C (LGMD2C), were injected with rANXA6 or control solution every 3 days for a total of 12 days. B-C) Creatine kinase (CK) and lactate dehydrogenase (LDH), clinically validated serum biomarkers of muscle injury, were then evaluated. Treatment with rANXA6 reduced serum CK and LDH compared to control, indicating enhanced repair of chronically injured muscle tissue.

Since recombinant annexin A6 protected against acute membrane injury in wildtype muscle in vivo, it was next assessed whether exposure to recombinant annexin A6 would protect against membrane injury in the context of chronic muscle disease. Mutations in the gene γ-sarcoglycan (SGCG) cause Limb-Girdle muscular dystrophy 2C (LGMD2C) in both mice and humans. To determine the if recombinant annexin A6 could facilitate repair in a chronic injury setting, sgcg-null mice were injected once every 3 days for 12 days with recombinant protein or control solution and then serum biomarkers of muscle damage, creatine kinase (CK) and lactate dehydrogenase (LDH), were quantified (FIG. 14A). Systemic treatment with recombinant annexin A6 reduced both serum CK and LDH levels in sgcg-null mice (FIGS. 14B and 14C). These results demonstrated that systemic recombinant annexin A6 promotes membrane repair in a model of chronic muscle disease.

Discussion

Annexins promote bleb formation at the site of membrane injury. It was found that increased expression of annexins in muscle fibers decreased injury-associated $Ca^{2+}$ fluorescence accumulation within myofibers. This reduction correlated with extracellular bleb formation arising at the site of annexin repair caps. We found that annexin A2 and A6 induced the formation of membranous blebs containing the $Ca^{2+}$-binding protein GCaMP5G emanating from the repair cap. Furthermore, overexpression of annexins A1, A2, and A6 each reduced endpoint $Ca^{2+}$ fluorescence accumulation within the myofiber after injury. Annexin A6 overexpression resulted in the most sustained effect on reducing injury-associated $Ca^{2+}$ accumulation inducing the formation of large GCaMP5G-containing blebs. A model is contemplated in which annexin A6 facilitates $Ca^{2+}$ and protein excretion into blebs whose formation was further induced by annexin A1 and annexin A2. In artificial membrane patches, the presence of annexin A1 or annexin A2 induced bleb formation at sites of membrane imperfection (Boye et al., 2018). In contrast, the presence of annexin A6 induced contraction of artificial membrane into large folds, in a $Ca^{2+}$-dependent manner (Boye et al., 2018). The difference between annexin A6 inducing blebs in live myofibers or folds in artificial membrane is likely do to the presence of endogenously expressed annexin A1 and A2 in isolated myofibers compared with exposure to single recombinant annexin protein in the artificial membrane studies. Without being bound by theory, it is hypothesized that within the macromolecular repair complex, annexins actively participate in bleb formation which acts to remove large membrane lesions facilitating wound closure, excision of damaged membrane, and reduction of $Ca^{2+}$ at the injury site.

Similar to the data described herein, others have shown that in damaged *Xenopus oocytes*, GCaMP5G fluorescence quickly localized in a ring around the site of membrane disruption, fading by approximately 5 minutes post injury, as healing progressed (Davenport et al., 2016). Overexpression of annexin A1-GFP in injured *Xenopus oocytes* resulted in annexin A1 positive blebs originating from the site of damage (Davenport et al., 2016). However, the effect of annexin overexpression on GCaMP5G fluorescence was not assessed. These data combined suggest that bleb formation, as a mechanism of membrane repair, is conserved across species and tissue types, and is facilitated by the presence of annexin proteins.

Annexin A6 protects against muscle membrane injury and enhances membrane repair. As shown herein, annexin proteins, including annexin A1, A2, and A6, localize to the site of membrane injury facilitating membrane repair cap and bleb formation. Mutation of annexin A6 abrogated repair cap formation, decreasing repair capacity, resulting in increased dye uptake. On the other hand, pretreatment with recombinant annexin A6 reduced dye uptake after laser-induced muscle injury and after toxin-induced muscle injury in vivo. This data, however, does not distinguish between annexin A6 enhancing membrane repair, reducing membrane injury, or a combination of both mechanisms. As a therapeutic tool, enhancing the cells' ability to repair and/or reduce injury through stabilizing the cell membrane are both beneficial avenues that can lead to improved cell survival. Previous studies have shown that annexin A6 is upregulated in muscle from models of chronic muscular dystrophy (Demonbreun et al., 2016a; Demonbreun et al., 2014; Swaggart et al., 2014). Additional proteomic approaches in the mdx mouse model have shown that annexin A1, A2, and A6 are enriched in mdx muscle membrane, again, suggesting a role for annexins at the membrane of injured cells (Murphy et al., 2018). Annexins bind membrane phospholipids, including phosphatidylserine, which is exposed during membrane disruption. Phosphatidylserine rearrangement upon injury provides a likely binding target for extracellular annexins to facilitate membrane folding, blebbing, and rolling at sites of membrane damage and imperfection (Boye et al., 2018). Based on the data herein, upregulation of annexin A6 is a compensatory mechanism to facilitate excision of defective membrane in fibers undergoing chronic damage. It is further contemplated that recombinant annexin A6 can facilitate membrane repair and reduce the susceptibility to injury long-term in chronic models of disease and in tissues beyond skeletal muscle.

Combinatorial approaches to improve membrane repair. As shown herein, recombinant annexin A6 protected normal and dystrophic muscle from laser-induced membrane injury. In addition, both intramuscular and systemic administration of recombinant annexin A6 protected against toxin-induced muscle membrane injury in vivo. Intriguingly, glucocorticoid administration increased annexin expression in muscle and this correlated with enhanced muscle repair in multiple mouse models of muscular dystrophy including mdx (DMD), dysferlin-null (LGMD2B), and γ-sarcoglycan-null (LGMD2C) mice (Quattrocelli et al., 2017a; Quattrocelli et al., 2017c). Importantly, glucocorticoid treatment also increased the expression of mitsugumin 53 (also known as MG53 or Trim 72), a repair protein that localizes to the site of membrane injury and is considered a "molecular band-aid" improving cellular wound healing. Similar to the annexins, MG53 is upregulated in chronic muscle injury and enhances repair in dystrophic muscles, as well as other tissues like heart, lung, kidney (Waddell et al., 2011). (Duann et al., 2015; He et al., 2012; Jia et al., 2014; Liu et al., 2015; Weisleder et al., 2012). MG53 is a component of the annexin-mediated repair complex, localizing juxtaposed to the annexin repair cap (Demonbreun et al., 2016b). It is contemplated that co-administration of recombinant annexin A6 with glucocorticoids and/or MG53 will further strengthen clinical relevance of these therapeutics for conditions resulting from membrane lesions.

In summary, the data provided herein demonstrate that annexins promote the formation of blebs released at the site of muscle membrane insult, with annexin A6 being the most effective at facilitating this process. Furthermore, recombinant annexin A6 protects against membrane injury of normal and dystrophic muscle. These data identify annexin A6 as a therapeutic target that enhances membrane repair capacity in healthy and diseased muscle.

Example 3

This example details the results of additional and updated experiments that were performed.

Membrane repair is essential to cell survival. In skeletal muscle, injury often associates with plasma membrane disruption. Additionally, muscular dystrophy is linked to mutations in genes that produce fragile membranes or reduce membrane repair. Methods to enhance repair and reduce susceptibility to injury could benefit muscle in both acute and chronic injury settings. Annexins are a family of membrane-associated $Ca^{2+}$-binding proteins implicated in repair, and annexin A6 was previously identified as a genetic modifier of muscle injury and disease. Annexin A6 forms the repair cap over the site of membrane disruption. To elucidate how annexins facilitate repair, annexin cap formation was visualized during injury. Annexin cap size was found to be positively correlated with increasing $Ca^{2+}$ concentrations. It was also found that annexin overexpression promoted external blebs enriched in $Ca^{2+}$ fluorescence and correlated with a reduction of intracellular $Ca^{2+}$ fluorescence at the injury site. Annexin A6 overexpression reduced membrane injury, consistent with enhanced repair. Treatment with recombinant annexin A6 protected against acute muscle injury in vitro and in vivo. Moreover, administration of recombinant annexin A6 in a model of muscular dystrophy reduced serum creatinine kinase, a biomarker of disease. These data identified annexins as mediators of membrane-associated $Ca^{2+}$ release during membrane repair and annexin A6 as a therapeutic target to enhance membrane repair capacity.

Annexin A6 forms a repair cap at the site of muscle membrane disruption. The data herein demonstrated that adding exogenous recombinant annexin A6 (rANXA6) promotes membrane resealing and recovery from injury.

Introduction

Plasma membrane repair occurs after membrane disruption and is a highly conserved process. The active process required for resealing membrane disruptions is thought to rely on $Ca^{2+}$-dependent vesicle fusion and local cytoskeletal remodeling (McNeil P L, and Khakee R. Disruptions of muscle fiber plasma membranes. Role in exercise-induced damage. Am J Pathol. 1992; 140(5):1097-109; McNeil P L, and Kirchhausen T. An emergency response team for membrane repair. Nat Rev Mol Cell Biol. 2005; 6(6):499-505). Other models suggest that membrane repair is mediated through the fusion of lysosomal vesicles, lateral diffusion of membrane to the site of injury, and the extrusion of membranous blebs (Rodriguez A, Webster P, Ortego J, and Andrews N W. Lysosomes behave as $Ca^{2+}$-regulated exocytic vesicles in fibroblasts and epithelial cells. J Cell Biol. 1997; 137(1):93-104; Reddy A, Caler E V, and Andrews N W. Plasma membrane repair is mediated by Ca(2+)-regulated exocytosis of lysosomes. Cell. 2001; 106(2):157-69; Demonbreun A R, Quattrocelli M, Barefield D Y, Allen M V, Swanson K E, and McNally E M. An actin-dependent annexin complex mediates plasma membrane repair in muscle. The Journal of cell biology. 2016; 213(6):705-18; McDade J R, Archambeau A, and Michele D E. Rapid actin-cytoskeleton-dependent recruitment of plasma membrane-derived dysferlin at wounds is critical for muscle membrane repair. FASEB J. 2014; 28(8):3660-70; Babiychuk E B, Monastyrskaya K, Potez S, and Draeger A. Blebbing confers resistance against cell lysis. Cell Death Differ. 2011; 18(1):80-9). These models are not mutually exclusive and may depend on the type and extent of damage. Skeletal muscle is highly dependent on plasma membrane repair as mutation in genes encoding repair proteins lead to muscle disease (Bansal D, Miyake K, Vogel S S, Groh S, Chen C C, Williamson R, et al. Defective membrane repair in dysferlin-deficient muscular dystrophy. Nature. 2003; 423(6936):168-72; Bashir R, Britton S, Strachan T, Keers S, Vafiadaki E, Lako M, et al. A gene related to *Caenorhabditis elegans* spermatogenesis factor fer-1 is mutated in limb-girdle muscular dystrophy type 2B. Nat Genet. 1998; 20(1):37-42; Demonbreun A R, Swanson K E, Rossi A E, Deveaux H K, Earley J U, Allen M V, et al. Eps 15 Homology Domain (EHD)-1 Remodels Transverse Tubules in Skeletal Muscle. PLOS One. 2015; 10(9):e0136679; Demonbreun A R, and McNally E M. Plasma Membrane Repair in Health and Disease. Curr Top Membr. 2016; 77:67-96; Defour A, Medikayala S, Van der Meulen J H, Hogarth M W, Holdreith N, Malatras A, et al. Annexin A2 links poor myofiber repair with inflammation and adipogenic replacement of the injured muscle. Human molecular genetics. 2017; 26(11):1979-91; Cai C, Masumiya H, Weisleder N, Matsuda N, Nishi M, Hwang M, et al. MG53 nucleates assembly of cell membrane repair machinery. Nat Cell Biol. 2009; 11(1):56-64).

The annexins are a family of $Ca^{2+}$-binding proteins that regulate lipid binding, cytoskeletal reorganization, and membrane folding, steps necessary for membrane repair (Jimenez A J, and Perez F. Plasma membrane repair: the adaptable cell life-insurance. Curr Opin Cell Biol. 2017; 47:99-107; Lauritzen S P, Boye T L, and Nylandsted J. Annexins are instrumental for efficient plasma membrane repair in cancer cells. Semin Cell Dev Biol. 2015; 45:32-8; Bizzarro V, Petrella A, and Parente L. Annexin A1: novel roles in skeletal muscle biology. J Cell Physiol. 2012; 227(8):3007-15; Grewal T, Hoque M, Conway J R W, Reverter M, Wahba M, Beevi S S, et al. Annexin A6-A multifunctional scaffold in cell motility. Cell Adh Migr. 2017; 11(3):288-304; Boye T L, Jeppesen J C, Maeda K, Pezeshkian W, Solovyeva V, Nylandsted J, et al. Annexins induce curvature on free-edge membranes displaying distinct morphologies. Sci Rep. 2018; 8(1):10309; Boye T L, Maeda K, Pezeshkian W, Sonder S L, Haeger S C, Gerke V, et al. Annexin A4 and A6 induce membrane curvature and constriction during cell membrane repair. Nat Commun. 2017; 8(1):1623). Individual annexin repeat domains coordinate $Ca^{2+}$ binding with unique annexin-specific type II or type III binding sites. Differential $Ca^{2+}$ affinity of the type II and type III binding sites provides each annexin a unique ability to respond to a range of intracellular $Ca^{2+}$ levels and phospholipid binding (Blackwood R A, and Ernst J D. Characterization of Ca2(+)-dependent phospholipid binding, vesicle aggregation and membrane fusion by annexins. The Biochemical journal. 1990; 266(1):195-200). Annexins have the ability to self- and hetero-oligomerize (Zaks W J, and Creutz C E. Ca(2+)-dependent annexin self-association on membrane surfaces. Biochemistry. 1991; 30(40):9607-15). Typical annexins like A1 and A2 contain one annexin core composed of four annexin repeat domains. In contrast, annexin A6 contains two annexin cores and thus eight annexin repeat domains (Benz J, Bergner A, Hofmann A, Demange P, Gottig P, Liemann S, et al. The structure of recombinant human annexin VI in crystals and membrane-bound. J Mol Biol. 1996; 260(5):638-43). Annexin A6's duplicated structure makes it possible for the amino- and carboxyl-terminal annexin core domains to bind one or two distinct membranes making annexin A6 a prime target for facilitating membrane coalescence and folding required during membrane repair (Boye T L, Jeppesen J C, Maeda K, Pezeshkian W, Solovyeva V, Nylandsted J, et al. Annexins induce curvature on free-edge membranes displaying distinct morphologies. Sci Rep. 2018; 8(1):10309; Boye T L, Maeda K, Pezeshkian W, Sonder S L, Haeger S C, Gerke V, et al. Annexin A4 and A6 induce membrane curvature and constriction during cell membrane repair. Nat Commun. 2017; 8(1):1623; Buzhynskyy N, Golczak M, Lai-Kee-Him J, Lambert O, Tessier B, Gounou C, et al. Annexin-A6 presents two modes of association with phospholipid membranes. A combined QCM-D, AFM and cryo-TEM study. Journal of structural biology. 2009; 168(1):107-16).

Annexins have a high affinity for phosphatidylserine, phosphatidylinositol, and cholesterol, which are highly enriched in the sarcolemma (Gerke V, Creutz C E, and Moss S E. Annexins: linking $Ca^{2+}$ signalling to membrane dynamics. Nat Rev Mol Cell Biol. 2005; 6(6):449-61; Fiehn W, Peter J B, Mead J F, and Gan-Elepano M. Lipids and fatty acids of sarcolemma, sarcoplasmic reticulum, and mitochondria from rat skeletal muscle. The Journal of biological chemistry. 1971; 246(18):5617-20). Multiple annexins, including annexins A1, A2, and A6, have been implicated in membrane repair in skeletal muscle, as well as *Xenopus oocytes*, human trophoblasts, and HeLa cancer cells, suggesting a conserved mechanism (Demonbreun A R, Quattrocelli M, Barefield D Y, Allen M V, Swanson K E, and McNally E M. An actin-dependent annexin complex mediates plasma membrane repair in muscle. The Journal of cell biology. 2016; 213(6):705-18; Babbin B A, Laukoetter M G, Nava P, Koch S, Lee W Y, Capaldo C T, et al. Annexin A1 regulates intestinal mucosal injury, inflammation, and repair.

J Immunol. 2008; 181(7):5035-44; Lennon N J, Kho A, Bacskai B J, Perlmutter S L, Hyman B T, and Brown R H, Jr. Dysferlin interacts with annexins A1 and A2 and mediates sarcolemmal wound-healing. The Journal of biological chemistry. 2003; 278(50):50466-73; McNeil A K, Rescher U, Gerke V, and McNeil P L. Requirement for annexin A1 in plasma membrane repair. The Journal of biological chemistry. 2006; 281(46):35202-7; Roostalu U, and Strahle U. In vivo imaging of molecular interactions at damaged sarcolemma. Dev Cell. 2012; 22(3):515-29; Davenport N R, Sonnemann K J, Eliceiri K W, and Bement W M. Membrane dynamics during cellular wound repair. Mol Biol Cell. 2016; 27(14):2272-85; Carmeille R, Degrelle S A, Plawinski L, Bouvet F, Gounou C, Evain-Brion D, et al. Annexin-A5 promotes membrane resealing in human trophoblasts. Biochimica et biophysica acta. 2015; 1853(9):2033-44; Bement W M, Mandato C A, and Kirsch M N. Wound-induced assembly and closure of an actomyosin purse string in *Xenopus oocytes*. Curr Biol. 1999; 9(11):579-87). Annexins are recruited to the injured membrane in a sequential manner forming a macromolecular repair complex at the membrane lesion referred to as a repair cap (Demonbreun A R, Quattrocelli M, Barefield D Y, Allen M V, Swanson K E, and McNally E M. An actin-dependent annexin complex mediates plasma membrane repair in muscle. The Journal of cell biology. 2016; 213(6):705-18; Boye T L, Maeda K, Pezeshkian W, Sonder S L, Haeger S C, Gerke V, et al. Annexin A4 and A6 induce membrane curvature and constriction during cell membrane repair. Nat Commun. 2017; 8(1):1623; Roostalu U, and Strahle U. In vivo imaging of molecular interactions at damaged sarcolemma. Dev Cell. 2012; 22(3):515-29). A polymorphism in Anxa6, the gene encoding annexin A6, was previously identified in several commonly used experimental mouse strains that correlated with impaired muscle repair (Demonbreun A R, Allen M V, Warner J L, Barefield D Y, Krishnan S, Swanson K E, et al. Enhanced Muscular Dystrophy from Loss of Dysferlin Is Accompanied by Impaired Annexin A6 Translocation after Sarcolemmal Disruption. Am J Pathol. 2016; 186(6):1610-22; Quattrocelli M, Capote J, Ohiri, J C, Warner J L, Vo A H, Earley J U, et al. Genetic modifiers of muscular dystrophy act on sarcolemmal resealing and recovery from injury. PLOS Genet. 2017; 13(10):e1007070; Swaggart K A, Demonbreun A R, Vo A H, Swanson K E, Kim E Y, Fahrenbach J P, et al. Annexin A6 modifies muscular dystrophy by mediating sarcolemmal repair. Proceedings of the National Academy of Sciences of the United States of America. 2014; 111(16):6004-9). This polymorphism produces a truncated annexin A6 protein that acts in a dominant-negative manner to reduce repair cap formation and interferes with sarcolemmal repair. Additional studies in mice have shown that loss of annexin A2 results in poor myofiber repair (Defour A, Medikayala S, Van der Meulen J H, Hogarth M W, Holdreith N, Malatras A, et al. Annexin A2 links poor myofiber repair with inflammation and adipogenic replacement of the injured muscle. Human molecular genetics. 2017; 26(11):1979-91). These data suggest that there is a coordinated recruitment of annexin proteins to the repair cap facilitated by dynamic protein-protein interactions.

Herein, the kinetics of annexin A1, A2, and A6 were assessed in repair cap formation after membrane injury at multiple $Ca^{2+}$ concentrations. The repair cap formed by annexins A1, A2, and A6 increased with increasing $Ca^{2+}$ concentrations, while mutations in $Ca^{2+}$-coordinating residues interfered with normal annexin repair cap formation. Annexin overexpression promoted the formation of external blebs at the site of membrane injury that were released from the repair cap. Overexpression of annexin A6 resulted in the formation of larger blebs being released from the repair cap. These vesicles were enriched in $Ca^{2+}$-binding marker protein GCaMP5G, and this enrichment of $Ca^{2+}$ correlated with a reduction of intracellular $Ca^{2+}$ fluorescence near the injury site. Annexin A6 overexpression promoted membrane repair, while mutation of residue E233, a critical $Ca^{2+}$-coordinating residue in annexin A6, interfered with annexin repair complex formation and decreased repair capacity. Local and systemic administration of recombinant annexin A6 reduced muscle damage in vivo. These data identified a new role for annexins in bleb release from muscle membrane lesions during membrane repair and identify annexin A6 as a therapeutic target to protect against muscle injury.

Methods

Animals. Wildtype mice from the 129T2/SvEmsJ background were bred and housed in a specific pathogen free facility on a 12-hour light/dark cycle and fed ad libitum in accordance with the Northwestern University's Institutional Animal Care and Use Committee regulations. 129T2/SvEmsJ (129T2) mice were purchased from the Jackson Laboratory (Ben Harbor, ME; Stock #002065). mdx/hLTBP4 mice were generated as described in (Quattrocelli M, Capote J, Ohiri J C, Warner J L, Vo A H, Earley J U, et al. Genetic modifiers of muscular dystrophy act on sarcolemmal resealing and recovery from injury. PLOS Genet. 2017; 13(10):e1007070; Ceco E, Bogdanovich S, Gardner B, Miller T, DeJesus A, Earley J U, et al. Targeting latent TGFbeta release in muscular dystrophy. Science translational medicine. 2014; 6(259):259ra144). Sgcg-null mice were generated as described in (Hack A A, Cordier L, Shoturma D I, Lam M Y, Sweeney H L, and McNally E M. Muscle degeneration without mechanical injury in sarcoglycan deficiency. Proceedings of the National Academy of Sciences of the United States of America. 1999; 96(19):10723-8). Two to three-month-old male and female were used for all wildtype mouse experiments. Sgcg-null cohorts were age and sex-matched with mice between 2-5 months old.

Plasmids. Plasmids encoding annexin A1, A2 and A6 with a carboxyl-terminal turboGFP tag were obtained from Origene (Rockville, MD). Subcloning of annexin A1, A2, and A6 to replace the GFP tag with tdTomato (Addgene) was performed by Mutagenix (Suwanee, GA). Site directed mutagenesis was performed by Mutagenix on annexin A1-GFP, A2-GFP and A6-GFP to create the $Ca^{2+}$-binding mutants A1-D171A-GFP, A2-D161A-GFP, A6-D149A-GFP, and A6-E233A-GFP. Constructs were sequenced to verify mutagenesis. Plasmid DNA was isolated using the Qiagen endo-free Maxi prep kit (Qiagen #12362). The $Ca^{2+}$ sensor GCaMP5G was purchased from (Addgene #31788).

Sequence comparison and protein schematics Protein ribbon diagrams were generated using Swiss-PdbViewer using solved crystal structures of annexin A1 (1MCX), annexin A2 (2HYW), and annexin A6 (1AVC) available on www.rcsb.org. Clustal Omega from the European Bioinformatics Institute (EMBL-EBI) was used to align annexin sequences from www.ncbi.nlm.nih.gov annexin A1 (NM_010730; SEQ ID NO: 37), annexin A2 (NM_007585; SEQ ID NO: 38), annexin A6 (NM_013472; SEQ ID NO: 39), and annexin A6-encoding sequencing from multiple species (*Homo sapiens* (AAH17046.1; SEQ ID NO: 40, *macaca* (AFE65315.1; SEQ ID NO: 41), *canis*

(XP_005619331.1; SEQ ID NO: 42), *rattus* (NP_077070.2; SEQ ID NO: 43) and *mus* (NP_038500.2; SEQ ID NO: 44).

Electroporation, myofiber isolation, laser injury, cap and vesicle measurement. Flexor digitorum brevis (FDB) fibers were transfected with endo-free plasmid DNA by in vivo electroporation. Methods were described previously in (Demonbreun A R, Quattrocelli M, Barefield D Y, Allen M V, Swanson K E, and McNally E M. An actin-dependent annexin complex mediates plasma membrane repair in muscle. The Journal of cell biology. 2016; 213(6):705-18; Demonbreun A R, and McNally E M. DNA Electroporation, Isolation and Imaging of Myofibers. Journal of visualized experiments: JoVE. 2015; 106(106):e53551; DiFranco M, Quinonez M, Capote J, and Vergara J. DNA transfection of mammalian skeletal muscles using in vivo electroporation. Journal of visualized experiments: JoVE. 2009; 32(32)). Z-stack projections were acquired from consecutive acquisitions after the final time-lapse frame, approximately 4 minutes post. damage, with a 0.125 μM step size between slices. Z-stack renderings were constructed in FIJI. Measurement of the cap area and feret diameter were conducted from a single slice near the middle of the z-stack using FIJI imaging tools. Fibers expressing similar levels of tagged or GCaMP5G protein were compared. GCaMP5G $Ca^{2+}$ fluorescence was measured from the acquired timelapse images, using a standard rectangular ROI, placed inside the myofiber below the site of damage using FIJI. Fluorescence was expressed as F/F0. External vesicle number and GCaMP5G area were measured from endpoint z-stacks and max projection images using FIJI. Vesicles were considered external if they were found outside the sarcolemma assessed in brightfield and fluorescent channels. All measurements were acquired from myofibers isolated from at least n≥3 mice, n≥3 myofibers per mouse.

For recombinant myofibers studies, myofibers were isolated from mdx/hLTBP4 mice as described above. Myofibers were incubated in Ringer's media with or without 25 μg/ml recombinant annexin A6 (5186-A6-050, R&D systems). FM 4-64 (2.5 μm) was added to the myofibers just prior to imaging. Images were acquired and quantitated as described above. FM 4-64 area was measured using FIJI at imaging endpoint from a single slice near the middle of the z-stack. Z-stack step size (0.125 μm) was acquired from cap end to end.

Myofiber quality control was based on a number of characteristics including using adherent myofibers with intact sarcomere structure detected through brightfield imaging. Myofibers appeared devoid of tears or ruptures induced during the isolation protocol. The region of the myofiber selected for damage was linear and not located on a nucleus or neuromuscular junction. Additionally, fluorescence intensity within both the red and green channels suggested similar expression levels prior to damage.

Figure 19:
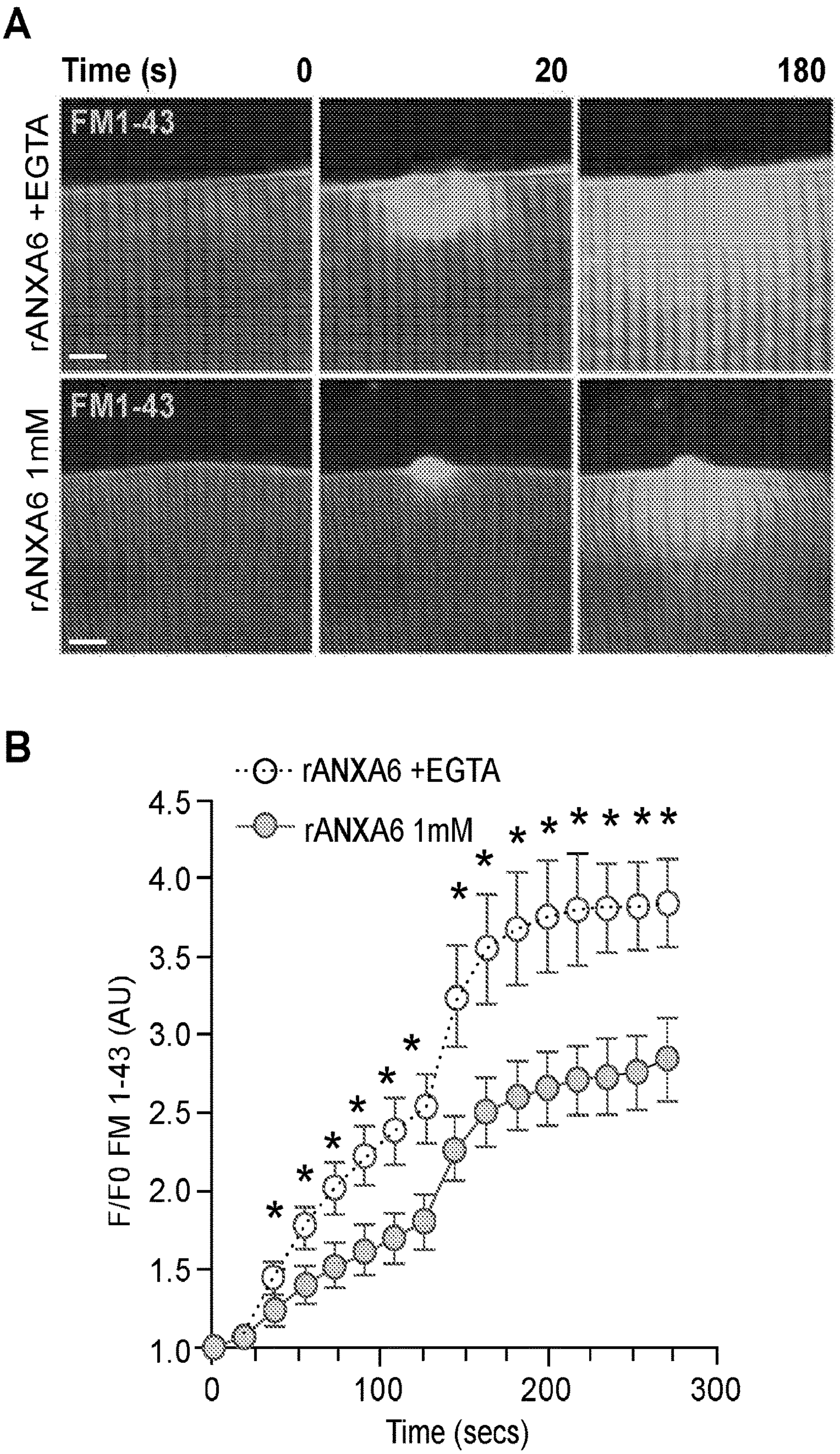
FIG. 19 shows $Ca^{2+}$-dependency of the protective effects of recombinant annexin A6. A and B) Wildtype myofibers were isolated and loaded with the fluorescence marker of membrane damage, FM 1-43 (green). Myofibers were pretreated with recombinant annexin A6 (rANXA6) then damaged in 1 mM $Ca^{2+}$ solution or 0 mM $Ca^{2+}$+EGTA, a calcium chelator. FM 1-43 fluorescence uptake over time was significantly reduced at 1 mM $Ca^{2+}$ compared to when EGTA was present. Scale 5 μm. Data are expressed as mean±SEM. Differences were tested by 2-way ANOVA with Bonferroni's multiple comparisons test * $p<0.05$, (n≥10 myofibers per condition; n=3 mice per condition).

Multiphoton laser injury and imaging. Fibers were subjected to laser-induced damage at room temperature using the Nikon A1R-MP multiphoton microscope. Imaging was performed using a 25×1.1NA objective directed by the NIS-Elements AR imaging software. Green fluorescence protein (GFP) and FM 4-64 were excited using a 920 nm wavelength laser and emission wavelengths of 575 nm and 629 nm were collected respectively. To induce laser damage on isolated myofibers, a diffraction limited spot (diameter approximately 410 nm) was created on the lateral membrane of the myofiber using a 920 nm wavelength laser at 10-15% laser power for 1 s. Time lapse images were collected as follows: one image was collected prior to damage, one image upon damage, then every 8 seconds for 80 seconds (10 images) followed by every 30 seconds for 5 minutes (10 images). At the end of the time lapsed image series, z-stack images were collected at 250 nm intervals through the damaged site on the myofiber directed by the NIS-Elements AR imaging software. The multiphoton was used to acquire data presented in FIG. 5, FIG. 10D and FIG. 19.

For recombinant protein calcium studies, myofibers were isolated from wildtype mice as described above. Myofibers were incubated in 20 μg/ml recombinant annexin A6 (5186-A6-050, R&D systems) in 1 mM $Ca^{2+}$ Ringers or 0 mM $Ca^{2+}$+EGTA. FM 1-43 (2.5 μm) was added to the myofibers just prior to imaging. Images were acquired and quantitated as described above. FM 1-43 fluorescence over time was measured using FIJI and plotted overtime as F/F0.

Cardiotoxin Injury and analysis. Tibialis anterior muscle of wildtype mice were injected with 25 μg/ml recombinant annexin A6 (5186-A6-050, R&D systems) or Ringers in sedated mice (3% isoflurane, 0.8 l/min $O_2$). For systemic administration, wildtype mice were injected with 1 mg/kg recombinant annexin A6 (5186-A6-050, R&D systems) or PBS diluted in EBD (5 μl/g body weight) into the retro-orbital cavity of sedated mice (3% isoflurane, 0.8 l/min $O_2$). Additionally, mice were injected with Evans' blue dye at 5 μl/g body weight (E-2129; Sigma-Aldrich, St. Louis, MO) dissolved in phosphate-buffered saline at 10 mg/ml cardiotoxin injury was performed injecting 20 μl of a 10 μM cardiotoxin solution in PBS in tibialis anterior or gastroc/soleus muscles in sedated animals (3% isoflurane, 0.8 l/min $O_2$) 2 hours post pretreatment. Cardiotoxin was released down the midline of the muscle to induce a homogenous area of injury at the center of the muscle. 3 hours post cardiotoxin injection muscle was harvested.

Evans blue dye uptake. Sections (10 μm thick) from the center of frozen-embedded muscles were collected on the cryostat (chamber, −20° C.; sample, −15° C.; catalog number CM1950; Leica, Wetzlar, Germany). Tissue sections were fixed with methanol for 2 minutes, rinsed and mounted with vectashield with DAPI (H-1200, Vector Laboratories). Imaging was performed using a Zeiss Axio Observer A1 microscope (Zeiss, Oberkochen, Germany), using a 10× objective. ZEN software (Zeiss, Jena, Germany) was used for acquiring images. Fluorescence quantitation, surface plots, and muscle area were performed using FIJI (NIH). For whole tissue dye quantification, whole tissue was dissected, finely minced, weighed, and incubated at 55° C. in 1 ml of formamide for 2 hours. Spectrophotometric absorbance was measured at 620 nm.

Serum collection and CK analysis. Mice were sedated (3% isoflurane, 0.8 l/min $O_2$) and blood was collected by means of retro-orbital puncture with heparinized capillary tubes (20-362-566; Fisher Scientific, Waltham, MA) into Microtainer™ Gold Top Serum Separator (365967 Becton Dickinson, Franklin Lakes, NJ) and centrifuged at 8,000×g for 10 minutes. The plasma fractions were frozen and stored at −80° C. Serum creatine kinase (CK) was analyzed in duplicate for each mouse using the EnzyChrom Creatine Kinase Assay (ECPK-100; BioAssay Systems, Hayward, CA) following manufacturer's instructions as described (Demonbreun A R, Allen M V, Warner J L, Barefield D Y, Krishnan S, Swanson K E, et al. Enhanced Muscular Dystrophy from Loss of Dysferlin Is Accompanied by Impaired Annexin A6 Translocation after Sarcolemmal Disruption. Am J Pathol. 2016; 186(6):1610-22). Results were acquired with the Synergy HTX multi-mode plate reader (BioTek®, Winooski, VT).

Short-term chronic dosing regimen. Sgcg-null mice were sedated (3% isoflurane, 0.8 l/min $O_2$) and blood collected as described above. While sedated, mice were injected with 1 mg/kg recombinant annexin A6 (5186-A6-050, R&D systems) or PBS into the right retro-orbital cavity once every 3 days for a total of 5 injections and then blood drawn on day 14 post initial injection. An additional cohort of Sgcg-null mice had blood drawn as described above immediately prior to the first protein injection. Then, 1 mg/kg recombinant annexin A6 or annexin A2 (both produced by Northwestern's Protein Production Core) was injected into the right retro-orbital cavity of sedated mice, once every 3 days for a total of 5 injections and then blood drawn on day 14 post initial injection.

Exercise Injury. Sgcg-null mice were sedated (3% isoflurane, 0.8 l/min $O_2$) and pre-exercise blood was collected by means of left retro-orbital puncture as described above. While sedated, mice were then injected 1 mg/kg recombinant annexin A6 (5186-A6-050, R&D systems) or PBS+1 mg/kg BSA into the right retro-orbital cavity at 9 am and 5 μm for 5 consecutive injection over 48 hours. Two hours post the 5th RO-injection, mice were subjected to 60 mins of treadmill running at 10 m/min at a 15° decline. Thirty minutes post exercise, blood was collected from the left retro-orbital cavity. Serum creatine kinase (CK) was analyzed as described above. Injections, exercise, and blood draws were performed blinded to treatment group.

Protein production. Recombinant mouse annexin A6 and mouse annexin A2 were produced and purified by the Northwestern's recombinant protein production core. Briefly, mouse annexin A6 (MG222645, Origene, Rockville, MD) and annexin A2 (MG205064, Origene, Rockville, MD) were subcloned into the pCMV6-AC-HIS backbone (PS100002, Origene, Rockville, MD). Plasmid was transfected and expressed with ExpiCHO expression system (A29133, ThermoFisher Scientific, Waltham, MA). Carboxy-terminally tagged recombinant protein was purified with Ni-charged MagBeads (L00295; GenScript, Piscataway, NJ) and purity evaluated through SDS-Page. Protein purity was additionally validated through immunoblot using anti-HIS (MAB050; R&D Systems, Minneapolis, MN) and anti-annexin A6 (ab31026, Abcam) or anti-annexin A2 (ab154113, Abcam) antibodies. Protein was diluted in phosphate buffered saline and stored at −80° C.

Calcium kinetics. FDB muscle was electroporated and isolated as described above. Myofibers were damaged in Ringers solution with $Ca^{2+}$ concentrations of 2 mM, 1 mM, 0.5 mM, 0.25 mM, 0.175 mM, 0.1 mM, 0.050 mM, and 0 mM. EDTA was added as a $Ca^{2+}$ chelating agent in only in the 0 mM $Ca^{2+}$ Ringers. Myofibers were isolated directly into 2 mM, 1 mM and 0.5 mM Ringers for those experiments respectively. For experiments using less than 0.5 mM $Ca^{2+}$ myofibers were isolated in 0.5 mM $Ca^{2+}$ Ringers and then diluted with 0 mM EDTA-free $Ca^{2+}$ Ringers. For 0 mM experiments, myofibers were isolated in 0.5 mM $Ca^{2+}$ Ringers and then replaced with 0 mM $Ca^{2+}$+EDTA Ringers just prior to imaging. Co-electroporation of wildtype annexin+wildtype annexin constructs was performed in one mouse foot, while the contralateral foot was co-electroporated with wildtype annexin+mutant annexin. All measurements were acquired from myofibers isolated from at least n≥2 mice, n≥3 myofibers per mouse at each $Ca^{2+}$ concentration. Area-$Ca^{2+}$ curves were fitted with a Hill Curve at $Ca^{2+}$ concentrations ranging from 0-2 mM. Kinetic parameters were calculated using Prism Graphpad.

Calcium and pH indicator dye measurements. Wildtype FDBs were isolated and plated in Ringers on Matek glass-bottom dishes as described above. Twenty minutes prior to imaging, myofibers were loaded with Fluo-4 AM at 37° C. (F10489, ThermoFisher Scientific, Waltham, MA) or pHrodo AM (P35373, ThermoFisher Scientific, Waltham, MA) as described in the instruction manual. Fibers were rinsed once with Ringers then subsequently damaged and imaged on the Nikon A1R GaSP, as described above.

Fluorescence intensity was measured using FIJI (NIH). phRodo change in fluorescence intensity was calculated as F/F0. Data was acquired from n=3 mice per experiment from multiple myofibers per mouse. Additionally, wildtype myofibers were incubated in 0 mM $Ca^{2+}$ for 1 hour., preloaded with Fluo-4 AM for 20 minutes prior to imaging, rinsed and then damaged on the MP+ in the presence of 0 mM external $Ca^{2+}$ with or without EGTA in the external Ringers Solution.

Cardiotoxin injection and histology. Wildtype mice were sedated (3% isoflurane, 0.8 l/min $O_2$) and then injected 1 mg/kg recombinant annexin A6 (5186-A6-050, R&D systems) or PBS+1 mg/kg BSA into the right retro-orbital cavity and allowed to recover. Two hours post injection mice were sedated for a second time. While sedated the tibialis anterior muscles were injected along the midline with 10 μm cardiotoxin in 20 ul of PBS as described above. Seven days post injection, the muscle was isolated and frozen. Muscle sections were acquired every 100 μm from muscle tendon into the mid belly, fixed and stained with hematoxylin and eosin. Imaging was performed using a Zeiss Axio Observer A1 microscope (Zeiss, Oberkochen, Germany), using a 10× objective. ZEN software (Zeiss, Jena, Germany) was used for acquiring tiled images. Percent injury area was calculated as the average injured area (containing internal myonuclei) divided by total muscle area of 3 sections per muscle. One muscle from each group was excluded due to technical error in tissue processing. Damage area was measured using FIJI (NIH).

Single cell $Ca^{2+}$ and shortening measurements. Isolated FDB fibers were plated on laminin coated glass-bottomed 35 mm dishes for one hour and then cultured overnight in DMEM with 10% FBS and 1% penicillin/streptomycin at 37° C. in a 10% $CO_2$ incubator. One hour prior to data acquisition, the medium was removed and cells were incubated in Tyrode buffer (119 mM NaCl, 5 mM KCl, 25 mM HEPES, 2 mM $CaCl_2$), 2 mM $MgCl_2$) with 10 μM Indo-1 AM (TefLabs) for 1 hour at 37° C. in a 10% $CO_2$ incubator. Dishes were then filled with Tyrode buffer, mounted on a custom stage and platinum pacing electrodes were inserted into the dish. Stimulation was elicited using a 701C high-powered stimulator controlled by the 950A software (Aurora Scientific). Stimulation was performed at 40 and 80 Hz, 5 ms pulse width, 100 ms duration. Ratiometric $Ca^{2+}$ signals were collected with two photomultiplier tubes and a FluoroDaq controller. Video sarcomere length was recorded with a high-speed camera and fast Fourier transform using the Aurora Scientific 900B-VSL system (Aurora, Ontario). Ten transients were collected over 20 seconds and averaged together per cell per frequency.

Statistical analysis. Statistical analyses were performed with Prism (Graphpad, La Jolla, CA). Comparisons relied on ANOVA ((1way ANOVA for 1 variable, 2way ANOVA for two variables (typically area and $Ca^{2+}$ concentration)). Otherwise, unpaired two-tailed t-tests were performed. P-values of less than or equal to 0.05 were considered significant. Error bars represent+/−standard error of the mean (SEM).

Study approval. The study was conducted with the approval of Northwestern University's Institutional Animal Care and Use Committee (Chicago, IL).

Figure 23:
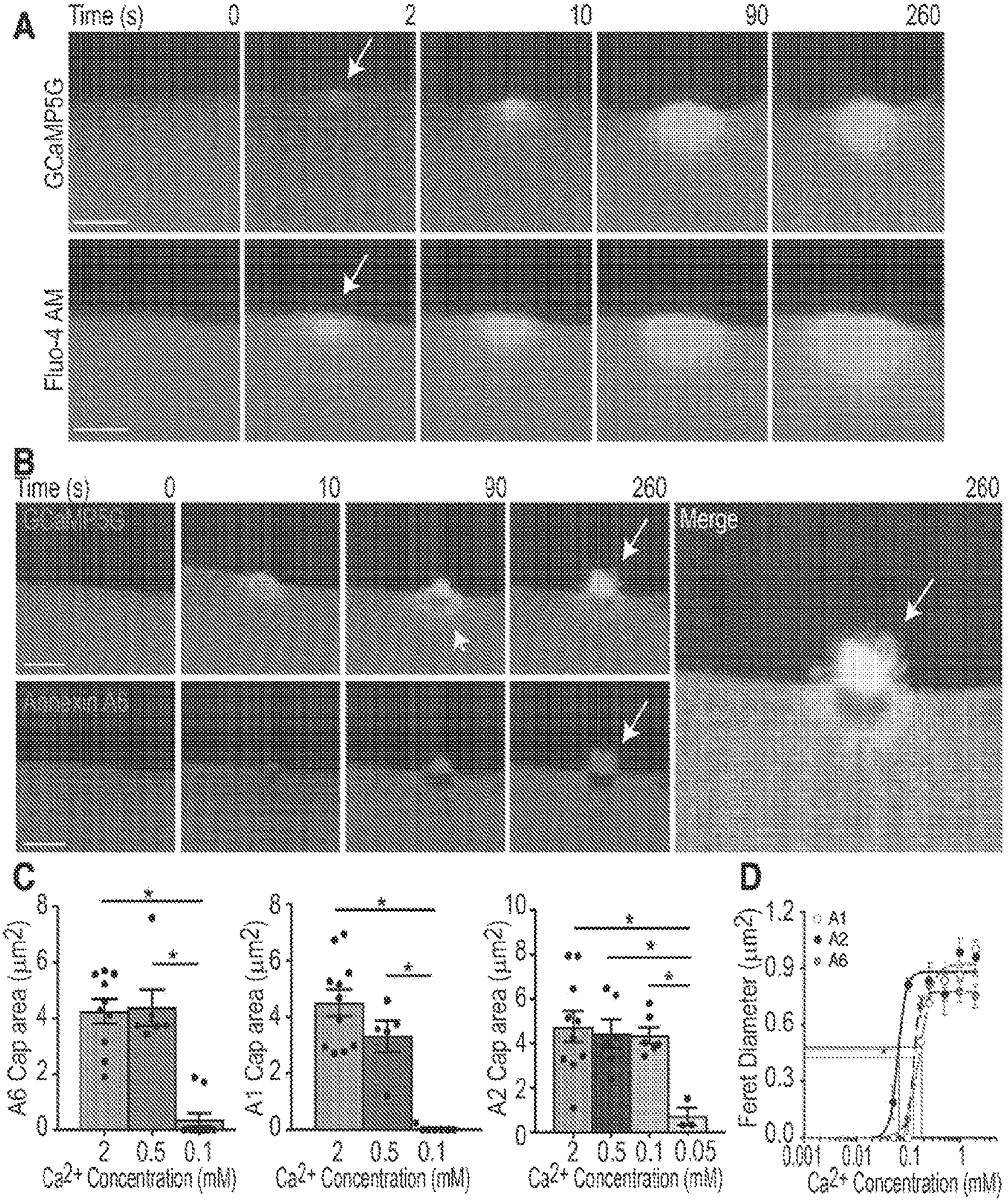
FIG. 23 shows $Ca^{2+}$-dependent annexin repair cap recruitment at the site of injury. Myofibers were generated to express the $Ca^{2+}$ indicator GCaMP5G (green), and time-lapse single slice images were assessed at time points after membrane disruption. (A) GCaMP5G fluorescence was present at the site of injury, at 2 seconds (arrow), indicating the presence of $Ca^{2+}$ immediately after damage at the site of injury (top panel). These data were validated with a non-protein $Ca^{2+}$ indicator, Fluo-4 AM (green, bottom panel). (B) Time-lapse images of myofibers co-electroporated with GCaMP5G and annexin A6-tdTomato (A6, red). GCaMP5G fluorescence was present at the site of injury localized around the annexin A6-free zone (arrowhead) and at the annexin A6 cap (arrow). GCaMP5G colocalized (merge, yellow, arrow) with the annexin A6 repair cap. Scale bar 5 μm. (C) Myofibers expressing fluorescently tagged annexins A1, A2 or A6 were injured at multiple $Ca^{2+}$ concentrations. Annexin A1 and A6 repair cap size was reduced at 0.1 mM $Ca^{2+}$ compared to 2 mM and 0.5 mM. Annexin A2 repair cap area was significantly reduced at 0.05 mM $Ca^{2+}$ compared to 2 mM, 0.5 mM, and 0.1 mM $Ca^{2+}$. (D) Cap kinetics were plotted as cap feret diameter over a range of $Ca^{2+}$ concentrations. Annexin A2 had a statistically significant leftward shift in $Km_{1/2}$ followed by annexin A6 then A1. Scale 5 μm. Data are expressed as mean±SEM. Differences were tested by one-way-ANOVA test with Tukey's multiple comparisons test (C) *p<0.05, (n≥5 myofibers per condition).
Figure 24:
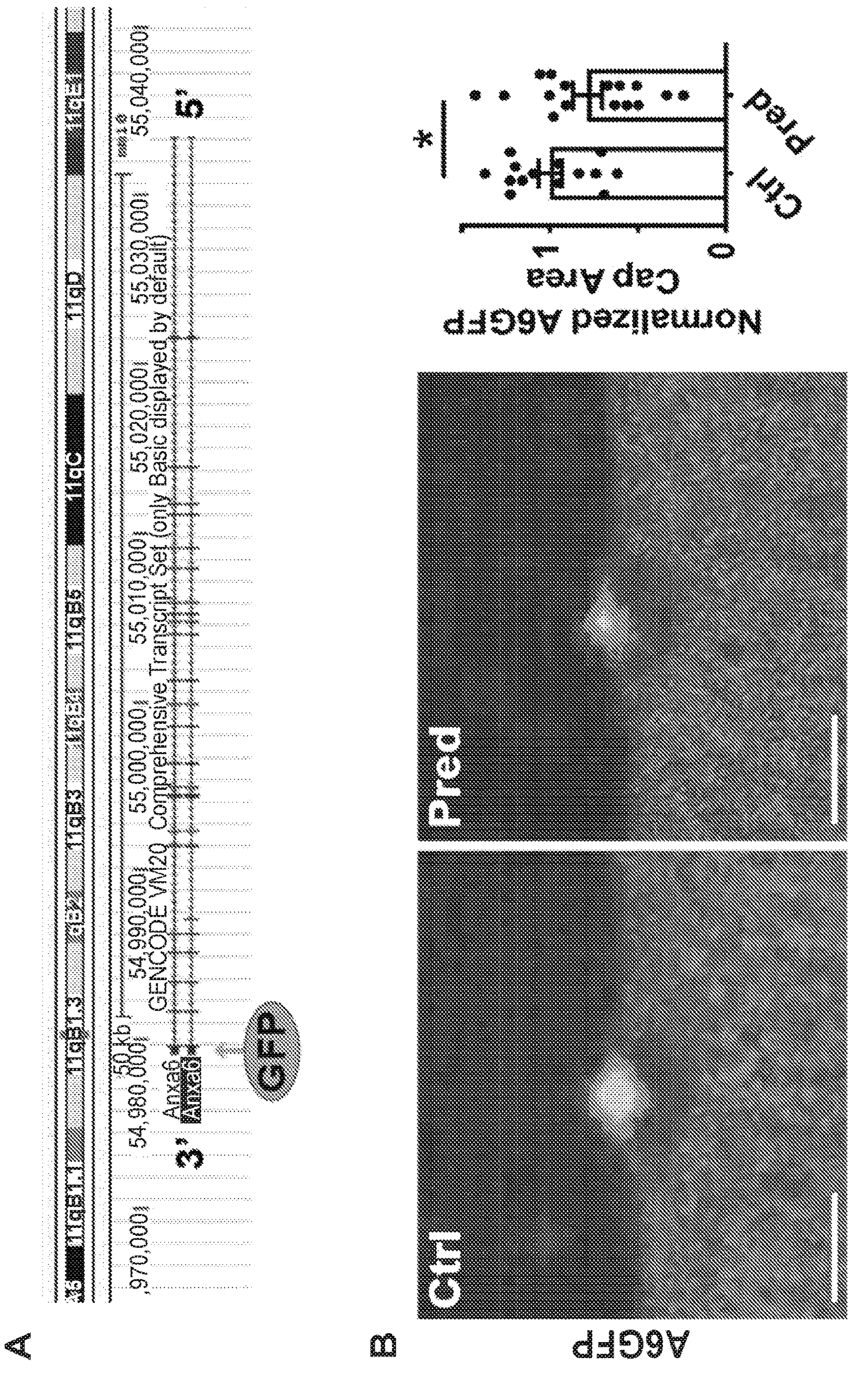
FIG. 24 shows genetically-encoded annexin A6GFP responds to prednisone exposure. A) Targeting strategy for generating genetically-encoded annexin A6GFP in mice. B) Mice were injected with the prednisone (pred) or control (Ctrl) into the intraperitoneal cavity. Twenty-four hours post injection, myofibers were isolated and subjected to laser injury. Annexin A6GFP repair cap size was reduced in response to prednisone administration, indicative of protection against injury. Scale 5 μm. * p<0.05. t-test n≥3 mice per treatment.

Results $Ca^{2+}$ localizes to the repair cap upon membrane damage. Activation of muscle membrane repair requires the presence of external $Ca^{2+}$ (Bansal D, Miyake K, Vogel S S, Groh S, Chen C C, Williamson R, et al. Defective membrane repair in dysferlin-deficient muscular dystrophy. Nature. 2003; 423(6936):168-72). Annexin proteins have previously been shown to aggregate into repair caps at the site of injury bordered by annexin-free zone within the cytoplasm under the repair cap (Demonbreun A R, Quattrocelli M, Barefield D Y, Allen M V, Swanson K E, and McNally E M. An actin-dependent annexin complex mediates plasma membrane repair in muscle. The Journal of cell biology. 2016; 213(6):705-18; Demonbreun A R, Allen M V, Warner J L, Barefield D Y, Krishnan S, Swanson K E, et al. Enhanced Muscular Dystrophy from Loss of Dysferlin Is Accompanied by Impaired Annexin A6 Translocation after Sarcolemmal Disruption. Am J Pathol. 2016; 186(6):1610-22; Swaggart K A, Demonbreun A R, Vo A H, Swanson K E, Kim E Y, Fahrenbach J P, et al. Annexin A6 modifies muscular dystrophy by mediating sarcolemmal repair. Proceedings of the National Academy of Sciences of the United States of America. 2014; 111(16):6004-9; Quattrocelli M, Barefield D Y, Warner J L, Vo A H, Hadhazy M, Earley J U, et al. Intermittent glucocorticoid steroid dosing enhances muscle repair without eliciting muscle atrophy. J Clin Invest. 2017; 127(6):2418-32). To visualize $Ca^{2+}$ dynamics at the site of injury in real-time, an in vivo fluorescent $Ca^{2+}$ indicator protein, GCaMP5G, was utilized. GCaMP5G is a fusion protein composed of green fluorescent protein (GFP), the calcium-binding protein calmodulin, and the calmodulin M13 binding peptide. GCaMP5G has minimal fluorescence when not bound to $Ca^{2+}$, and $Ca^{2+}$ binding results in a conformational change within the protein increasing the fluorescence intensity of GFP (Akerboom J, Chen T W, Wardill T J, Tian L, Marvin J S, Mutlu S, et al. Optimization of a GCaMP calcium indicator for neural activity imaging. J Neurosci. 2012; 32(40):13819-40). Wildtype flexor digitorum brevis (FDB) muscle was electroporated with the GCaMP5G plasmid and then injured the plasma membrane using laser ablation (Demonbreun A R, Quattrocelli M, Barefield D Y, Allen M V, Swanson K E, and McNally E M. An actin-dependent annexin complex mediates plasma membrane repair in muscle. The Journal of cell biology. 2016; 213(6):705-18; Demonbreun A R, and McNally E M. DNA Electroporation, Isolation and Imaging of Myofibers. Journal of visualized experiments: JoVE. 2015; 106(106): e53551). Within two seconds of membrane injury (arrow), GCaMP5G fluorescence accumulated in the cytoplasm at the site of injury. GCaMP5G fluorescence intensity progressively increased through 260 seconds of imaging (FIG. 23A, top panel).

Figure 15:
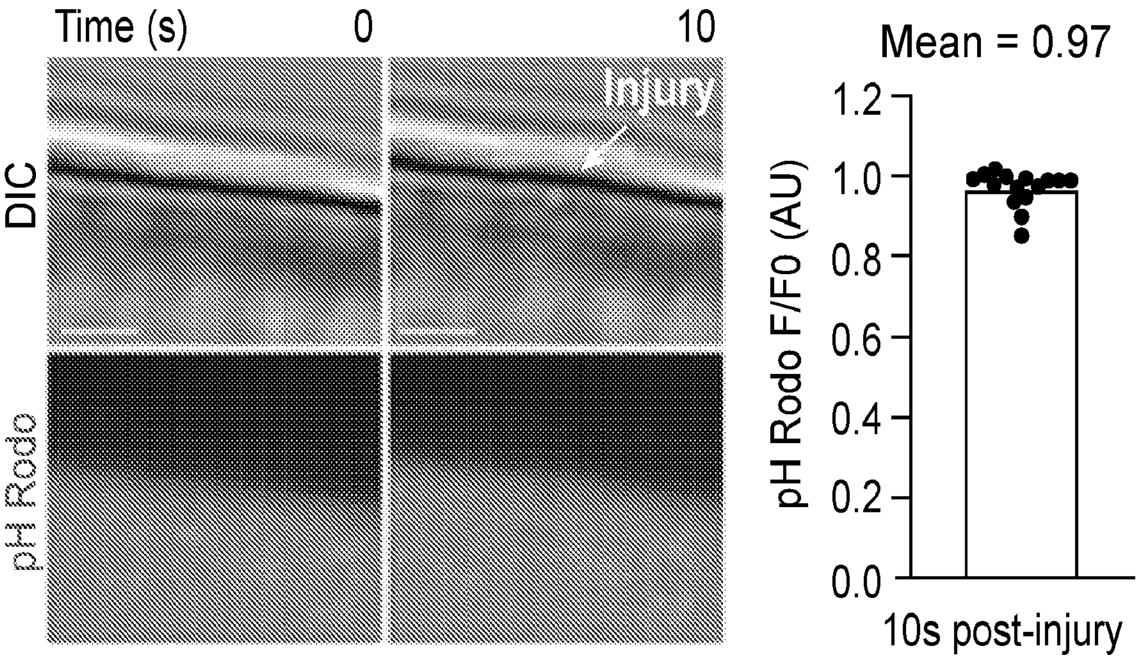
FIG. 15 shows the lack of visible pH change immediately after membrane injury. Myofibers were laser injured in the presence of the pH fluorescence indicator pH Rodo AM. The pH remained unchanged between preinjury (0s) and post-injury (10 s) expressed as F/F0 mean=0.97, where a value of 1 is identical. Scale 5 μm.

To ensure these results were not a reflection of protein aggregation of the GCaMP5G sensor, wildtype myofibers were injured in the presence of Fluo-4 AM. Fluo-4 AM is a non-protein, $Ca^{2+}$ indicator dye that increases fluorescence intensity upon binding $Ca^{2+}$ and is routinely used to measure $Ca^{2+}$ dynamics. Similar to GCaMP5G fluorescence, Fluo-4 AM fluorescence intensity increased at the site of laser-induced membrane injury 2 seconds post damage (arrow) and continued to increase intensity through the 260 seconds of imaging (FIG. 23A, bottom panel). In myofibers co-electroporated with plasmids expressing GCaMP5G and annexin A6 with a carboxyl-terminal tdTomato fluorescent tag, GCaMP5G fluorescence localized in a ring around the annexin A6-free zone (FIG. 23B, arrowhead) and co-localized with annexin A6 at the repair cap (FIG. 23B, arrow, merge). It was also evaluated whether pH changed with injury using pHrodo fluorescence, a non-protein pH indicator dye that changes fluorescence with different pH levels. No change from the preinjury state (0 s) compared to 10 s post injury was noted, when $Ca^{2+}$ indicator fluorescence is already increased at the site of injury (FIG. 15). This temporal sequence is consistent with $Ca^{2+}$ accumulation at the site of injury facilitating annexin translocation and assembly into repair caps.

Annexin repair caps exhibit differential $Ca^{2+}$ sensitivity during repair cap recruitment. Annexin proteins are $Ca^{2+}$-dependent phospholipid and actin binding proteins that contain four annexin repeat domains or eight in the case of annexin A6 (FIG. 2). Annexin repeat domains bind $Ca^{2+}$, but are distinct from the $Ca^{2+}$ binding of C2 domains and EF-hands seen in other classes of repair proteins (Gerke V, and Moss S E. Annexins: from structure to function. Physiol Rev. 2002; 82(2):331-71). Annexins coordinate $Ca^{2+}$ and bind membranes from their convex face (FIG. 2), and both type II and type III $Ca^{2+}$ binding sites have been described in annexin proteins. To further define the $Ca^{2+}$ requirements in annexin-mediated sarcolemmal repair in myofibers, annexin A1, A2, or A6 repair cap formation was examined at multiple $Ca^{2+}$ concentrations. Cap size was measured from the center of a z-stack, and the type of fluorescent tag, turboGFP or tdTomato, did not alter assessed parameters (FIGS. 3A and 3B). Annexin A1 and A6 repair cap size was $Ca^{2+}$-dependent, with the largest repair caps forming at 2 mM and smaller repair caps forming at 0.1 mM, while annexin A2 repair caps were not significantly reduced until 0.05 mM $Ca^{2+}$ (FIGS. 23C and 23D). Repair cap area was plotted as a function of $Ca^{2+}$ concentration using a modified Hill equation. Annexin A2 formed a repair cap at the lowest concentration of $Ca^{2+}$, 0.05 mM, while annexins A1 and A6 did not form a discernable cap at $Ca^{2+}$ concentrations lower than 0.1 mM $Ca^{2+}$, seen as the significant leftward annexin A2 curve with a $Km_{1/2}$ of 0.067 mM compared to A6 and A1, which showed $Km_{1/2}$ of 0.12 mM and 0.17 mM, respectively (FIG. 23D). Annexin A1 and A6 repair cap size and rate was highly dependent on $Ca^{2+}$ concentration (FIG. 4). The rate of annexin A2 cap formation and cap size was similar at 2 mM, 0.5 mM and 0.1 mM $Ca^{2+}$, while annexin A1 and A6 rates decreased with lower $Ca^{2+}$ concentrations, suggesting a high $Ca^{2+}$ affinity for annexin A2 (FIG. 4). To ensure that repair cap formation was not artifact due to the type of laser injury, we induced laser injury on both the Nikon A1R GaSP confocal and the Nikon A1R MP+ multiphoton confocal. Injury induced by a multiphoton laser is more focused producing less collateral damage. Annexin A6 repair caps appeared comparable with both types of lasers (FIG. 5). These data indicate that annexin A1, A2, and A6 repair cap formation is influenced by the level of $Ca^{2+}$ present during myofiber repair with annexin A2 being the most $Ca^{2+}$ sensitive of the three annexins studied.

Annexin overexpression promotes bleb formation at the site of membrane injury. Membrane repair studies in *Lytechinus pictus* and *Xenopus oocytes* have observed membranous structures emerging and erupting from the site of membrane repair (Davenport N R, Sonnemann K J, Eliceiri K W, and Bement W M. Membrane dynamics during cellular wound repair. Mol Biol Cell. 2016; 27(14):2272-85; Bi G Q, Alderton J M, and Steinhardt R A. Calcium-regulated exocytosis is required for cell membrane resealing. The Journal of cell biology. 1995; 131(6 Pt 2):1747-58). Additionally, in artificial membrane preparations, the addition of recombinant annexins induced membrane folding or blebbing in a $Ca^{2+}$-dependent manner at sites of membrane imperfection (Boye T L, Jeppesen J C, Maeda K, Pezeshkian W, Solovyeva V, Nylandsted J, et al. Annexins induce curvature on free-edge membranes displaying distinct morphologies.

Figure 16:
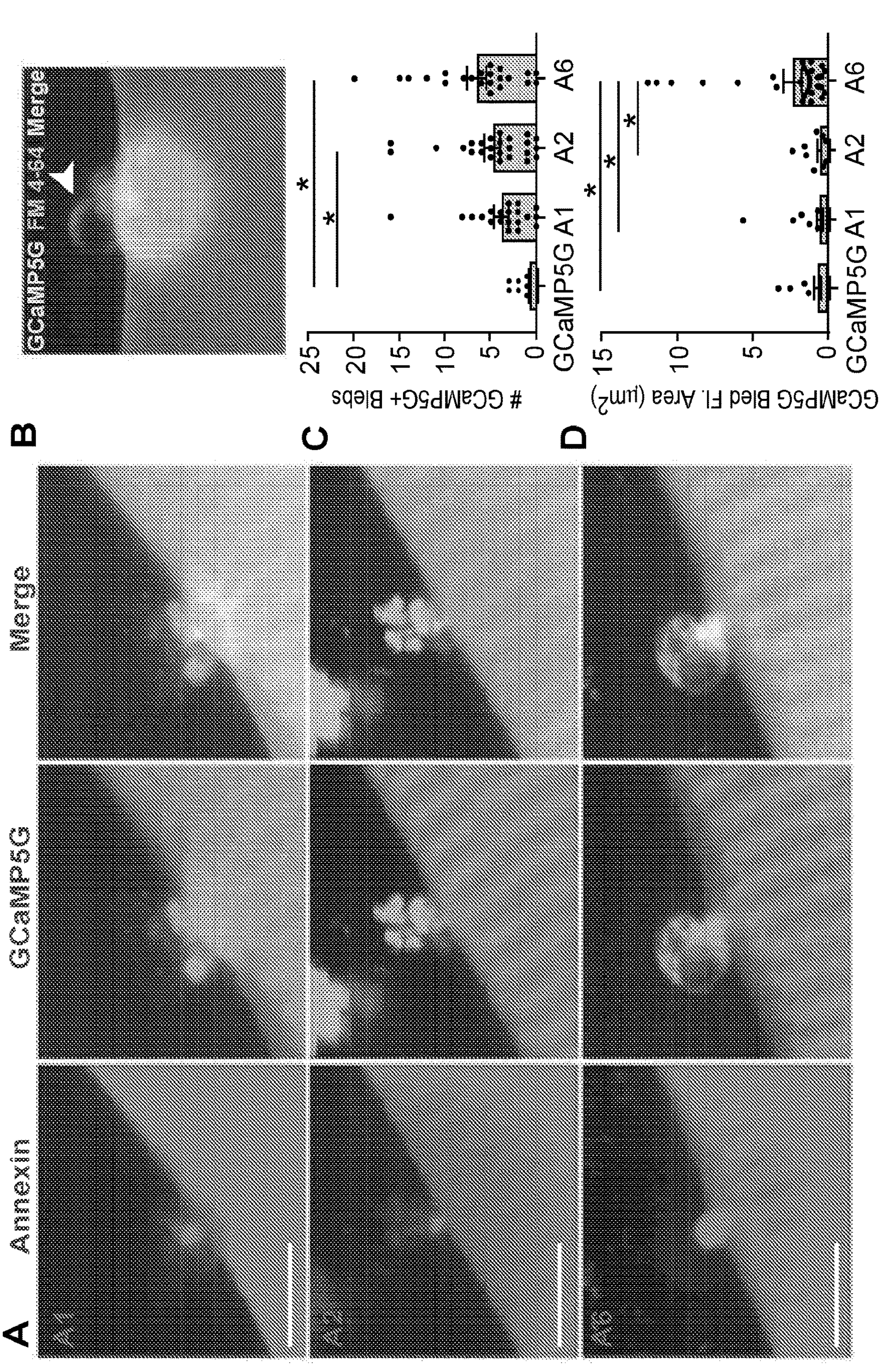
FIG. 16 shows annexin expression promoted release of blebs from the site if myofiber repair. Myofibers were electroporated with the $Ca^{2+}$ indicator GCaMP5G (green) with or without tdTomato-labelled annexin A1, annexin A2, or annexin A6. $Ca^{2+}$ area and fluorescence were assessed after membrane damage. (A) High magnification z-projection images illustrate external blebs filled with the $Ca^{2+}$ indicator emanating from the lesion when annexin A1, A2, or A6 was co-expressed and a corresponding reduction of $Ca^{2+}$ indicator within the myofiber when compared to GCaMP5G alone (B). (B) Membrane marked by FM 4-64 shows GCaMP5G-negative vesicles form in the absence of annexin overexpression. (C) Expression of annexin A6 or A2 resulted in an increased number of GCaMP5G-positive blebs. (D) Expression of annexin A6 resulted in the formation of the largest GCaMP5G-positive blebs. Data are expressed as mean±SEM. Differences were tested by one-way-ANOVA test with Tukey's multiple comparisons test $*p<0.05$, (n≥16 myofibers from n≥3 mice per condition).

Sci Rep. 2018; 8(1):10309; Boye T L, Maeda K, Pezeshkian W, Sonder S L, Haeger S C, Gerke V, et al. Annexin A4 and A6 induce membrane curvature and constriction during cell membrane repair. Nat Commun. 2017; 8(1):1623). It was investigated whether similar findings could be observed at the site of muscle membrane injury in live skeletal myofibers. GCaMP5G was expressed alone or in combination with annexin A1, A2 or A6 in skeletal myofibers. It was found that overexpression of annexins promoted the formation of extracellular blebs emanating from annexin repair caps at the membrane lesion (FIG. 16A, red channel). These blebs appeared after the formation of repair caps and were seen at the extracellular tip of the repair cap, coincident with FM 4-64 fluorescence (FIGS. 16A and 16B). FM 4-64 is a membrane impermeable dye that is non-fluorescent in aqueous solution and increases fluorescence intensity as it binds membrane phospholipids exposed during injury; FM 4-64 is commonly used as a marker of membrane injury (Bansal D, Miyake K, Vogel S S, Groh S, Chen C C, Williamson R, et al. Defective membrane repair in dysferlin-deficient muscular dystrophy. Nature. 2003; 423(6936):168-72; Cai C, Masumiya H, Weisleder N, Matsuda N, Nishi M, Hwang M, et al. MG53 nucleates assembly of cell membrane repair machinery. Nat Cell Biol. 2009; 11(1):56-64; Demonbreun A R, and McNally E M. DNA Electroporation, Isolation and Imaging of Myofibers. Journal of visualized experiments: JoVE. 2015; 106(106):e53551; Yeung T, Heit B, Dubuisson J F, Fairn G D, Chiu B, Inman R, et al. Contribution of phosphatidylserine to membrane surface charge and protein targeting during phagosome maturation. The Journal of cell biology. 2009; 185(5):917-28; Zweifach A. FM1-43 reports plasma membrane phospholipid scrambling in T-lymphocytes. The Biochemical journal. 2000; 349(Pt 1):255-60). Overexpression of annexin A6 and annexin A2 induced significantly more blebs than were observed after annexin A1 overexpression or GCaMP5G alone (FIGS. 16C and 16D). Furthermore, annexin-induced blebs were enriched for GCaMP5G, and annexin A6 induced the formation of significantly larger GCaMP5G-containing blebs as compared to annexin A1, A2, or GCaMP5G alone (FIG. 16A, green channel, and 16D). A z-stack compilation demonstrated large annexin A6-induced GCaMP5G-positive blebs emanating from the site of injury. In contrast, annexin A2 resulted in smaller blebs extruding from the repair cap. These data indicate that annexins not only form a repair cap at the site of membrane disruption, but that these caps serve as sites for excretion of extracellular components enriched for $Ca^{2+}$-binding proteins.

Figure 17:
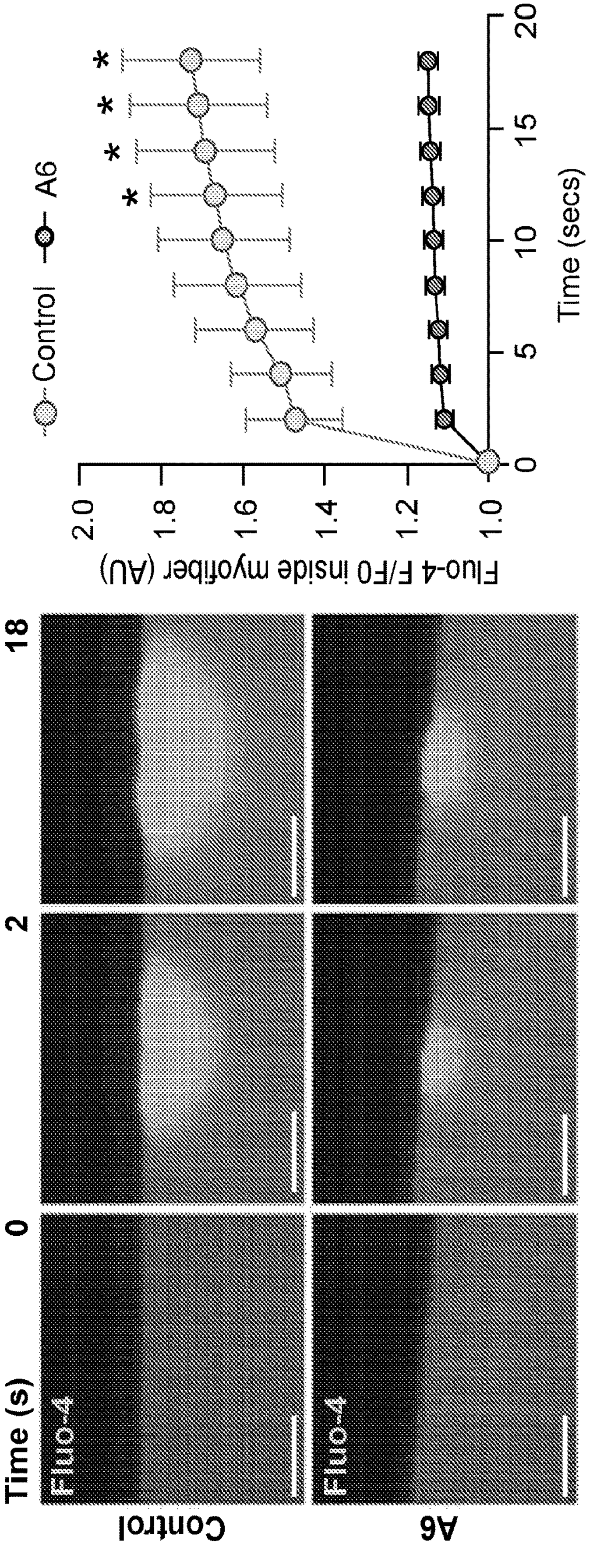
FIG. 17 shows decreased Fluo-4 $Ca^{2+}$ levels at that site of injury with annexin A6 expression. Myofibers were preloaded with the fluorescent $Ca^{2+}$ indicator dye, Fluo-4, and the sarcolemma subsequently injured with a confocal laser. Myofibers overexpressing annexin A6 had significantly decreased levels of internal Fluo-4 $Ca^{2+}$ fluorescence at the site of membrane injury compared to control myofibers, similar to results obtained with the protein-based $Ca^{2+}$ indicator GCaMP5G. Scale 5 μm. Data are expressed as mean±SEM. Differences were tested by 2-way ANOVA with Bonferroni's multiple comparisons test * $p<0.05$, (n=3 mice; n≥8 myofibers per condition).

Decreased intracellular $Ca^{2+}$ fluorescence at the site of injury with annexin overexpression. Time lapse imaging of the $Ca^{2+}$ indicator GCaMP5G after laser injury suggested intracellular $Ca^{2+}$ was decreasing concomitant with extracellular bleb formation suggesting that these blebs serve to reduce intracellular $Ca^{2+}$ accumulation through excretion. The annexin-induced reduction in intracellular $Ca^{2+}$ fluorescence could be seen for all three annexins A1, A2 and A6, but was most evident for annexin A2 and A6 (FIG. 7A). Over the 240 seconds of imaging, overexpression of annexin A6 induced the most significant reduction in intracellular $Ca^{2+}$, visualized as internal GCaMP5G $Ca^{2+}$ fluorescence (FIG. 7B). Detailed analysis of the first 20 seconds post injury showed a significant reduction in internal GCaMP5G $Ca^{2+}$ fluorescence with annexin A2 and A6, but not annexin A1, when compared to GCaMP5G alone (FIG. 7C). Baseline GCaMP5G fluorescence intensity prior to injury was not significantly different between groups (FIG. 7D). Reduction in internal $Ca^{2+}$ fluorescence at the lesion with annexin A6 expression was confirmed using Fluo-4 AM (FIG. 17). Thus, annexin expression induced a reduction of $Ca^{2+}$ signal within the injured myofiber concomitant with enhanced egress of $Ca^{2+}$-binding protein-filled blebs. Moreover, annexin A6 was the most effective of the three annexins tested at sustaining this response.

Overexpression of $Ca^{2+}$-binding proteins like annexins may have unexpected effects on intracellular $Ca^{2+}$ signaling and cellular function. Therefore, the $Ca^{2+}$ handling and contractile properties of isolated myofibers overexpressing annexin A6 was evaluated compared to controls. Isolated myofibers expressing annexin A6 were loaded with the ratiometric $Ca^{2+}$ indicator dye Indo-1, and we observed no differences in $Ca^{2+}$ cycling at 40 or 80 Hz stimulation frequencies between annexin A6 or control fibers (FIGS. 8A, 8B, and 8C). Unloaded cell shortening was also unaffected by the presence of overexpressed annexin A6 (FIGS. 8D, 8E, and 8F). These results demonstrated that annexin A6 overexpression was well-tolerated by myofibers.

Annexin A6 $Ca^{2+}$ binding is required for repair cap formation and myofiber repair. Mutation of annexin A1 residue D171 and annexin A2 residue D161 were previously shown to inhibit annexin membrane translocation in HEK cells (McNeil A K, Rescher U, Gerke V, and McNeil P L. Requirement for annexin A1 in plasma membrane repair. The Journal of biological chemistry. 2006; 281(46):35202-7; Jost M, Thiel C, Weber K, and Gerke V. Mapping of three unique Ca(2+)-binding sites in human annexin II. Eur J Biochem. 1992; 207(3):923-30). It was queried whether these mutations would inhibit translocation and formation of the macromolecular annexin repair cap formed after muscle membrane injury in live myofibers. Alignment of annexins A1, A2 and A6 protein sequences was used to identify the conserved residues within the consensus sequence of type II $Ca^{2+}$ binding sites across all three annexin proteins (FIG. 2). In order to disrupt $Ca^{2+}$ binding in annexin A1, A2, and A6, site-directed mutagenesis was performed to convert the aspartic acid residue in the first type II $Ca^{2+}$ binding site into an alanine residue (A1D171A, A2D161A, A6D149A, respectively) (FIG. 9A). E233A was also generated in annexin A6, to create a similar change in the $Ca^{2+}$ binding site in the second annexin repeat domain of annexin A6. Each construct also contained turboGFP or tdTomato at the C-terminus. To assess the effect of homotypic annexin interactions during repair cap formation, myofibers were co-electroporated with wildtype+wildtype (A6+A6) or wildtype+mutant (A6+A6E233A) annexin combinations. Mutation of E233 in annexin A6 acted in a dominant-negative fashion significantly decreasing cap size of the co-expressed wildtype annexin A6 protein (FIG. 10A). Prior structural studies suggested that D149 in the first annexin repeat domain of annexin A6 did not bind $Ca^{2+}$ (Avila-Sakar A J, Creutz C E, and Kretsinger R H. Crystal structure of bovine annexin VI in a calcium-bound state. Biochimica et biophysica acta. 1998; 1387(1-2):103-16), and consistent with this, the D149A mutant in annexin A6 had little effect on cap size (FIG. 9B, right panel). The repair cap feret diameter was plotted as a function of $Ca^{2+}$ concentration using a modified Hill equation. Expression of mutant annexin A6E233A significantly reduced the cap diameter (DMAX) of the co-expressed wildtype annexin A6 protein (FIG. 10B). To assess the effect of heterotypic annexin interactions on repair cap formation, myofibers were co-electroporated with various combinations of wildtype and mutant annexin constructs. Co-expression of mutant annexin A6E233A resulted in a significant reduction in annexin A1, A2, and A6 cap size compared to A1+A6, A2+A6, A6+A6 controls, respectively (FIG. 10C). Together, these data showed that annexin proteins interact in a homotypic and heterotypic fashion influencing annexin repair complex-assembly and that the mutant annexin A6 protein is sufficient to negatively modulate annexin complex assembly during repair.

$Ca^{2+}$-binding of both annexin A1 and A2 was also required for repair cap formation. A1D171A and A2D161A mutant cap size was reduced compared to wildtype annexin A1 and A2 controls, respectively. Expression of mutant annexin A1D171A and A2D161A significantly reduced the repair cap diameter (DMAX) of the respective co-expressed wildtype annexin protein (FIG. 9B, left and middle panels). Despite the ability of mutant annexin A1D171A and A2D161A to significantly decrease co-expressed wildtype annexin A1 and A2 cap size, respectively, A1D171A or A2D171A had minimal effect of wildtype annexin A6 cap size (FIG. 9C): These data showed that annexin A1 and A2 interact in a homotypic fashion influencing self-cap assembly, while A6 localization to the repair cap is minimally modulated by annexin A1 and A2 localization.

To determine the effect of dominant negative annexin A6 on the assembly of annexins A1, A2, and A6 at the repair cap and membrane repair capacity, laser injury was similarly performed on isolated myofibers in the presence of FM 4-64. Myofibers expressing annexin A6E233A-GFP had increased FM 4-64 fluorescence area after laser injury compared to control myofibers expressing wildtype annexin A6-GFP (FIG. 10D). These results indicate that a functional annexin repair complex is required for proper membrane repair and annexin A6 participates in orchestrating complex formation.

Figure 18:
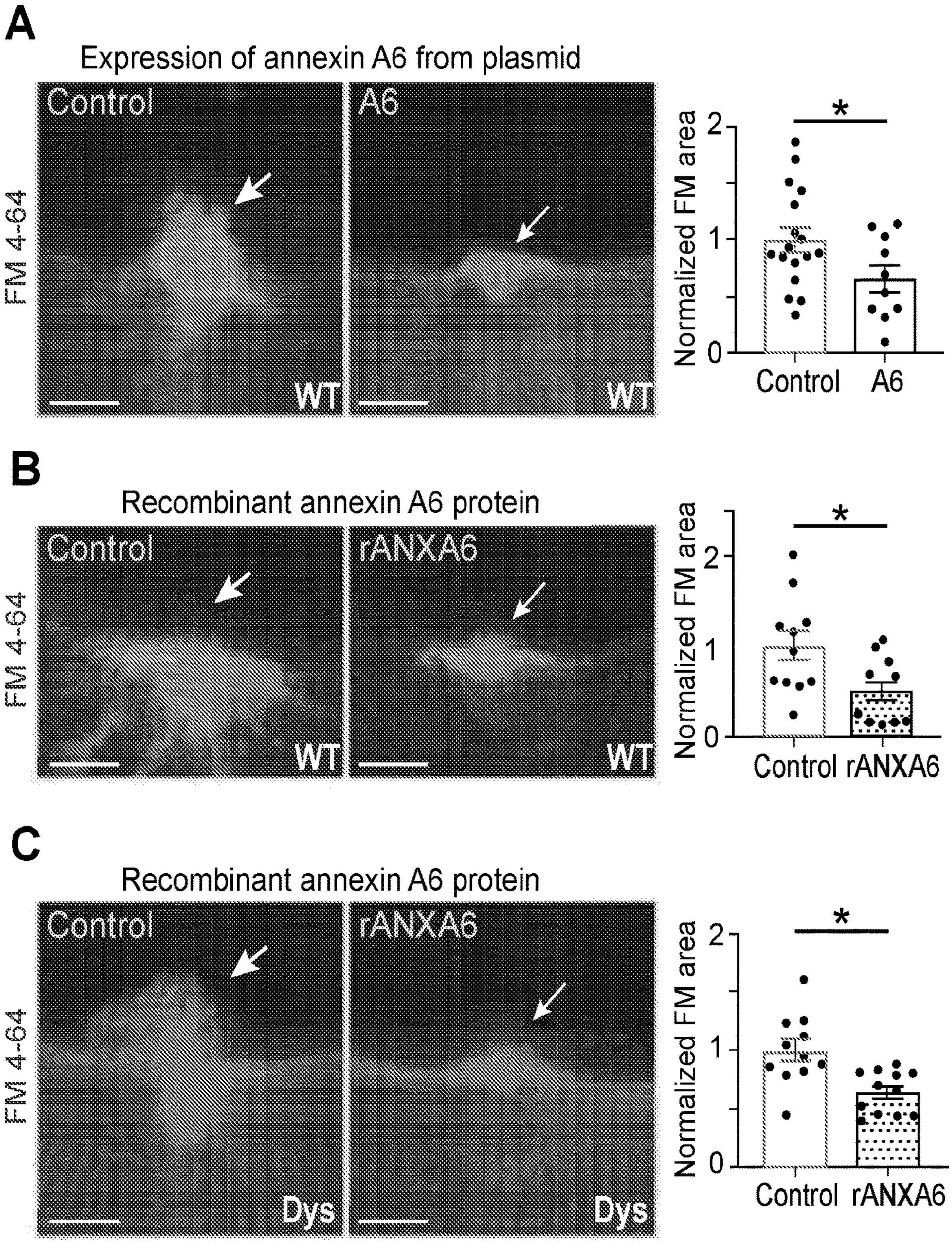
FIG. 18 shows that annexin A6 enhanced membrane repair capacity of healthy and dystrophic myofibers in vitro. (A) Plasmid expression of annexin A6 in wildtype (WT) myofibers reduced FM 4-64 dye uptake, a marker of membrane damage, after laser-induced injury as compared to control myofibers. (B) Wildtype myofibers injured in the presence of extracellular recombinant annexin A6 (rANXA6) had significantly less FM 4-64 dye uptake compared to control myofibers. (C) Dystrophic (Dys) myofibers injured in the presence of recombinant annexin A6 (rANXA6) had significantly less FM 4-64 dye uptake than control myofibers. Scale 5 μm. Data are expressed as mean±SEM. Differences were tested by two-tailed t-test * $p<0.05$, (n=10 myofibers from n=3 mice per condition).

Annexin A6 protected against laser-induced myofiber injury in vitro in a $Ca^{2+}$-dependent manner. Since annexin A6 facilitates the formation of the macromolecular repair cap complex and was the most efficient at forming large, $Ca^{2+}$-filled blebs at the site of membrane injury, it was assessed whether expression of annexin A6 would reduce membrane injury in wildtype myofibers. Wildtype myofibers were electroporated with annexin A6-GFP or mock electroporated and then laser damaged in the presence of FM 4-64 to mark the injury area. Wildtype myofibers overexpressing annexin A6 had decreased FM 4-64 dye uptake after laser-induced membrane injury compared to control myofibers (FIG. 18A). These results indicate that intracellular overexpression of annexin A6 is effective at improving membrane repair and/or protecting against laser-induced membrane injury in isolated myofibers.

Since intracellular annexin A6 targets phospholipids exposed at the site of membrane injury and enhances membrane repair capacity, we hypothesized that extracellular recombinant annexin A6 (rANXA6) would also localize to the site of injury and protect against membrane injury. Muscular dystrophy is a progressive muscle wasting disease, arising from loss-of-function mutations in critical cytoskeletal or membrane-associated proteins, often resulting in fragile plasma membranes. To determine if recombinant annexin A6 could protect against membrane insult in both healthy and dystrophic muscle, wildtype and dystrophic myofibers from a model representing Duchenne Muscular Dystrophy were isolated and incubated with recombinant annexin A6 or vehicle control. Laser injury was conducted in the presence of FM 4-64 to visualize the extent of injury. Treatment with extracellular recombinant annexin A6 reduced FM 4-64 fluorescence area compared to vehicle control-treated myofibers, indicating enhanced repair in both healthy and dystrophic myofibers (FIGS. 18B and 18C).

To assess whether recombinant annexin A6's protective effects required external $Ca^{2+}$, wildtype myofibers were pretreated with recombinant annexin A6, loaded with FM 1-43, a fluorescence marker of membrane damage similar to FM4-64, and subsequently damaged in solution containing 1 mM $Ca^{2+}$ or 0 mM $Ca^{2+}$+EGTA, a $Ca^{2+}$ chelator. FM 1-43 fluorescence accumulation at the lesion over time (F/F0) was significantly increased in the absence of $Ca^{2+}$ compared to in the presence of 1 mM $Ca^{2+}$ (FIGS. 19A and 19B). These data demonstrated that extracellular recombinant annexin A6 protects against membrane injury and/or enhances repair through extracellular exposure in a $Ca^{2+}$-dependent manner.

Recombinant annexin A6 protected against acute muscle injury in vivo. To determine the therapeutic potential of recombinant annexin A6 to protect against muscle injury in vivo, recombinant annexin A6 was utilized as a tool compound. Recombinant annexin A6 or vehicle control was injected intramuscularly into the tibialis anterior (TA) muscles of wildtype mice two hours prior to toxin-induced injury. Mice were injected intraperitoneally with Evan's blue dye, a vital tracer that is excluded by intact healthy myofibers but is readily taken up in injured permeable myofibers (Jennische E, and Hansson H A. Postischemic skeletal muscle injury: patterns of injury in relation to adequacy of reperfusion. Exp Mol Pathol. 1986; 44(3):272-80). Three hours post-cardiotoxin injury muscle was evaluated for Evan's blue dye uptake (FIG. 12A). Gross imaging showed that pretreatment with recombinant annexin A6 reduced cardiotoxin-induced muscle damage in vivo, as seen as less dye (blue) uptake compared to controls (FIG. 12B). Fluorescence imaging showed a 50% decrease in dye (red) uptake with recombinant annexin A6 pretreatment compared to control muscle (FIG. 12C). Surface plot profiles illustrate reduced dye fluorescence in tibialis anterior muscle pretreated with intramuscular recombinant annexin A6 (FIG. 12D).

Figure 20:
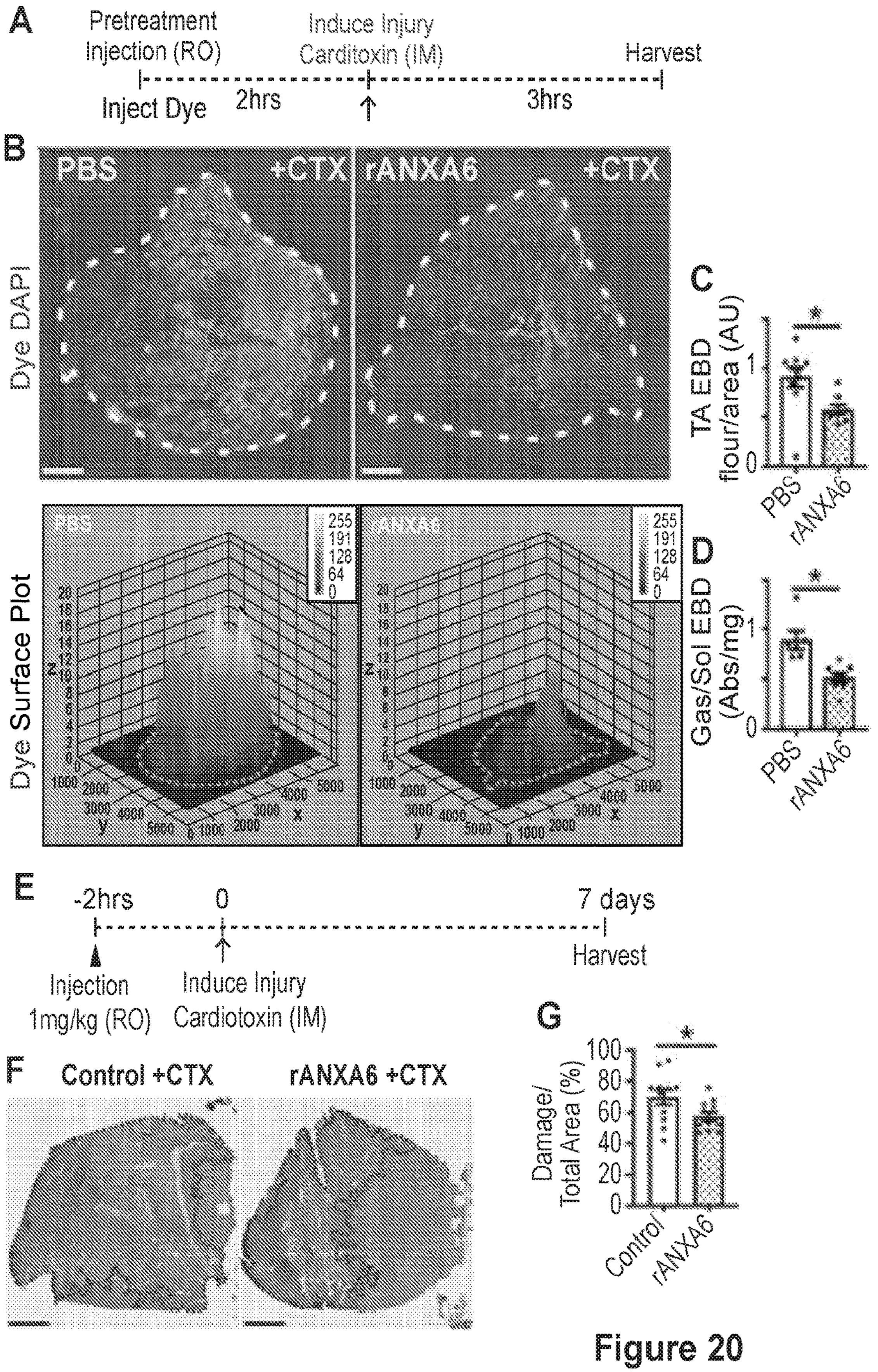
FIG. 20 shows systemic delivery using retro-orbital injection of recombinant annexin A6 protected against muscle damage in vivo. (A) Wildtype mice were injected intravenously with recombinant human annexin A6 (rANXA6) or control solution. Following this, muscles were damaged with cardiotoxin (CTX). (B-C) Immunofluorescence imaging revealed approximately 38% less dye uptake (red) in muscle pretreated with rANXA6. Dotted lines outline the tibialis anterior muscle sections (top panel). DAPI (blue) marks nuclei. Surface plots of dye uptake depict reduced fluorescence in muscle pretreated with rANXA6. (D) Whole tissue spectroscopic analysis of injured gastrocnemius/soleus muscles revealed a 58% reduction in dye uptake with rANXA6 pretreatment compared to control muscle. (E) Wildtype mice were injected intravenously with rANXA6 or control solution. Two hours later tibialis anterior muscles were damaged with cardiotoxin. Seven days post injury muscles were harvested. (F & G) Hematoxylin and eosin images were quantified and show a reduction in percent myofiber damage (dotted lines), in rANXA6 treated mice compared to controls. B, Scale 1 mm. F, Scale 500 μm. Data are expressed as mean±SEM. Differences were tested by two-tailed t-test * $p<0.05$, (B, C, D n≥3 mice, n≥6 legs per condition; F, G n≥6 mice; n≥11 muscles per condition).

Although intramuscular injection of annexin A6 was effective at reducing acute injury, this route of application is not optimal for large muscle groups, internal tissues, or treatment of chronic diseases. Therefore, the efficacy of recombinant annexin A6 administered systemically via retro-orbital (RO) injection in the protection against acute muscle injury was examined. Recombinant annexin A6 or vehicle was injected into the retro-orbital cavity two hours prior to toxin-induced injury. Mice were simultaneously injected with Evan's blue dye. Three hours post-cardiotoxin injury muscle was evaluated for Evan's blue dye uptake (FIG. 20A). Fluorescence imaging showed a 38% decrease in dye (red) uptake with recombinant annexin A6 pretreatment compared to vehicle control (FIGS. 20B and 20C). Surface plot profiles illustrate reduced dye fluorescence in muscle pretreated with systemic recombinant annexin A6 (FIG. 20C). In addition, whole tissue spectroscopic analysis of injured gastrocnemius/soleus muscles revealed a 58% reduction in dye uptake with rANXA6 pretreatment compared to vehicle treated (FIG. 20D). These results demonstrated that local and systemic administration of recombinant annexin A6 protects against acute muscle injury in vivo.

To determine if recombinant annexin A6 administration enhanced myocyte survival and/or recovery from injury, mice were administered recombinant annexin A6 or BSA control, at 1 mg/kg, through retro-orbital systemic injection. Two hours post protein administration, cardiotoxin was injected into the tibialis anterior muscles to induce focal muscle injury. Muscle was harvested 7 days post injury and histology evaluated for injury area (FIG. 20E). Pretreament with recombinant annexin A6 reduced the percentage of injured muscle, marked by internal myonuclei (black dotted outline), at 7 days post insult (FIGS. 20F and 20G). These data illustrated that systemic administration of recombinant annexin A6 protects against acute muscle injury enhancing myocyte survival/recovery from injury.

Recombinant annexin A6 protected against chronic muscle injury in vivo.

Figure 22:
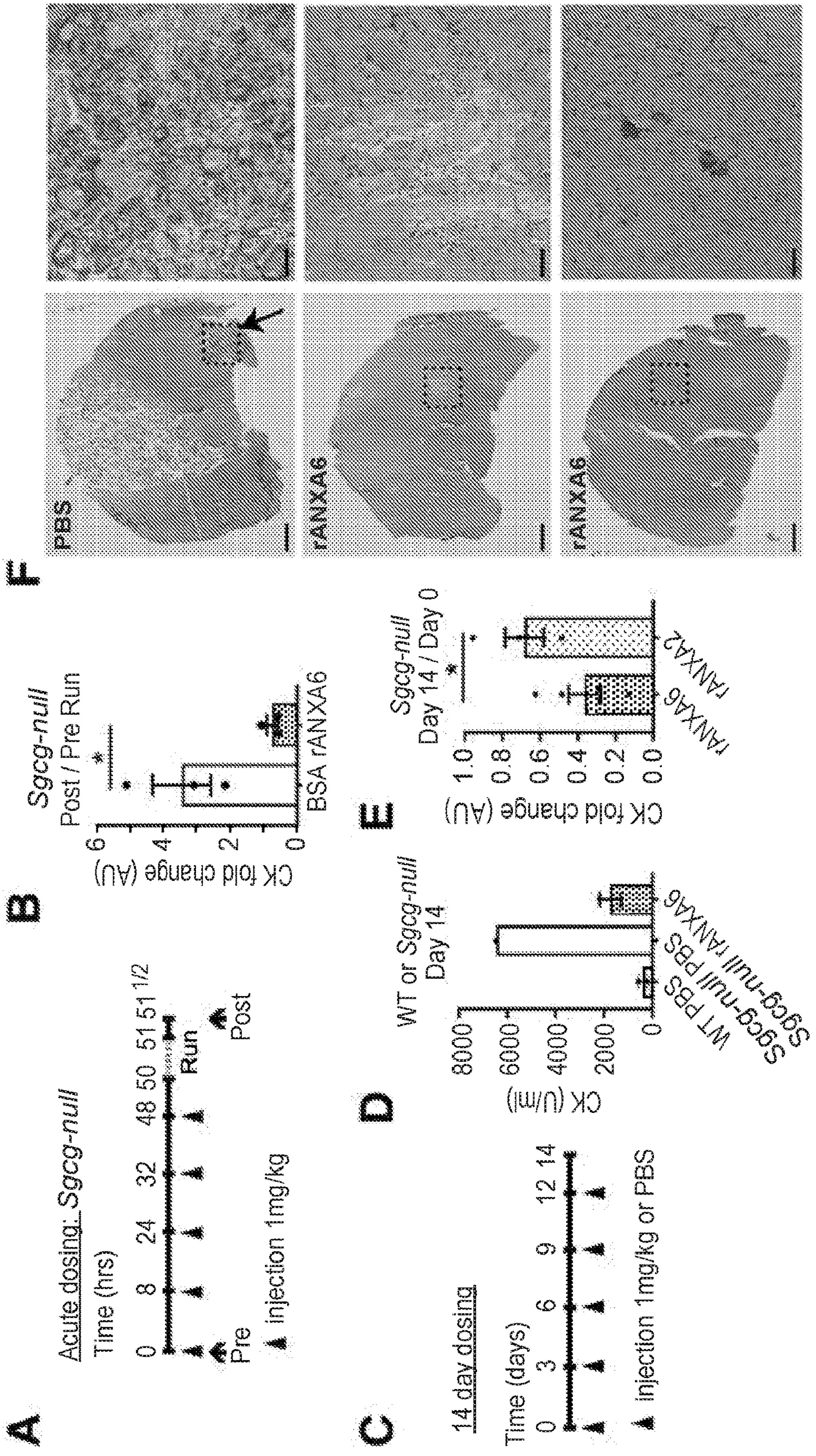
FIG. 22 shows that recombinant annexin A6 protected against muscle damage in a mouse model of muscular dystrophy in vivo. (A-B) Sgcg-null mice, a model of Limb Girdle Muscular Dystrophy 2C, were injected intravenously with recombinant human annexin A6 (rANXA6) or BSA control solution five times over 48 hours. Prior to injections, serum CK was measured. Two hours after the 5th injection, mice were subjected to 60 minutes of downhill running. Thirty minutes post exercise, serum CK was measured. The fold change in CK post/pre running was significantly reduced with rANXA6 administration compared to BSA-injected controls, consistent with a reduction in muscle injury from acute running. (C-D) Sgcg-null mice were injected intravenously every 3 days over 14 days with rANXA6 or control. On day 14, serum creatine kinase was evaluated. Serum CK in Sgcg-null mice treated with rANXA6 was lower than PBS control. (E) Sgcg-null mice were injected intravenously every 3 days for 14 days with rANXA6 or recombinant annexin A2. The serum CK fold change post/pretreatment (Day 14/Day 0) was significantly reduced in Sgcg-null mice treated with recombinant annexin A6 compared to annexin A2. (F) Histological analysis of gastrocnemius/soleus muscles from Sgcg-null mice shown in part D injected with PBS or recombinant annexin A6. Low magnification on the left and high magnification on the right of boxed area. F, Scale 500 μm (left), Scale 50 μm (right). Data are expressed as mean±SEM. Differences were tested by two-tailed t-test (B & E) * $p<0.05$, (n=3 mice per condition, except part D).

The ability of recombinant annexin A6, administered systemically, to protect against muscle damage in the Sgcg-null mouse model of Limb Girdle Muscular Dystrophy type 2C (LGMD2C) (Hack A A, Cordier L, Shoturma D I, Lam M Y, Sweeney H L, and McNally E M. Muscle degeneration without mechanical injury in sarcoglycan deficiency. Proceedings of the National Academy of Sciences of the United States of America. 1999; 96(19):10723-8) was assessed next. Sgcg-null mice lack γ-sarcoglycan, an integral membrane component of the dystrophin glycoprotein complex required for membrane stability and function. Humans and mice lacking γ-sarcoglycan develop progressive muscle disease, reduced muscle function and elevated serum creatine kinase (CK), a serum biomarker of muscle injury and membrane leak. To determine if recombinant annexin A6 protected in dystrophic muscle, Sgcg-null mice were treated systemically with recombinant annexin A6 or BSA control over 48 hours (FIG. 22A). Mice were then subjected to 60 minutes of treadmill running to induce physiological muscle damage and CK release. Recombinant annexin A6 reduced the fold change of CK kinase post exercise to pretreatment, consistent with improved membrane resealing (FIGS. 22A and 22B). Recombinant annexin A6 was also injected over a two-week interval in Sgcg-null mice. 1 mg/kg of recombinant annexin A6 was injected once every three days for 14 days (FIG. 22C). Administration of recombinant annexin A6 significantly decreased levels of serum creatine kinase (CK) compared to control treatment at day 14 (FIG. 22D). Annexin A6 was more effective than annexin A2 at reducing intracellular $Ca^{2+}$ after injury (FIG. 16D). Using the same 14-day dosing regimen in Sgcg-null mice, short-term systemic administration of recombinant annexin A6 significantly reduced serum CK levels compared to recombinant annexin A2 (FIG. 22E). The gastrocnemius/soleus muscle from recombinant annexin treated mice showed qualitatively less injury (FIG. 22F). These data showed that extracellular recombinant annexin A6 protects against injury or enhances repair in chronically injured, dystrophic mouse muscle, in vivo.

Discussion

Annexins promote calcium-filled bleb formation at the site of membrane injury. Plasma membrane instability is inherent to many forms of muscular dystrophy and thought to contribute to dysregulated $Ca^{2+}$ homoeostasis and disease pathogenesis. Molkentin and colleagues showed that transgenic overexpression of TRPC3 was sufficient to increase myofiber $Ca^{2+}$ influx and result in a dystrophy-like phenotype (Millay D P, Goonasekera S A, Sargent M A, Maillet M, Aronow B J, and Molkentin J D. Calcium influx is sufficient to induce muscular dystrophy through a TRPC-dependent mechanism.

Proceedings of the National Academy of Sciences of the United States of America. 2009; 106(45):19023-8). Correspondingly, transgenic overexpression of SERCA1 reduced cytosolic $Ca^{2+}$ levels and mitigated dystrophic muscle pathology implicating $Ca^{2+}$ in disease progression (Goonasekera S A, Lam C K, Millay D P, Sargent M A, Hajjar R J, Kranias E G, et al. Mitigation of muscular dystrophy in mice by SERCA overexpression in skeletal muscle. J Clin Invest. 2011; 121(3):1044-52). As shown and described herein, increased expression of annexins in muscle fibers decreased injury-associated $Ca^{2+}$ fluorescence within myofibers. This reduction of $Ca^{2+}$-associated fluorescence was at the injury site and correlated with extracellular bleb formation emanating from annexin repair caps. Both annexin A2 or A6 could induce the formation of membranous blebs containing the $Ca^{2+}$-binding protein GCaMP5G. Furthermore, overexpression of annexins A1, A2, and A6 each reduced endpoint $Ca^{2+}$ fluorescence accumulation within the myofiber after injury. Of the three annexins tested, annexin A6 overexpression resulted in the most sustained effect on reducing injury-associated $Ca^{2+}$ accumulation inducing the formation of large GCaMP5G-containing blebs. In HEK293 cells damaged with streptolysin O (SLO), the presence of extracellular membranous blebs correlated with increased cell survival and reduction in cytoplasmic $Ca^{2+}$ levels, a process facilitated by annexin A1 (Babiychuk E B, Monastyrskaya K, Potez S, and Draeger A. Blebbing confers resistance against cell lysis. Cell Death Differ. 2011; 18(1):80-9). Davenport and colleagues showed overexpression of annexin A1-GFP in injured *Xenopus oocytes* resulted in annexin A1 positive blebs originating from the site of damage (Davenport N R, Sonnemann K J, Eliceiri K W, and Bement W M. Membrane dynamics during cellular wound repair. Mol Biol Cell. 2016; 27(14):2272-85). However, the effects of annexins A2 or A6 overexpression were not assessed in either study. These data combined suggest bleb formation as a mechanism of membrane repair is conserved across species and tissue types and is facilitated by the presence of annexin proteins.

Without being bound by theory, it is contemplated that annexin A6 facilitates cytoplasmic $Ca^{2+}$ and protein excretion into extracellular blebs whose formation is further induced by annexin A1 and annexin A2. In artificial membrane patches, the presence of annexin A1 or annexin A2 induced bleb formation at sites of membrane imperfection (Boye T L, Jeppesen J C, Maeda K, Pezeshkian W, Solovyeva V, Nylandsted J, et al. Annexins induce curvature on free-edge membranes displaying distinct morphologies. Sci Rep. 2018; 8(1):10309). In contrast, the presence of annexin A6 induced $Ca^{2+}$-dependent contraction of artificial membrane into large folds (Boye T L, Jeppesen J C, Maeda K, Pezeshkian W, Solovyeva V, Nylandsted J, et al. Annexins induce curvature on free-edge membranes displaying distinct morphologies. Sci Rep. 2018; 8(1):10309). The difference between annexin A6 inducing blebs in live myofibers or folds in artificial membrane may reflect the presence of endogenously expressed annexin A1 and A2 in isolated myofibers compared with exposure to single recombinant annexin protein in the artificial membrane studies. Without being bound by theory, it is contemplated that within the macromolecular repair complex, multiple annexins actively participate in bleb formation, which acts to remove large membrane lesions facilitating wound closure, excision of damaged membrane, and reduction of $Ca^{2+}$ at the injury site.

Annexin A6 protects against muscle membrane injury and enhances membrane repair. We showed that annexin proteins, including annexin A1, A2, and A6, localize to the site of membrane injury facilitating membrane repair cap and bleb formation. Mutation of annexin A6 abrogated repair cap formation, decreasing repair capacity, resulting in increased dye uptake. On the other hand, pretreatment with recombinant annexin A6 reduced dye uptake after laser-induced muscle injury and after toxin-induced muscle injury in vivo. As a therapeutic tool, enhancing the cells' ability to repair and/or reduce injury through stabilizing the cell membrane are both beneficial avenues that can lead to improved cell survival. Previous studies have shown that annexin A6 is upregulated in muscle from models of chronic muscular dystrophy (Demonbreun A R, Allen M V, Warner J L, Barefield D Y, Krishnan S, Swanson K E, et al. Enhanced Muscular Dystrophy from Loss of Dysferlin Is Accompanied by Impaired Annexin A6 Translocation after Sarcolemmal Disruption. Am J Pathol. 2016; 186(6):1610-22; Swaggart K A, Demonbreun A R, Vo A H, Swanson K E, Kim E Y, Fahrenbach J P, et al. Annexin A6 modifies muscular dystrophy by mediating sarcolemmal repair. Proceedings of the National Academy of Sciences of the United States of America. 2014; 111(16):6004-9; Demonbreun A R, Rossi A E, Alvarez M G, Swanson K E, Deveaux H K, Earley J U, et al. Dysferlin and myoferlin regulate transverse tubule formation and glycerol sensitivity. Am J Pathol. 2014; 184(1):248-59). Proteomic profiling of mdx mouse muscle showed that annexins A1 and A2 are enriched in mdx muscle membrane, consistent with a role for annexins at the membrane of injured muscle cells (Murphy S, Zweyer M, Henry M, Meleady P, Mundegar R R, Swandulla D, et al. Proteomic analysis of the sarcolemma-enriched fraction from dystrophic mdx-4cv skeletal muscle. J Proteomics. 2018). Annexins bind membrane phospholipids, including phosphatidylserine, which is exposed during membrane disruption. Phosphatidylserine rearrangement after injury provides an optimal binding target for extracellular annexins to facilitate membrane folding, blebbing, and rolling at sites of membrane damage and imperfection (Boye T L, Jeppesen J C, Maeda K, Pezeshkian W, Solovyeva V, Nylandsted J, et al. Annexins induce curvature on free-edge membranes displaying distinct morphologies. Sci Rep. 2018; 8(1): 10309). Upregulation of annexins is contemplated to be a compensatory mechanism to facilitate excision of defective membrane in fibers undergoing chronic damage.

Additional studies of cardiac muscle injury further suggest a role for annexin proteins in modulating the repair response. Administration of recombinant annexin A1 or the N-terminal annexin A1 peptide (AC2-26) elicited a cardioprotective response in a rat model of myocardial ischemia-reperfusion-induced injury (La M, D'Amico M, Bandiera S, Di Filippo C, Oliani S M, Gavins F N, et al. Annexin 1 peptides protect against experimental myocardial ischemia-reperfusion: analysis of their mechanism of action. FASEB J. 2001; 15(12):2247-56). Meng et al demonstrated that downregulation of annexin A3 resulted in cardioprotection, decreasing rat myocardial infarct size through activation of AKT signaling (Meng H, Zhang Y, An S T, and Chen Y. Annexin A3 gene silencing promotes myocardial cell repair through activation of the PI3K/Akt signaling pathway in rats with acute myocardial infarction. J Cell Physiol. 2019; 234(7):10535-46). In addition to membrane reorganization, annexins act as scaffolds regulating multiple downstream intracellular signaling cascades important for orchestrating repair from injury. Both intra- and extra-cellular functions of annexin proteins should be considered when evaluating the therapeutic potential of annexin proteins.

The studies presented herein indicate that human recombinant annexin A6 protein is a suitable biologic to protect against acute muscle injury. It is shown herein that human recombinant annexin A6 was capable of resealing injured membrane in mouse models, confirming functional activity of the human recombinant protein in a mouse preclinical model. Human and mouse annexin A6 proteins are 94.35% identical at the amino acid level with increasing percent amino acid conservation between humans and rat (94.65%), dog (95.54%), and monkey (98.96%), and this high degree of similarly is consistent with human recombinant protein having efficacy in a mouse model (FIG. 21). The current studies are limited by available recombinant protein, and further studies are needed to determine if recombinant annexin A6 can facilitate membrane repair and reduce the susceptibility to injury long-term in chronic models of muscle disease and in tissues beyond skeletal muscle. Annexin A6 was originally identified in a mouse model of muscular dystrophy as a genetic modifier of muscle membrane leak, and annexin A6 was subsequently shown to modify injury response in healthy mouse muscle (Swaggart K A, Demonbreun A R, Vo A H, Swanson K E, Kim E Y, Fahrenbach J P, et al. Annexin A6 modifies muscular dystrophy by mediating sarcolemmal repair. Proceedings of the National Academy of Sciences of the United States of America. 2014; 111(16):6004-9). It is contemplated herein that enhancing repair through administration of recombinant annexin A6 protein will provide similar protection in dystrophic muscle but would require long term intermittent dosing. Future studies will require optimizing mammalian recombinant annexin A6 protein production to generate sufficient quantities of purified protein.

Combinatorial approaches to improve membrane repair. Recombinant annexin A6 and its ability to protect normal and dystrophic muscle from laser-induced membrane injury is described and shown herein. In addition, both intramuscular and systemic administration of recombinant annexin A6 protected against toxin-induced muscle membrane injury in vivo. It was previously found that glucocorticoid administration increased annexin expression in muscle, and this correlated with enhanced muscle repair in multiple mouse models of muscular dystrophy including mdx (DMD), dysferlin-null (Limb Girdle Muscular Dystrophy 2B), and γ-sarcoglycan-null (Limb Girdle Muscular Dystrophy 2C) mice (Quattrocelli M, Barefield D Y, Warner J L, Vo A H, Hadhazy M, Earley J U, et al. Intermittent glucocorticoid steroid dosing enhances muscle repair without eliciting muscle atrophy. J Clin Invest. 2017; 127(6):2418-32; Quattrocelli M, Salamone I M, Page P G, Warner J L, Demonbreun A R, and McNally E M. Intermittent Glucocorticoid Dosing Improves Muscle Repair and Function in Mice with Limb-Girdle Muscular Dystrophy. Am J Pathol. 2017; 187(11): 2520-35). Glucocorticoid treatment also increased the expression of the Trim72 gene that encodes mitsugumin 53 (known as MG53), a repair protein that localizes to the site of membrane injury and considered a "molecular band-aid" for improving cellular wound healing. Similar to the annexins, MG53 is upregulated in chronic muscle injury and enhances repair in dystrophic muscles, as well as other tissues like heart, lung, kidney (Waddell L B, Lemckert F A, Zheng X F, Tran J, Evesson F J, Hawkes J M, et al. Dysferlin, annexin A1, and mitsugumin 53 are upregulated in muscular dystrophy and localize to longitudinal tubules of the T-system with stretch. J Neuropathol Exp Neurol. 2011; 70(4):302-13; Duann P, Li H, Lin P, Tan T, Wang Z, Chen K, et al. MG53-mediated cell membrane repair protects against acute kidney injury. Science translational medicine. 2015; 7(279):279ra36; He B, Tang R H, Weisleder N, Xiao B, Yuan Z, Cai C, et al. Enhancing muscle membrane repair by gene delivery of MG53 ameliorates muscular dystrophy and heart failure in delta-Sarcoglycan-deficient hamsters. Molecular therapy: the journal of the American Society of Gene Therapy. 2012; 20(4):727-35; Jia Y, Chen K, Lin P, Lieber G, Nishi M, Yan R, et al. Treatment of acute lung injury by targeting MG53-mediated cell membrane repair. Nat Commun. 2014; 5:4387; Liu J, Zhu H, Zheng Y, Xu Z, Li L, Tan T, et al. Cardioprotection of recombinant human MG53 protein in a porcine model of ischemia and reperfusion injury. Journal of molecular and cellular cardiology. 2015; 80:10-9; Weisleder N, Takizawa N, Lin P, Wang X, Cao C, Zhang Y, et al. Recombinant MG53 protein modulates therapeutic cell membrane repair in treatment of muscular dystrophy. Science translational medicine. 2012; 4(139):139ra85). MG53 is a component of the annexin-mediated repair complex, localizing adjacent to the annexin repair cap (Demonbreun A R, Quattrocelli M, Barefield D Y, Allen M V, Swanson K E, and McNally E M. An actin-dependent annexin complex mediates plasma membrane repair in muscle. The Journal of cell biology. 2016; 213(6): 705-18).

Example 4

Additional experiments were designed and conducted to evaluate the role of endogenous annexin A6, annexin A6 in heart, and annexin A6 in additional models of muscular dystrophy.

Methods

Animals. Genetically-encoded annexin A6GFP mice were generated and backcrossed onto the 129T2/SvEmsJ background. Dysferlin-null mice on the 129T2/SvEmsJ background were previously generated (Demonbreun et al. HMG 2011). Sgcg-null mice were generated as described in (Hack et al PNAS 1999). Mice were bred and housed in a specific pathogen free facility on a 12-hour light/dark cycle and fed ad libitum in accordance with the Northwestern University's Institutional Animal Care and Use Committee regulations. 129T2/SvEmsJ (129T2) mice were originally purchased from the Jackson Laboratory (Ben Harbor, ME; Stock #002065). Two to three-month-old male and female were used for all experiments. All animal experiments were approved in accordance with the Northwestern University's Institutional Animal Care and Use Committee regulations.

Genomic structure schematic. Annexin A6 genomic structure was visualized using UCSC genome browser.

Myofiber isolation. Flexor digitorum brevis (FDB) fibers were isolated with methods that were described previously in (Demonbreun and McNally, 2015; Demonbreun et al., 2016b; DiFranco et al., 2009). Briefly, fibers were dissociated in 0.2% BSA plus collagenase type II (Cat #17101, Thermo Fisher Scientific, Waltham, MA) for 60 minutes at 37 degrees in 10% $CO_2$. Fibers were then moved to Ringers solution and placed on MatTek confocal microscopy dishes (Cat #P35G-1.5-14-C, MatTek, Ashland MA).

Immunofluorescence microscopy. Mice were systemically injected with recombinant annexin A6 with a C-terminal HIS tag (R&D). Muscle was harvested and flash frozen. Muscle sections (10 μm thick) from the center of frozen-embedded muscles were collected on the cryostat (chamber, −20° C.; sample, −15° C.; catalog number CM1950; Leica, Wetzlar, Germany) for immunostaining. Tissues were fixed with 4% paraformaldehyde for 10 minutes on ice. Block and permeabilization were with 0.1% Triton (catalog number X-100; Sigma-Aldrich), 10% fetal bovine serum, and PBS for 60 minutes. For laminin detection, anti-laminin antibody was used at a dilution of 1:100 and for HIS detection, anti-HIS antibody was used at 1:100 overnight at 4° C. Hoechst labelled nuclei. Sections were PBS rinsed, incubated with secondary antibody for 1 hour, PBS rinsed, and mounted. Imaging was performed using a Zeiss Axio Observer A1 microscope (Zeiss, Oberkochen, Germany).

Cardiomyocyte isolation. Mice were treated with 50 U heparin intraperitoneally 20 minutes before sacrifice. Mice were anesthetized under 5% vaporized isoflurane mixed with 100% oxygen. A thoracotomy was performed and the heart and lungs rapidly excised and submerged into ice-cold Tyrode solution without calcium (143-mM NaCl, 2.5-mM KCl, 16-mM $MgCl_2$, 11-mM glucose, 25-mM $NaHCO_3$, pH adjusted to 7.4). The ascending aorta was dissected out of the surrounding tissue and cannulated with an animal feeding needle (7900, Cadence Science, Staunton, Virginia) and secured with a 6-0 silk suture. The heart was initially perfused with 1 ml of ice-cold calcium-free Tyrode solution before being transferred to a Langendorff apparatus (Radnoti, Covina, California). Hearts were perfused with 37° C. calcium-free Tyrode solution using a constant pressure (65-cm vertical distance between the buffer reservoir and cannula tip) for 1 to 2 minutes before perfusion for 5.5 minutes with digestion solution (0.15% collagenase type 2 [Worthington Biochemical, Lakewood, New Jersey], 0.1% 2,3-butanedione monoxime, 0.1% glucose, 100-U/ml penicillin/streptomycin, 112-mM NaCl, 4.7-mM KCl, 0.6-mM $KH2PO_4$, 40-μM $CaCl_2$), 0.6-mM Na2HPO4, 1.2-mM MgSO4, 30-μM phenol red, 21.4-mM $NaHCO_3$, 10-mM HEPES, and 30-mM taurine; pH adjusted to 7.4). The heart was removed from the cannula, triturated with a transfer pipette, and filtered through a 100-μm cell strainer. Cardiomyocytes were allowed to pellet by gravity for 7 minutes, followed by aspiration of digestion media and washing with stop buffer (formulated identically to digestion solution except with no collagenase and with 1% bovine serum albumin). Cells were again allowed to gravity pellet followed by a wash in stop buffer without bovine serum albumin. Cardiomyocytes were tolerated to calcium by adding Tyrode buffer with 0.3-mM $CaCl_2$) dropwise. Cell culture dishes were coated with 20 μg/ml laminin (23017-015; Gibco, Thermo Fisher Scientific, Waltham, Massachusetts) for 1 hour at room temperature. Laminin solution was aspirated followed by plating of cardiomyocytes for 1 hour to allow cell adhesion before experimentation.

Multiphoton laser injury and imaging. Isolated fibers were subjected to laser-induced damage at room temperature using the Nikon A1R-MP multiphoton microscope. Imaging was performed using a 25×1.1NA objective directed by the NIS-Elements AR imaging software. Green fluorescence protein (GFP) and FM 4-64 were excited using a 920 nm wavelength laser and emission wavelengths of 575 nm and 629 nm were collected respectively. To induce laser damage on isolated myofibers, a diffraction limited spot (diameter approximately 410 nm) was created on the lateral membrane of the myofiber using a 920 nm wavelength laser at 10-15% laser power for 1 second. Time lapse images were collected as follows: one image was collected prior to damage, one image upon damage, then every 8 s for 80 s (10 images) followed by every 30 seconds for 5 min (10 images). At the end of the time lapsed image series, z-stack images were collected at 250 nm intervals through the damaged site on the myofiber directed by the NIS-Elements AR imaging software. Fluorescence intensity and cap area were measured using Fiji (NIH).

For recombinant protein studies, myofibers were isolated from mice as described above. Myofibers were incubated in 10-40 μg/ml recombinant annexin A6 (5186-A6-050, R&D systems) in 1 mM $Ca^{2+}$ Ringers or BSA control. Cap size was assessed from acquired images in FIJI. FM 4-64 (2.5 μm) was added to the myofibers just prior to imaging. Images were acquired and quantitated as described above. FM 4-64 fluorescence at endpoint was measured using FIJI.

For prednisone studies, prednisone (catalog P6254) was resuspended in DMSO (catalog D2650, Sigma-Aldrich) at 5 mg/ml. Dosing was based on pretreatment weights (1 mg/kg body weight) in 30 μl total PBS. Mice were injected at 7 am on the day prior to imaging. On injection days, stock solutions stored at −20° C. were diluted into sterile Eppendorf tubes containing sterile PBS (catalog 14190, Life Technologies). Sterile BD Micro-Fine IV Insulin Syringes (catalog 14-829-1A, Fisher Scientific) were used to inject the I.P. cavity of non-sedated animals. 24 hours post injection myofibers were harvest and then imaged the same day.

Statistical analysis. Statistical analyses were performed with Prism (Graphpad, La Jolla, CA). Comparisons relied on ANOVA (1way ANOVA for 1 variable). Otherwise, unpaired two-tailed t-tests were performed. P value less than or equal to 0.05 was considered significant. Data were presented as single values were appropriate. Error bars represent+/−standard error of the mean (SEM).

Results of the experiments are shown in FIGS. 24-28.

Glucocorticoid steroids modify endogenous annexin A6GFP localization, protecting against insult. Gene editing was used to introduce a GFP tag at the carboxyl terminus of the Anxa6 locus in mice to create Anxa6$^{em1(GFP)}$ mice. These mice offer the advantage of examining genomically-encoded annexin A6 under the control of the Anxa6 promoter and regulatory sequences. Because Anxa6$^{em1(GFP)}$ mice express annexin A6 protein under the control of the Anxa6 gene, expression levels are at normal to lower levels than plasmid encoded annexin A6-GFP. This animal model allows for the examination of a range of annexin A6 protein expression in real time. Glucocorticoid steroids, including prednisone, have been shown to upregulate annexin A1 and A6 expression. Furthermore, prednisone administration protected against membrane injury, reducing plasmid overexpressed annexin GFP cap formation after laser injury. To determine if prednisone modulated genomically-encoded annexin A6GFP cap kinetics, Anxa6$^{em1(GFP)}$ mice were injected with 1 mg/kg prednisone or control DMSO into the intraperitoneal cavity. Twenty-four hours post injection, myofibers were isolated and subjected to laser injury. Annexin A6GFP cap size was reduced in myofibers treated with prednisone compared to controls (FIG. 24), indicating responsiveness of annexin A6GFP protein to steroid administration. This illustrated the potential of external agents to modify endogenous annexin A6 expression to elicit protection against injury.

Figure 25:
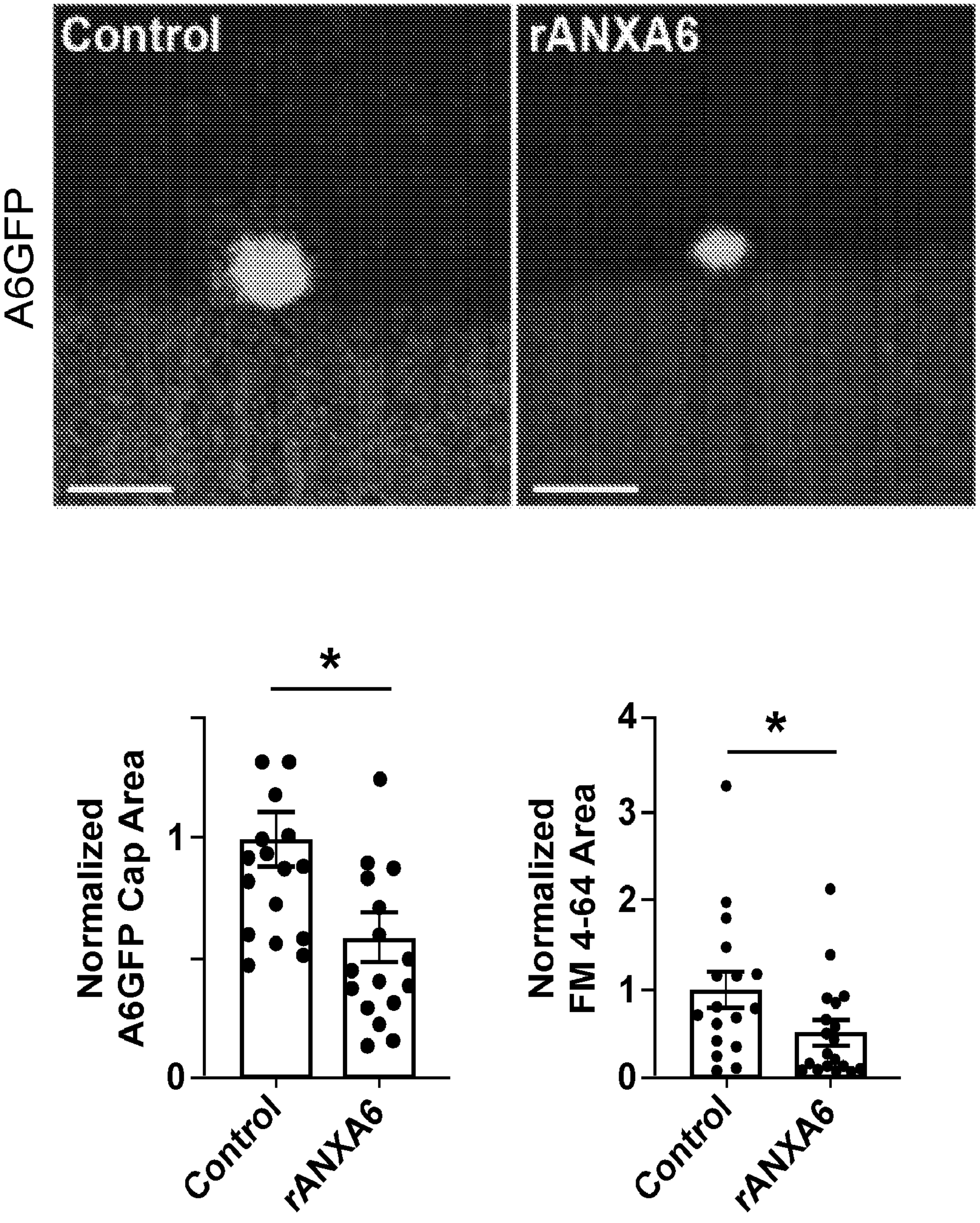
FIG. 25 shows recombinant annexin A6 pretreatment reduces genetically-encoded annexin A6GFP cap size and dye influx, indicating enhanced protection against injury. Myofibers were isolated, pretreated with recombinant annexin A6 (rANAXA6) and subsequently subjected to laser-induced membrane injury. Z-stack imaging revealed annexin A6GFP repair cap size was reduced in the presence of recombinant annexin A6, indicative of protection against injury. This correlated with a reduction in FM 4-64 uptake, a marker of membrane injury, in the presence of rANXA6. Scale 5 μm. *p<0.05. t-test. n≥3 mice per treatment.

Recombinant annexin A6 promotes skeletal muscle repair. It was shown that recombinant annexin A6 protected against laser-induced injury by reducing FM dye uptake in healthy and dystrophic myofibers. To further elucidate the mechanism by which recombinant annexin A6 confers protection, Anxa6$^{em1(GFP)}$ myofibers were pretreated with recombinant annexin A6 protein or control. Subsequently, myofibers were incubated in FM 4-64 dye and subjected to laser injury. Myofibers pretreated with recombinant annexin A6 had smaller annexin A6GFP repair caps and a concomitant reduction in FM dye uptake, compared to control myofibers (FIG. 25). These data indicated that recombinant annexin A6 participates in orchestrating the endogenous repair complex, enhancing membrane protection and repair, reducing membrane leak.

Figure 26:
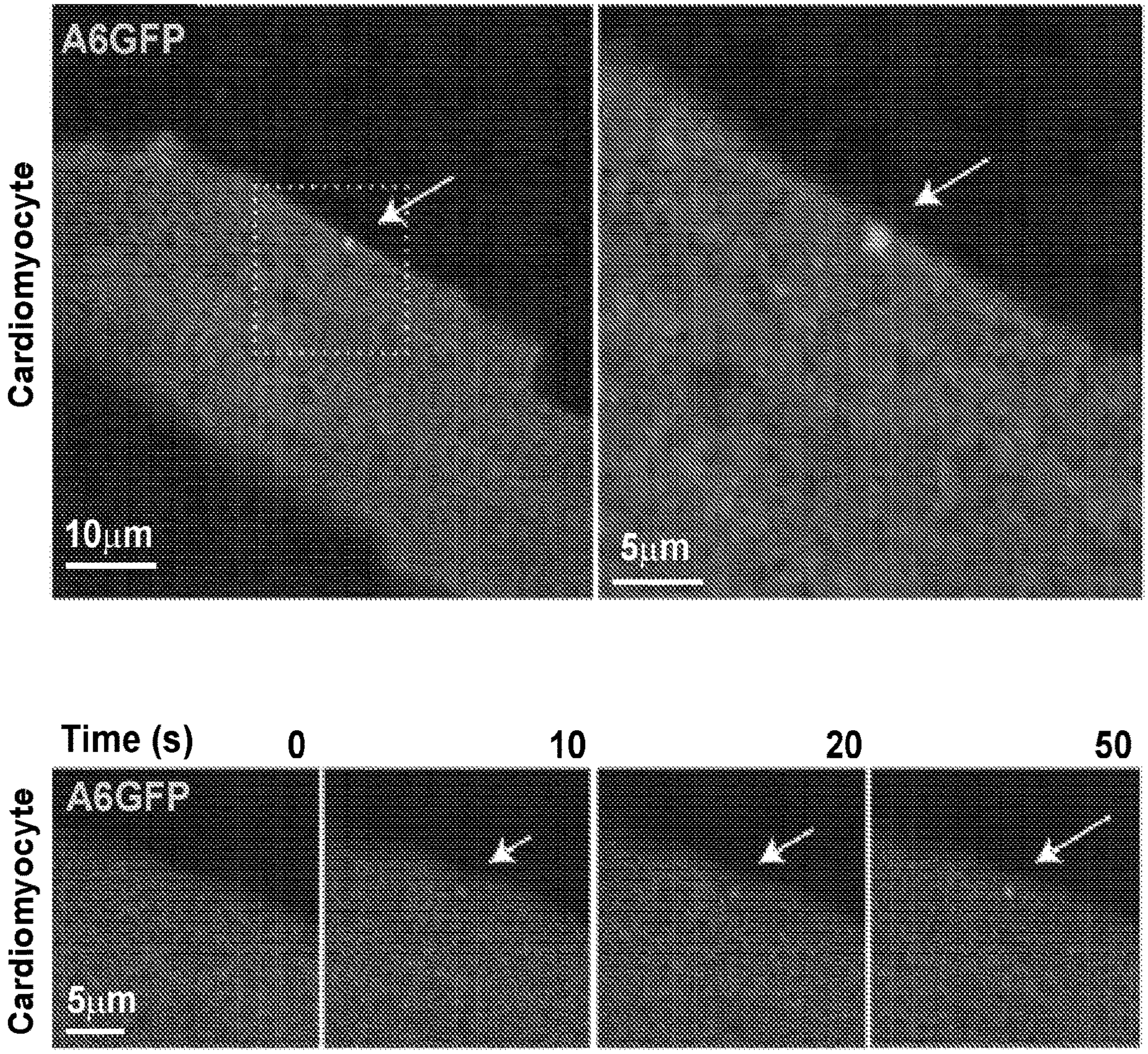
FIG. 26 shows genetically-encoded annexin A6GFP localizes at the site of cardiomyocyte membrane injury. Adult cardiomyocytes were isolated from $AnxaG^{em1(GFP)}$ mice and subsequently laser-damaged. Annexin A6GFP (green) localizes in a repair cap (white arrow, left image) at the site of injury. Area within the dotted box is magnified on the right. Timelapse imaging shows that annexin A6GFP localizes in a repair cap (white arrow) at the site of injury over 50 seconds of imaging, in adult cardiomyocytes isolated from $Anxa6^{em1(GFP)}$ mice. Scale 5 μm or 10 μm.
Figure 27:
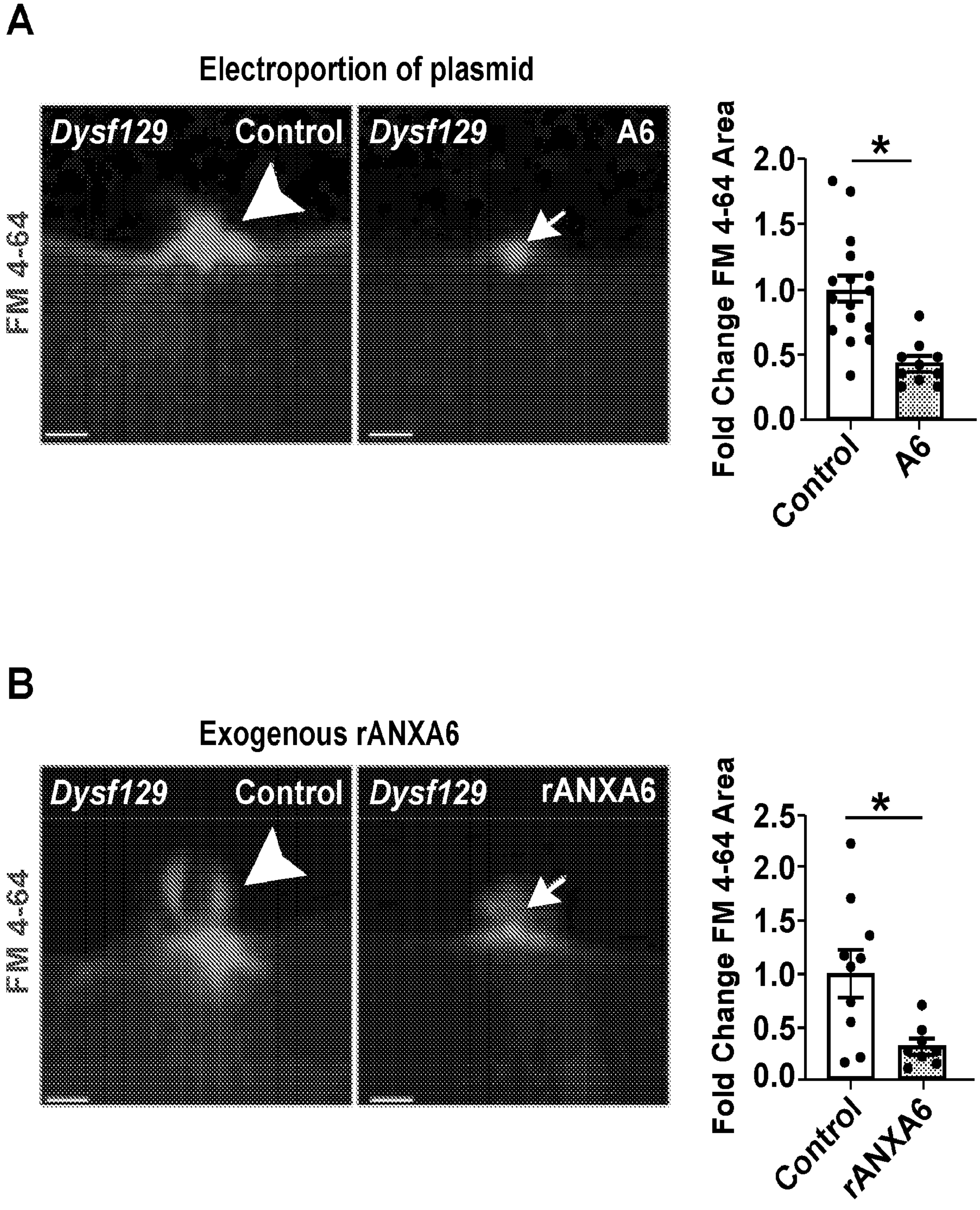
FIG. 27 shows annexin A6 enhanced membrane repair capacity of dystrophic, dysferlin-null myofibers in vitro, protecting against injury. A) Plasmid expression of annexin A6 in dysferlin-null (Dysf129) myofibers reduced FM 4-64 dye uptake (small arrow), a marker of membrane damage, after laser-induced injury as compared to control myofibers (arrowhead). B) Pretreatment with recombinant annexin A6 decreased FM 4-64 uptake (small arrow) compared to control (arrowhead) after laser injury in dysferlin-null (Dysf129) myofibers. Scale 5 μm. Data are expressed as mean±SEM. Differences were tested by two-tailed t-test * p<0.05, (n≥9 myofibers per condition).

Annexin A6GFP is expressed in the heart and forms repair caps in injured cardiomyocytes. Annexin A6 was identified as a modifier of membrane leak in the heart, however, methods to evaluate cardiomyocyte repair were previously lacking. It was hypothesized that if endogenous annexin A6GFP was expressed in the heart that this new Anxa6$^{em1(GFP)}$ mouse model could be used as a tool to evaluate endogenous cardiomyocyte membrane repair. To determine if endogenous annexin A6GFP played a role in membrane repair in tissues beyond skeletal muscle, Anxa6$^{em1(GFP)}$ cardiomyocytes were isolated and subjected to laser injury. Endogenous annexin A6GFP localized in a sarcomeric pattern in live, isolated cardiomyocytes, similar to skeletal myofibers (FIG. 26). Within seconds of laser-induced damage, annexin A6GFP localized to the membrane lesion organizing into a repair cap in the cardiomyocyte (FIG. 26, white arrow). A magnified image of the white dotted box depicting a bright annexin A6GFP repair cap is shown in the image on the right (FIG. 26). Timelapse images illustrating the progression of annexin A6GFP localization into the repair cap (arrow) in an isolated cardiomyocyte is shown up to 50 seconds post injury (FIG. 26). These data showed that endogenous annexin A6GFP localizes to the site of membrane injury forming a repair cap at the membrane lesion in live, adult cardiomyocytes, suggesting a broad role for annexin A6 in membrane repair.

Annexin A6 enhances repair in a model of Limb Girdle Muscular Dystrophy 2B (LGMD2B). Dysferlin is a $Ca^{2+}$-binding, membrane-associated protein implicated in membrane repair. Loss-of-function mutations is dysferlin reduce membrane repair capacity resulting in Limb Girdle Muscular Dystrophy 2B (LGMD2B). It was hypothesized that agents that enhance repair or reduce injury susceptibility could provide therapeutic benefit for treating LGMD2B. To test this hypothesis, mice lacking dysferlin on the 129 background (Dysf129) were electroporated with annexin A6 plasmid and then were subjected to laser injury in the presence of FM 4-64. Myofibers overexpressing annexin A6 had a significant reduction in FM 4-64 dye uptake after injury (FIG. 27A). Since plasmid overexpression protected dysferlin-null myofibers from injury, we next tested the effectiveness of recombinant annexin A6. To determine if recombinant annexin A6 could protect against membrane insult in dystrophic, dysferlin-null muscle, myofibers from Dysf129 mice were isolated and incubated with recombinant annexin A6 or vehicle control. Laser injury was conducted in the presence of FM 4-64 to visualize the extent of injury. Treatment with extracellular recombinant annexin A6 reduced FM 4-64 fluorescence area compared to vehicle control-treated myofibers (FIG. 27B). These data indicated that annexin A6 enhances repair and protects against injury of dystrophic, LGMD2B myofibers.

Figure 28:
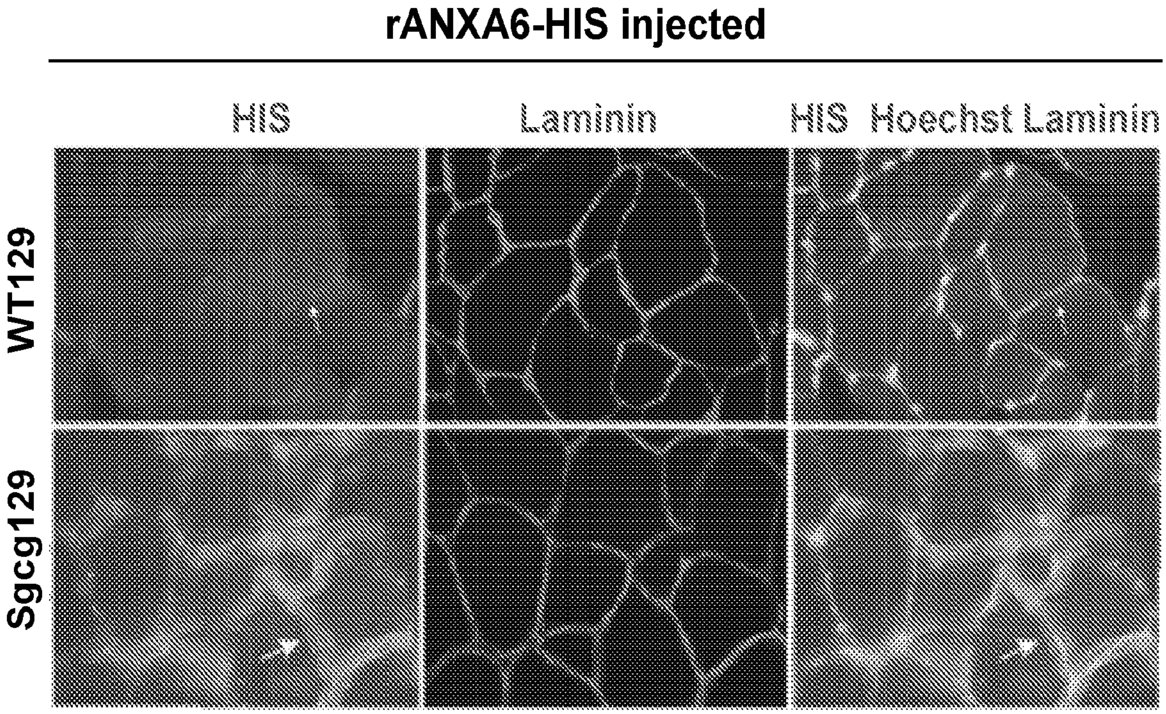
FIG. 28 shows recombinant Annexin A6 localizes to the sarcolemma of dystrophic, of Limb girdle muscular dystrophy 2C muscle. Recombinant annexin A6 (rANXA6) with a carboxy-terminal HIS tag was injected in healthy, wildtype mice or a mouse model of Limb girdle muscular dystrophy 2C, Sgcg-null, that undergoes chronic membrane disruption. Mice were on the 129Sv/EmsJ background. anti-HIS fluorescence intensity was increased at the plasma membrane of Sgcg-null muscle, visualized through anti-laminin staining, compared to wildtype controls. Hoechst labeled nuclei.

Recombinant annexin A6 localizes to the sarcolemma in a model of Limb Girdle Muscular Dystrophy 2C (LGMD2C). Since recombinant annexin A6 protected against membrane injury, the localization ability of recombinant annexin A6, administered systemically, was assessed in the Sgcg-null mouse model of LGMD2C compared to wildtype controls. Sgcg-null mice lack γ-sarcoglycan, an integral membrane component of the dystrophin glycoprotein complex required for membrane stability and function. Recombinant annexin A6 localized to the muscle membrane of chronically injured, Sgcg-null mice, visualized by strong anti-HIS immunofluorescence signal colocalizing with anti-laminin membrane staining (FIG. 28). In comparison, minimal sarcolemma anti-HIS fluorescence was present in uninjured, wildtype muscle membrane (FIG. 28). These data illustrated that recombinant annexin A6 localizes to the membrane of chronically injured muscle.

Example 5

This example details the production of recombinant annexin A6 protein (rANXA6) expressed from plasmids in both mammalian cells and prokaryotic cells.

Figure 29:
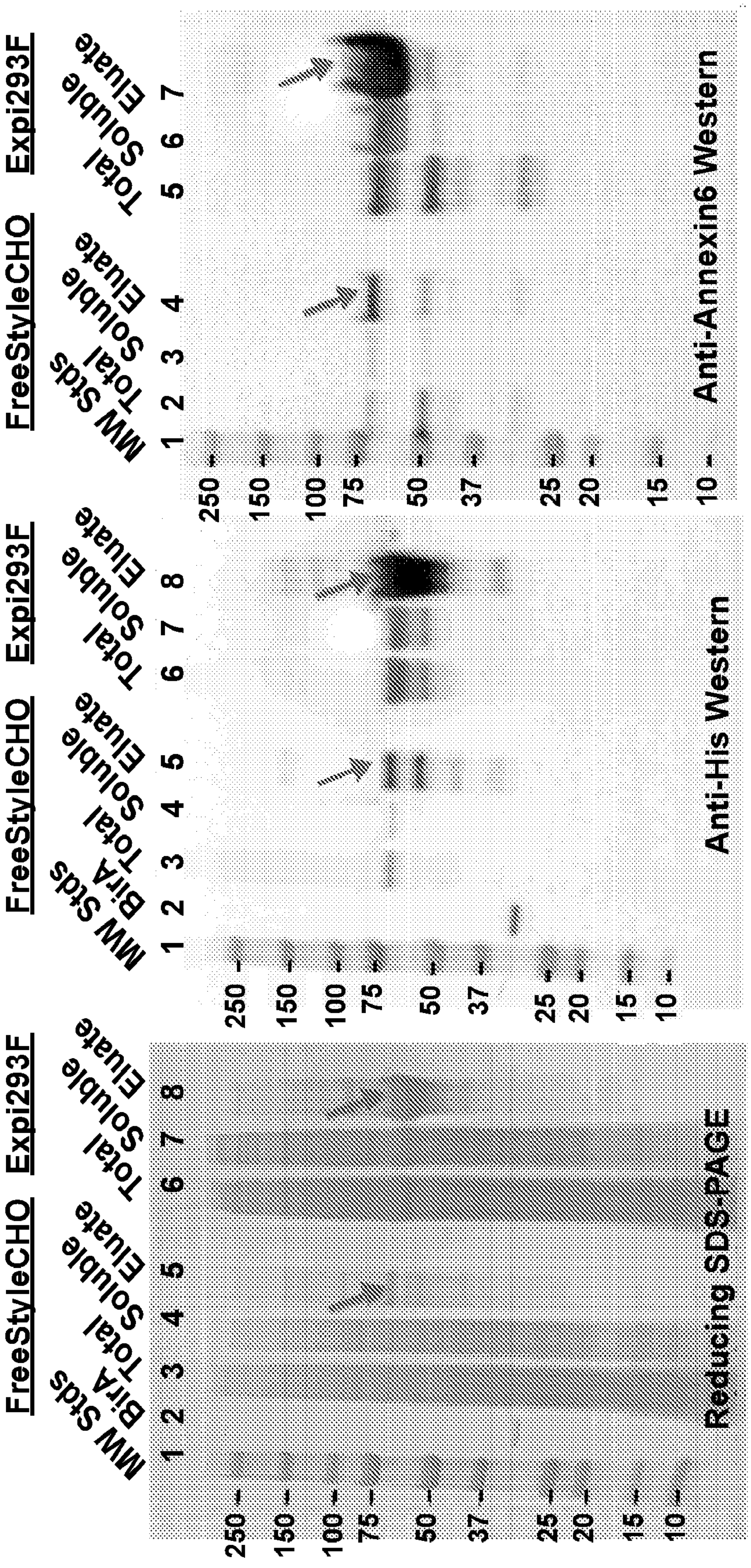
FIG. 29 shows results of SDS-PAGE (left panel) and Western blot analysis (middle and right panels) of recombinant annexin A6 protein expressed in mammalian cells. The middle panel is blotted anti-HIS as the recombinant annexin A6 was made with a C-terminal HIS epitope tag for detection and purification purposes. Right panel was blotted against A6 itself.

Production of rANXA6Protein in Mammalian Cells rANXA6 protein production was carried out in a total volume of 4 liters using two mammalian cell lines (Expi293F™ Cells and FreeStyle™ CHO—S Cells, ThermoFisher Scientific). The estimated yield (as determined by Coomassie staining (FIG. 29)) was 15 mg/L from the Expi293F™ Cells and 2.3 mg/L from the FreeStyle™ CHO—S Cells. The recombinant protein was also evaluated by immunoblot analysis to detect annexin A6 and an anti-HIS antibody to detect the C-terminal HIS tag found on the recombinantly-produced rANXA6 protein (FIG. 29).

The buffers and Immobilized metal affinity chromatography (IMAC) protocols are indicated below in Table 1.

TABLE 1

| Pellet processing buffers<br>Buffers - Lysis and IMAC | |
|---|---|
| Pellet re-suspension buffer (5 ml cell pellet re-suspended in 1 ml lysis buffer) | 50 mM Tris-HCl pH 7.5<br>150 mM NaCl<br>5 mM Imidazole<br>1% TX-100<br>1 mM DTT<br>1 mM EGTA<br>1 mM PMSF<br>1 Roche Protease tablet per 50 ml buffer |
| IMAC pulldown Buffer A (IMAC wash & equilibration buffer) | 25 mM Tris-HCl pH 7.5<br>150 mM NaCl<br>5 mM Imidazole<br>1 mM DTT<br>1 mM PMSF<br>1 Roche Protease tablet per 50 ml buffer |
| IMAC pulldown Buffer B (elution buffer) | 25 mM Tris-HCl pH 7.5,<br>150 mM NaCl<br>500 mM Imidazole,<br>1 mM DTT<br>1 mM PMSF<br>1 Roche Protease tablet per 50 ml buffer |
| Column type | PhyTip ™ Micro-Scale Affinity Column (10 μl resin) |

Purification of Annexin 6 (ANXA6) from Expi293F™ Cells. The protein lysate was loaded on to an IMAC column and eluted by 500 mM imidazole. The yield at this stage was determined to be approximately 270 mg. The relevant fractions were pooled and loaded on to an Ion Exchange Q (IExQ) column, and the indicated fractions were pooled. At this stage the yield was approximately 208 mg. These pools were loaded on to a S200 26/60 column in 1×PBS. The final yield was approximately 77 mg. The purity of the recombinant protein was determined to be greater than 95%.

Absolute size exclusion chromatography (aSEC) indicated that the protein was in a monomeric state, and mass spectrometry (MS) showed multiple modifications.

Purification of Annexin 6 (ANXA6) from FreeStyle™ CHO—S Cells. The protein lysate was loaded on to an IMAC column and eluted by 500 mM imidazole. The yield at this point was approximately 78 mg. The relevant fractions were pooled and loaded on to an Ion Exchange Q (IExQ) column, and the indicated fractions were combined in two separate pools. The yield at this stage was approximately 24 mg (approximately 12 mg in each pool). The pools were run on an S200 26/60 column (SEC Run for Pool1 and Pool2). The final yield was determined to be: Pool1=2.25 mg and Pool2=1.9 mg.

Absolute size exclusion chromatography (aSEC) and MS did not show any difference between Pool1 and Pool2, and no difference was detected between the recombinant proteins expressed in Expi293F™ Cells and FreeStyle™ CHO—S Cells.

Production of rANXA6 Protein in Prokaryotic Cells

The rANXA6 protein was also purified from prokaryotic cells. rANXA6 protein production was carried out in a 4 liter low endotoxin purification method in *E. coli* cells (Rosetta (DE3) competent cells) in TB media. The cells were grown at 30 C for 4 hours and 18 hours. Isopropyl β-D-1-thiogalactopyranoside (IPTG) inducer was used at 0.4 mM. The composition of the various buffers used is shown in Table 2. The total yield obtained using the method was 308 mg (approximately 2.5 mg/mL).

TABLE 2

Buffer compositions.

| Buffer | Composition |
|---|---|
| Lysis | 50 mM Tris-HCl pH 7.5, 150 mM NaCl, 5 mM Imidazole, 1% TX-100, 1 mM DTT, 1 mM EGTA, 1 mM PMSF, PI tab |
| Wash | 25 mM Tris-HCl pH 7.5, 150 mM NaCl, 5 mM Imidazole, 1 mM DTT, 1 mM PMSF, PI tablet |
| Elution | 50 mM Tris-HCl pH 7.5, 150 mM NaCl, 500 mM Imidazole, 1% TX-100, 1 mM DTT, 1 mM PMSF, PI tablet |

Figure 30:
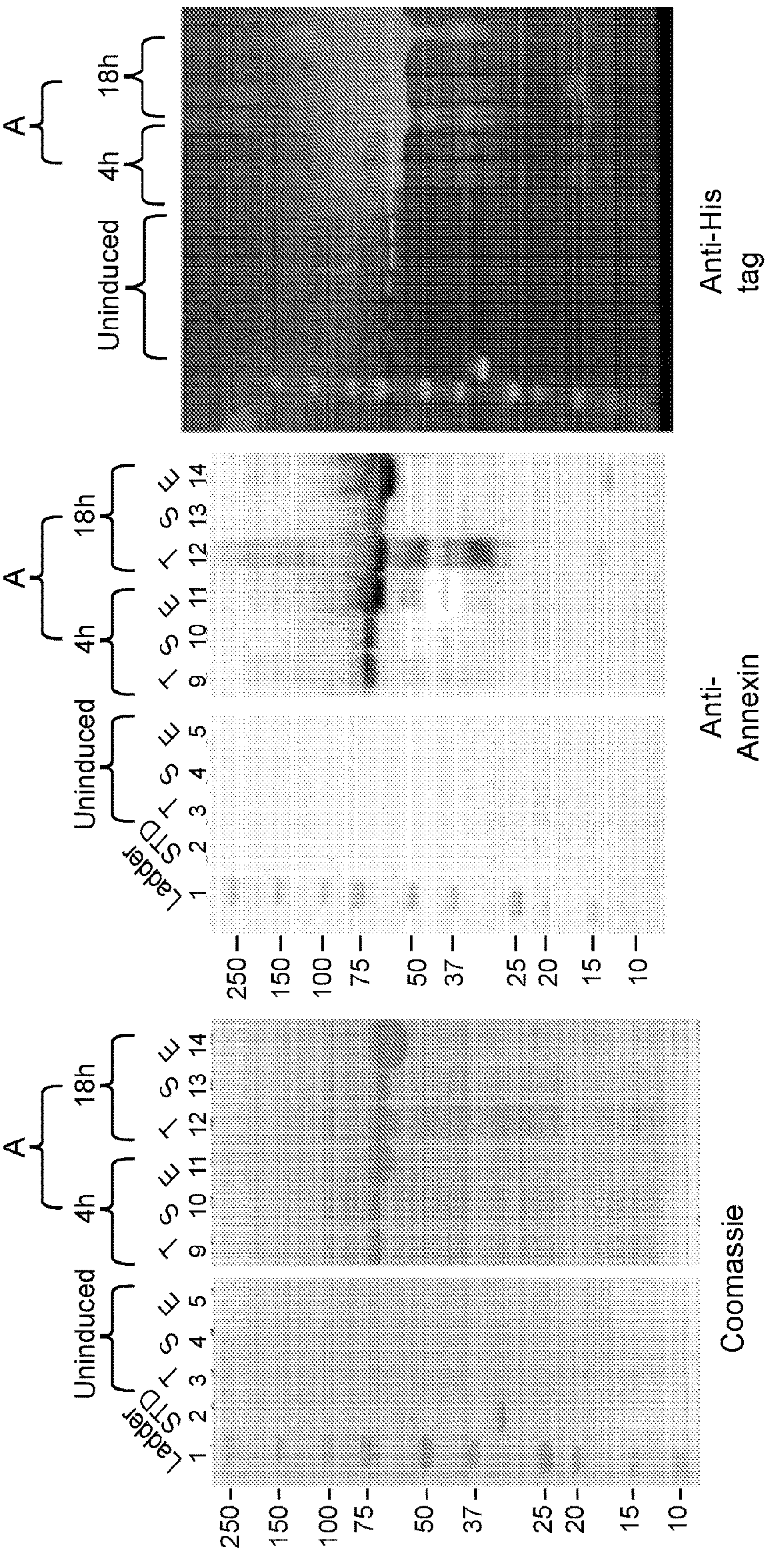
FIG. 30 shows results of SDS-PAGE (Coomassie stained) (left panel) and Western blot analysis (middle and right panels) of recombinant annexin A6 protein expressed in prokaryotic cells. Lanes in left and middle panels are labeled T (total), S (soluble), and E (eluate). The contents of the lanes in the right panel mirror those of the left and middle panels. The middle panel is blotted for annexin A6. The right panel is blotted for anti-HIS as the recombinant annexin A6 was made with a C-terminal HIS tag for purification purposes.

The recombinant protein was analyzed by Coomassie staining and immunoblot analysis, as shown in FIG. 30.

Purification of Annexin 6 (ANXA6) from *E. coli* Cells. The protein lysate was loaded on to an IMAC column and eluted by 500 mM imidazole. The yield at this stage was determined to be approximately 546 mg. The relevant fractions were pooled and loaded on to an Ion Exchange Q (IExQ) column, and the indicated fractions were pooled. The yield at this stage was approximately 408 mg. These pools were loaded on to a S200 26/60 column in 1×PBS. After three runs the final yield was approximately 306 mg. The final endotoxin level was approximately 4 EU/mg/10.5 EU/mL. The purity of the recombinant protein was determined to be greater than 95%.

Absolute size exclusion chromatography (aSEC) indicated that the protein was in a monomeric state, and mass spectrometry (MS) showed multiple modifications.

Example 6

This example details experiments comparing the function of rANXA6 produced in mammalian cells with rANXA6 produced in prokaryotic cells. These experiments were conducted to test whether the activity of an annexin protein (in this case, rANXA6) differed based on whether the annexin protein was produced in mammalian cells versus prokaryotic cells. The predicted posttranslational modification signature for annexin A6 was determined using PTMcode (http://ptmcode.embl.de) and is shown in Table 3. Various forms of posttranslational modification (PTM) identified through mass spectrometry (MS) (e.g., acetylation, nitrosylation, phosphorylation) are indicated in Table 3.

TABLE 3

Posttranslational modifications of annexin A6 protein expressed in prokaryotic cells and mammalian cells.

| PTMcode prediction | AA | POSITION | Type | CHO | *E coli*[4] | CHO (Batch 1)[5] | CHO (Batch 2)[5] | *E coli* (Batch 1)[5] | *E coli* (Batch 2)[5] | HEK (Batch 1)[5] | HEK (Batch 2)[5] |
|---|---|---|---|---|---|---|---|---|---|---|---|
| Acetylation[3] | A[3] | 2[3] | | | | | | | | | |
| acetylation[1] | K[1] | 34[1] | | x[1] | x[1] | x[1] | x[1] | x[1] | x[1] | x[1] | x[1] |
| acetylation[1] | K[1] | 40[1] | | x[1] | | | | | | | |
| acetylation[2] | K[2] | 63[2] | | | x[2] | | | | | | |
| acetylation[2] | K[2] | 68[2] | | | x[2] | | | | | | |
| acetylation[1] | K[1] | 75[1] | | | x[1] | | | x[1] | x[1] | | |
| acetylation[2] | K[2] | 81[2] | | | x[2] | | | x[2] | x[2] | | |
| acetylation[1] | K[1] | 99[1] | | | x[1] | | | | | | |
| acetylation[1] | K[1] | 102[1] | | | | x[1] | | x[1] | x[1] | x[1] | |
| acetylation[1] | K[1] | 113[1] | | | x[1] | x[1] | | x[1] | x[1] | x[1] | |
| acetylation[1] | K[1] | 156[1] | | x[1] | | | | | | | |
| acetylation[1] | K[1] | 220[1] | | | x[1] | | | | | | |
| acetylation[1] | K[1] | 240[1] | | | x[1] | | | x[1] | x[1] | | |
| acetylation[3] | K[3] | 265[3] | | | | | | | | | |
| acetylation[2] | K[2] | 306[2] | | | x[2] | | | x[2] | | | |
| acetylation[3] | K[3] | 314[3] | | | | | | | | | |
| acetylation[1] | K[1] | 319[1] | | | x[1] | | | x[1] | | x[1] | |
| acetylation[1] | K[1] | 354[1] | | | x[1] | | | | | | |
| acetylation[1] | K[1] | 370[1] | | | x[1] | | | | | | |
| acetylation[1] | K[1] | 377[1] | | | x[1] | | | | x[1] | | |
| acetylation[2] | K[2] | 418[2] | | | x[2] | | | x[2] | x[2] | x[2] | |
| acetylation[3] | K[3] | 445[3] | | | | | | | | | |
| acetylation[1] | K[1] | 446[1] | | | | | | | x[1] | | |
| acetylation[3] | K[3] | 483[3] | | | | | | | | | |
| acetylation[1] | K[1] | 540[1] | | | x[1] | | | | | | |
| acetylation[1] | K[1] | 598[1] | | | x[1] | | x[1] | | x[1] | x[1] | x[1] |
| acetylation[1] | K[1] | 600[1] | | x[1] | x[1] | | x[1] | | | | x[1] |
| acetylation[1] | K[1] | 607[1] | | x[1] | x[1] | | | | x[1] | | |
| acetylation[2] | K[2] | 613[2] | | | | x[2] | | | | | |
| acetylation[2] | K[2] | 620[2] | | x[2] | x[2] | | | | x[2] | | |
| acetylation[1] | K[1] | 647[1] | | | x[1] | | | | | x[1] | |
| nitrosylation[3] | C[3] | 96[3] | | | | | | | | | |
| nitrosylation[3] | C[3] | 114[3] | | | | | | | | | |
| nitrosylation[3] | C[3] | 552[3] | | | | | | | | | |
| phosphorylation[3] | Y[3] | 30[3] | | | | | | | | | |
| phosphorylation[3] | S[3] | 51[3] | | | | | | | | | |
| phosphorylation[3] | Y[3] | 95[3] | | | | | | | | | |
| phosphorylation[3] | S[3] | 106[3] | | | | | | | | | |
| phosphorylation[3] | T[3] | 110[3] | | | | | | | | | |
| phosphorylation[3] | Y[3] | 201[3] | | | | | | | | | |
| phosphorylation[3] | S[3] | 229[3] | | | | | | | | | |
| phosphorylation[3] | S[3] | 251[3] | | | | | | | | | |
| phosphorylation[3] | T[3] | 269[3] | | | | | | | | | |
| phosphorylation[1] | T[1] | 273[1] | | | | | x[1] | | | | |
| phosphorylation[1] | S[1] | 321[1] | | x[1] | x[1] | | | | | | |
| phosphorylation[1] | Y[1] | 340[1] | | | x[1] | | | | | | |
| phosphorylation[2] | T[2] | 381[2] | | | | | | | | | x[2] |
| phosphorylation[3] | T[3] | 391[3] | | | | | | | | | |
| phosphorylation[3] | T[3] | 464[3] | | | | | | | | | |
| phosphorylation[3] | Y[3] | 609[3] | | | | | | | | | |
| phosphorylation[3] | S[3] | 628[3] | | | | | | | | | |
| ubiquitination[1] | K[1] | 9[1] | | | | | | | | x[1] | |
| ubiquitination[1] | K[1] | 40[1] | | x[1] | x[1] | | | | x[1] | | |
| ubiquitination[1] | K[1] | 75[1] | | | x[1] | | x[1] | | | | |
| ubiquitination[3] | K[3] | 102[3] | | | | | | | | | |
| ubiquitination[1] | K[1] | 156[1] | | x[1] | x[1] | | | | x[1] | | x[1] |
| ubiquitination[1] | K[1] | 220[1] | | | x[1] | | | | | | |
| ubiquitination[1] | K[1] | 240[1] | | | x[1] | | x[1] | | x[1] | | x[1] |
| ubiquitination[1] | K[1] | 319[1] | | | x[1] | | | | x[1] | | |
| ubiquitination[1] | K[1] | 354[1] | | | x[1] | | | | | | |
| ubiquitination[1] | K[1] | 370[1] | | | x[1] | | | | | | |
| ubiquitination[2] | K[2] | 377[2] | | | x | | | | | | |
| ubiquitination[1] | K[1] | 418[1] | | | x[1] | | x[1] | | x[1] | | x[1] |
| ubiquitination[3] | K[3] | 478[3] | | | | | | | | | |
| ubiquitination[1] | K[1] | 483[1] | | | | | | | x[1] | | |
| ubiquitination[1] | K[1] | 540[1] | | | x[1] | | | | | | |
| ubiquitination[1] | K[1] | 568[1] | | | | | | | x[1] | | |
| ubiquitination[1] | K[1] | 580[1] | | | | | x[1] | | x[1] | | x[1] |
| ubiquitination[1] | K[1] | 598[1] | | | x[1] | | x[1] | | | | x[1] |
| ubiquitination[1] | K[1] | 600[1] | | x[1] | x[1] | | x[1] | | | | x[1] |
| ubiquitination | K[1] | 607[1] | | x[1] | x[1] | | | | x[1] | | x[1] |
| ubiquitination | K[1] | 620[1] | | x[1] | x[1] | | x[1] | | | x[1] | |
| ubiquitination | K[1] | 647[1] | | | x[1] | | | | | | |
| methylation[1] | R[1] | 11[1] | di[1] | | x[1] | | x[1] | x[1] | x[1] | | x[1] |
| methylation[1] | K[1] | 34[1] | mono/tri[1] | x[1] | x[1] | x[1] | x[1] | x[1] | x[1] | | x[1] |

TABLE 3-continued

Posttranslational modifications of annexin A6 protein expressed in prokaryotic cells and mammalian cells.

| PTMcode prediction | AA | POSITION | Type | CHO | *E coli*[4] | CHO (Batch 1)[5] | CHO (Batch 2)[5] | *E coli* (Batch 1)[5] | *E coli* (Batch 2)[5] | HEK (Batch 1)[5] | HEK (Batch 2)[5] |
|---|---|---|---|---|---|---|---|---|---|---|---|
| methylation[1] | K[1] | 40[1] | mono[1] | | | x[1] | | x[1] | x[1] | x[1] | |
| methylation[1] | K[1] | 63[1] | mono[1] | | | | | x[1] | | | |
| methylation[1] | K[1] | 68[1] | di[1] | | | x[1] | | | | | |
| methylation[1] | K[1] | 99[1] | mono[1] | | x[1] | | | x[1] | | | |
| methylation[1] | K[1] | 102[1] | di[1] | | | x[1] | | | | | |
| methylation[1] | K[1] | 113[1] | mono/tri[1] | | x[1] | x[1] | x[1] | x[1] | x[1] | x[1] | x[1] |
| methylation[1] | R[1] | 122[1] | mono[1] | | x[1] | | | | | | |
| methylation[1] | R[1] | 140[1] | mono[1] | | x[1] | | | | x[1] | x[1] | |
| methylation[1] | K[1] | 156[1] | di[1] | x[1] | x[1] | | | | x[1] | x[1] | |
| methylation[1] | R[1] | 166[1] | di[1] | | x[1] | | | x[1] | x[1] | | |
| methylation[1] | K[1] | 191[1] | mono[1] | x[1] | x[1] | | | | | | |
| methylation[1] | K[1] | 231[1] | mono[1] | | | | x[1] | | | | |
| methylation[1] | K/R[1] | 319[1] | tri[1] | | x[1] | | | | | x[1] | |
| methylation[1] | R[1] | 368[1] | di[1] | | | | | x[1] | | | |
| methylation[1] | K[1] | 370[1] | tri[1] | | x[1] | | | | | | |
| methylation[1] | K/R[1] | 418[1] | mono/di[1] | | | | | x[1] | | x[1] | |
| methylation[1] | K[1] | 456[1] | mono[1] | | | | | | x[1] | | |
| methylation[1] | K[1] | 478[1] | mono[1] | x[1] | x[1] | | | x[1] | | | |
| methylation[1] | K[1] | 483[1] | tri[1] | x[1] | x[1] | | | x[1] | | | |
| methylation[1] | K/R[1] | 520[1] | di[1] | | x[1] | | | x[1] | | | |
| methylation[1] | R[1] | 540[1] | mono/di[1] | | x[1] | x[1] | x[1] | x[1] | x[1] | x[1] | x[1] |
| methylation[1] | R[1] | 546[1] | mono/di[1] | | x[1] | x[1] | | | x[1] | x[1] | |
| methylation[1] | R[1] | 554[1] | mono[1] | | x[1] | x[1] | | | x[1] | x[1] | |
| methylation[1] | K[1] | 579[1] | mono[1] | | | | | | x[1] | | |
| methylation[1] | K/R[1] | 587[1] | mono/di[1] | | x[1] | | | x[1] | x[1] | | |
| methylation[1] | K[1] | 598[1] | di[1] | | x[1] | | | x[1] | | | |
| methylation[1] | K[1] | 600[1] | di[1] | | | | | x[1] | | | |
| methylation[1] | K[1] | 620[1] | di[1] | | | | | x[1] | | | |
| methylation[1] | K[1] | 639[1] | mono[1] | | | | | | | | x[1] |
| methylation[1] | K[1] | 644[1] | tri[1] | | x[1] | | | | | | |
| methylation[1] | K[1] | 647[1] | tri[1] | | x[1] | | | | | x[1] | |
| N-linked glycosylation | | | | NA | NA | NA | None found | NA | None found | NA | None found |

[1]= identified by mass spectrometry
[2]= in silico predicted and detected by mass spectrometry
[3]= in silico predicted but not detected
[4]= results in this column were obtained using annexin A6 protein obtained from R&D Systems, Inc. (Minneapolis, MN) catalog number 5186-A6-050
[5]= results in these columns were obtained using annexin A6 protein obtained from a contract research organization (CRO; Evotec SE (Princeton, NJ)) (see Example 5 for general protocols)
Batch 1 = small milliliter (mL) sized production
Batch 2 = medium liter-sized production As shown in Table 3, the posttranslational modification signature of annexin A6 differs depending on whether the protein is expressed in prokaryotic cells or mammalian cells. It would be expected, therefore, that the altered posttranslational modification signature would result in a change in activity between the annexin A6 protein produced in prokaryotic cells versus mammalian cells. Unexpectedly, however, it was found that the annexin A6 protein produced in prokaryotic cells performed as well as the protein that was produced in mammalian cells in the myofiber injury experiments described below.

Myofiber isolation, laser injury, and dye measurement. For recombinant myofibers studies, myofibers were isolated from wildtype mice. Myofibers were incubated in Ringer's media with 13 μg/ml or 130 μg/ml human recombinant annexin, *E coli* or HEK cell produced. Bovine serum albumin (BSA) was used as a negative control. FM 4-64 (2.5 μm) was added to the myofibers just prior to imaging. Fibers were subjected to laser-induced damage at room temperature using the Nikon A1R-MP multiphoton microscope. Imaging was performed using a 25×1.1NA objective directed by the NIS-Elements AR imaging software. FM 4-64 was excited using a 920 nm wavelength laser and emission wavelengths of 575 nm and 629 nm were collected, respectively. To induce laser damage on isolated myofibers, a diffraction limited spot (diameter approximately 410 nm) was created on the lateral membrane of the myofiber using a 920 nm wavelength laser at 10-15% laser power for 1 second. FM 4-64 area was measured using FIJI from a single slice near the middle of the z-stack. Myofiber quality control was based on a number of characteristics including using adherent myofibers with intact sarcomere structure. Myofibers appeared devoid of tears or ruptures induced during the isolation protocol. The region of the myofiber selected for damage was linear and not located on a nucleus or neuromuscular junction.

Figure 31:
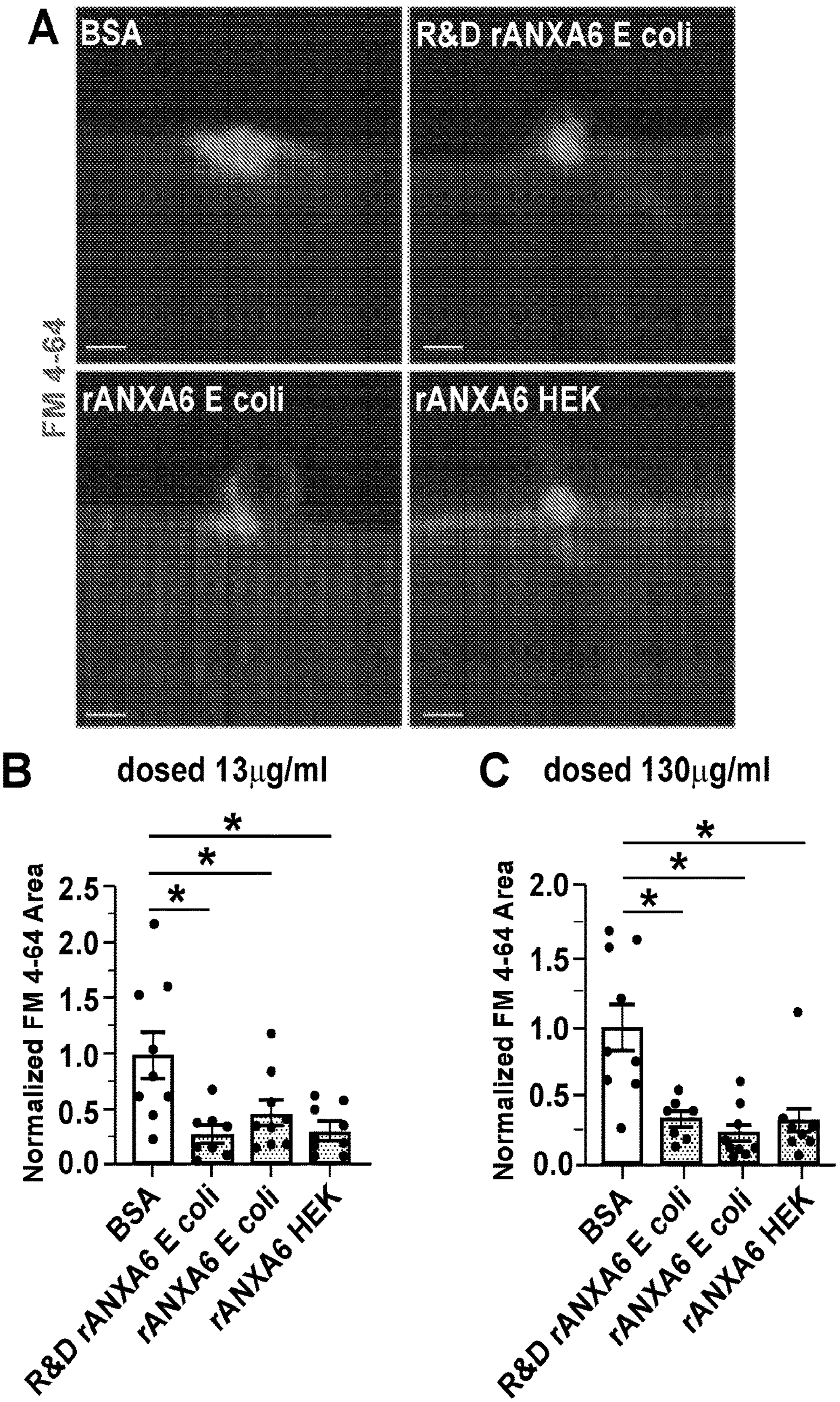
FIG. 31 shows in panels A, B, and C that Wildtype myofibers injured in the presence of extracellular recombinant annexin A6 (rANXA6), produced in *E coli* or mammalian HEK cells, had significantly less FM 4-64 dye uptake compared to BSA control treated myofibers, indicating protection against membrane injury and enhanced repair with rANXA6 treatment. (B & C) The beneficial effects of rANXA6 on membrane repair were not significantly different between *E coli* produced rANXA6, which was obtained commercially through R&D Systems or produced by a contract research organization (CRO; Evotec SE), compared to mammalian HEK cell produced rANXA6 protein at 13 μg/ml and 130 μg/ml. Scale=5 μm. Data are expressed as mean±SEM. Differences were tested by two-tailed t-test * p<0.05, (n≥8 myofibers from n≥3 mice per condition).

Statistical analyses were performed with Prism (Graphpad, La Jolla, CA). Comparisons relied on ANOVA (1way ANOVA for 1 variable). P-values of less than or equal to 0.05 were considered significant. Error bars represent+/− standard error of the mean (SEM). Results are shown in FIG. 31.

These experiments demonstrated that myofibers injured in the presence of extracellular recombinant annexin A6 (rANXA6), produced in *E coli* or mammalian cells, had similar beneficial effects on enhancing membrane repair and protecting against injury. This was demonstrated across multiple doses, 13 mg/ml and 130 mg/ml, measured as a reduction in FM 4-64 dye uptake after laser injury compared to BSA control treated myofibers.

Example 7

This example was designed to test the necessity of the amino acid sequence VAAEIL (exon 21 of annexin A6) (SEQ ID NO: 47) in facilitating the localization and organization of the annexin repair cap at the site of membrane injury.

Methods

Animals. Wildtype mice from the 129T2/SvEmsJ background were bred and housed in a specific pathogen free facility on a 12-hour light/dark cycle and fed ad libitum in accordance with the Northwestern University's Institutional Animal Care and Use Committee regulations. 129T2/SvEmsJ (129T2) mice were purchased from the Jackson Laboratory (Ben Harbor, ME; Stock #002065). Two to three-month-old male and female were used for all wildtype mouse experiments.

Plasmids. Plasmids encoding annexin A6 with a carboxyl-terminal turboGFP tag were obtained from Origene (Rockville, MD). Subcloning of annexin A6 to replace the GFP tag with tdTomato (Addgene) was performed by Mutagenix (Suwanee, GA). Site directed mutagenesis was performed by Mutagenix on annexin A6-GFP to generate the construct lacking the VAAEIL (SEQ ID NO: 47) sequence. Plasmid DNA was isolated using the Qiagen endo-free Maxi prep kit (Qiagen #12362).

Electroporation, myofiber isolation, laser injury, cap and vesicle measurement. Flexor digitorum brevis (FDB) fibers were transfected with endo-free plasmid DNA by in vivo electroporation. Methods were described previously in Demonbreun et al JoVE 2015. Briefly, the hindlimb footpad was injected with 10 μl of hyaluronidase (8 units) (H4272, Sigma, St. Louis, MO). Two hours post injection up to 20 ul of 2 μg/μl endotoxin free plasmid was injected into the footpad. Electroporation was conducted by applying 20 pulses, 20 ms in duration/each, at 1 Hz, at 100 V/cm. Animals were allowed to recover for a minimum of seven days and not more than ten days after electroporation to avoid examining injured muscle and to allow sufficient time for plasmid expression.

FDB muscle was removed and individual myofibers were isolated and imaged (Demonbreun et al., JoVE, 2015). Fibers were dissected and laser damaged as described (Demonbreun et al., JoVE2015; Swaggart et al., PNAS 2014). Briefly, fibers were dissociated in 0.2% BSA plus collagenase type II (Cat #17101, Life Technologies, Grand Island, NY) for up to 90 minutes with intermittent trituration at 37 degrees in 10% $CO_2$. Fibers were then moved to Ringers solution and placed on MatTek confocal microscopy dishes (Cat #P35G-1.5-14-C, MatTek, Ashland MA). After one hour, fibers were adhered and the Ringers was replaced with 1 ml of fresh Ringers solution. Imaging and ablation was performed on the Nikon A1R laser scanning confocal equipped with GaSP detectors through a 60× Apo lambda 1.4 NA objective driven by Nikon Elements AR software. A single pixel set as 120 nm (0.0144 $\mu m^2$) was ablated using the 405 nm laser at 100% power for up to 5 seconds. Z-stack projections were acquired from consecutive acquisitions after the final time-lapse frame, approximately 4 minutes post damage, with a 0.125 μM step size between slices. Z-stack renderings were constructed in FIJI. Fibers expressing similar levels of tagged protein were compared.

Results

Figure 32:
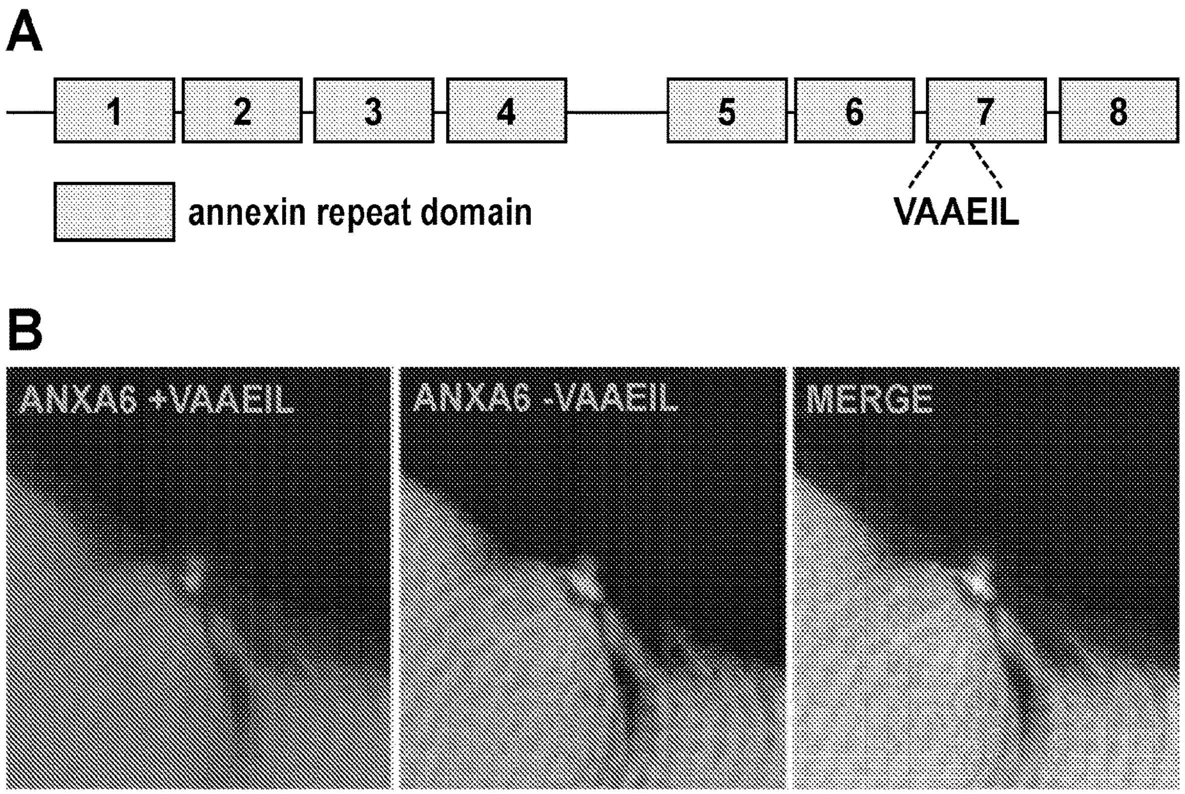
FIG. 32 demonstrates that annexin A6 lacking the amino acid sequence VAAEIL (SEQ ID NO: 47) localizes to the site of muscle membrane injury. A) Schematic showing the structure of annexin A6. The amino acid sequence, VAAEIL, is located in annexin repeat domain 7, exon 21. B) Myofibers were electroporated with GFP-labelled annexin A6 lacking VAAEIL (SEQ ID NO: 47) and tdTomato-labelled annexin A6. High magnification images show that annexin A6 lacking the VAAEIL (SEQ ID NO: 47) sequence partially colocalizes with annexin A6 in a repair cap at the site of muscle membrane injury.

It was then questioned whether the presence of the VAAEIL (SEQ ID NO: 47) sequence in annexin A6 influenced annexin A6 localization upon muscle membrane injury. Myofibers were electroporated with full-length annexin A6-tdTomato and A6-GFP lacking VAAEIL (SEQ ID NO: 47) and subsequently laser-injured. Annexin A6 isoforms with and without the VAAEIL (SEQ ID NO: 47) sequence localized to the site of muscle membrane injury forming a repair cap (FIG. 32). Annexin A6 lacking VAAEIL (SEQ ID NO: 47) partially colocalized with full-length annexin A6, forming a flatter repair cap at the membrane lesion. These data demonstrated that multiple annexin A6 isoforms, with and without the amino acids VAAEIL, participate in the muscle injury response.

ADDITIONAL REFERENCES

Akerboom, J., T. W. Chen, T. J. Wardill, L. Tian, J. S. Marvin, S. Mutlu, N. C. Calderon, F. Esposti, B. G. Borghuis, X. R. Sun, A. Gordus, M. B. Orger, R. Portugues, F. Engert, J. J. Macklin, A. Filosa, A. Aggarwal, R. A. Kerr, R. Takagi, S. Kracun, E. Shigetomi, B. S. Khakh, H. Baier, L. Lagnado, S. S. Wang, C. I. Bargmann, B. E. Kimmel, V. Jayaraman, K. Svoboda, D. S. Kim, E. R. Schreiter, and L. L. Looger. 2012. Optimization of a GCaMP calcium indicator for neural activity imaging. J Neurosci. 32:13819-13840.

Avila-Sakar, A. J., C. E. Creutz, and R. H. Kretsinger. 1998. Crystal structure of bovine annexin VI in a calcium-bound state. Biochimica et biophysica acta. 1387:103-116. Babbin, B. A., M. G. Laukoetter, P. Nava, S. Koch, W. Y. Lee, C. T. Capaldo, E.

Peatman, E. A. Severson, R. J. Flower, M. Perretti, C. A. Parkos, and A. Nusrat. 2008. Annexin A1 regulates intestinal mucosal injury, inflammation, and repair. J Immunol. 181:5035-5044.

Bansal, D., K. Miyake, S. S. Vogel, S. Groh, C. C. Chen, R. Williamson, P. L. McNeil, and K. P. Campbell. 2003. Defective membrane repair in dysferlin-deficient muscular dystrophy. Nature. 423:168-172.

Bashir, R., S. Britton, T. Strachan, S. Keers, E. Vafiadaki, M. Lako, I. Richard, S. Marchand, N. Bourg, Z. Argov, M. Sadeh, I. Mahjneh, G. Marconi, M. R. Passos-Bueno, S. Moreira Ede, M. Zatz, J. S. Beckmann, and K. Bushby. 1998. A gene related to *Caenorhabditis elegans* spermatogenesis factor fer-1 is mutated in limb-girdle muscular dystrophy type 2B. Nat Genet. 20:37-42.

Bement, W. M., C. A. Mandato, and M. N. Kirsch. 1999. Wound-induced assembly and closure of an actomyosin purse string in *Xenopus oocytes*. Curr Biol. 9:579-587.

Benz, J., A. Bergner, A. Hofmann, P. Demange, P. Gottig, S. Liemann, R. Huber, and D. Voges. 1996. The structure of recombinant human annexin VI in crystals and membrane-bound. J Mol Biol. 260:638-643.

Bi, G. Q., J. M. Alderton, and R. A. Steinhardt. 1995. Calcium-regulated exocytosis is required for cell membrane resealing. The Journal of cell biology. 131:1747-1758.

Bizzarro, V., A. Petrella, and L. Parente. 2012. Annexin A1: novel roles in skeletal muscle biology. J Cell Physiol. 227:3007-3015.

Blackwood, R. A., and J. D. Ernst. 1990. Characterization of Ca2(+)-dependent phospholipid binding, vesicle aggregation and membrane fusion by annexins. The Biochemical journal. 266:195-200.

Boye, T. L., J. C. Jeppesen, K. Maeda, W. Pezeshkian, V. Solovyeva, J. Nylandsted, and A. C. Simonsen. 2018. Annexins induce curvature on free-edge membranes displaying distinct morphologies. Sci Rep. 8:10309.

Boye, T. L., K. Maeda, W. Pezeshkian, S. L. Sonder, S. C. Haeger, V. Gerke, A. C. Simonsen, and J. Nylandsted. 2017. Annexin A4 and A6 induce membrane curvature and constriction during cell membrane repair. Nat Commun. 8:1623.

Buzhynskyy, N., M. Golczak, J. Lai-Kee-Him, O. Lambert, B. Tessier, C. Gounou, R. Berat, A. Simon, T. Granier, J. M. Chevalier, S. Mazeres, J. Bandorowicz-Pikula, S. Pikula, and A. R. Brisson. 2009. Annexin-A6 presents two modes of association with phospholipid membranes. A combined QCM-D, AFM and cryo-TEM study. Journal of structural biology. 168:107-116.

Cai, C., H. Masumiya, N. Weisleder, N. Matsuda, M. Nishi, M. Hwang, J. K. Ko, P. Lin, A. Thornton, X. Zhao, Z. Pan, S. Komazaki, M. Brotto, H. Takeshima, and J. Ma. 2009. MG53 nucleates assembly of cell membrane repair machinery. Nat Cell Biol. 11:56-64.

Carmeille, R., S. A. Degrelle, L. Plawinski, F. Bouvet, C. Gounou, D. Evain-Brion, A. R. Brisson, and A. Bouter. 2015. Annexin-A5 promotes membrane resealing in human trophoblasts. Biochimica et biophysica acta. 1853: 2033-2044.

Cagliani, R., F. Magri, A. Toscano, L. Merlini, F. Fortunato, C. Lamperti, C. Rodolico, A. Prelle, M. Sironi, M. Aguennouz, P. Ciscato, A. Uncini, M. Moggio, N. Bresolin, and G. P. Comi. 2005. Mutation finding in patients with dysferlin deficiency and role of the dysferlin interacting proteins annexin A1 and A2 in muscular dystrophies. Human mutation. 26:283.

Ceco, E., S. Bogdanovich, B. Gardner, T. Miller, A. DeJesus, J. U. Earley, M. Hadhazy, L. R. Smith, E. R. Barton, J. D. Molkentin, and E. M. McNally. 2014. Targeting latent TGFbeta release in muscular dystrophy. Science translational medicine. 6:259ra144.

Christmas, P., J. Callaway, J. Fallon, J. Jones, and H. T. Haigler. 1991. Selective secretion of annexin 1, a protein without a signal sequence, by the human prostate gland. *The Journal of biological chemistry.* 266:2499-2507.

Davenport, N. R., K. J. Sonnemann, K. W. Eliceiri, and W. M. Bement. 2016. Membrane dynamics during cellular wound repair. Mol Biol Cell. 27:2272-2285.

Defour, A., S. Medikayala, J. H. Van der Meulen, M. W. Hogarth, N. Holdreith, A. Malatras, W. Duddy, J. Boehler, K. Nagaraju, and J. K. Jaiswal. 2017. Annexin A2 links poor myofiber repair with inflammation and adipogenic replacement of the injured muscle. Human molecular genetics. 26:1979-1991.

de Laat, B., R. H. Derksen, I. J. Mackie, M. Roest, S. Schoormans, B. J. Woodhams, P. G. de Groot, and W. L. van Heerde. 2006. Annexin A5 polymorphism (-1C-->T) and the presence of anti-annexin A5 antibodies in the antiphospholipid syndrome. Annals of the rheumatic diseases. 65:1468-1472.

Demonbreun, A. R., M. V. Allen, J. L. Warner, D. Y. Barefield, S. Krishnan, K. E. Swanson, J. U. Earley, and E. M. McNally. 2016a. Enhanced Muscular Dystrophy from Loss of Dysferlin Is Accompanied by Impaired Annexin A6 Translocation after Sarcolemmal Disruption. Am J Pathol. 186:1610-1622.

Demonbreun, A. R., and E. M. McNally. 2015. DNA Electroporation, Isolation and Imaging of Myofibers. Journal of visualized experiments: JoVE. 106:e53551.

Demonbreun, A. R., and E. M. McNally. 2016. Plasma Membrane Repair in Health and Disease. Curr Top Membr. 77:67-96.

Demonbreun, A. R., M. Quattrocelli, D. Y. Barefield, M. V. Allen, K. E. Swanson, and E. M. McNally. 2016b. An actin-dependent annexin complex mediates plasma membrane repair in muscle. The Journal of cell biology. 213:705-718.

Demonbreun, A. R., A. E. Rossi, M. G. Alvarez, K. E. Swanson, H. K. Deveaux, J. U. Earley, M. Hadhazy, R. Vohra, G. A. Walter, P. Pytel, and E. M. McNally. 2014. Dysferlin and myoferlin regulate transverse tubule formation and glycerol sensitivity. Am J Pathol. 184:248-259.

Demonbreun, A. R., K. E. Swanson, A. E. Rossi, H. K. Deveaux, J. U. Earley, M. V. Allen, P. Arya, S. Bhattacharyya, H. Band, P. Pytel, and E. M. McNally. 2015. Eps 15 Homology Domain (EHD)-1 Remodels Transverse Tubules in Skeletal Muscle. PLOS One. 10:e0136679.

Deora, A. B., G. Kreitzer, A. T. Jacovina, and K. A. Hajjar. 2004. An annexin 2 phosphorylation switch mediates p11-dependent translocation of annexin 2 to the cell surface. *The Journal of biological chemistry.* 279:43411-43418.

DiFranco, M., M. Quinonez, J. Capote, and J. Vergara. 2009. DNA transfection of mammalian skeletal muscles using in vivo electroporation. Journal of visualized experiments: JoVE. 32.

Duann, P., H. Li, P. Lin, T. Tan, Z. Wang, K. Chen, X. Zhou, K. Gumpper, H. Zhu, T. Ludwig, P. J. Mohler, B. Rovin, W. T. Abraham, C. Zeng, and J. Ma. 2015. MG53-mediated cell membrane repair protects against acute kidney injury. Science translational medicine. 7:279ra236.

Echigoya Y, Lim K R Q, Nakamura A, and Yokota T. Multiple Exon Skipping in the Duchenne Muscular Dystrophy Hot Spots: Prospects and Challenges. J Pers Med 8, 2018.

Fiehn, W., J. B. Peter, J. F. Mead, and M. Gan-Elepano. 1971. Lipids and fatty acids of sarcolemma, sarcoplasmic reticulum, and mitochondria from rat skeletal muscle. The Journal of biological chemistry. 246:5617-5620.

Flanigan, K. M., E. Ceco, K. M. Lamar, Y. Kaminoh, D. M. Dunn, J. R. Mendell, W. M. King, A. Pestronk, J. M. Florence, K. D. Mathews, R. S. Finkel, K. J. Swoboda, E. Gappmaier, M. T. Howard, J. W. Day, C. McDonald, E. M. McNally, and R. B. Weiss. 2013. LTBP4 genotype predicts age of ambulatory loss in duchenne muscular dystrophy. Ann Neurol. 73:481-488.

Gerke, V., C. E. Creutz, and S. E. Moss. 2005. Annexins: linking $Ca^{2+}$ signalling to membrane dynamics. Nat Rev Mol Cell Biol. 6:449-461.

Gerke, V., and S. E. Moss. 2002. Annexins: from structure to function. Physiol Rev. 82:331-371.

Grewal, T., M. Hoque, J. R. W. Conway, M. Reverter, M. Wahba, S. S. Beevi, P. Timpson, C. Enrich, and C. Rentero. 2017. Annexin A6-A multifunctional scaffold in cell motility. Cell Adh Migr. 11:288-304.

Goulet, F., K. G. Moore, and A. C. Sartorelli. 1992. Glycosylation of annexin I and annexin II. *Biochemical and biophysical research communications.* 188:554-558.

Hack A A, et al. Gamma-sarcoglycan deficiency leads to muscle membrane defects and apoptosis independent of dystrophin. *J Cell Biol.* 1998; 142(5):1279-1287.

Hannon, R., J. D. Croxtall, S. J. Getting, F. Roviezzo, S. Yona, M. J. Paul-Clark, F. N. Gavins, M. Perretti, J. F. Morris, J. C. Buckingham, and R. J. Flower. 2003. Aberrant inflammation and resistance to glucocorticoids in annexin 1−/− mouse. *FASEB J.* 17:253-255.

He, B., R. H. Tang, N. Weisleder, B. Xiao, Z. Yuan, C. Cai, H. Zhu, P. Lin, C. Qiao, J. Li, C. Mayer, J. Li, J. Ma, and X. Xiao. 2012. Enhancing muscle membrane repair by gene delivery of MG53 ameliorates muscular dystrophy and heart failure in delta-Sarcoglycan-deficient hamsters. Molecular therapy: the journal of the American Society of Gene Therapy. 20:727-735.

Hoffman, E. P., R. H. Brown, Jr., and L. M. Kunkel. 1987. Dystrophin: the protein product of the Duchenne muscular dystrophy locus. Cell. 51:919-928.

Jennische, E., and H. A. Hansson. 1986. Postischemic skeletal muscle injury: patterns of injury in relation to adequacy of reperfusion. Exp Mol Pathol. 44:272-280.

Jia, Y., K. Chen, P. Lin, G. Lieber, M. Nishi, R. Yan, Z. Wang, Y. Yao, Y. Li, B. A. Whitson, P. Duann, H. Li, X. Zhou, H. Zhu, H. Takeshima, J. C. Hunter, R. L. McLeod, N. Weisleder, C. Zeng, and J. Ma. 2014. Treatment of acute lung injury by targeting MG53-mediated cell membrane repair. Nat Commun. 5:4387.

Jimenez, A. J., and F. Perez. 2017. Plasma membrane repair: the adaptable cell life-insurance. Curr Opin Cell Biol. 47:99-107.

Jost, M., C. Thiel, K. Weber, and V. Gerke. 1992. Mapping of three unique Ca(2+)-binding sites in human annexin II. Eur J Biochem. 207:923-930.

Kaetzel, M. A., Y. D. Mo, T. R. Mealy, B. Campos, W. Bergsma-Schutter, A. Brisson, J. R. Dedman, and B. A. Seaton. 2001. Phosphorylation mutants elucidate the mechanism of annexin IV-mediated membrane aggregation. Biochemistry. 40:4192-4199.

Lauritzen, S. P., T. L. Boye, and J. Nylandsted. 2015. Annexins are instrumental for efficient plasma membrane repair in cancer cells. Semin Cell Dev Biol. 45:32-38.

Lennon, N. J., A. Kho, B. J. Bacskai, S. L. Perlmutter, B. T. Hyman, and R. H. Brown, Jr. 2003. Dysferlin interacts with annexins A1 and A2 and mediates sarcolemmal wound-healing. The Journal of biological chemistry. 278: 50466-50473.

Li D, Mastaglia F L, Fletcher S, and Wilton S D. Precision Medicine through Antisense Oligonucleotide-Mediated Exon Skipping. Trends Pharmacol Sci 39:982-994, 2018.

Ling, Q., A. T. Jacovina, A. Deora, M. Febbraio, R. Simantov, R. L. Silverstein, B. Hempstead, W. H. Mark, and K. A. Hajjar. 2004. Annexin II regulates fibrin homeostasis and neoangiogenesis in vivo. The Journal of clinical investigation. 113:38-48.

Liu, J., H. Zhu, Y. Zheng, Z. Xu, L. Li, T. Tan, K. H. Park, J. Hou, C. Zhang, D. Li, R. Li, Z. Liu, N. Weisleder, D. Zhu, P. Lin, and J. Ma. 2015. Cardioprotection of recombinant human MG53 protein in a porcine model of ischemia and reperfusion injury. Journal of molecular and cellular cardiology. 80:10-19.

McDade, J. R., A. Archambeau, and D. E. Michele. 2014. Rapid actin-cytoskeleton-dependent recruitment of plasma membrane-derived dysferlin at wounds is critical for muscle membrane repair. FASEB J. 28:3660-3670.

McNeil, A. K., U. Rescher, V. Gerke, and P. L. McNeil. 2006. Requirement for annexin A1 in plasma membrane repair. The Journal of biological chemistry. 281:35202-35207.

McNeil, P. L., and R. Khakee. 1992. Disruptions of muscle fiber plasma membranes. Role in exercise-induced damage. Am J Pathol. 140:1097-1109.

McNeil, P. L., and T. Kirchhausen. 2005. An emergency response team for membrane repair. Nat Rev Mol Cell Biol. 6:499-505.

Min Y L, Bassel-Duby R, and Olson E N. CRISPR Correction of Duchenne Muscular Dystrophy. Annu Rev Med, 2018.

Murphy, S., M. Zweyer, M. Henry, P. Meleady, R. R. Mundegar, D. Swandulla, and K. Ohlendieck. 2018. Proteomic analysis of the sarcolemma-enriched fraction from dystrophic mdx-4cv skeletal muscle. J Proteomics.

Petrof, B. J., J. B. Shrager, H. H. Stedman, A. M. Kelly, and H. L. Sweeney. 1993. Dystrophin protects the sarcolemma from stresses developed during muscle contraction. Proceedings of the National Academy of Sciences of the United States of America. 90:3710-3714.

Quattrocelli, M., D. Y. Barefield, J. L. Warner, A. H. Vo, M. Hadhazy, J. U. Earley, A. R. Demonbreun, and E. M. McNally. 2017a. Intermittent glucocorticoid steroid dosing enhances muscle repair without eliciting muscle atrophy. J Clin Invest. 127:2418-2432.

Quattrocelli, M., J. Capote, J. C. Ohiri, J. L. Warner, A. H. Vo, J. U. Earley, M. Hadhazy, A. R. Demonbreun, M. J. Spencer, and E. M. McNally. 2017b. Genetic modifiers of muscular dystrophy act on sarcolemmal resealing and recovery from injury. PLOS Genet. 13:e1007070.

Quattrocelli, M., I. M. Salamone, P. G. Page, J. L. Warner, A. R. Demonbreun, and E. M. McNally. 2017c. Intermittent Glucocorticoid Dosing Improves Muscle Repair and Function in Mice with Limb-Girdle Muscular Dystrophy. Am J Pathol. 187:2520-2535.

Reddy, A., E. V. Caler, and N. W. Andrews. 2001. Plasma membrane repair is mediated by Ca(2+)-regulated exocytosis of lysosomes. Cell. 106:157-169.

Rodriguez, A., P. Webster, J. Ortego, and N. W. Andrews. 1997. Lysosomes behave as $Ca^{2+}$-regulated exocytic vesicles in fibroblasts and epithelial cells. J Cell Biol. 137:93-104.

Roostalu, U., and U. Strahle. 2012. In vivo imaging of molecular interactions at damaged sarcolemma. Dev Cell. 22:515-529.

Swaggart, K. A., A. R. Demonbreun, A. H. Vo, K. E. Swanson, E. Y. Kim, J. P. Fahrenbach, J. Holley-Cuthrell, A. Eskin, Z. Chen, K. Squire, A. Heydemann, A. A. Palmer, S. F. Nelson, and E. M. McNally. 2014. Annexin A6 modifies muscular dystrophy by mediating sarcolemmal repair. Proceedings of the National Academy of Sciences of the United States of America. 111:6004-6009.

Waddell, L. B., F. A. Lemckert, X. F. Zheng, J. Tran, F. J. Evesson, J. M. Hawkes, A. Lek, N. E. Street, P. Lin, N. F. Clarke, A. P. Landstrom, M. J. Ackerman, N. Weisleder, J. Ma, K. N. North, and S. T. Cooper. 2011. Dysferlin, annexin A1, and mitsugumin 53 are upregulated in muscular dystrophy and localize to longitudinal tubules of the T-system with stretch. J Neuropathol Exp Neurol. 70:302-313.

Wallner, B. P., R. J. Mattaliano, C. Hession, R. L. Cate, R. Tizard, L. K. Sinclair, C. Foeller, E. P. Chow, J. L. Browing, K. L. Ramachandran, and et al. 1986. Cloning and expression of human lipocortin, a phospholipase A2 inhibitor with potential anti-inflammatory activity. *Nature.* 320:77-81.

Weisleder, N., N. Takizawa, P. Lin, X. Wang, C. Cao, Y. Zhang, T. Tan, C. Ferrante, H. Zhu, P. J. Chen, R. Yan, M. Sterling, X. Zhao, M. Hwang, M. Takeshima, C. Cai, H. Cheng, H. Takeshima, R. P. Xiao, and J. Ma. 2012. Recombinant MG53 protein modulates therapeutic cell membrane repair in treatment of muscular dystrophy. Science translational medicine. 4:139ra185.

Yeung, T., B. Heit, J. F. Dubuisson, G. D. Fairn, B. Chiu, R. Inman, A. Kapus, M. Swanson, and S. Grinstein. 2009. Contribution of phosphatidylserine to membrane surface charge and protein targeting during phagosome maturation. The Journal of cell biology. 185:917-928.

Zaks, W. J., and C. E. Creutz. 1991. Ca(2+)-dependent annexin self-association on membrane surfaces. Biochemistry. 30:9607-9615.

Zhang Y, Long C, Bassel-Duby R, and Olson E N. Myoediting: Toward Prevention of Muscular Dystrophy by Therapeutic Genome Editing. Physiol Rev 98:1205-1240, 2018.

Zweifach, A. 2000. FM1-43 reports plasma membrane phospholipid scrambling in T-lymphocytes. The Biochemical journal. 349:255-260.

What is claimed is:

1. A method of treating a cellular membrane injury comprising administering to a patient in need thereof a therapeutically effective amount of a composition comprising an agent that increases the activity of an annexin protein, wherein the agent is:

a protein having at least 90% sequence identity to annexin A6 (SEQ ID NO: 7, SEQ ID NO: 8, or a combination thereof), or a modified form thereof, or a polynucleotide capable of expressing an extracellular protein having at least 90% sequence identity to annexin A6 (SEQ ID NO: 7, SEQ ID NO: 8, or a combination thereof), or a modified form thereof.

2. A method of delaying onset, enhancing recovery from cellular membrane injury, or preventing a cellular membrane injury comprising administering to a patient in need thereof a therapeutically effective amount of a composition comprising an agent that increases the activity of an annexin protein, wherein the agent is:

a protein having at least 90% sequence identity to annexin A6 (SEQ ID NO: 7, SEQ ID NO: 8, or a combination thereof), or a modified form thereof, or a polynucleotide capable of expressing an extracellular protein having at least 90% sequence identity to annexin A6 (SEQ ID NO: 7, SEQ ID NO: 8, or a combination thereof), or a modified form thereof.

3. The method of claim 1, wherein the patient suffers from an acute injury.

4. The method of claim 3, wherein the acute injury results from surgery, a burn, a toxin, a chemical, radiation-induced injury, acute myocardial injury, acute muscle injury, acute lung injury, acute epithelial injury, acute epidermal injury, acute kidney injury, acute liver injury, vascular injury, an excessive mechanical force, or trauma.

5. The method of claim 1, wherein the patient suffers from a chronic disorder.

6. The method of claim 5, wherein the chronic disorder is Becker Muscular Dystrophy (BMD), Duchenne Muscular Dystrophy (DMD), Limb Girdle Muscular Dystrophy, congenital Muscular Dystrophy, Emery-Dreifuss Muscular Dystrophy (EDMD), Myotonic Dystrophy, Fascioscapulohumeral Dystrophy (FSHD), Oculopharyngeal Muscular Dystrophy, Distal Muscular Dystrophy, cystic fibrosis, pulmonary fibrosis, muscle atrophy, cerebral palsy, an epithelial disorder, an epidermal disorder, a kidney disorder, a liver disorder, sarcopenia, cardiomyopathy, Alzheimer's disease, stroke and ischemic injury, neural trauma, Huntington's disease, or Parkinson's disease.

7. The method of claim 6, wherein the cardiomyopathy is hypertrophic, dilated, congenital, arrhythmogenic, restrictive, ischemic, or heart failure.

8. The method of claim 1, further comprising administering an effective amount of a second agent, wherein the second agent is selected from the group consisting of mitsugumin 53 (MG53), a modulator of latent TGF-β binding protein 4 (LTBP4), a modulator of transforming growth factor β (TGF-β) activity, a modulator of androgen response, a modulator of an inflammatory response, a promoter of muscle growth, a chemotherapeutic agent, a modulator of fibrosis, and a combination thereof.

9. The method of claim 1, wherein the polynucleotide is contained in a vector.

10. The method of claim 9 wherein the vector is a viral vector.

11. The method of claim 10 wherein the viral vector is selected from the group consisting of a herpes virus vector, an adeno-associated virus (AAV) vector, an adeno virus vector, and a lentiviral vector.

12. The method of claim 11 wherein the AAV vector is recombinant AAV5, AAV6, AAV8, AAV9, or AAV74.

13. The method of claim 1, wherein the composition is a pharmaceutical composition comprising a pharmaceutically acceptable carrier, buffer, and/or diluent.

14. The method of claim 1, wherein the protein or the extracellular protein has at least 95% or at least 99% sequence identity to annexin A6 as depicted in SEQ ID NO: 7, SEQ ID NO: 8 or a combination thereof, or a post-translationally modified form thereof.

15. The method of claim 1, wherein the protein or the extracellular protein is annexin A6 as depicted in SEQ ID NO: 7, SEQ ID NO: 8, or a combination thereof.

16. The method of claim 1, wherein the composition further comprises a protein having at least 90%, at least 95%, or at least 99%, sequence identity to annexin A2 as depicted in SEQ ID NO: 2 or SEQ ID NO: 3 or a post-translationally modified form thereof, or the composition further comprises a polynucleotide that encodes an annexin protein having at least 90%, at least 95%, or at least 99% sequence identity to annexin A2 as depicted in SEQ ID NO: 2 or SEQ ID NO: 3 or a modified form thereof.

17. The method of claim 1, wherein the composition further comprises a protein having at least 90%, at least 95%, or at least 99% sequence identity to annexin A1 as depicted in SEQ ID NO: 1 or a post-translationally modified form thereof, or the composition further comprises a polynucleotide that encodes an annexin protein having at least 90%, at least 95%, or at least 99% sequence identity to annexin A1 as depicted in SEQ ID NO: 1 or a modified form thereof.

18. The method of claim 1, wherein the composition further comprises:

annexin A2 as depicted in SEQ ID NO: 2 or SEQ ID NO: 3 or a post-translationally modified form thereof; or a polynucleotide that encodes annexin A2 as depicted in SEQ ID NO: 2 or SEQ ID NO: 3; and/or annexin A1 as depicted in SEQ ID NO: 1 or a post-translationally modified form thereof; or a polynucleotide that encodes annexin A1 as depicted in SEQ ID NO: 1.

19. The method of claim 13, wherein purity of annexin A6 in the composition is about 90% or higher as measured by standard release assay.

20. The method of claim 13, wherein the composition has an endotoxin level that is less than 0.50000 endotoxin units per milligram (EU/mg).

21. The method of claim 1, wherein the post-translationally modified form is biotinylated, glycosylated, PEGylated, and/or polysialylated.

22. The method of claim 1, wherein the annexin A6 as set out in SEQ ID NO: 7 and/or SEQ ID NO: 8 is produced in a prokaryotic cell.

23. The method of claim 2, wherein the patient suffers from a chronic disorder.

24. The method of claim 23, wherein the chronic disorder is Becker Muscular Dystrophy (BMD), Duchenne Muscular Dystrophy (DMD), Limb Girdle Muscular Dystrophy, congenital Muscular Dystrophy, Emery-Dreifuss Muscular Dystrophy (EDMD), Myotonic Dystrophy, Fascioscapulohumeral Dystrophy (FSHD), Oculopharyngeal Muscular Dystrophy, Distal Muscular Dystrophy, cystic fibrosis, pulmonary fibrosis, muscle atrophy, cerebral palsy, an epithelial disorder, an epidermal disorder, a kidney disorder, a liver disorder, sarcopenia, cardiomyopathy, Alzheimer's disease, stroke and ischemic injury, neural trauma, Huntington's disease, or Parkinson's disease.

25. The method of claim 24, wherein the cardiomyopathy is hypertrophic, dilated, congenital, arrhythmogenic, restrictive, ischemic, or heart failure.

26. The method of claim 2, further comprising administering an effective amount of a second agent, wherein the second agent is selected from the group consisting of mitsugumin 53 (MG53), a modulator of latent TGF-β binding protein 4 (LTBP4), a modulator of transforming growth factor β (TGF-β) activity, a modulator of androgen response, a modulator of an inflammatory response, a promoter of muscle growth, a chemotherapeutic agent, a modulator of fibrosis, and a combination thereof.

27. The method of claim 2, wherein the composition is a pharmaceutical composition comprising a pharmaceutically acceptable carrier, buffer, and/or diluent.

28. The method of claim 2, wherein the protein or the extracellular protein has at least 95% or at least 99% sequence identity to annexin A6 as depicted in SEQ ID NO: 7, SEQ ID NO: 8 or a combination thereof, or a post-translationally modified form thereof.

29. The method of claim 2, wherein the protein or the extracellular protein is annexin A6 as depicted in SEQ ID NO: 7, SEQ ID NO: 8, or a combination thereof.

30. The method of claim 2, wherein the composition further comprises a protein having at least 90%, at least 95%, or at least 99%, sequence identity to annexin A2 as depicted in SEQ ID NO: 2 or SEQ ID NO: 3 or a post-translationally modified form thereof, or the composition further comprises a polynucleotide that encodes an annexin protein having at least 90%, at least 95%, or at least 99% sequence identity to annexin A2 as depicted in SEQ ID NO: 2 or SEQ ID NO: 3 or a modified form thereof.

31. The method of claim 2, wherein the composition further comprises a protein having at least 90%, at least 95%, or at least 99% sequence identity to annexin A1 as depicted in SEQ ID NO: 1 or a post-translationally modified form thereof, or the composition further comprises a polynucleotide that encodes an annexin protein having at least 90%, at least 95%, or at least 99% sequence identity to annexin A1 as depicted in SEQ ID NO: 1 or a modified form thereof.

32. The method of claim 2, wherein the composition further comprises:

annexin A2 as depicted in SEQ ID NO: 2 or SEQ ID NO: 3 or a post-translationally modified form thereof; or a polynucleotide that encodes annexin A2 as depicted in SEQ ID NO: 2 or SEQ ID NO: 3; and/or annexin A1 as depicted in SEQ ID NO: 1 or a post-translationally modified form thereof; or a polynucleotide that encodes annexin A1 as depicted in SEQ ID NO: 1.

33. The method of claim 27, wherein purity of annexin A6 in the composition is about 90% or higher as measured by standard release assay.

34. The method of claim 27, wherein the composition has an endotoxin level that is less than 0.50000 endotoxin units per milligram (EU/mg).

35. The method of claim 2, wherein the post-translationally modified form is biotinylated, glycosylated, PEGylated, and/or polysialylated.

36. The method of claim 2, wherein the annexin A6 as set out in SEQ ID NO: 7 and/or SEQ ID NO: 8 is produced in a prokaryotic cell.

* * * * *

SEQUENCE LISTING

```
<160> NUMBER OF SEQ ID NOS: 47

<210> SEQ ID NO 1
<211> LENGTH: 346
<212> TYPE: PRT
<213> ORGANISM: Homo sapiens
<220> FEATURE:
<221> NAME/KEY: MISC_FEATURE
<223> OTHER INFORMATION: NP_000691.1 annexin A1

<400> SEQUENCE: 1

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
```

```
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345


<210> SEQ ID NO 2
<211> LENGTH: 357
<212> TYPE: PRT
<213> ORGANISM: Homo sapiens
<220> FEATURE:
<221> NAME/KEY: MISC_FEATURE
<223> OTHER INFORMATION: NP_001002858.1 annexin A2 isoform 1

<400> SEQUENCE: 2

Met Gly Arg Gln Leu Ala Gly Cys Gly Asp Ala Gly Lys Lys Ala Ser
1               5                   10                  15

Phe Lys Met Ser Thr Val His Glu Ile Leu Cys Lys Leu Ser Leu Glu
            20                  25                  30

Gly Asp His Ser Thr Pro Pro Ser Ala Tyr Gly Ser Val Lys Ala Tyr
        35                  40                  45

Thr Asn Phe Asp Ala Glu Arg Asp Ala Leu Asn Ile Glu Thr Ala Ile
    50                  55                  60

Lys Thr Lys Gly Val Asp Glu Val Thr Ile Val Asn Ile Leu Thr Asn
65                  70                  75                  80

Arg Ser Asn Ala Gln Arg Gln Asp Ile Ala Phe Ala Tyr Gln Arg Arg
                85                  90                  95

Thr Lys Lys Glu Leu Ala Ser Ala Leu Lys Ser Ala Leu Ser Gly His
            100                 105                 110

Leu Glu Thr Val Ile Leu Gly Leu Leu Lys Thr Pro Ala Gln Tyr Asp
        115                 120                 125

Ala Ser Glu Leu Lys Ala Ser Met Lys Gly Leu Gly Thr Asp Glu Asp
    130                 135                 140

Ser Leu Ile Glu Ile Ile Cys Ser Arg Thr Asn Gln Glu Leu Gln Glu
145                 150                 155                 160

Ile Asn Arg Val Tyr Lys Glu Met Tyr Lys Thr Asp Leu Glu Lys Asp
                165                 170                 175

Ile Ile Ser Asp Thr Ser Gly Asp Phe Arg Lys Leu Met Val Ala Leu
            180                 185                 190

Ala Lys Gly Arg Arg Ala Glu Asp Gly Ser Val Ile Asp Tyr Glu Leu
        195                 200                 205

Ile Asp Gln Asp Ala Arg Asp Leu Tyr Asp Ala Gly Val Lys Arg Lys
    210                 215                 220

Gly Thr Asp Val Pro Lys Trp Ile Ser Ile Met Thr Glu Arg Ser Val
225                 230                 235                 240

Pro His Leu Gln Lys Val Phe Asp Arg Tyr Lys Ser Tyr Ser Pro Tyr
                245                 250                 255

Asp Met Leu Glu Ser Ile Arg Lys Glu Val Lys Gly Asp Leu Glu Asn
            260                 265                 270

Ala Phe Leu Asn Leu Val Gln Cys Ile Gln Asn Lys Pro Leu Tyr Phe
        275                 280                 285

Ala Asp Arg Leu Tyr Asp Ser Met Lys Gly Lys Gly Thr Arg Asp Lys
    290                 295                 300
```

```
Val Leu Ile Arg Ile Met Val Ser Arg Ser Glu Val Asp Met Leu Lys
305                 310                 315                 320

Ile Arg Ser Glu Phe Lys Arg Lys Tyr Gly Lys Ser Leu Tyr Tyr Tyr
                325                 330                 335

Ile Gln Gln Asp Thr Lys Gly Asp Tyr Gln Lys Ala Leu Leu Tyr Leu
            340                 345                 350

Cys Gly Gly Asp Asp
        355


<210> SEQ ID NO 3
<211> LENGTH: 339
<212> TYPE: PRT
<213> ORGANISM: Homo sapiens
<220> FEATURE:
<221> NAME/KEY: MISC_FEATURE
<223> OTHER INFORMATION: NP_001129487.1 annexin A2 isoform 2

<400> SEQUENCE: 3

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
    210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
    290                 295                 300
```

```
Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp


<210> SEQ ID NO 4
<211> LENGTH: 323
<212> TYPE: PRT
<213> ORGANISM: Homo sapiens
<220> FEATURE:
<221> NAME/KEY: MISC_FEATURE
<223> OTHER INFORMATION: NP_005130.1 annexin A3

<400> SEQUENCE: 4

Met Ala Ser Ile Trp Val Gly His Arg Gly Thr Val Arg Asp Tyr Pro
1               5                   10                  15

Asp Phe Ser Pro Ser Val Asp Ala Glu Ala Ile Gln Lys Ala Ile Arg
            20                  25                  30

Gly Ile Gly Thr Asp Glu Lys Met Leu Ile Ser Ile Leu Thr Glu Arg
        35                  40                  45

Ser Asn Ala Gln Arg Gln Leu Ile Val Lys Glu Tyr Gln Ala Ala Tyr
    50                  55                  60

Gly Lys Glu Leu Lys Asp Asp Leu Lys Gly Asp Leu Ser Gly His Phe
65                  70                  75                  80

Glu His Leu Met Val Ala Leu Val Thr Pro Pro Ala Val Phe Asp Ala
                85                  90                  95

Lys Gln Leu Lys Lys Ser Met Lys Gly Ala Gly Thr Asn Glu Asp Ala
            100                 105                 110

Leu Ile Glu Ile Leu Thr Thr Arg Thr Ser Arg Gln Met Lys Asp Ile
        115                 120                 125

Ser Gln Ala Tyr Tyr Thr Val Tyr Lys Lys Ser Leu Gly Asp Asp Ile
    130                 135                 140

Ser Ser Glu Thr Ser Gly Asp Phe Arg Lys Ala Leu Leu Thr Leu Ala
145                 150                 155                 160

Asp Gly Arg Arg Asp Glu Ser Leu Lys Val Asp Glu His Leu Ala Lys
                165                 170                 175

Gln Asp Ala Gln Ile Leu Tyr Lys Ala Gly Glu Asn Arg Trp Gly Thr
            180                 185                 190

Asp Glu Asp Lys Phe Thr Glu Ile Leu Cys Leu Arg Ser Phe Pro Gln
        195                 200                 205

Leu Lys Leu Thr Phe Asp Glu Tyr Arg Asn Ile Ser Gln Lys Asp Ile
    210                 215                 220

Val Asp Ser Ile Lys Gly Glu Leu Ser Gly His Phe Glu Asp Leu Leu
225                 230                 235                 240

Leu Ala Ile Val Asn Cys Val Arg Asn Thr Pro Ala Phe Leu Ala Glu
                245                 250                 255

Arg Leu His Arg Ala Leu Lys Gly Ile Gly Thr Asp Glu Phe Thr Leu
            260                 265                 270

Asn Arg Ile Met Val Ser Arg Ser Glu Ile Asp Leu Leu Asp Ile Arg
        275                 280                 285

Thr Glu Phe Lys Lys His Tyr Gly Tyr Ser Leu Tyr Ser Ala Ile Lys
    290                 295                 300

Ser Asp Thr Ser Gly Asp Tyr Glu Ile Thr Leu Leu Lys Ile Cys Gly
305                 310                 315                 320
```

Gly Asp Asp

<210> SEQ ID NO 5
<211> LENGTH: 321
<212> TYPE: PRT
<213> ORGANISM: Homo sapiens
<220> FEATURE:
<221> NAME/KEY: MISC_FEATURE
<223> OTHER INFORMATION: NP_001144.1 annexin A4 isoform a

<400> SEQUENCE: 5

Met Ala Met Ala Thr Lys Gly Gly Thr Val Lys Ala Ala Ser Gly Phe
1 5 10 15

Asn Ala Met Glu Asp Ala Gln Thr Leu Arg Lys Ala Met Lys Gly Leu
20 25 30

Gly Thr Asp Glu Asp Ala Ile Ile Ser Val Leu Ala Tyr Arg Asn Thr
35 40 45

Ala Gln Arg Gln Glu Ile Arg Thr Ala Tyr Lys Ser Thr Ile Gly Arg
50 55 60

Asp Leu Ile Asp Asp Leu Lys Ser Glu Leu Ser Gly Asn Phe Glu Gln
65 70 75 80

Val Ile Val Gly Met Met Thr Pro Thr Val Leu Tyr Asp Val Gln Glu
85 90 95

Leu Arg Arg Ala Met Lys Gly Ala Gly Thr Asp Glu Gly Cys Leu Ile
100 105 110

Glu Ile Leu Ala Ser Arg Thr Pro Glu Glu Ile Arg Arg Ile Ser Gln
115 120 125

Thr Tyr Gln Gln Gln Tyr Gly Arg Ser Leu Glu Asp Asp Ile Arg Ser
130 135 140

Asp Thr Ser Phe Met Phe Gln Arg Val Leu Val Ser Leu Ser Ala Gly
145 150 155 160

Gly Arg Asp Glu Gly Asn Tyr Leu Asp Asp Ala Leu Val Arg Gln Asp
165 170 175

Ala Gln Asp Leu Tyr Glu Ala Gly Glu Lys Lys Trp Gly Thr Asp Glu
180 185 190

Val Lys Phe Leu Thr Val Leu Cys Ser Arg Asn Arg Asn His Leu Leu
195 200 205

His Val Phe Asp Glu Tyr Lys Arg Ile Ser Gln Lys Asp Ile Glu Gln
210 215 220

Ser Ile Lys Ser Glu Thr Ser Gly Ser Phe Glu Asp Ala Leu Leu Ala
225 230 235 240

Ile Val Lys Cys Met Arg Asn Lys Ser Ala Tyr Phe Ala Glu Lys Leu
245 250 255

Tyr Lys Ser Met Lys Gly Leu Gly Thr Asp Asp Asn Thr Leu Ile Arg
260 265 270

Val Met Val Ser Arg Ala Glu Ile Asp Met Leu Asp Ile Arg Ala His
275 280 285

Phe Lys Arg Leu Tyr Gly Lys Ser Leu Tyr Ser Phe Ile Lys Gly Asp
290 295 300

Thr Ser Gly Asp Tyr Arg Lys Val Leu Leu Val Leu Cys Gly Gly Asp
305 310 315 320

Asp

<210> SEQ ID NO 6
<211> LENGTH: 320

<212> TYPE: PRT
<213> ORGANISM: Homo sapiens
<220> FEATURE:
<221> NAME/KEY: MISC_FEATURE
<223> OTHER INFORMATION: NP_001145.1 annexin A5

<400> SEQUENCE: 6

```
Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
            20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
    50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
        195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320
```

<210> SEQ ID NO 7
<211> LENGTH: 673
<212> TYPE: PRT
<213> ORGANISM: Homo sapiens
<220> FEATURE:
<221> NAME/KEY: MISC_FEATURE
<223> OTHER INFORMATION: NP_001146.2 annexin A6 isoform 1

<400> SEQUENCE: 7

-continued

```
Met Ala Lys Pro Ala Gln Gly Ala Lys Tyr Arg Gly Ser Ile His Asp
1               5                   10                  15

Phe Pro Gly Phe Asp Pro Asn Gln Asp Ala Glu Ala Leu Tyr Thr Ala
            20                  25                  30

Met Lys Gly Phe Gly Ser Asp Lys Glu Ala Ile Leu Asp Ile Ile Thr
        35                  40                  45

Ser Arg Ser Asn Arg Gln Arg Gln Glu Val Cys Gln Ser Tyr Lys Ser
    50                  55                  60

Leu Tyr Gly Lys Asp Leu Ile Ala Asp Leu Lys Tyr Glu Leu Thr Gly
65                  70                  75                  80

Lys Phe Glu Arg Leu Ile Val Gly Leu Met Arg Pro Pro Ala Tyr Cys
                85                  90                  95

Asp Ala Lys Glu Ile Lys Asp Ala Ile Ser Gly Ile Gly Thr Asp Glu
            100                 105                 110

Lys Cys Leu Ile Glu Ile Leu Ala Ser Arg Thr Asn Glu Gln Met His
        115                 120                 125

Gln Leu Val Ala Ala Tyr Lys Asp Ala Tyr Glu Arg Asp Leu Glu Ala
    130                 135                 140

Asp Ile Ile Gly Asp Thr Ser Gly His Phe Gln Lys Met Leu Val Val
145                 150                 155                 160

Leu Leu Gln Gly Thr Arg Glu Glu Asp Asp Val Val Ser Glu Asp Leu
                165                 170                 175

Val Gln Gln Asp Val Gln Asp Leu Tyr Glu Ala Gly Glu Leu Lys Trp
            180                 185                 190

Gly Thr Asp Glu Ala Gln Phe Ile Tyr Ile Leu Gly Asn Arg Ser Lys
        195                 200                 205

Gln His Leu Arg Leu Val Phe Asp Glu Tyr Leu Lys Thr Thr Gly Lys
    210                 215                 220

Pro Ile Glu Ala Ser Ile Arg Gly Glu Leu Ser Gly Asp Phe Glu Lys
225                 230                 235                 240

Leu Met Leu Ala Val Val Lys Cys Ile Arg Ser Thr Pro Glu Tyr Phe
                245                 250                 255

Ala Glu Arg Leu Phe Lys Ala Met Lys Gly Leu Gly Thr Arg Asp Asn
            260                 265                 270

Thr Leu Ile Arg Ile Met Val Ser Arg Ser Glu Leu Asp Met Leu Asp
        275                 280                 285

Ile Arg Glu Ile Phe Arg Thr Lys Tyr Glu Lys Ser Leu Tyr Ser Met
    290                 295                 300

Ile Lys Asn Asp Thr Ser Gly Glu Tyr Lys Lys Thr Leu Leu Lys Leu
305                 310                 315                 320

Ser Gly Gly Asp Asp Asp Ala Ala Gly Gln Phe Phe Pro Glu Ala Ala
                325                 330                 335

Gln Val Ala Tyr Gln Met Trp Glu Leu Ser Ala Val Ala Arg Val Glu
            340                 345                 350

Leu Lys Gly Thr Val Arg Pro Ala Asn Asp Phe Asn Pro Asp Ala Asp
        355                 360                 365

Ala Lys Ala Leu Arg Lys Ala Met Lys Gly Leu Gly Thr Asp Glu Asp
    370                 375                 380

Thr Ile Ile Asp Ile Ile Thr His Arg Ser Asn Val Gln Arg Gln Gln
385                 390                 395                 400

Ile Arg Gln Thr Phe Lys Ser His Phe Gly Arg Asp Leu Met Thr Asp
                405                 410                 415

Leu Lys Ser Glu Ile Ser Gly Asp Leu Ala Arg Leu Ile Leu Gly Leu
```

420 425 430

Met Met Pro Pro Ala His Tyr Asp Ala Lys Gln Leu Lys Lys Ala Met
435 440 445

Glu Gly Ala Gly Thr Asp Glu Lys Ala Leu Ile Glu Ile Leu Ala Thr
450 455 460

Arg Thr Asn Ala Glu Ile Arg Ala Ile Asn Glu Ala Tyr Lys Glu Asp
465 470 475 480

Tyr His Lys Ser Leu Glu Asp Ala Leu Ser Ser Asp Thr Ser Gly His
485 490 495

Phe Arg Arg Ile Leu Ile Ser Leu Ala Thr Gly His Arg Glu Glu Gly
500 505 510

Gly Glu Asn Leu Asp Gln Ala Arg Glu Asp Ala Gln Val Ala Ala Glu
515 520 525

Ile Leu Glu Ile Ala Asp Thr Pro Ser Gly Asp Lys Thr Ser Leu Glu
530 535 540

Thr Arg Phe Met Thr Ile Leu Cys Thr Arg Ser Tyr Pro His Leu Arg
545 550 555 560

Arg Val Phe Gln Glu Phe Ile Lys Met Thr Asn Tyr Asp Val Glu His
565 570 575

Thr Ile Lys Lys Glu Met Ser Gly Asp Val Arg Asp Ala Phe Val Ala
580 585 590

Ile Val Gln Ser Val Lys Asn Lys Pro Leu Phe Phe Ala Asp Lys Leu
595 600 605

Tyr Lys Ser Met Lys Gly Ala Gly Thr Asp Glu Lys Thr Leu Thr Arg
610 615 620

Ile Met Val Ser Arg Ser Glu Ile Asp Leu Leu Asn Ile Arg Arg Glu
625 630 635 640

Phe Ile Glu Lys Tyr Asp Lys Ser Leu His Gln Ala Ile Glu Gly Asp
645 650 655

Thr Ser Gly Asp Phe Leu Lys Ala Leu Leu Ala Leu Cys Gly Gly Glu
660 665 670

Asp

<210> SEQ ID NO 8
<211> LENGTH: 641
<212> TYPE: PRT
<213> ORGANISM: Homo sapiens
<220> FEATURE:
<221> NAME/KEY: MISC_FEATURE
<223> OTHER INFORMATION: NP_001180473.1 annexin A6 isoform 2

<400> SEQUENCE: 8

Met Lys Gly Phe Gly Ser Asp Lys Glu Ala Ile Leu Asp Ile Ile Thr
1 5 10 15

Ser Arg Ser Asn Arg Gln Arg Gln Glu Val Cys Gln Ser Tyr Lys Ser
20 25 30

Leu Tyr Gly Lys Asp Leu Ile Ala Asp Leu Lys Tyr Glu Leu Thr Gly
35 40 45

Lys Phe Glu Arg Leu Ile Val Gly Leu Met Arg Pro Pro Ala Tyr Cys
50 55 60

Asp Ala Lys Glu Ile Lys Asp Ala Ile Ser Gly Ile Gly Thr Asp Glu
65 70 75 80

Lys Cys Leu Ile Glu Ile Leu Ala Ser Arg Thr Asn Glu Gln Met His
85 90 95

Gln Leu Val Ala Ala Tyr Lys Asp Ala Tyr Glu Arg Asp Leu Glu Ala

```
            100                 105                 110

Asp Ile Ile Gly Asp Thr Ser Gly His Phe Gln Lys Met Leu Val Val
        115                 120                 125

Leu Leu Gln Gly Thr Arg Glu Glu Asp Asp Val Val Ser Glu Asp Leu
    130                 135                 140

Val Gln Gln Asp Val Gln Asp Leu Tyr Glu Ala Gly Glu Leu Lys Trp
145                 150                 155                 160

Gly Thr Asp Glu Ala Gln Phe Ile Tyr Ile Leu Gly Asn Arg Ser Lys
                165                 170                 175

Gln His Leu Arg Leu Val Phe Asp Glu Tyr Leu Lys Thr Thr Gly Lys
            180                 185                 190

Pro Ile Glu Ala Ser Ile Arg Gly Glu Leu Ser Gly Asp Phe Glu Lys
        195                 200                 205

Leu Met Leu Ala Val Val Lys Cys Ile Arg Ser Thr Pro Glu Tyr Phe
    210                 215                 220

Ala Glu Arg Leu Phe Lys Ala Met Lys Gly Leu Gly Thr Arg Asp Asn
225                 230                 235                 240

Thr Leu Ile Arg Ile Met Val Ser Arg Ser Glu Leu Asp Met Leu Asp
                245                 250                 255

Ile Arg Glu Ile Phe Arg Thr Lys Tyr Glu Lys Ser Leu Tyr Ser Met
            260                 265                 270

Ile Lys Asn Asp Thr Ser Gly Glu Tyr Lys Lys Thr Leu Leu Lys Leu
        275                 280                 285

Ser Gly Gly Asp Asp Asp Ala Ala Gly Gln Phe Phe Pro Glu Ala Ala
    290                 295                 300

Gln Val Ala Tyr Gln Met Trp Glu Leu Ser Ala Val Ala Arg Val Glu
305                 310                 315                 320

Leu Lys Gly Thr Val Arg Pro Ala Asn Asp Phe Asn Pro Asp Ala Asp
                325                 330                 335

Ala Lys Ala Leu Arg Lys Ala Met Lys Gly Leu Gly Thr Asp Glu Asp
            340                 345                 350

Thr Ile Ile Asp Ile Ile Thr His Arg Ser Asn Val Gln Arg Gln Gln
        355                 360                 365

Ile Arg Gln Thr Phe Lys Ser His Phe Gly Arg Asp Leu Met Thr Asp
    370                 375                 380

Leu Lys Ser Glu Ile Ser Gly Asp Leu Ala Arg Leu Ile Leu Gly Leu
385                 390                 395                 400

Met Met Pro Pro Ala His Tyr Asp Ala Lys Gln Leu Lys Lys Ala Met
                405                 410                 415

Glu Gly Ala Gly Thr Asp Glu Lys Ala Leu Ile Glu Ile Leu Ala Thr
            420                 425                 430

Arg Thr Asn Ala Glu Ile Arg Ala Ile Asn Glu Ala Tyr Lys Glu Asp
        435                 440                 445

Tyr His Lys Ser Leu Glu Asp Ala Leu Ser Ser Asp Thr Ser Gly His
    450                 455                 460

Phe Arg Arg Ile Leu Ile Ser Leu Ala Thr Gly His Arg Glu Glu Gly
465                 470                 475                 480

Gly Glu Asn Leu Asp Gln Ala Arg Glu Asp Ala Gln Val Ala Ala Glu
                485                 490                 495

Ile Leu Glu Ile Ala Asp Thr Pro Ser Gly Asp Lys Thr Ser Leu Glu
            500                 505                 510

Thr Arg Phe Met Thr Ile Leu Cys Thr Arg Ser Tyr Pro His Leu Arg
        515                 520                 525
```

```
Arg Val Phe Gln Glu Phe Ile Lys Met Thr Asn Tyr Asp Val Glu His
    530                 535                 540

Thr Ile Lys Lys Glu Met Ser Gly Asp Val Arg Asp Ala Phe Val Ala
545                 550                 555                 560

Ile Val Gln Ser Val Lys Asn Lys Pro Leu Phe Phe Ala Asp Lys Leu
                565                 570                 575

Tyr Lys Ser Met Lys Gly Ala Gly Thr Asp Glu Lys Thr Leu Thr Arg
            580                 585                 590

Ile Met Val Ser Arg Ser Glu Ile Asp Leu Leu Asn Ile Arg Arg Glu
        595                 600                 605

Phe Ile Glu Lys Tyr Asp Lys Ser Leu His Gln Ala Ile Glu Gly Asp
    610                 615                 620

Thr Ser Gly Asp Phe Leu Lys Ala Leu Leu Ala Leu Cys Gly Gly Glu
625                 630                 635                 640

Asp


<210> SEQ ID NO 9
<211> LENGTH: 466
<212> TYPE: PRT
<213> ORGANISM: Homo sapiens
<220> FEATURE:
<221> NAME/KEY: MISC_FEATURE
<223> OTHER INFORMATION: NP_001147.1 annexin A7 isoform 1

<400> SEQUENCE: 9

Met Ser Tyr Pro Gly Tyr Pro Pro Thr Gly Tyr Pro Pro Phe Pro Gly
1               5                   10                  15

Tyr Pro Pro Ala Gly Gln Glu Ser Ser Phe Pro Pro Ser Gly Gln Tyr
            20                  25                  30

Pro Tyr Pro Ser Gly Phe Pro Pro Met Gly Gly Gly Ala Tyr Pro Gln
        35                  40                  45

Val Pro Ser Ser Gly Tyr Pro Gly Ala Gly Gly Tyr Pro Ala Pro Gly
    50                  55                  60

Gly Tyr Pro Ala Pro Gly Gly Tyr Pro Gly Ala Pro Gln Pro Gly Gly
65                  70                  75                  80

Ala Pro Ser Tyr Pro Gly Val Pro Pro Gly Gln Gly Phe Gly Val Pro
                85                  90                  95

Pro Gly Gly Ala Gly Phe Ser Gly Tyr Pro Gln Pro Pro Ser Gln Ser
            100                 105                 110

Tyr Gly Gly Gly Pro Ala Gln Val Pro Leu Pro Gly Gly Phe Pro Gly
        115                 120                 125

Gly Gln Met Pro Ser Gln Tyr Pro Gly Gly Gln Pro Thr Tyr Pro Ser
    130                 135                 140

Gln Pro Ala Thr Val Thr Gln Val Thr Gln Gly Thr Ile Arg Pro Ala
145                 150                 155                 160

Ala Asn Phe Asp Ala Ile Arg Asp Ala Glu Ile Leu Arg Lys Ala Met
                165                 170                 175

Lys Gly Phe Gly Thr Asp Glu Gln Ala Ile Val Asp Val Val Ala Asn
            180                 185                 190

Arg Ser Asn Asp Gln Arg Gln Lys Ile Lys Ala Ala Phe Lys Thr Ser
        195                 200                 205

Tyr Gly Lys Asp Leu Ile Lys Asp Leu Lys Ser Glu Leu Ser Gly Asn
    210                 215                 220

Met Glu Glu Leu Ile Leu Ala Leu Phe Met Pro Pro Thr Tyr Tyr Asp
225                 230                 235                 240
```

```
Ala Trp Ser Leu Arg Lys Ala Met Gln Gly Ala Gly Thr Gln Glu Arg
                245                 250                 255

Val Leu Ile Glu Ile Leu Cys Thr Arg Thr Asn Gln Glu Ile Arg Glu
            260                 265                 270

Ile Val Arg Cys Tyr Gln Ser Glu Phe Gly Arg Asp Leu Glu Lys Asp
        275                 280                 285

Ile Arg Ser Asp Thr Ser Gly His Phe Glu Arg Leu Leu Val Ser Met
    290                 295                 300

Cys Gln Gly Asn Arg Asp Glu Asn Gln Ser Ile Asn His Gln Met Ala
305                 310                 315                 320

Gln Glu Asp Ala Gln Arg Leu Tyr Gln Ala Gly Glu Gly Arg Leu Gly
                325                 330                 335

Thr Asp Glu Ser Cys Phe Asn Met Ile Leu Ala Thr Arg Ser Phe Pro
            340                 345                 350

Gln Leu Arg Ala Thr Met Glu Ala Tyr Ser Arg Met Ala Asn Arg Asp
        355                 360                 365

Leu Leu Ser Ser Val Ser Arg Glu Phe Ser Gly Tyr Val Glu Ser Gly
    370                 375                 380

Leu Lys Thr Ile Leu Gln Cys Ala Leu Asn Arg Pro Ala Phe Phe Ala
385                 390                 395                 400

Glu Arg Leu Tyr Tyr Ala Met Lys Gly Ala Gly Thr Asp Asp Ser Thr
                405                 410                 415

Leu Val Arg Ile Val Val Thr Arg Ser Glu Ile Asp Leu Val Gln Ile
            420                 425                 430

Lys Gln Met Phe Ala Gln Met Tyr Gln Lys Thr Leu Gly Thr Met Ile
        435                 440                 445

Ala Gly Asp Thr Ser Gly Asp Tyr Arg Arg Leu Leu Leu Ala Ile Val
    450                 455                 460

Gly Gln
465
```

<210> SEQ ID NO 10
<211> LENGTH: 488
<212> TYPE: PRT
<213> ORGANISM: Homo sapiens
<220> FEATURE:
<221> NAME/KEY: MISC_FEATURE
<223> OTHER INFORMATION: NP_004025.1 annexin A7 isoform 2

<400> SEQUENCE: 10

```
Met Ser Tyr Pro Gly Tyr Pro Pro Thr Gly Tyr Pro Pro Phe Pro Gly
1               5                   10                  15

Tyr Pro Pro Ala Gly Gln Glu Ser Ser Phe Pro Pro Ser Gly Gln Tyr
            20                  25                  30

Pro Tyr Pro Ser Gly Phe Pro Pro Met Gly Gly Gly Ala Tyr Pro Gln
        35                  40                  45

Val Pro Ser Ser Gly Tyr Pro Gly Ala Gly Gly Tyr Pro Ala Pro Gly
    50                  55                  60

Gly Tyr Pro Ala Pro Gly Gly Tyr Pro Gly Ala Pro Gln Pro Gly Gly
65                  70                  75                  80

Ala Pro Ser Tyr Pro Gly Val Pro Pro Gly Gln Gly Phe Gly Val Pro
                85                  90                  95

Pro Gly Gly Ala Gly Phe Ser Gly Tyr Pro Gln Pro Pro Ser Gln Ser
            100                 105                 110

Tyr Gly Gly Gly Pro Ala Gln Val Pro Leu Pro Gly Gly Phe Pro Gly
```

```
        115                 120                 125

Gly Gln Met Pro Ser Gln Tyr Pro Gly Gly Gln Pro Thr Tyr Pro Ser
    130                 135                 140

Gln Ile Asn Thr Asp Ser Phe Ser Ser Tyr Pro Val Phe Ser Pro Val
145                 150                 155                 160

Ser Leu Asp Tyr Ser Ser Glu Pro Ala Thr Val Thr Gln Val Thr Gln
                165                 170                 175

Gly Thr Ile Arg Pro Ala Ala Asn Phe Asp Ala Ile Arg Asp Ala Glu
            180                 185                 190

Ile Leu Arg Lys Ala Met Lys Gly Phe Gly Thr Asp Glu Gln Ala Ile
        195                 200                 205

Val Asp Val Val Ala Asn Arg Ser Asn Asp Gln Arg Gln Lys Ile Lys
    210                 215                 220

Ala Ala Phe Lys Thr Ser Tyr Gly Lys Asp Leu Ile Lys Asp Leu Lys
225                 230                 235                 240

Ser Glu Leu Ser Gly Asn Met Glu Glu Leu Ile Leu Ala Leu Phe Met
                245                 250                 255

Pro Pro Thr Tyr Tyr Asp Ala Trp Ser Leu Arg Lys Ala Met Gln Gly
            260                 265                 270

Ala Gly Thr Gln Glu Arg Val Leu Ile Glu Ile Leu Cys Thr Arg Thr
        275                 280                 285

Asn Gln Glu Ile Arg Glu Ile Val Arg Cys Tyr Gln Ser Glu Phe Gly
    290                 295                 300

Arg Asp Leu Glu Lys Asp Ile Arg Ser Asp Thr Ser Gly His Phe Glu
305                 310                 315                 320

Arg Leu Leu Val Ser Met Cys Gln Gly Asn Arg Asp Glu Asn Gln Ser
                325                 330                 335

Ile Asn His Gln Met Ala Gln Glu Asp Ala Gln Arg Leu Tyr Gln Ala
            340                 345                 350

Gly Glu Gly Arg Leu Gly Thr Asp Glu Ser Cys Phe Asn Met Ile Leu
        355                 360                 365

Ala Thr Arg Ser Phe Pro Gln Leu Arg Ala Thr Met Glu Ala Tyr Ser
    370                 375                 380

Arg Met Ala Asn Arg Asp Leu Leu Ser Ser Val Ser Arg Glu Phe Ser
385                 390                 395                 400

Gly Tyr Val Glu Ser Gly Leu Lys Thr Ile Leu Gln Cys Ala Leu Asn
                405                 410                 415

Arg Pro Ala Phe Phe Ala Glu Arg Leu Tyr Tyr Ala Met Lys Gly Ala
            420                 425                 430

Gly Thr Asp Asp Ser Thr Leu Val Arg Ile Val Val Thr Arg Ser Glu
        435                 440                 445

Ile Asp Leu Val Gln Ile Lys Gln Met Phe Ala Gln Met Tyr Gln Lys
    450                 455                 460

Thr Leu Gly Thr Met Ile Ala Gly Asp Thr Ser Gly Asp Tyr Arg Arg
465                 470                 475                 480

Leu Leu Leu Ala Ile Val Gly Gln
                485
```

<210> SEQ ID NO 11
<211> LENGTH: 365
<212> TYPE: PRT
<213> ORGANISM: Homo sapiens
<220> FEATURE:
<221> NAME/KEY: MISC_FEATURE
<223> OTHER INFORMATION: NP_001258631.1 annexin A8 isoform 1

<400> SEQUENCE: 11

```
Met Ala Trp Trp Lys Ser Trp Ile Glu Gln Glu Gly Val Thr Val Lys
1               5                   10                  15

Ser Ser Ser His Phe Asn Pro Asp Pro Asp Ala Glu Thr Leu Tyr Lys
            20                  25                  30

Ala Met Lys Gly Ile Gly Val Gly Ser Gln Leu Leu Ser His Gln Ala
        35                  40                  45

Ala Ala Phe Ala Phe Pro Ser Ser Ala Leu Thr Ser Val Ser Pro Trp
    50                  55                  60

Gly Gln Gln Gly His Leu Cys Cys Asn Pro Ala Gly Thr Asn Glu Gln
65                  70                  75                  80

Ala Ile Ile Asp Val Leu Thr Lys Arg Ser Asn Thr Gln Arg Gln Gln
                85                  90                  95

Ile Ala Lys Ser Phe Lys Ala Gln Phe Gly Lys Asp Leu Thr Glu Thr
            100                 105                 110

Leu Lys Ser Glu Leu Ser Gly Lys Phe Glu Arg Leu Ile Val Ala Leu
        115                 120                 125

Met Tyr Pro Pro Tyr Arg Tyr Glu Ala Lys Glu Leu His Asp Ala Met
    130                 135                 140

Lys Gly Leu Gly Thr Lys Glu Gly Val Ile Ile Glu Ile Leu Ala Ser
145                 150                 155                 160

Arg Thr Lys Asn Gln Leu Arg Glu Ile Met Lys Ala Tyr Glu Glu Asp
                165                 170                 175

Tyr Gly Ser Ser Leu Glu Glu Asp Ile Gln Ala Asp Thr Ser Gly Tyr
            180                 185                 190

Leu Glu Arg Ile Leu Val Cys Leu Leu Gln Gly Ser Arg Asp Asp Val
        195                 200                 205

Ser Ser Phe Val Asp Pro Gly Leu Ala Leu Gln Asp Ala Gln Asp Leu
    210                 215                 220

Tyr Ala Ala Gly Glu Lys Ile Arg Gly Thr Asp Glu Met Lys Phe Ile
225                 230                 235                 240

Thr Ile Leu Cys Thr Arg Ser Ala Thr His Leu Leu Arg Val Phe Glu
                245                 250                 255

Glu Tyr Glu Lys Ile Ala Asn Lys Ser Ile Glu Asp Ser Ile Lys Ser
            260                 265                 270

Glu Thr His Gly Ser Leu Glu Glu Ala Met Leu Thr Val Val Lys Cys
        275                 280                 285

Thr Gln Asn Leu His Ser Tyr Phe Ala Glu Arg Leu Tyr Tyr Ala Met
    290                 295                 300

Lys Gly Ala Gly Thr Arg Asp Gly Thr Leu Ile Arg Asn Ile Val Ser
305                 310                 315                 320

Arg Ser Glu Ile Asp Leu Asn Leu Ile Lys Cys His Phe Lys Lys Met
                325                 330                 335

Tyr Gly Lys Thr Leu Ser Ser Met Ile Met Glu Asp Thr Ser Gly Asp
            340                 345                 350

Tyr Lys Asn Ala Leu Leu Ser Leu Val Gly Ser Asp Pro
        355                 360                 365
```

<210> SEQ ID NO 12
<211> LENGTH: 327
<212> TYPE: PRT
<213> ORGANISM: Homo sapiens
<220> FEATURE:
<221> NAME/KEY: MISC_FEATURE
<223> OTHER INFORMATION: NP_001035173.1 annexin A8 isoform 2

<400> SEQUENCE: 12

Met Ala Trp Trp Lys Ser Trp Ile Glu Gln Glu Gly Val Thr Val Lys
1 5 10 15

Ser Ser Ser His Phe Asn Pro Asp Pro Asp Ala Glu Thr Leu Tyr Lys
20 25 30

Ala Met Lys Gly Ile Gly Thr Asn Glu Gln Ala Ile Ile Asp Val Leu
35 40 45

Thr Lys Arg Ser Asn Thr Gln Arg Gln Gln Ile Ala Lys Ser Phe Lys
50 55 60

Ala Gln Phe Gly Lys Asp Leu Thr Glu Thr Leu Lys Ser Glu Leu Ser
65 70 75 80

Gly Lys Phe Glu Arg Leu Ile Val Ala Leu Met Tyr Pro Pro Tyr Arg
85 90 95

Tyr Glu Ala Lys Glu Leu His Asp Ala Met Lys Gly Leu Gly Thr Lys
100 105 110

Glu Gly Val Ile Ile Glu Ile Leu Ala Ser Arg Thr Lys Asn Gln Leu
115 120 125

Arg Glu Ile Met Lys Ala Tyr Glu Glu Asp Tyr Gly Ser Ser Leu Glu
130 135 140

Glu Asp Ile Gln Ala Asp Thr Ser Gly Tyr Leu Glu Arg Ile Leu Val
145 150 155 160

Cys Leu Leu Gln Gly Ser Arg Asp Asp Val Ser Ser Phe Val Asp Pro
165 170 175

Gly Leu Ala Leu Gln Asp Ala Gln Asp Leu Tyr Ala Ala Gly Glu Lys
180 185 190

Ile Arg Gly Thr Asp Glu Met Lys Phe Ile Thr Ile Leu Cys Thr Arg
195 200 205

Ser Ala Thr His Leu Leu Arg Val Phe Glu Glu Tyr Glu Lys Ile Ala
210 215 220

Asn Lys Ser Ile Glu Asp Ser Ile Lys Ser Glu Thr His Gly Ser Leu
225 230 235 240

Glu Glu Ala Met Leu Thr Val Val Lys Cys Thr Gln Asn Leu His Ser
245 250 255

Tyr Phe Ala Glu Arg Leu Tyr Tyr Ala Met Lys Gly Ala Gly Thr Arg
260 265 270

Asp Gly Thr Leu Ile Arg Asn Ile Val Ser Arg Ser Glu Ile Asp Leu
275 280 285

Asn Leu Ile Lys Cys His Phe Lys Lys Met Tyr Gly Lys Thr Leu Ser
290 295 300

Ser Met Ile Met Glu Asp Thr Ser Gly Asp Tyr Lys Asn Ala Leu Leu
305 310 315 320

Ser Leu Val Gly Ser Asp Pro
325

<210> SEQ ID NO 13
<211> LENGTH: 345
<212> TYPE: PRT
<213> ORGANISM: Homo sapiens
<220> FEATURE:
<221> NAME/KEY: MISC_FEATURE
<223> OTHER INFORMATION: NP_003559.2 annexin A9

<400> SEQUENCE: 13

Met Ser Val Thr Gly Gly Lys Met Ala Pro Ser Leu Thr Gln Glu Ile

```
1               5                   10                  15

Leu Ser His Leu Gly Leu Ala Ser Lys Thr Ala Ala Trp Gly Thr Leu
            20                  25                  30

Gly Thr Leu Arg Thr Phe Leu Asn Phe Ser Val Asp Lys Asp Ala Gln
        35                  40                  45

Arg Leu Leu Arg Ala Ile Thr Gly Gln Gly Val Asp Arg Ser Ala Ile
    50                  55                  60

Val Asp Val Leu Thr Asn Arg Ser Arg Glu Gln Arg Gln Leu Ile Ser
65                  70                  75                  80

Arg Asn Phe Gln Glu Arg Thr Gln Gln Asp Leu Met Lys Ser Leu Gln
                85                  90                  95

Ala Ala Leu Ser Gly Asn Leu Glu Arg Ile Val Met Ala Leu Leu Gln
            100                 105                 110

Pro Thr Ala Gln Phe Asp Ala Gln Glu Leu Arg Thr Ala Leu Lys Ala
        115                 120                 125

Ser Asp Ser Ala Val Asp Val Ala Ile Glu Ile Leu Ala Thr Arg Thr
    130                 135                 140

Pro Pro Gln Leu Gln Glu Cys Leu Ala Val Tyr Lys His Asn Phe Gln
145                 150                 155                 160

Val Glu Ala Val Asp Asp Ile Thr Ser Glu Thr Ser Gly Ile Leu Gln
                165                 170                 175

Asp Leu Leu Leu Ala Leu Ala Lys Gly Gly Arg Asp Ser Tyr Ser Gly
            180                 185                 190

Ile Ile Asp Tyr Asn Leu Ala Glu Gln Asp Val Gln Ala Leu Gln Arg
        195                 200                 205

Ala Glu Gly Pro Ser Arg Glu Glu Thr Trp Val Pro Val Phe Thr Gln
    210                 215                 220

Arg Asn Pro Glu His Leu Ile Arg Val Phe Asp Gln Tyr Gln Arg Ser
225                 230                 235                 240

Thr Gly Gln Glu Leu Glu Glu Ala Val Gln Asn Arg Phe His Gly Asp
                245                 250                 255

Ala Gln Val Ala Leu Leu Gly Leu Ala Ser Val Ile Lys Asn Thr Pro
            260                 265                 270

Leu Tyr Phe Ala Asp Lys Leu His Gln Ala Leu Gln Glu Thr Glu Pro
        275                 280                 285

Asn Tyr Gln Val Leu Ile Arg Ile Leu Ile Ser Arg Cys Glu Thr Asp
    290                 295                 300

Leu Leu Ser Ile Arg Ala Glu Phe Arg Lys Lys Phe Gly Lys Ser Leu
305                 310                 315                 320

Tyr Ser Ser Leu Gln Asp Ala Val Lys Gly Asp Cys Gln Ser Ala Leu
                325                 330                 335

Leu Ala Leu Cys Arg Ala Glu Asp Met
            340                 345


<210> SEQ ID NO 14
<211> LENGTH: 324
<212> TYPE: PRT
<213> ORGANISM: Homo sapiens
<220> FEATURE:
<221> NAME/KEY: MISC_FEATURE
<223> OTHER INFORMATION: NP_009124.2 annexin A10

<400> SEQUENCE: 14

Met Phe Cys Gly Asp Tyr Val Gln Gly Thr Ile Phe Pro Ala Pro Asn
1               5                   10                  15
```

```
Phe Asn Pro Ile Met Asp Ala Gln Met Leu Gly Gly Ala Leu Gln Gly
            20                  25                  30

Phe Asp Cys Asp Lys Asp Met Leu Ile Asn Ile Leu Thr Gln Arg Cys
        35                  40                  45

Asn Ala Gln Arg Met Met Ile Ala Glu Ala Tyr Gln Ser Met Tyr Gly
    50                  55                  60

Arg Asp Leu Ile Gly Asp Met Arg Glu Gln Leu Ser Asp His Phe Lys
65                  70                  75                  80

Asp Val Met Ala Gly Leu Met Tyr Pro Pro Pro Leu Tyr Asp Ala His
                85                  90                  95

Glu Leu Trp His Ala Met Lys Gly Val Gly Thr Asp Glu Asn Cys Leu
            100                 105                 110

Ile Glu Ile Leu Ala Ser Arg Thr Asn Gly Glu Ile Phe Gln Met Arg
        115                 120                 125

Glu Ala Tyr Cys Leu Gln Tyr Ser Asn Asn Leu Gln Glu Asp Ile Tyr
    130                 135                 140

Ser Glu Thr Ser Gly His Phe Arg Asp Thr Leu Met Asn Leu Val Gln
145                 150                 155                 160

Gly Thr Arg Glu Glu Gly Tyr Thr Asp Pro Ala Met Ala Ala Gln Asp
                165                 170                 175

Ala Met Val Leu Trp Glu Ala Cys Gln Gln Lys Thr Gly Glu His Lys
            180                 185                 190

Thr Met Leu Gln Met Ile Leu Cys Asn Lys Ser Tyr Gln Gln Leu Arg
        195                 200                 205

Leu Val Phe Gln Glu Phe Gln Asn Ile Ser Gly Gln Asp Met Val Asp
    210                 215                 220

Ala Ile Asn Glu Cys Tyr Asp Gly Tyr Phe Gln Glu Leu Leu Val Ala
225                 230                 235                 240

Ile Val Leu Cys Val Arg Asp Lys Pro Ala Tyr Phe Ala Tyr Arg Leu
                245                 250                 255

Tyr Ser Ala Ile His Asp Phe Gly Phe His Asn Lys Thr Val Ile Arg
            260                 265                 270

Ile Leu Ile Ala Arg Ser Glu Ile Asp Leu Leu Thr Ile Arg Lys Arg
        275                 280                 285

Tyr Lys Glu Arg Tyr Gly Lys Ser Leu Phe His Asp Ile Arg Asn Phe
    290                 295                 300

Ala Ser Gly His Tyr Lys Lys Ala Leu Leu Ala Ile Cys Ala Gly Asp
305                 310                 315                 320

Ala Glu Asp Tyr


<210> SEQ ID NO 15
<211> LENGTH: 505
<212> TYPE: PRT
<213> ORGANISM: Homo sapiens
<220> FEATURE:
<221> NAME/KEY: MISC_FEATURE
<223> OTHER INFORMATION: NP_665875.1 annexin A11 isoform 1

<400> SEQUENCE: 15

Met Ser Tyr Pro Gly Tyr Pro Pro Pro Pro Gly Gly Tyr Pro Pro Ala
1               5                   10                  15

Ala Pro Gly Gly Gly Pro Trp Gly Gly Ala Ala Tyr Pro Pro Pro Pro
            20                  25                  30

Ser Met Pro Pro Ile Gly Leu Asp Asn Val Ala Thr Tyr Ala Gly Gln
        35                  40                  45
```

```
Phe Asn Gln Asp Tyr Leu Ser Gly Met Ala Ala Asn Met Ser Gly Thr
    50                  55                  60

Phe Gly Gly Ala Asn Met Pro Asn Leu Tyr Pro Gly Ala Pro Gly Ala
65                  70                  75                  80

Gly Tyr Pro Pro Val Pro Pro Gly Gly Phe Gly Gln Pro Pro Ser Ala
                85                  90                  95

Gln Gln Pro Val Pro Pro Tyr Gly Met Tyr Pro Pro Pro Gly Gly Asn
            100                 105                 110

Pro Pro Ser Arg Met Pro Ser Tyr Pro Pro Tyr Pro Gly Ala Pro Val
        115                 120                 125

Pro Gly Gln Pro Met Pro Pro Pro Gly Gln Gln Pro Pro Gly Ala Tyr
    130                 135                 140

Pro Gly Gln Pro Pro Val Thr Tyr Pro Gly Gln Pro Pro Val Pro Leu
145                 150                 155                 160

Pro Gly Gln Gln Gln Pro Val Pro Ser Tyr Pro Gly Tyr Pro Gly Ser
                165                 170                 175

Gly Thr Val Thr Pro Ala Val Pro Pro Thr Gln Phe Gly Ser Arg Gly
            180                 185                 190

Thr Ile Thr Asp Ala Pro Gly Phe Asp Pro Leu Arg Asp Ala Glu Val
        195                 200                 205

Leu Arg Lys Ala Met Lys Gly Phe Gly Thr Asp Glu Gln Ala Ile Ile
    210                 215                 220

Asp Cys Leu Gly Ser Arg Ser Asn Lys Gln Arg Gln Gln Ile Leu Leu
225                 230                 235                 240

Ser Phe Lys Thr Ala Tyr Gly Lys Asp Leu Ile Lys Asp Leu Lys Ser
                245                 250                 255

Glu Leu Ser Gly Asn Phe Glu Lys Thr Ile Leu Ala Leu Met Lys Thr
            260                 265                 270

Pro Val Leu Phe Asp Ile Tyr Glu Ile Lys Glu Ala Ile Lys Gly Val
        275                 280                 285

Gly Thr Asp Glu Ala Cys Leu Ile Glu Ile Leu Ala Ser Arg Ser Asn
    290                 295                 300

Glu His Ile Arg Glu Leu Asn Arg Ala Tyr Lys Ala Glu Phe Lys Lys
305                 310                 315                 320

Thr Leu Glu Glu Ala Ile Arg Ser Asp Thr Ser Gly His Phe Gln Arg
                325                 330                 335

Leu Leu Ile Ser Leu Ser Gln Gly Asn Arg Asp Glu Ser Thr Asn Val
            340                 345                 350

Asp Met Ser Leu Ala Gln Arg Asp Ala Gln Glu Leu Tyr Ala Ala Gly
        355                 360                 365

Glu Asn Arg Leu Gly Thr Asp Glu Ser Lys Phe Asn Ala Val Leu Cys
    370                 375                 380

Ser Arg Ser Arg Ala His Leu Val Ala Val Phe Asn Glu Tyr Gln Arg
385                 390                 395                 400

Met Thr Gly Arg Asp Ile Glu Lys Ser Ile Cys Arg Glu Met Ser Gly
                405                 410                 415

Asp Leu Glu Glu Gly Met Leu Ala Val Val Lys Cys Leu Lys Asn Thr
            420                 425                 430

Pro Ala Phe Phe Ala Glu Arg Leu Asn Lys Ala Met Arg Gly Ala Gly
        435                 440                 445

Thr Lys Asp Arg Thr Leu Ile Arg Ile Met Val Ser Arg Ser Glu Thr
    450                 455                 460

Asp Leu Leu Asp Ile Arg Ser Glu Tyr Lys Arg Met Tyr Gly Lys Ser
```

465 470 475 480

Leu Tyr His Asp Ile Ser Gly Asp Thr Ser Gly Asp Tyr Arg Lys Ile
485 490 495

Leu Leu Lys Ile Cys Gly Gly Asn Asp
500 505

<210> SEQ ID NO 16
<211> LENGTH: 472
<212> TYPE: PRT
<213> ORGANISM: Homo sapiens
<220> FEATURE:
<221> NAME/KEY: MISC_FEATURE
<223> OTHER INFORMATION: NP_001265338.1 annexin A11 isoform 2

<400> SEQUENCE: 16

Met Pro Pro Ile Gly Leu Asp Asn Val Ala Thr Tyr Ala Gly Gln Phe
1 5 10 15

Asn Gln Asp Tyr Leu Ser Gly Met Ala Ala Asn Met Ser Gly Thr Phe
20 25 30

Gly Gly Ala Asn Met Pro Asn Leu Tyr Pro Gly Ala Pro Gly Ala Gly
35 40 45

Tyr Pro Pro Val Pro Pro Gly Gly Phe Gly Gln Pro Pro Ser Ala Gln
50 55 60

Gln Pro Val Pro Pro Tyr Gly Met Tyr Pro Pro Pro Gly Gly Asn Pro
65 70 75 80

Pro Ser Arg Met Pro Ser Tyr Pro Pro Tyr Pro Gly Ala Pro Val Pro
85 90 95

Gly Gln Pro Met Pro Pro Pro Gly Gln Gln Pro Pro Gly Ala Tyr Pro
100 105 110

Gly Gln Pro Pro Val Thr Tyr Pro Gly Gln Pro Pro Val Pro Leu Pro
115 120 125

Gly Gln Gln Gln Pro Val Pro Ser Tyr Pro Gly Tyr Pro Gly Ser Gly
130 135 140

Thr Val Thr Pro Ala Val Pro Pro Thr Gln Phe Gly Ser Arg Gly Thr
145 150 155 160

Ile Thr Asp Ala Pro Gly Phe Asp Pro Leu Arg Asp Ala Glu Val Leu
165 170 175

Arg Lys Ala Met Lys Gly Phe Gly Thr Asp Glu Gln Ala Ile Ile Asp
180 185 190

Cys Leu Gly Ser Arg Ser Asn Lys Gln Arg Gln Gln Ile Leu Leu Ser
195 200 205

Phe Lys Thr Ala Tyr Gly Lys Asp Leu Ile Lys Asp Leu Lys Ser Glu
210 215 220

Leu Ser Gly Asn Phe Glu Lys Thr Ile Leu Ala Leu Met Lys Thr Pro
225 230 235 240

Val Leu Phe Asp Ile Tyr Glu Ile Lys Glu Ala Ile Lys Gly Val Gly
245 250 255

Thr Asp Glu Ala Cys Leu Ile Glu Ile Leu Ala Ser Arg Ser Asn Glu
260 265 270

His Ile Arg Glu Leu Asn Arg Ala Tyr Lys Ala Glu Phe Lys Lys Thr
275 280 285

Leu Glu Glu Ala Ile Arg Ser Asp Thr Ser Gly His Phe Gln Arg Leu
290 295 300

Leu Ile Ser Leu Ser Gln Gly Asn Arg Asp Glu Ser Thr Asn Val Asp
305 310 315 320

```
Met Ser Leu Ala Gln Arg Asp Ala Gln Glu Leu Tyr Ala Ala Gly Glu
                325                 330                 335

Asn Arg Leu Gly Thr Asp Glu Ser Lys Phe Asn Ala Val Leu Cys Ser
            340                 345                 350

Arg Ser Arg Ala His Leu Val Ala Val Phe Asn Glu Tyr Gln Arg Met
        355                 360                 365

Thr Gly Arg Asp Ile Glu Lys Ser Ile Cys Arg Glu Met Ser Gly Asp
    370                 375                 380

Leu Glu Glu Gly Met Leu Ala Val Val Lys Cys Leu Lys Asn Thr Pro
385                 390                 395                 400

Ala Phe Phe Ala Glu Arg Leu Asn Lys Ala Met Arg Gly Ala Gly Thr
                405                 410                 415

Lys Asp Arg Thr Leu Ile Arg Ile Met Val Ser Arg Ser Glu Thr Asp
            420                 425                 430

Leu Leu Asp Ile Arg Ser Glu Tyr Lys Arg Met Tyr Gly Lys Ser Leu
        435                 440                 445

Tyr His Asp Ile Ser Gly Asp Thr Ser Gly Asp Tyr Arg Lys Ile Leu
    450                 455                 460

Leu Lys Ile Cys Gly Gly Asn Asp
465                 470


<210> SEQ ID NO 17
<211> LENGTH: 316
<212> TYPE: PRT
<213> ORGANISM: Homo sapiens
<220> FEATURE:
<221> NAME/KEY: MISC_FEATURE
<223> OTHER INFORMATION: NP_004297.2 annexin A13 isoform a

<400> SEQUENCE: 17

Met Gly Asn Arg His Ala Lys Ala Ser Ser Pro Gln Gly Phe Asp Val
1               5                   10                  15

Asp Arg Asp Ala Lys Lys Leu Asn Lys Ala Cys Lys Gly Met Gly Thr
            20                  25                  30

Asn Glu Ala Ala Ile Ile Glu Ile Leu Ser Gly Arg Thr Ser Asp Glu
        35                  40                  45

Arg Gln Gln Ile Lys Gln Lys Tyr Lys Ala Thr Tyr Gly Lys Glu Leu
    50                  55                  60

Glu Glu Val Leu Lys Ser Glu Leu Ser Gly Asn Phe Glu Lys Thr Ala
65                  70                  75                  80

Leu Ala Leu Leu Asp Arg Pro Ser Glu Tyr Ala Ala Arg Gln Leu Gln
                85                  90                  95

Lys Ala Met Lys Gly Leu Gly Thr Asp Glu Ser Val Leu Ile Glu Val
            100                 105                 110

Leu Cys Thr Arg Thr Asn Lys Glu Ile Ile Ala Ile Lys Glu Ala Tyr
        115                 120                 125

Gln Arg Leu Phe Asp Arg Ser Leu Glu Ser Asp Val Lys Gly Asp Thr
    130                 135                 140

Ser Gly Asn Leu Lys Lys Ile Leu Val Ser Leu Leu Gln Ala Asn Arg
145                 150                 155                 160

Asn Glu Gly Asp Asp Val Asp Lys Asp Leu Ala Gly Gln Asp Ala Lys
                165                 170                 175

Asp Leu Tyr Asp Ala Gly Glu Gly Arg Trp Gly Thr Asp Glu Leu Ala
            180                 185                 190

Phe Asn Glu Val Leu Ala Lys Arg Ser Tyr Lys Gln Leu Arg Ala Thr
        195                 200                 205
```

```
Phe Gln Ala Tyr Gln Ile Leu Ile Gly Lys Asp Ile Glu Glu Ala Ile
    210                 215                 220

Glu Glu Glu Thr Ser Gly Asp Leu Gln Lys Ala Tyr Leu Thr Leu Val
225                 230                 235                 240

Arg Cys Ala Gln Asp Cys Glu Asp Tyr Phe Ala Glu Arg Leu Tyr Lys
                245                 250                 255

Ser Met Lys Gly Ala Gly Thr Asp Glu Glu Thr Leu Ile Arg Ile Val
            260                 265                 270

Val Thr Arg Ala Glu Val Asp Leu Gln Gly Ile Lys Ala Lys Phe Gln
        275                 280                 285

Glu Lys Tyr Gln Lys Ser Leu Ser Asp Met Val Arg Ser Asp Thr Ser
    290                 295                 300

Gly Asp Phe Arg Lys Leu Leu Val Ala Leu Leu His
305                 310                 315


<210> SEQ ID NO 18
<211> LENGTH: 358
<212> TYPE: PRT
<213> ORGANISM: Homo sapiens
<220> FEATURE:
<221> NAME/KEY: MISC_FEATURE
<223> OTHER INFORMATION: NP_001003954.1 annexin A13 isoform b

<400> SEQUENCE: 18

Ile Met Gly Asn Arg His Ser Gln Ser Tyr Thr Leu Ser Glu Gly Ser
1               5                   10                  15

Gln Gln Leu Pro Lys Gly Asp Ser Gln Pro Ser Thr Val Val Gln Pro
            20                  25                  30

Leu Ser His Pro Ser Arg Asn Gly Glu Pro Glu Ala Pro Gln Pro Ala
        35                  40                  45

Lys Ala Ser Ser Pro Gln Gly Phe Asp Val Asp Arg Asp Ala Lys Lys
    50                  55                  60

Leu Asn Lys Ala Cys Lys Gly Met Gly Thr Asn Glu Ala Ala Ile Ile
65                  70                  75                  80

Glu Ile Leu Ser Gly Arg Thr Ser Asp Glu Arg Gln Gln Ile Lys Gln
                85                  90                  95

Lys Tyr Lys Ala Thr Tyr Gly Lys Glu Leu Glu Glu Val Leu Lys Ser
            100                 105                 110

Glu Leu Ser Gly Asn Phe Glu Lys Thr Ala Leu Ala Leu Leu Asp Arg
        115                 120                 125

Pro Ser Glu Tyr Ala Ala Arg Gln Leu Gln Lys Ala Met Lys Gly Leu
    130                 135                 140

Gly Thr Asp Glu Ser Val Leu Ile Glu Val Leu Cys Thr Arg Thr Asn
145                 150                 155                 160

Lys Glu Ile Ile Ala Ile Lys Glu Ala Tyr Gln Arg Leu Phe Asp Arg
                165                 170                 175

Ser Leu Glu Ser Asp Val Lys Gly Asp Thr Ser Gly Asn Leu Lys Lys
            180                 185                 190

Ile Leu Val Ser Leu Leu Gln Ala Asn Arg Asn Glu Gly Asp Asp Val
        195                 200                 205

Asp Lys Asp Leu Ala Gly Gln Asp Ala Lys Asp Leu Tyr Asp Ala Gly
    210                 215                 220

Glu Gly Arg Trp Gly Thr Asp Glu Leu Ala Phe Asn Glu Val Leu Ala
225                 230                 235                 240

Lys Arg Ser Tyr Lys Gln Leu Arg Ala Thr Phe Gln Ala Tyr Gln Ile
```

```
            245                 250                 255

Leu Ile Gly Lys Asp Ile Glu Glu Ala Ile Glu Glu Glu Thr Ser Gly
            260                 265                 270

Asp Leu Gln Lys Ala Tyr Leu Thr Leu Val Arg Cys Ala Gln Asp Cys
        275                 280                 285

Glu Asp Tyr Phe Ala Glu Arg Leu Tyr Lys Ser Met Lys Gly Ala Gly
    290                 295                 300

Thr Asp Glu Glu Thr Leu Ile Arg Ile Val Val Thr Arg Ala Glu Val
305                 310                 315                 320

Asp Leu Gln Gly Ile Lys Ala Lys Phe Gln Glu Lys Tyr Gln Lys Ser
                325                 330                 335

Leu Ser Asp Met Val Arg Ser Asp Thr Ser Gly Asp Phe Arg Lys Leu
            340                 345                 350

Leu Val Ala Leu Leu His
        355


<210> SEQ ID NO 19
<211> LENGTH: 1401
<212> TYPE: DNA
<213> ORGANISM: Homo sapiens
<220> FEATURE:
<221> NAME/KEY: misc_feature
<223> OTHER INFORMATION: NM_000700.3 Homo sapiens annexin A1 (ANXA1),
      mRNA

<400> SEQUENCE: 19

agtgtgaaat cttcagagaa gaatttctct ttagttcttt gcaagaaggt agagataaag     60

acactttttc aaaaatggca atggtatcag aattcctcaa gcaggcctgg tttattgaaa    120

atgaagagca ggaatatgtt caaactgtga agtcatccaa aggtggtccc ggatcagcgg    180

tgagccccta tcctaccttc aatccatcct cggatgtcgc tgccttgcat aaggccataa    240

tggttaaagg tgtggatgaa gcaaccatca ttgacattct aactaagcga aacaatgcac    300

agcgtcaaca gatcaaagca gcatatctcc aggaaacagg aaagcccctg gatgaaacac    360

tgaagaaagc ccttacaggt caccttgagg aggttgtttt agctctgcta aaaactccag    420

cgcaatttga tgctgatgaa cttcgtgctg ccatgaaggg ccttggaact gatgaagata    480

ctctaattga gattttggca tcaagaacta acaaagaaat cagagacatt aacagggtct    540

acagagagga actgaagaga gatctggcca aagacataac ctcagacaca tctggagatt    600

ttcggaacgc tttgctttct cttgctaagg gtgaccgatc tgaggacttt ggtgtgaatg    660

aagacttggc tgattcagat gccagggcct tgtatgaagc aggagaaagg agaaagggga    720

cagacgtaaa cgtgttcaat accatcctta ccaccagaag ctatccacaa cttcgcagag    780

tgtttcagaa atacaccaag tacagtaagc atgacatgaa caaagttctg gacctggagt    840

tgaaaggtga cattgagaaa tgcctcacag ctatcgtgaa gtgcgccaca agcaaaccag    900

ctttctttgc agagaagctt catcaagcca tgaaaggtgt tggaactcgc cataaggcat    960

tgatcaggat tatggtttcc cgttctgaaa ttgacatgaa tgatatcaaa gcattctatc   1020

agaagatgta tggtatctcc ctttgccaag ccatcctgga tgaaaccaaa ggagattatg   1080

agaaaatcct ggtggctctt tgtggaggaa actaaacatt cccttgatgg tctcaagcta   1140

tgatcagaag actttaatta tatattttca tcctataagc ttaaatagga aagtttcttc   1200

aacaggatta cagtgtagct acctacatgc tgaaaaatat agcctttaaa tcatttttat   1260

attataactc tgtataatag agataagtcc atttttttaaa aatgttttcc ccaaaccata   1320
```

aaaccctata caagttgttc tagtaacaat acatgagaaa gatgtctatg tagctgaaaa 1380
taaaatgacg tcacaagaca a 1401

<210> SEQ ID NO 20
<211> LENGTH: 1632
<212> TYPE: DNA
<213> ORGANISM: Homo sapiens
<220> FEATURE:
<221> NAME/KEY: misc_feature
<223> OTHER INFORMATION: NM_001002858.2 Homo sapiens annexin A2 (ANXA2), transcript variant 1, mRNA

<400> SEQUENCE: 20
gctcagcatt tggggacgct ctcagctctc ggcgcacggc ccaggtaagc ggggcgcgcc 60
ctgcccgccc gcgatgggcc gccagctagc ggggtgtgga gacgctggga agaaggcttc 120
cttcaaaatg tctactgttc acgaaatcct gtgcaagctc agcttggagg gtgatcactc 180
tacaccccca agtgcatatg ggtctgtcaa agcctatact aactttgatg ctgagcggga 240
tgctttgaac attgaaacag ccatcaagac caaaggtgtg gatgaggtca ccattgtcaa 300
cattttgacc aaccgcagca atgcacagag acaggatatt gccttcgcct accagagaag 360
gaccaaaaag gaacttgcat cagcactgaa gtcagcctta tctggccacc tggagacggt 420
gattttgggc ctattgaaga cacctgctca gtatgacgct tctgagctaa aagcttccat 480
gaaggggctg ggaaccgacg aggactctct cattgagatc atctgctcca gaaccaacca 540
ggagctgcag gaaattaaca gagtctacaa ggaaatgtac aagactgatc tggagaagga 600
cattatttcg gacacatctg gtgacttccg caagctgatg gttgccctgg caaagggtag 660
aagagcagag gatggctctg tcattgatta tgaactgatt gaccaagatg ctcgggatct 720
ctatgacgct ggagtgaaga ggaaaggaac tgatgttccc aagtggatca gcatcatgac 780
cgagcggagc gtgccccacc tccagaaagt atttgatagg tacaagagtt acagccctta 840
tgacatgttg gaaagcatca ggaaagaggt taaaggagac ctggaaaatg ctttcctgaa 900
cctggttcag tgcattcaga acaagcccct gtattttgct gatcggctgt atgactccat 960
gaagggcaag gggacgcgag ataaggtcct gatcagaatc atggtctccc gcagtgaagt 1020
ggacatgttg aaaattaggt ctgaattcaa gagaaagtac ggcaagtccc tgtactatta 1080
tatccagcaa gacactaagg gcgactacca gaaagcgctg ctgtacctgt gtggtggaga 1140
tgactgaagc ccgacacggc ctgagcgtcc agaaatggtg ctcaccatgc ttccagctaa 1200
caggtctaga aaaccagctt gcgaataaca gtccccgtgg ccatccctgt gagggtgacg 1260
ttagcattac ccccaacctc attttagttg cctaagcatt gcctggcctt cctgtctagt 1320
ctctcctgta agccaaagaa atgaacattc caaggagttg gaagtgaagt ctatgatgtg 1380
aaacactttg cctcctgtgt actgtgtcat aaacagatga ataaactgaa tttgtacttt 1440
agaaacacgt actttgtggc cctgctttca actgaattgt ttgaaaatta aacgtgcttg 1500
gggttcagct ggtgaggctg tccctgtagg aagaaagctc tgggactgag ctgtacagta 1560
tggttgcccc tatccaagtg tcgctattta agttaaattt aaatgaaata aaataaaata 1620
aaatcaaaaa aa 1632

<210> SEQ ID NO 21
<211> LENGTH: 1432
<212> TYPE: DNA
<213> ORGANISM: Homo sapiens
<220> FEATURE:
<221> NAME/KEY: misc_feature
<223> OTHER INFORMATION: NM_005139.3 Homo sapiens annexin A3 (ANXA3), mRNA

<400> SEQUENCE: 21
agcgcggagc acctgcgccc gcggctgaca ccttcgctcg cagtttgttc gcagtttact 60
cgcacaccag tttcccccac cgcgctttgg attagtgtga tctcagctca aggcaaaggt 120
gggatatcat ggcatctatc tgggttggac accgaggaac agtaagagat tatccagact 180
ttagcccatc agtggatgct gaagctattc agaaagcaat cagaggaatt ggaactgatg 240
agaaaatgct catcagcatt ctgactgaga ggtcaaatgc acagcggcag ctgattgtta 300
aggaatatca agcagcatat ggaaaggagc tgaaagatga cttgaagggt gatctctctg 360
gccactttga gcatctcatg gtggccctag tgactccacc agcagtcttt gatgcaaagc 420
agctaaagaa atccatgaag ggcgcgggaa caaacgaaga tgccttgatt gaaatcttaa 480
ctaccaggac aagcaggcaa atgaaggata tctctcaagc ctattataca gtatacaaga 540
agagtcttgg agatgacatt agttccgaaa catctggtga cttccggaaa gctctgttga 600
ctttggcaga tggcagaaga gatgaaagtc tgaaagtgga tgagcatctg gccaaacaag 660
atgcccagat tctctataaa gctggtgaga acagatgggg cacggatgaa gacaaattca 720
ctgagatcct gtgtttaagg agctttcctc aattaaaact aacatttgat gaatacagaa 780
atatcagcca aaaggacatt gtggacagca taaaaggaga attatctggg cattttgaag 840
acttactgtt ggccatagtt aattgtgtga ggaacacgcc ggccttttta gccgaaagac 900
tgcatcgagc cttgaagggt attggaactg atgagtttac tctgaaccga ataatggtgt 960
ccagatcaga aattgacctt ttggacattc gaacagagtt caagaagcat tatggctatt 1020
ccctatattc agcaattaaa tcggatactt ctggagacta tgaaatcaca ctcttaaaaa 1080
tctgtggtgg agatgactga accaagaaga taatctccaa aggtccacga tgggctttcc 1140
caacagctcc accttacttc ttctcatact atttaagaga acaagcaaat ataaacagca 1200
acttgtgttc ctaacaggaa ttttcattgt tctataacaa caacaacaaa agcgattatt 1260
attttagagc atctcattta taatgtagca gctcataaat gaaattgaaa atggtattaa 1320
agatctgcaa ctactatcca acttatattt ctgctttcaa agttaagaat ctttatagtt 1380
ctactccatt aaatataaag caagataata aaaattgttg cttttgttaa aa 1432

<210> SEQ ID NO 22
<211> LENGTH: 2651
<212> TYPE: DNA
<213> ORGANISM: Homo sapiens
<220> FEATURE:
<221> NAME/KEY: misc_feature
<223> OTHER INFORMATION: NM_001153.5 Homo sapiens annexin A4 (ANXA4), transcript variant 2, mRNA

<400> SEQUENCE: 22
gtgacctccg cagccgcaga ggaggagcgc agcccggcct cgaagaactt ctgcttgggt 60
ggctgaactc tgatcttgac ctagagtcat ggccatggca accaaaggag gtactgtcaa 120
agctgcttca ggattcaatg ccatggaaga tgcccagacc ctgaggaagg ccatgaaagg 180
gctcggcacc gatgaagacg ccattattag cgtccttgcc taccgcaaca ccgcccagcg 240
ccaggagatc aggacagcct acaagagcac catcggcagg gacttgatag acgacctgaa 300
gtcagaactg agtggcaact tcgagcaggt gattgtgggg atgatgacgc ccacggtgct 360
gtatgacgtg caagagctgc gaagggccat gaagggagcc ggcactgatg agggctgcct 420

```
aattgagatc ctggcctccc ggacccctga ggagatccgg cgcataagcc aaacctacca    480
gcagcaatat ggacggagcc ttgaagatga cattcgctct gacacatcgt tcatgttcca    540
gcgagtgctg gtgtctctgt cagctggtgg gagggatgaa ggaaattatc tggacgatgc    600
tctcgtgaga caggatgccc aggacctgta tgaggctgga gagaagaaat gggggacaga    660
tgaggtgaaa tttctaactg ttctctgttc ccggaaccga aatcacctgt tgcatgtgtt    720
tgatgaatac aaaaggatat cacagaagga tattgaacag agtattaaat ctgaaacatc    780
tggtagcttt gaagatgctc tgctggctat agtaaagtgc atgaggaaca aatctgcata    840
ttttgctgaa aagctctata aatcgatgaa gggcttgggc accgatgata acaccctcat    900
cagagtgatg gtttctcgag cagaaattga catgttggat atccgggcac acttcaagag    960
actctatgga aagtctctgt actcgttcat caagggtgac acatctggag actacaggaa   1020
agtactgctt gttctctgtg gaggagatga ttaaaataaa aatcccagaa ggacaggagg   1080
attctcaaca ctttgaattt ttttaacttc atttttctac actgctatta tcattatctc   1140
agaatgctta tttccaatta aaacgcctac agctgcctcc tagaatatag actgtctgta   1200
ttattattca cctataatta gtcattatga tgctttaaag ctgtacttgc atttcaaagc   1260
ttataagata taaatggaga ttttaaagta gaaataaata tgtattccat gtttttaaaa   1320
gattactttc tactttgtgt ttcacagaca ttgaatatat taaattattc catatttttct  1380
tttcagtgaa aaatttttta aatggaagac tgttctaaaa tcactttttt ccctaatcca   1440
atttttagag tggctagtag tttcttcatt tgaaattgta agcatccggt cagtaagaat   1500
gcccatccag ttttctatat ttcatagtca aagccttgaa agcatctaca aatctctttt   1560
tttaggtttt gtccatagca tcagttgatc cttactaagt ttttcatggg agacttcctt   1620
catcacatct tatgttgaaa tcactttctg tagtcaaagt ataccaaaac caatttatct   1680
gaactaaatt ctaaagtatg gttatacaaa ccatatacat ctggttacca aacataaatg   1740
ctgaacattc catattatta tagttaatgt cttaatccag cttgcaagtg aatggaaaaa   1800
aaaataagct tcaaactagg tattctggga atgatgtaat gctctgaatt tagtatgata   1860
taaagaaaac ttttttgtgc taaaaatact ttttaaaatc aattttgttg attgtagtaa   1920
tttctatttg cactgtgcct ttcaactcca gaaacattct gaagatgtac ttggatttaa   1980
ttaaaaagtt cactttgtaa gaacgtggaa aaataatttt aatttaaaaa tggtgttttt   2040
aggccggggg cgggggctca cgccagtaat cccaacactt tgggaggcca aggcgggtgg   2100
atcacctaag gtcaggagtt caagactagc ctggccaaca tggagaaact gcatctctac   2160
taaaaatata aaaattagcc gggtgtggtg gctggtgcct gtaatcccag ccactcggag   2220
gctgagtcag ggagaactgc ttgaacccag gaggcaggag gcaaaggttg cagtgagccg   2280
agatcacgcc agcctgggcg acagagcgag aatccatcta aaaaaaaaaa aaaaaaaagt   2340
gtctttaaag tgaggtatag tctttctctg atccactttt caccttctga ggtttttcat   2400
cttggcccct gaaaggagct atttttgaag gacttgtgtt actcagtttc tacaggaatt   2460
acaagataag aaaaaaaaaa tcatatttag tcttatgcgt gcctactggc taatgttcac   2520
atatgccaaa cactactcaa taacataaaa taatgtatga acttattctc tggaaatgag   2580
tgatgccctc tgctctaagt agaccattta tattaaatat cataaatgta taaaggacat   2640
tcatattctt a                                                        2651
```

<210> SEQ ID NO 23
<211> LENGTH: 1638

<212> TYPE: DNA
<213> ORGANISM: Homo sapiens
<220> FEATURE:
<221> NAME/KEY: misc_feature
<223> OTHER INFORMATION: NM_001154.4 Homo sapiens annexin A5 (ANXA5), mRNA

<400> SEQUENCE: 23
agtctaggtg cagctgccgg atccttcagc gtctgcatct cggcgtcgcc ccgcgtaccg 60
tcgcccggct ctccgccgct ctcccggggt ttcggggcac ttgggtccca cagtctggtc 120
ctgcttcacc ttcccctgac ctgagtagtc gccatggcac aggttctcag aggcactgtg 180
actgacttcc ctggatttga tgagcgggct gatgcagaaa ctcttcggaa ggctatgaaa 240
ggcttgggca cagatgagga gagcatcctg actctgttga catcccgaag taatgctcag 300
cgccaggaaa tctctgcagc ttttaagact ctgtttggca gggatcttct ggatgacctg 360
aaatcagaac taactggaaa atttgaaaaa ttaattgtgg ctctgatgaa accctctcgg 420
ctttatgatg cttatgaact gaaacatgcc ttgaagggag ctggaacaaa tgaaaaagta 480
ctgacagaaa ttattgcttc aaggacacct gaagaactga gagccatcaa acaagtttat 540
gaagaagaat atggctcaag cctggaagat gacgtggtgg gggacacttc agggtactac 600
cagcggatgt tggtggttct ccttcaggct aacagagacc ctgatgctgg aattgatgaa 660
gctcaagttg aacaagatgc tcaggcttta tttcaggctg gagaacttaa atgggggaca 720
gatgaagaaa agtttatcac catctttgga acacgaagtg tgtctcattt gagaaaggtg 780
tttgacaagt acatgactat atcaggattt caaattgagg aaaccattga ccgcgagact 840
tctggcaatt tagagcaact actccttgct gttgtgaaat ctattcgaag tatacctgcc 900
taccttgcag agaccctcta ttatgctatg aagggagctg ggacagatga tcataccctc 960
atcagagtca tggtttccag gagtgagatt gatctgttta acatcaggaa ggagtttagg 1020
aagaattttg ccacctctct ttattccatg attaagggag atacatctgg ggactataag 1080
aaagctcttc tgctgctctg tggagaagat gactaacgtg tcacggggaa gagctccctg 1140
ctgtgtgcct gcaccacccc actgccttcc ttcagcacct ttagctgcat ttgtatgcca 1200
gtgcttaaca cattgcctta ttcatactag catgctcatg accaacacat acacgtcata 1260
gaagaaaata gtggtgcttc tttctgatct ctagtggaga tctctttgac tgctgtagta 1320
ctaaagtgta cttaatgtta ctaagtttaa tgcctggcca ttttccattt atatatattt 1380
tttaagaggc tagagtgctt ttagcctttt ttaaaaactc catttatatt acatttgtaa 1440
ccatgatact ttaatcagaa gcttagcctt gaaattgtga actcttggaa atgttattag 1500
tgaagttcgc aactaaacta aacctgtaaa attatgatga ttgtattcaa aagattaatg 1560
aaaaataaac atttctgtcc ccctgaatta tgtgtacatg tgtgtttaga tttattatta 1620
aatttattta acaatgtt 1638

<210> SEQ ID NO 24
<211> LENGTH: 2889
<212> TYPE: DNA
<213> ORGANISM: Homo sapiens
<220> FEATURE:
<221> NAME/KEY: misc_feature
<223> OTHER INFORMATION: NM_001155.5 Homo sapiens annexin A6 (ANXA6), transcript variant 1, mRNA

<400> SEQUENCE: 24
gcggttgctg ctgggctaac gggctccgat ccagcgagcg ctgcgtcctc gagtccctgc 60

```
gcccgtgcgt ccgtctgcga cccgaggcct ccgctgcgcg tggattctgc tgcgaaccgg    120
agaccatggc caaaccagca cagggtgcca agtaccgggg ctccatccat gacttcccag    180
gctttgaccc caaccaggat gccgaggctc tgtacactgc catgaagggc tttggcagtg    240
acaaggaggc catactggac ataatcacct cacggagcaa caggcagagg caggaggtct    300
gccagagcta caagtccctc tacggcaagg acctcattgc tgatttaaag tatgaattga    360
cgggcaagtt tgaacggttg attgtgggcc tgatgaggcc acctgcctat tgtgatgcca    420
aagaaattaa agatgccatc tcgggcattg gcactgatga gaagtgcctc attgagatct    480
tggcttcccg gaccaatgag cagatgcacc agctggtggc agcatacaaa gatgcctacg    540
agcgggacct ggaggctgac atcatcggcg acacctctgg ccacttccag aagatgcttg    600
tggtcctgct ccagggaacc agggaggagg atgacgtagt gagcgaggac ctggtacaac    660
aggatgtcca ggacctatac gaggcagggg aactgaaatg ggaacagat gaagcccagt     720
tcatttacat cttgggaaat cgcagcaagc agcatcttcg gttggtgttc gatgagtatc    780
tgaagaccac agggaagccg attgaagcca gcatccgagg ggagctgtct ggggactttg    840
agaagctaat gctggccgta gtgaagtgta tccggagcac cccggaatat tttgctgaaa    900
ggctcttcaa ggctatgaag ggcctgggga ctcgggacaa caccctgatc cgcatcatgg    960
tctcccgtag tgagttggac atgctcgaca ttcgggagat cttccggacc aagtatgaga   1020
agtccctcta cagcatgatc aagaatgaca cctctggcga gtacaagaag actctgctga   1080
agctgtctgg gggagatgat gatgctgctg gccagttctt cccggaggca gcgcaggtgg   1140
cctatcagat gtgggaactt agtgcagtgg cccgagtaga gctgaaggga actgtgcgcc   1200
cagccaatga cttcaaccct gacgcagatg ccaaagcgct gcggaaagcc atgaagggac   1260
tcgggactga cgaagacaca atcatcgata tcatcacgca ccgcagcaat gtccagcggc   1320
agcagatccg gcagaccttc aagtctcact ttggccggga cttaatgact gacctgaagt   1380
ctgagatctc tggagacctg gcaaggctga ttctggggct catgatgcca ccggcccatt   1440
acgatgccaa gcagttgaag aaggccatgg agggagccgg cacagatgaa aaggctctta   1500
ttgaaatcct ggccactcgg accaatgctg aaatccgggc catcaatgag gcctataagg   1560
aggactatca caagtccctg gaggatgctc tgagctcaga cacatctggc cacttcagga   1620
ggatcctcat ttctctggcc acggggcatc gtgaggaggg aggagaaaac ctggaccagg   1680
cacgggaaga tgcccaggtg gctgctgaga tcttggaaat agcagacaca cctagtggag   1740
acaaaacttc cttggagaca cgtttcatga cgatcctgtg tacccggagc tatccgcacc   1800
tccggagagt cttccaggag ttcatcaaga tgaccaacta tgacgtggag cacaccatca   1860
agaaggagat gtctggggat gtcagggatg catttgtggc cattgttcaa agtgtcaaga   1920
acaagcctct cttctttgcc gacaaacttt acaaatccat gaagggtgct ggcacagatg   1980
agaagactct gaccaggatc atggtatccc gcagtgagat tgacctgctc aacatccgga   2040
gggaattcat tgagaaatat gacaagtctc tccaccaagc cattgagggt gacacctccg   2100
gagacttcct gaaggccttg ctggctctct gtggtggtga ggactagggc cacagctttg   2160
gcgggcactt ctgccaagaa atggttatca gcaccagccg ccatggccaa gcctgattgt   2220
tccagctcca gagactaagg aaggggcagg ggtgggggga ggggttgggt tgggctctta   2280
tcttcagtgg agcttaggaa acgctcccac tcccacgggc catcgagggc ccagcacggc   2340
tgagcggctg aaaaaccgta gccatagatc ctgtccacct ccactcccct ctgaccctca   2400
ggctttccca gcttcctccc cttgctacag cctctgccct ggtttgggct atgtcagatc   2460
```

caaaaacatc ctgaacctct gtctgtaaaa tgagtagtgt ctgtactttg aatgaggggg 2520
ttggtggcag gggccagttg aatgtgctgg gcggggtggt gggaaggata gtaaatgtgc 2580
tggggcaaac tgacaaatct tcccatccat ttcaccaccc atctccatcc aggccgcgct 2640
agagtactgg accaggaatt tggatgcctg ggttcaaatc tgcatctgcc atgcacttgt 2700
ttctgacctt aggccagccc ctttccctcc ctgagtctct attttcttat ctacaatgag 2760
acagttggac aaaaaaatct tggcttccct tctaacatta acttcctaaa gtatgcctcc 2820
gattcattcc cttgacactt tttatttcta aggaagaaat aaaaagagat acacaaacac 2880
ataaacaca 2889

<210> SEQ ID NO 25
<211> LENGTH: 2879
<212> TYPE: DNA
<213> ORGANISM: Homo sapiens
<220> FEATURE:
<221> NAME/KEY: misc_feature
<223> OTHER INFORMATION: NM_001193544.1 Homo sapiens annexin A6 (ANXA6), transcript variant 2, mRNA

<400> SEQUENCE: 25
agagaccaga gagcatccag aggcctggcc ggggtcctgc agtgcagacg ttgggaggca 60
cggagacggg gagaggggga ggcggtccag gactcactct gctccacctc tgactccttg 120
aagggtgcca agtaccgggg ctccatccat gacttcccag gctttgaccc caaccaggat 180
gccgaggctc tgtacactgc catgaagggc tttggcagtg acaaggaggc catactggac 240
ataatcacct cacggagcaa caggcagagg caggaggtct gccagagcta caagtccctc 300
tacggcaagg acctcattgc tgatttaaag tatgaattga cgggcaagtt tgaacggttg 360
attgtgggcc tgatgaggcc acctgcctat tgtgatgcca aagaaattaa agatgccatc 420
tcgggcattg gcactgatga gaagtgcctc attgagatct tggcttcccg gaccaatgag 480
cagatgcacc agctggtggc agcatacaaa gatgcctacg agcgggacct ggaggctgac 540
atcatcggcg acacctctgg ccacttccag aagatgcttg tggtcctgct ccagggaacc 600
agggaggagg atgacgtagt gagcgaggac ctggtacaac aggatgtcca ggacctatac 660
gaggcagggg aactgaaatg ggaacagat gaagcccagt tcatttacat cttgggaaat 720
cgcagcaagc agcatcttcg gttggtgttc gatgagtatc tgaagaccac agggaagccg 780
attgaagcca gcatccgagg ggagctgtct ggggactttg agaagctaat gctggccgta 840
gtgaagtgta tccggagcac cccggaatat tttgctgaaa ggctcttcaa ggctatgaag 900
ggcctgggga ctcgggacaa caccctgatc cgcatcatgg tctcccgtag tgagttggac 960
atgctcgaca ttcgggagat cttccggacc aagtatgaga agtccctcta cagcatgatc 1020
aagaatgaca cctctggcga gtacaagaag actctgctga agctgtctgg gggagatgat 1080
gatgctgctg gccagttctt cccggaggca gcgcaggtgg cctatcagat gtgggaactt 1140
agtgcagtgg cccgagtaga gctgaaggga actgtgcgcc cagccaatga cttcaaccct 1200
gacgcagatg ccaaagcgct gcggaaagcc atgaagggac tcgggactga cgaagacaca 1260
atcatcgata tcatcacgca ccgcagcaat gtccagcggc agcagatccg gcagaccttc 1320
aagtctcact ttggccggga cttaatgact gacctgaagt ctgagatctc tggagacctg 1380
gcaaggctga ttctggggct catgatgcca ccggcccatt acgatgccaa gcagttgaag 1440
aaggccatgg agggagccgg cacagatgaa aaggctctta ttgaaatcct ggccactcgg 1500
accaatgctg aaatccgggc catcaatgag gcctataagg aggactatca caagtccctg 1560
gaggatgctc tgagctcaga cacatctggc cacttcagga ggatcctcat ttctctggcc 1620
acggggcatc gtgaggaggg aggagaaaac ctggaccagg cacgggaaga tgcccaggtg 1680
gctgctgaga tcttggaaat agcagacaca cctagtggag acaaaacttc cttggagaca 1740
cgtttcatga cgatcctgtg tacccggagc tatccgcacc tccggagagt cttccaggag 1800
ttcatcaaga tgaccaacta tgacgtggag cacaccatca agaaggagat gtctggggat 1860
gtcagggatg catttgtggc cattgttcaa agtgtcaaga acaagcctct cttctttgcc 1920
gacaaacttt acaaatccat gaagggtgct ggcacagatg agaagactct gaccaggatc 1980
atggtatccc gcagtgagat tgacctgctc aacatccgga gggaattcat tgagaaatat 2040
gacaagtctc tccaccaagc cattgagggt gacacctccg gagacttcct gaaggccttg 2100
ctggctctct gtggtggtga ggactagggc cacagctttg gcgggcactt ctgccaagaa 2160
atggttatca gcaccagccg ccatggccaa gcctgattgt tccagctcca gagactaagg 2220
aaggggcagg ggtgggggga ggggttgggt tgggctctta tcttcagtgg agcttaggaa 2280
acgctcccac tcccacgggc catcgagggc ccagcacggc tgagcggctg aaaaaccgta 2340
gccatagatc ctgtccacct ccactcccct ctgaccctca ggctttccca gcttcctccc 2400
cttgctacag cctctgccct ggtttgggct atgtcagatc caaaaacatc ctgaacctct 2460
gtctgtaaaa tgagtagtgt ctgtactttg aatgaggggg ttggtggcag ggccagttg 2520 aatgtgctgg gcggggtggt gggaaggata gtaaatgtgc tggggcaaac tgacaaatct 2580
tcccatccat ttcaccaccc atctccatcc aggccgcgct agagtactgg accaggaatt 2640
tggatgcctg ggttcaaatc tgcatctgcc atgcacttgt ttctgacctt aggccagccc 2700
ctttccctcc ctgagtctct attttcttat ctacaatgag acagttggac aaaaaaatct 2760
tggcttccct tctaacatta acttcctaaa gtatgcctcc gattcattcc cttgacactt 2820
tttatttcta aggaagaaat aaaaagagat acacaaacac ataaacacaa aaaaaaaaa 2879

<210> SEQ ID NO 26
<211> LENGTH: 2443
<212> TYPE: DNA
<213> ORGANISM: Homo sapiens
<220> FEATURE:
<221> NAME/KEY: misc_feature
<223> OTHER INFORMATION: NM_001156.5 Homo sapiens annexin A7 (ANXA7),
      transcript variant 1, mRNA

<400> SEQUENCE: 26
atcttgcggg agaccgggtt gggctgtgac gctgctgctg gggtcagaat gtcataccca 60
ggctatcccc caacaggcta cccacctttc cctggatatc ctcctgcagg tcaggagtca 120
tcttttcccc cttctggtca gtatccttat cctagtggct ttcctccaat gggaggaggt 180
gcctacccac aagtgccaag tagtggctac ccaggagctg gaggctaccc tgcgcctgga 240
ggttatccag cccctggagg ctatcctggt gccccacagc caggggggagc tccatcctat 300 cccggagttc ctccaggcca aggatttgga gtcccaccag gtggagcagg cttttctggg 360
tatccacagc caccttcaca gtcttatgga ggtggtccag cacaggttcc actacctggt 420
ggctttcctg gaggacagat gccttctcag tatcctggag gacaacctac ttaccctagt 480
cagcctgcca cagtgactca ggtcactcaa ggaactatcc gaccagctgc caacttcgat 540
gctataagag atgcagaaat tcttcgtaag gcaatgaagg gttttgggac agatgagcag 600
gcaattgtgg atgtggtggc caaccgttcc aatgatcaga ggcaaaaaat taaagcagca 660

```
tttaagacct cctatggcaa ggatttaatc aaagatctca aatcagagtt aagtggaaat    720
atggaagaac tgatcctggc cctcttcatg cctcctacgt attacgatgc ctggagctta    780
cggaaagcaa tgcagggagc aggaactcag gaacgtgtat tgattgagat tttgtgcaca    840
agaacaaatc aggaaatccg agaaattgtc agatgttatc agtcagaatt tggacgagac    900
cttgaaaagg acattaggtc agatacatca ggacattttg aacgtttact tgtgtccatg    960
tgccagggaa atcgtgatga gaaccagagt ataaaccacc aaatggctca ggaagatgct   1020
cagcgtctct atcaagctgg tgaggggaga ctagggaccg atgaatcttg ctttaacatg   1080
atccttgcca caagaagctt tcctcagctg agagctacca tggaggctta ttctaggatg   1140
gctaatcgag acttgttaag cagtgtgagc cgtgagtttt ccggatatgt agaaagtggt   1200
ttgaagacca tcttgcagtg tgccctgaac cgccctgcct tctttgctga gaggctctac   1260
tatgctatga aggtgctggg cacagatgac tccaccctgg tccggattgt ggtcactcga   1320
agtgagattg accttgtaca aataaaacag atgttcgctc agatgtatca gaagactctg   1380
ggcacaatga ttgcaggtga cacgagtgga gattaccgaa gacttcttct ggctattgtg   1440
ggccagtagg agggattttt tttttttaa tgaaaaaaaa tttctattca tagcttatcc   1500
ttcagagcaa tgacctgcat gcagcaatat caaacatcag ctaaccgaaa gagctttctg   1560
tcaaggaccg tatcagggta atgtgcttgg tttgcacatg ttgttattgc cttaattcta   1620
attttatttt gttctctaca tacaatcaat gtaaagccat atcacaatga tacagtaata   1680
ttgcaatgtt tgtaaacctt cattcttact agtttcattc taatcaagat gtcaaattga   1740
ataaaaatca cagcaatctc tgattctgtg taataatatt gaataatttt ttagaaggtt   1800
actgaaagct ctgccttccg gaatccctct aagtctgctt gatagagtgg atagtgtgtt   1860
aaaactgtgt actttaaaaa aaaattcaac ctttacatct agaataattt gcatctcatt   1920
ttgcctaaat tggttctgta ttcataaaca ctttccacat agaaaataga ttagtattac   1980
ctgtggcacc ttttaagaaa gggtcaaatg tttatatgct taagatacat agcctacttt   2040
tttttcgcag ttgttttctt tttttaaatt gagttatgac aaataaaaaa ttgcatatat   2100
ttaaggtgta caatatggtg ttttgatatc agcattcctt gtgtaatgat tccacaatta   2160
aggtcaggct aattacgtat ctgtcacctt gacatagtta ccattttttc atgtgtggtg   2220
aaaacactta agatctacta ccttagcaaa ttttaagtgt tcagtacatt attaactata   2280
gatactgtgc tctacattaa acctctagca tttattcgtt ttataactga aagtttatac   2340
cctttgacca acatctcccc atttccccca cctctcacct ggacaaccac cactgtgttt   2400
aagttcagct attttagatt ccacgtataa atggtataca ata                      2443
```

<210> SEQ ID NO 27
<211> LENGTH: 2550
<212> TYPE: DNA
<213> ORGANISM: Homo sapiens
<220> FEATURE:
<221> NAME/KEY: misc_feature
<223> OTHER INFORMATION: NM_004034.3 Homo sapiens annexin A7 (ANXA7),
transcript variant 2, mRNA

<400> SEQUENCE: 27

```
gcccaccctg ggcccgcccc cggctccatc ttgcgggaga ccgggttggg ctgtgacgct     60
gctgctgggg tcagaatgtc atacccaggc tatcccccaa caggctaccc acctttccct    120
ggatatcctc ctgcaggtca ggagtcatct tttcccccctt ctggtcagta tccttatcct    180
```

```
agtggctttc ctccaatggg aggaggtgcc tacccacaag tgccaagtag tggctaccca    240
ggagctggag gctaccctgc gcctggaggt tatccagccc ctggaggcta tcctggtgcc    300
ccacagccag gggagctcc atcctatccc ggagttcctc caggccaagg atttggagtc    360
ccaccaggtg gagcaggctt ttctgggtat ccacagccac cttcacagtc ttatggaggt    420
ggtccagcac aggttccact acctggtggc tttcctggag gacagatgcc ttctcagtat    480
cctggaggac aacctactta ccctagtcag atcaatacag attctttttc ttcctatcct    540
gttttctctc ctgtttcttt ggattatagc agtgaacctg ccacagtgac tcaggtcact    600
caaggaacta tccgaccagc tgccaacttc gatgctataa gagatgcaga aattcttcgt    660
aaggcaatga agggttttgg gacagatgag caggcaattg tggatgtggt ggccaaccgt    720
tccaatgatc agaggcaaaa aattaaagca gcatttaaga cctcctatgg caaggattta    780
atcaaagatc tcaaatcaga gttaagtgga aatatggaag aactgatcct ggccctcttc    840
atgcctccta cgtattacga tgcctggagc ttacggaaag caatgcaggg agcaggaact    900
caggaacgtg tattgattga gattttgtgc acaagaacaa atcaggaaat ccgagaaatt    960
gtcagatgtt atcagtcaga atttggacga gaccttgaaa aggacattag gtcagataca   1020
tcaggacatt ttgaacgttt acttgtgtcc atgtgccagg gaaatcgtga tgagaaccag   1080
agtataaacc accaaatggc tcaggaagat gctcagcgtc tctatcaagc tggtgagggg   1140
agactaggga ccgatgaatc ttgctttaac atgatccttg ccacaagaag ctttcctcag   1200
ctgagagcta ccatggaggc ttattctagg atggctaatc gagacttgtt aagcagtgtg   1260
agccgtgagt tttccggata tgtagaaagt ggtttgaaga ccatcttgca gtgtgccctg   1320
aaccgccctg ccttctttgc tgagaggctc tactatgcta tgaaaggtgc tggcacagat   1380
gactccaccc tggtccggat tgtggtcact cgaagtgaga ttgaccttgt acaaataaaa   1440
cagatgttcg ctcagatgta tcagaagact ctgggcacaa tgattgcagg tgacacgagt   1500
ggagattacc gaagacttct tctggctatt gtgggccagt aggagggatt ttttttttt    1560
taatgaaaaa aaatttctat tcatagctta tccttcagag caatgacctg catgcagcaa   1620
tatcaaacat cagctaaccg aaagagcttt ctgtcaagga ccgtatcagg gtaatgtgct   1680
tggtttgcac atgttgttat tgccttaatt ctaattttat tttgttctct acatacaatc   1740
aatgtaaagc catatcacaa tgatacagta atattgcaat gtttgtaaac cttcattctt   1800
actagtttca ttctaatcaa gatgtcaaat tgaataaaaa tcacagcaat ctctgattct   1860
gtgtaataat attgaataat tttttagaag gttactgaaa gctctgcctt ccggaatccc   1920
tctaagtctg cttgatagag tggatagtgt gttaaaactg tgtactttaa aaaaaaattc   1980
aacctttaca tctagaataa tttgcatctc attttgccta aattggttct gtattcataa   2040
acactttcca catagaaaat agattagtat tacctgtggc accttttaag aaagggtcaa   2100
atgtttatat gcttaagata catagcctac tttttttcg cagttgtttt cttttttaa     2160
attgagttat gacaaataaa aaattgcata tatttaaggt gtacaatatg gtgttttgat   2220
atcagcattc cttgtgtaat gattccacaa ttaaggtcag gctaattacg tatctgtcac   2280
cttgacatag ttaccatttt ttcatgtgtg gtgaaaacac ttaagatcta ctaccttagc   2340
aaattttaag tgttcagtac attattaact atagatactg tgctctacat taaacctcta   2400
gcatttattc gttttataac tgaaagttta taccctttga ccaacatctc cccattttcc   2460
ccacctctca cctggacaac caccactgtg tttaagttca gctattttag attccacgta   2520
taaatggtat acaataaaaa aaaaaaaaaa                                     2550
```

<210> SEQ ID NO 28
<211> LENGTH: 2205
<212> TYPE: DNA
<213> ORGANISM: Homo sapiens
<220> FEATURE:
<221> NAME/KEY: misc_feature
<223> OTHER INFORMATION: [0124] NM_001271702.1 Homo sapiens annexin A8 (ANXA8), transcript variant 1, mRNA

<400> SEQUENCE: 28

```
ctgggtgggg cctgggagcc acaggagatg cccaaagcca ggcagagccc gggggcgagg     60
ggacggcagg caggtgtggc gctgccctgg gcgggcttgc acccccacac ccaagtgagc    120
ggcctgctca ctcctcagct gcaggagcca gacgtgtgga gtcccagcag aggccaacct    180
gtgtctcttc atctccctgg gaaaggtgcc cccgaggtga aagagatggc ctggtggaaa    240
tcctggattg aacaggaggg tgtcacagtg aagagcagct cccacttcaa cccagaccct    300
gatgcagaga ccctctacaa agccatgaag gggatcggtg tcgggtccca actgctcagc    360
caccaagcag ctgccttcgc cttcccctcc tccgccctca ccagtgtgtc accctggggg    420
cagcagggtc acttgtgctg taaccctgca gggaccaacg agcaggctat catcgatgtg    480
ctcaccaaga gaagcaacac gcagcggcag cagatcgcca agtccttcaa ggctcagttc    540
ggcaaggacc tcactgagac cttgaagtct gagctcagtg gcaagtttga gaggctcatt    600
gtggccctta tgtacccgcc atacagatac gaagccaagg agctgcatga cgccatgaag    660
ggcttaggaa ccaaggaggg tgtcatcatt gagatcctgg cctctcggac caagaaccag    720
ctgcgggaga taatgaaggc gtatgaggaa gactatgggt ccagcctgga ggaggacatc    780
caagcagaca caagtggcta cctggagagg atcctggtgt gcctcctgca gggcagcagg    840
gatgatgtga gcagctttgt ggacccagga ctggccctcc aagacgcaca ggatctgtat    900
gcggcaggcg agaagattcg tgggactgat gagatgaaat tcatcaccat cctgtgcacg    960
cgcagtgcca ctcacctgct gagagtgttt gaagagtatg agaaaattgc caacaagagc   1020
attgaggaca gcatcaagag tgagacccat ggctcactgg aggaggccat gctcactgtg   1080
gtgaaatgca cccaaaacct ccacagctac tttgcagaga gactctacta tgccatgaag   1140
ggagcaggga cgcgtgatgg gaccctgata agaaacatcg tttcaaggag cgagattgac   1200
ttaaatctta tcaaatgtca cttcaagaag atgtacggca agaccctcag cagcatgatc   1260
atggaagaca ccagcggtga ctacaagaac gccctgctga gcctggtggg cagcgacccc   1320
tgaggcacag aagaacaaga gcaaagacca tgaagccaga gtctccagga ctcctcactc   1380
aacctcggcc atggacgcag gttgggtgtg agggggggtcc cagcctttcg gtcttctatt   1440
tccctatttc cagtgctttc cagccgggtt tctgacccag agggtggaac cggcctggac   1500
tcctcttccc aacttcctcc aggtcatttc ccagtgtgag cacaatgcca accttagtgt   1560
ttctccagcc agacagatgc ctcagcatga agggcttggg gacttgtgga tcattccttc   1620
ctccctgcag gagcttccca agctggtcac agagtctcct gggcacaggt tatacagacc   1680
ccagccccat tcccatctac tgaaacaggg tctccacaag aggggccagg gaatatgggt   1740
ttttaacaag cgtcttacaa aacacttctc tatcatgcag ccggagagct ggctgggagc   1800
ccttttgttt tagaacacac atccttcagc agctgagaaa cgaacacgaa tccatcccaa   1860
ccgagatgcc attaacattc atctaaaaat gttaggctct aaatggacga aaaattctct   1920
cgccatctta ataacaaaat aaactacaaa ttcctgaccc aaggacactg tgttataaga   1980
```

ggcgtgggct cccctggtgg ctgaccaggt cagctgccct ggccttgcac ccctctgcat 2040
gcagcacaga agggtgtgac catgccctca gcaccactct tgtccccact gaacggcaac 2100
tgagactggg tacctggaga ttctgaagtg cctttgctgt ggttttcaaa ataataaaga 2160
tttgtattca actcaaaaaa aaaaaaaaaa aaaaaaaaaa aaaaa 2205

<210> SEQ ID NO 29
<211> LENGTH: 2070
<212> TYPE: DNA
<213> ORGANISM: Homo sapiens
<220> FEATURE:
<221> NAME/KEY: misc_feature
<223> OTHER INFORMATION: NM_001040084.2 Homo sapiens annexin A8 (ANXA8), transcript variant 2, mRNA

<400> SEQUENCE: 29
ctgggtgggg cctgggagcc acaggagatg cccaaagcca ggcagagccc gggggcgagg 60
ggacggcagg caggtgtggc gctgccctgg gcgggcttgc acccccacac ccaagtgagc 120
ggcctgctca ctcctcagct gcaggagcca gacgtgtgga gtcccagcag aggccaacct 180
gtgtctcttc atctccctgg gaaaggtgcc cccgaggtga aagagatggc ctggtggaaa 240
tcctggattg aacaggaggg tgtcacagtg aagagcagct cccacttcaa cccagaccct 300
gatgcagaga ccctctacaa agccatgaag gggatcggga ccaacgagca ggctatcatc 360
gatgtgctca ccaagagaag caacacgcag cggcagcaga tcgccaagtc cttcaaggct 420
cagttcggca aggacctcac tgagaccttg aagtctgagc tcagtggcaa gtttgagagg 480
ctcattgtgg cccttatgta cccgccatac agatacgaag ccaaggagct gcatgacgcc 540
atgaagggct taggaaccaa ggagggtgtc atcattgaga tcctggcctc tcggaccaag 600
aaccagctgc gggagataat gaaggcgtat gaggaagact atgggtccag cctggaggag 660
gacatccaag cagacacaag tggctacctg gagaggatcc tggtgtgcct cctgcagggc 720
agcagggatg atgtgagcag ctttgtggac ccaggactgg ccctccaaga cgcacaggat 780
ctgtatgcgg caggcgagaa gattcgtggg actgatgaga tgaaattcat caccatcctg 840
tgcacgcgca gtgccactca cctgctgaga gtgtttgaag agtatgagaa aattgccaac 900
aagagcattg aggacagcat caagagtgag acccatggct cactggagga ggccatgctc 960
actgtggtga aatgcaccca aaacctccac agctactttg cagagagact ctactatgcc 1020
atgaagggag cagggacgcg tgatgggacc ctgataagaa acatcgtttc aaggagcgag 1080
attgacttaa atcttatcaa atgtcacttc aagaagatgt acggcaagac cctcagcagc 1140
atgatcatgg aagacaccag cggtgactac aagaacgccc tgctgagcct ggtgggcagc 1200
gacccctgag gcacagaaga acaagagcaa agaccatgaa gccagagtct ccaggactcc 1260
tcactcaacc tcggccatgg acgcaggttg ggtgtgaggg gggtcccagc ctttcggtct 1320
tctatttccc tatttccagt gctttccagc cgggtttctg acccagaggg tggaaccggc 1380
ctggactcct cttcccaact tcctccaggt catttcccag tgtgagcaca atgccaacct 1440
tagtgtttct ccagccagac agatgcctca gcatgaaggg cttggggact tgtggatcat 1500
tccttcctcc ctgcaggagc ttcccaagct ggtcacagag tctcctgggc acaggttata 1560
cagaccccag ccccattccc atctactgaa acagggtctc cacaagaggg gccagggaat 1620
atgggttttt aacaagcgtc ttacaaaaca cttctctatc atgcagccgg agagctggct 1680
gggagccctt ttgttttaga acacacatcc ttcagcagct gagaaacgaa cacgaatcca 1740
tcccaaccga gatgccatta acattcatct aaaaatgtta ggctctaaat ggacgaaaaa 1800
ttctctcgcc atcttaataa caaaataaac tacaaattcc tgacccaagg acactgtgtt 1860
ataagaggcg tgggctcccc tggtggctga ccaggtcagc tgccctggcc ttgcacccct 1920
ctgcatgcag cacagaaggg tgtgaccatg ccctcagcac cactcttgtc cccactgaac 1980
ggcaactgag actgggtacc tggagattct gaagtgcctt tgctgtggtt ttcaaaataa 2040
taaagatttg tattcaactc aaaaaaaaaa 2070

<210> SEQ ID NO 30
<211> LENGTH: 1551
<212> TYPE: DNA
<213> ORGANISM: Homo sapiens
<220> FEATURE:
<221> NAME/KEY: misc_feature
<223> OTHER INFORMATION: NM_003568.3 Homo sapiens annexin A9 (ANXA9), mRNA

<400> SEQUENCE: 30
ctctaccagg ccacaccgga ggcagtgctc acacaggcaa gctaccaggc cacaacaacg 60
acacccacct cacctctggc acctctgagc atccacgtac ttgcaagaac tcttgctcac 120
atcagctaag agattgcacc tgctgaccta gagattccgg cctgtgctcc tgtgctgctg 180
agcagggcaa ccagtagcac catgtctgtg actggcggga agatggcacc gtccctcacc 240
caggagatcc tcagccacct gggcctggcc agcaagactg cagcgtgggg gaccctgggc 300
accctcagga ccttcttgaa cttcagcgtg gacaaggatg cgcagaggct actgagggcc 360
attactggcc aaggcgtgga ccgcagtgcc attgtggacg tgctgaccaa ccggagcaga 420
gagcaaaggc agctcatctc acgaaacttc caggagcgca cccaacagga cctgatgaag 480
tctctacagg cagcactttc cggcaacctg gagaggattg tgatggctct gctgcagccc 540
acagcccagt ttgacgccca ggaattgagg acagctctga aggcctcaga ttctgctgtg 600
gacgtggcca ttgaaattct tgccactcga accccaccc agctgcagga gtgcctggca 660
gtctacaaac acaatttcca ggtggaggct gtggatgaca tcacatctga gaccagtggc 720
atcttgcagg acctgctgtt ggccctggcc aaggggggcc gtgacagcta ctctggaatc 780
attgactata atctggcaga acaagatgtc caggcactgc agcgggcaga aggacctagc 840
agagaggaaa catgggtccc agtcttcacc cagcgaaatc ctgaacacct catccgagtg 900
tttgatcagt accagcggag cactgggcaa gagctggagg aggctgtcca gaaccgtttc 960
catggagatg ctcaggtggc tctgctcggc ctagcttcgg tgatcaagaa cacaccgctg 1020
tactttgctg acaaacttca tcaagccctc caggaaactg agcccaatta ccaagtcctg 1080
attcgcatcc ttatctctcg atgtgagact gaccttctga gtatcagagc tgagttcagg 1140
aagaaatttg ggaagtccct ctactcttct ctccaggatg cagtgaaagg ggattgccag 1200
tcagccctcc tggccttgtg cagggctgaa gacatgtgag acttccctgc ccccaccccac 1260 atgacatccg aggatctgag atttccgtgt ttggctgaac ctgggagacc agctgggcct 1320
ccaagtagga taacccctca ctgagcacca cattctctag cttcttgttg aggctggaac 1380
tgtttcttta aaatccctta attttcccat ctcaaaatta tatctgtacc tgggtcatcc 1440
agctccttct tgggtgtggg gaaatgagtt ttctttgata gtttctgcct cactcatccc 1500
tcctgtaccc tggccagaac atctcactga tactcgaatt cttttggcaa a 1551

<210> SEQ ID NO 31
<211> LENGTH: 1447
<212> TYPE: DNA

<213> ORGANISM: Homo sapiens
<220> FEATURE:
<221> NAME/KEY: misc_feature
<223> OTHER INFORMATION: NM_007193.4 Homo sapiens annexin A10 (ANXA10),
mRNA

<400> SEQUENCE: 31
atccagattt gcttttacat tttcttgcct gagtctgagg tgaacagtga acatatttac 60
atttgattta acagtgaacc ttaattcttt ctggcttcac agtgaaacaa gtttatgcaa 120
tcgatcaaat attttcatcc ctgaggttaa caattaccat caaaatgttt tgtggagact 180
atgtgcaagg aaccatcttc ccagctccca atttcaatcc cataatggat gcccaaatgc 240
taggaggagc actccaagga tttgactgtg acaaagacat gctgatcaac attctgactc 300
agcgctgcaa tgcacaaagg atgatgattg cagaggcata ccagagcatg tatggccggg 360
acctgattgg ggatatgagg gagcagcttt cggatcactt caaagatgtg atggctggcc 420
tcatgtaccc accaccactg tatgatgctc atgagctctg gcatgccatg aagggagtag 480
gcactgatga gaattgcctc attgaaatac tagcttcaag aacaaatgga gaaattttcc 540
agatgcgaga agcctactgc ttgcaataca gcaataacct ccaagaggac atttattcag 600
agacctcagg acacttcaga gatactctca tgaacttggt ccaggggacc agagaggaag 660
gatatacaga ccctgcgatg gctgctcagg atgcaatggt cctatgggaa gcctgtcagc 720
agaagacggg ggagcacaaa accatgctgc aaatgatcct gtgcaacaag agctaccagc 780
agctgcggct ggttttccag gaatttcaaa atatttctgg gcaagatatg gtagatgcca 840
ttaatgaatg ttatgatgga tactttcagg agctgctggt tgcaattgtt ctctgtgttc 900
gagacaaacc agcctatttt gcttatagat tatatagtgc aattcatgac tttggtttcc 960
ataataaaac tgtaatcagg attctcattg ccagaagtga aatagacctg ctgaccataa 1020
ggaaacgata caaagagcga tatggaaaat ccctatttca tgatatcaga aattttgctt 1080
cagggcatta taagaaagca ctgcttgcca tctgtgctgg tgatgctgag gactactaaa 1140
atgaagagga cttggagtac tgtgcactcc tctttctaga cacttccaaa tagagatttt 1200
ctcacaaatt tgtactgttc atggcactat taacaaaact atacaatcat attttctctt 1260
ctatctttga aattattcta agccaaagaa aactatgaat gaaagtatat gatactgaat 1320
ttgcctacta tcctgaattt gcctactatc taatcagcaa ttaaataaat tgtgcatgat 1380
ggaataatag aaaaattgca ttggaataga ttttatttaa atgtgaacca tcaacaacct 1440
acaacaa 1447

<210> SEQ ID NO 32
<211> LENGTH: 6734
<212> TYPE: DNA
<213> ORGANISM: Homo sapiens
<220> FEATURE:
<221> NAME/KEY: misc_feature
<223> OTHER INFORMATION: NM_145868.2 Homo sapiens annexin A11 (ANXA11),
transcript variant b, mRNA

<400> SEQUENCE: 32
ggagttttcc gcccggcgct gacggctgct gcgcccgcgg ctccccagtg ccccgagtgc 60
cccgcgggcc ccgcgagcgg gagtgggacc cagcccctag gcagaaccca ggcgccgcgc 120
ccgggacgcc cgcggagaga gccactcccg cccacgtccc atttcgcccc tcgcgtccgg 180
agtccccgtg gccaggtgtg tgtctgggga agagacttac agaagtggag ttgctgagtc 240
aaagatctaa ccatgagcta ccctggctat cccccgcccc caggtggcta cccaccagct 300

```
gcaccaggtg gtggtccctg gggaggtgct gcctaccctc ctccgcccag catgcccccc    360
atcgggctgg ataacgtggc cacctatgcg gggcagttca accaggacta tctctcggga    420
atggcggcca acatgtctgg gacatttgga ggagccaaca tgcccaacct gtaccctggg    480
gcccctgggg ctggctaccc accagtgccc cctggcggct ttgggcagcc cccctctgcc    540
cagcagcctg ttcctcccta tgggatgtat ccacccccag gaggaaaccc accctccagg    600
atgccctcat atccgccata cccaggggcc cctgtgccgg gccagcccat gccacccccc    660
ggacagcagc ccccaggggc ctaccctggg cagccaccag tgacctaccc tggtcagcct    720
ccagtgccac tccctgggca gcagcagcca gtgccgagct acccaggata cccggggtct    780
gggactgtca cccccgctgt gcccccaacc cagtttggaa gccgaggcac catcactgat    840
gctcccggct ttgaccccct gcgagatgcc gaggtcctgc ggaaggccat gaaaggcttc    900
gggacggatg agcaggccat cattgactgc ctggggagtc gctccaacaa gcagcggcag    960
cagatcctac tttccttcaa gacggcttac ggcaaggatt tgatcaaaga tctgaaatct   1020
gaactgtcag gaaactttga gaagacaatc ttggctctga tgaagacccc agtcctcttt   1080
gacatttatg agataaagga agccatcaag gggttggca ctgatgaagc ctgcctgatt    1140
gagatcctcg cttcccgcag caatgagcac atccgagaat taaacagagc ctacaaagca   1200
gaattcaaaa agaccctgga agaggccatt cgaagcgaca catcagggca cttccagcgg   1260
ctcctcatct ctctctctca gggaaaccgt gatgaaagca caaacgtgga catgtcactc   1320
gcccagagag atgcccagga gctgtatgcg gccggggaga accgcctggg aacagacgag   1380
tccaagttca atgcggttct gtgctcccgg agccgggccc acctggtagc agttttcaat   1440
gagtaccaga gaatgacagg ccgggacatt gagaagagca tctgccggga gatgtccggg   1500
gacctggagg agggcatgct ggccgtggtg aaatgtctca agaataccc agccttcttt    1560
gcggagaggc tcaacaaggc catgaggggg gcaggaacaa aggaccggac cctgattcgc   1620
atcatggtgt ctcgcagcga gaccgacctc ctggacatca gatcagagta taagcggatg   1680
tacggcaagt cgctgtacca cgacatctcg ggagatactt caggggatta ccggaagatt   1740
ctgctgaaga tctgtggtgg caatgactga acagtgactg gtggctcact tctgcccacc   1800
tgccggcaac accagtgcca ggaaaaggcc aaaagaatgt ctgtttctaa caaatccaca   1860
aatagccccg agattcaccg tcctagagct taggcctgtc ttccacccct cctgacccgt   1920
atagtgtgcc acaggacctg ggtcggtcta gaactctctc aggatgcctt ttctacccca   1980
tccctcacag cctcttgctg ctaaaataga tgtttcattt ttctgactca tgcaatcatt   2040
cccctttgcc tgtggctaag acttggcttc atttcgtcat gtaattgtat atttttattt   2100
ggaggcatat tttcttttct tacagtcatt gccagacaga ggcatacaag tctgtttgct   2160
gcatacacat ttctggtgag ggcgactggg tgggtgaagc accgtgtcct cgctgaggag   2220
agaaagggag gcgtgcctga gaaggtagcc tgtgcatctg gtgagtgtgt cacgagcttt   2280
gttactgcca aactcactcc tttttagaaa aaacaaaaaa aaagggccag aaagtcattc   2340
cttccatctt ccttgcagaa accacgagaa caaagccagt tccctgtcag tgacagggct   2400
tcttgtaatt tgtggtatgt gccttaaacc tgaatgtctg tagccaaaac ttgtttccac   2460
attaagagtc agccagctct ggaatggtct ggaaatgtct tcctggtacc aacttgtttt   2520
cttctgcttg attctgccct gtggctcaga ggtctggcct tatcagccag tgaaagttca   2580
tgtaacctta cgtagagatt tgtgtgcagg aaaccctgag catacactag tttgcaggga   2640
```

ctcgtaagga catgggaagg gaggttcccg aaatccaggc aggaggccca gacacctgaa 2700
aggcaaaggg atcttggttg gttgcaggtg cagtgaagtc cactgaaggt gtggtgcgaa 2760
gaatgcagtc cttcacccag gtcccaggag ggaagaaggg tgtgtgctaa ttcctggtgc 2820
ccctcggcgg gggccagaga gaaggatggg gacaacccag agagtcacaa gaccagtgcc 2880
tcccctcagg gtgcctccag gctgaaaggg gctcctggct ctggtctctg gggaccctgt 2940
gcccgttggt tggtggtgtg agggaagaga atccataaga gagtttctga gaattatggt 3000
gtcatgtcca gaagctagag cttaccttgc atcaggggtc tccacccact ccttttccaa 3060
cctcctgcgt tgaggtttag aaaagagaga atcgactagg cactatggct cacgcctgta 3120
atccaaggac tttgggaagc tgaggtgaga ggatcacttg agctcaggag ttcaagacta 3180
gcctagccaa cagcgagacc cctgtctcta ctaaaaaatt tggccaggcg tggtggctca 3240
cggctgtaat cccagcactt tgggaggtga ggcgggcaga tcacctgagg tcaggagttc 3300
gagacccagc ctggccaaca tggtgaaacc ccatctctac taaaaataca aaaattagcc 3360
aggcatggtg gcacattcct gtaatcccag ctacacagga tgctgaggca ggagaatcac 3420
ttgaacccag gaggcagagg ttgtagtgag ctgagatcac accattgcac ttcaacctgg 3480
gtggacagag tgagactctg tctcaaaaaa aaaaaaaaat ttacctggca ttgtagtgca 3540
ttccctatag tcggctactc tggaggctga ggcaggaaga tccttagagc ccaagaaatt 3600
gaggccgtag taagctgtga ttacaccact gcactccagc ctggacaaca gagcgagacc 3660
ttgtctcaaa tgagaaaaaa acaaaaagaa atgggagaat ccagagagac taggctagat 3720
caagcctgct gggtcctggc aggagcccca gggagtagct catctgcaga catttgcttg 3780
aggactaccc cctaaacata aaggaagaat gacatccgaa gggtgtggag cagccatgag 3840
ctgagaacta gcctggtcta cctgagattg atggcaggtc ctggtcaaca cgtcagctct 3900
gcgtcagagt ccatgcctca agcccaagct gaagccccat ccctgctgct ctcccaagaa 3960
ctcctctgct agggcaggcc ccttgccctt gggtgccagg tgggacctgc ctgatgggat 4020
ggggtgcttg gcatatacaa cttgccatga actcaaggtg accctggggg cctcctgaat 4080
tgtgatgggg cctagaacca atgtgctctg atgtgaccat attctgtgac attaccttgc 4140
cctgtttact ccaaagttcc cagcctggtg cccagcaggc aatattgcac ctacagacac 4200
atttactttg gtttccaaag tgtttttaga catttgaatt tgttgccaac atttaaacat 4260
tgagagattt catattttta aaaatctgga attctggctt ctcttgaaaa ctcagaaatt 4320
ctggcactat ggggcttgca ttcctgcatg gctggagctg agttgcagct gccccttag 4380
gcctgtactc cttatttgct ataggctccg tcttgtatta cactaagccc atgtcaccca 4440
tttggctcct gcaggccttt gggtttgaga ccctggtcta cacacttgga gaccacctgt 4500
tgtaaagtac atggatgtgc tttggtcaag gaatagacca aggtggatat ccaggccaga 4560
gtgactcagc gagtttaggt cacaggcgta tactccactt gttatataac ctgcttgtgt 4620
aagttcatac ttggctcaaa gccactattg tttggaaaag gtataactgc cctgctgacg 4680
ctgtacagat gttcttgggc tcggatgggc atggctccac gtggtgtgca ctagcaccca 4740
gagagagtga agctattgac ccctgtaagg gagagtgacc atctggcaga tagatagagg 4800
ggagccagga catggctcag cttgtgccca gagggagagt taagccgctg accctgtagc 4860
cagggagtgc acctgcaagc atgggggtgg caggagccac agagctggct gctgagagga 4920
gctgcagatc tggagaagac agcctaggta aaggtggaca gtgtgagagc tgctgatgag 4980
atagctgctg aataaaacta cattttacct gcctatggcc cgccaggttt tctttcagct 5040
atcgcccatc cacccagtcc cctcgaacct cagcatgggc tggaacctga ccctgggcat 5100
gacatttggc atagttgtgg acctgacacc tgtgtttgtc ctagtcctgt ttctccctgc 5160
cttcctgttc ctctcgctgc cctcatggtc actcccaaga gatccaaccc atgttaagta 5220
tgggctggag gactgcatga atgcctcatg atcttcccag aggcaaaggc acctactgcc 5280
ttccaaggtc agtgggaggt tgggatcaac actgtttatt atgcttagga caaaaaagat 5340
agggagaaag atgtgcaacc ttacaggtca tctttctggg atagaacaca atgggtcttc 5400
tcctgcctcc tggatatgtt agtcaaggcc agtccatgct acacatctag tctgacttct 5460
aaaatagaag caccagatga attcagccct gagagaattt tcagcagctg tgggggcgct 5520
ggaggaaaca ctattaaata gttttgcacc tgagacagat agcctcactc gcctcaccct 5580
agtcctggtg gcatttgtct caggtgcaaa atttaagaaa gaaaccttgg agtgctcacc 5640
ctgtggctgg gtagatggtc ctaaagtggt ggttttcaag cctgagtgtg tatcaggatc 5700
atcaggggag cttgctaaag agcagttcct gcggtcagac cctcatgcat tttgagcagg 5760
tgtggggact gggaaactgc atctgtaacc tgctgtaatc taacgcttat ctaaatacta 5820
ctgtgctcac acagagaaca ccgcaaaagt agaggtgttc ctccagaggg caggtgagca 5880
gatggcacag tctgcttgga attcagtcag gtgatgagag atgagatgag gcactcctag 5940
ctttgggaag agggagctga aagatgaacc tttgcaggtg cccacggtca aagtggtggt 6000
ttaatgccat gccatgccca ttttctgttg gccttggcag ggagttacag ccctacctta 6060
ggacctggct ccttatttct gctgtaggct ctttcctgcc ctggccgaga tggagtggaa 6120
tgagacctag aaacatcaag ctaaatacat gtcctcagaa agataaaggt ttacattttc 6180
acccccatca aatctgaaag ctctctgcct gtgtttttct aagggatagg gacatcatta 6240
ctcagtccac aacctggact catgtagggt cccctgtcag taaaggagtc agtcaagccc 6300
accaggtata ccaaggactc ttaccctcag cccctactcc ttggaaagct gccccttggc 6360
ctaatattgg tgtttagctt gagcctgact ccttctcaac actaagagct gatgaagtcc 6420
tgaagcagaa agagctctga cctgagagtc aaacatcctt attctgatct cagctcagcc 6480
cctgatttgt tgtgtgaccc tggatatgtc acttcctgtc tttttgactt tttaaaatga 6540
agggtagact agaggagagc ttctaaaact ttaatgtggt caacgaaatg gaataggaaa 6600
ttccacaagt ctgtccttcc acaaaagcag caaataaggt ggcaaaaact caaatttatg 6660
ggaactctgg aaacgaattg aaagtttaca gcaatcaggt gaatacctaa gaataaaagc 6720
tggatttagt aaga 6734

<210> SEQ ID NO 33
<211> LENGTH: 2804
<212> TYPE: DNA
<213> ORGANISM: Homo sapiens
<220> FEATURE:
<221> NAME/KEY: misc_feature
<223> OTHER INFORMATION: NM_001278409.1 Homo sapiens annexin A11
(ANXA11), transcript variant f, mRNA

<400> SEQUENCE: 33
gcactgcctc tggcacctgg ggcagccgcg cccgcggagt tttccgcccg gcgctgacgg 60
ctgctgcgcc cgcggctccc cagtgccccg agtgccccgc gggccccgcg agcgggagtg 120
ggacccagcc cctaggcaga acccaggcgc cgcgcccggg acgcccgcgg agagagccac 180
tcccgcccac gtcccatttc gcccctcgcg tccggagtcc ccgtggccag gtgtgtgtct 240

```
ggggaagaga cttacagaag tggagttgct gagtcaaaga tctaaccatg agctaccctg    300
gctatccccc gcccccaggt ggctacccac cagctgcacc aggttggctg gcactggcct    360
gggttctctc tctatagtag aaatcctgcc atccagatcc tgccactgcc acctttgcta    420
gcacagctga gcagcctctg agcagcaaga gaggaggagg caggaaattt agggaaggtt    480
cttcctggag ggtctggagc cctggagatg aagagccgat ccgaagctgc catgtagagg    540
aaagcatcta acaggccaga ggccccatga tgatgtcgaa tgcccatcgg gcacccagct    600
gagccctgca ggtggtggtc cctggggagg tgctgcctac cctcctccgc ccagcatgcc    660
ccccatcggg ctggataacg tggccaccta tgcggggcag ttcaaccagg actatctctc    720
gggaatggcg gccaacatgt ctgggacatt tggaggagcc aacatgccca acctgtaccc    780
tggggcccct ggggctggct acccaccagt gccccctggc ggctttgggc agccccccctc    840
tgcccagcag cctgttcctc cctatgggat gtatccaccc ccaggaggaa acccaccctc    900
caggatgccc tcatatccgc catacccagg ggcccctgtg ccgggccagc ccatgccacc    960
ccccggacag cagcccccag gggcctaccc tgggcagcca ccagtgacct accctggtca   1020
gcctccagtg ccactccctg ggcagcagca gccagtgccg agctacccag gatacccggg   1080
gtctgggact gtcacccccg ctgtgccccc aacccagttt ggaagccgag gcaccatcac   1140
tgatgctccc ggctttgacc ccctgcgaga tgccgaggtc ctgcggaagg ccatgaaagg   1200
cttcgggacg gatgagcagg ccatcattga ctgcctgggg agtcgctcca acaagcagcg   1260
gcagcagatc ctactttcct tcaagacggc ttacggcaag gatttgatca aagatctgaa   1320
atctgaactg tcaggaaact ttgagaagac aatcttggct ctgatgaaga ccccagtcct   1380
ctttgacatt tatgagataa aggaagccat caagggggtt ggcactgatg aagcctgcct   1440
gattgagatc ctcgcttccc gcagcaatga gcacatccga gaattaaaca gagcctacaa   1500
agcagaattc aaaaagaccc tggaagaggc cattcgaagc gacacatcag ggcacttcca   1560
gcggctcctc atctctctct ctcagggaaa ccgtgatgaa agcacaaacg tggacatgtc   1620
actcgcccag agagatgccc aggagctgta tgcggccggg gagaaccgcc tgggaacaga   1680
cgagtccaag ttcaatgcgg ttctgtgctc ccggagccgg gcccacctgg tagcagtttt   1740
caatgagtac cagagaatga caggccggga cattgagaag agcatctgcc gggagatgtc   1800
cggggacctg gaggagggca tgctggccgt ggtgaaatgt ctcaagaata ccccagcctt   1860
ctttgcggag aggctcaaca aggccatgag gggggcagga acaaaggacc ggaccctgat   1920
tcgcatcatg gtgtctcgca gcgagaccga cctcctggac atcagatcag agtataagcg   1980
gatgtacggc aagtcgctgt accacgacat ctcgggagat acttcagggg attaccggaa   2040
gattctgctg aagatctgtg gtggcaatga ctgaacagtg actggtggct cacttctgcc   2100
cacctgccgg caacaccagt gccaggaaaa ggccaaaaga atgtctgttt ctaacaaatc   2160
cacaaatagc cccgagattc accgtcctag agcttaggcc tgtcttccac ccctcctgac   2220
ccgtatagtg tgccacagga cctgggtcgg tctagaactc tctcaggatg ccttttctac   2280
cccatccctc acagcctctt gctgctaaaa tagatgtttc atttttctga ctcatgcaat   2340
cattcccctt tgcctgtggc taagacttgg cttcatttcg tcatgtaatt gtatattttt   2400
atttggaggc atattttctt ttcttacagt cattgccaga cagaggcata caagtctgtt   2460
tgctgcatac acatttctgg tgagggcgac tgggtgggtg aagcaccgtg tcctcgctga   2520
ggagagaaag ggaggcgtgc ctgagaaggt agcctgtgca tctggtgagt gtgtcacgag   2580
ctttgttact gccaaactca ctccttttta gaaaaaacaa aaaaaaaggg ccagaaagtc   2640
```

attccttcca tcttccttgc agaaaccacg agaacaaagc cagttccctg tcagtgacag 2700
ggcttcttgt aatttgtggt atgtgcctta aacctgaatg tctgtagcca aaacttgttt 2760
ccacattaag agtcagccag ctctggaatg gtctggaaat gtca 2804

<210> SEQ ID NO 34
<211> LENGTH: 1456
<212> TYPE: DNA
<213> ORGANISM: Homo sapiens
<220> FEATURE:
<221> NAME/KEY: misc_feature
<223> OTHER INFORMATION: NM_004306.4 Homo sapiens annexin A13 (ANXA13), transcript variant 1, mRNA

<400> SEQUENCE: 34
gcctgtagga ggactgatct cttgatgaaa tacagaaaaa ccatctcaga aaaaggaaaa 60
tgggcaatcg tcatgctaaa gcgagcagtc ctcagggttt tgatgtggat cgagatgcca 120
aaaagctgaa caaagcctgc aaaggaatgg ggaccaatga agcagccatc attgaaatct 180
tatcgggcag gacatcagat gagaggcaac aaatcaagca aaagtacaag gcaacgtacg 240
gcaaggagct ggaggaagta ctcaagagtg agctgagtgg aaacttcgag aagacagcgt 300
tggcccttct ggaccgtccc agcgagtacg ccgcccggca gctgcagaag gctatgaagg 360
gtctgggcac agatgagtcc gtcctcattg aggtcctgtg cacgaggacc aataaggaaa 420
tcatcgccat taaagaggcc taccaaaggc tatttgatag gagcctcgaa tcagatgtca 480
aaggtgatac aagtggaaac ctaaaaaaaa tcctggtgtc tctgctgcag gctaatcgca 540
atgaaggaga tgacgtggac aaagatctag ctggtcagga tgccaaagat ctgtatgatg 600
caggggaagg ccgctggggc actgatgagc ttgcgttcaa tgaagtcctg gccaagagga 660
gctacaagca gttacgagcc acctttcaag cctatcaaat tctcattggc aaagacatag 720
aagaagccat tgaagaagaa acatcaggcg acttgcagaa ggcctattta actctcgtga 780
gatgtgccca ggattgtgag gactattttg ctgaacgtct gtacaagtcg atgaagggtg 840
cggggaccga tgaggagacg ttgattcgca tagtcgtgac cagggccgag gtggaccttc 900
aggggatcaa agcaaagttc caagagaagt atcagaagtc tctctctgac atggttcgct 960
cagatacctc cggggacttc cggaaactgc tagtagccct cttgcactga gccaagccag 1020
ggcaatagga acacagggtg gaaccgcctt tgtcaagagc acattccaaa tcaaacttgc 1080
aaatgagact cccgcacgaa aacccttaag agtcccggat tactttcttg gcagcttaag 1140
tggcgcagcc aggccaagct gtgtaagtta agggcagtaa cgttaagatg cgtgggcagg 1200
gcaccttgaa ctctggctta gcaagcatct aggctgcctc ttcactttct tttagcatgg 1260
taactggatg ttttctaaac actaatgaaa tcagcagttg atgaaaaaac tatgcatttg 1320
taatggcaca tttagaagga tatgcatcac acaagtaagg tacaggaaag acaaaattaa 1380
acaatttatt aattttcctt ctgtgtgttc aatttgaaag cctcattgtt aattaaagtt 1440
gtggattatg cctcta 1456

<210> SEQ ID NO 35
<211> LENGTH: 1633
<212> TYPE: DNA
<213> ORGANISM: Homo sapiens
<220> FEATURE:
<221> NAME/KEY: misc_feature
<223> OTHER INFORMATION: NM_001003954.2 Homo sapiens annexin A13 (ANXA13), transcript variant 2, mRNA

<400> SEQUENCE: 35
attatgtccg gggggaaaac tgttgtaaac tttgcctgta ggaggactga tctcttaatg 60
aaatacagaa aaaccatctc agaaaaagga aaatgggcaa tcgtcatagc cagtcgtaca 120
ccctctcaga aggcagtcaa cagttgccta aaggggactc ccaaccctcg acagtcgtgc 180
agcctctcag ccacccatca cggaatggag agccagaggc cccacagcct gctaaagcga 240
gcagtcctca gggttttgat gtggatcgag atgccaaaaa gctgaacaaa gcctgcaaag 300
gaatggggac caatgaagca gccatcattg aaatcttatc gggcaggaca tcagatgaga 360
ggcaacaaat caagcaaaag tacaaggcaa cgtacggcaa ggagctggag gaagtactca 420
agagtgagct gagtggaaac ttcgagaaga cagcgttggc ccttctggac cgtcccagcg 480
agtacgccgc ccggcagctg cagaaggcta tgaagggtct gggcacagat gagtccgtcc 540
tcattgaggt cctgtgcacg aggaccaata aggaaatcat cgccattaaa gaggcctacc 600
aaaggctatt tgataggagc ctcgaatcag atgtcaaagg tgatacaagt ggaaacctaa 660
aaaaaatcct ggtgtctctg ctgcaggcta atcgcaatga aggagatgac gtggacaaag 720
atctagctgg tcaggatgcc aaagatctgt atgatgcagg ggaaggccgc tggggcactg 780
atgagcttgc gttcaatgaa gtcctggcca agaggagcta caagcagtta cgagccacct 840
ttcaagccta tcaaattctc attggcaaag acatagaaga agccattgaa gaagaaacat 900
caggcgactt gcagaaggcc tatttaactc tcgtgagatg tgcccaggat tgtgaggact 960
attttgctga acgtctgtac aagtcgatga agggtgcggg gaccgatgag gagacgttga 1020
ttcgcatagt cgtgaccagg gccgaggtgg accttcaggg gatcaaagca aagttccaag 1080
agaagtatca gaagtctctc tctgacatgg ttcgctcaga tacctccggg gacttccgga 1140
aactgctagt agccctcttg cactgagcca agccagggca ataggaacac agggtggaac 1200
cgcctttgtc aagagcacat tccaaatcaa acttgcaaat gagactcccg cacgaaaacc 1260
cttaagagtc ccggattact ttcttggcag cttaagtggc gcagccaggc caagctgtgt 1320
aagttaaggg cagtaacgtt aagatgcgtg ggcagggcac cttgaactct ggcttagcaa 1380
gcatctaggc tgcctcttca ctttctttta gcatggtaac tggatgtttt ctaaacacta 1440
atgaaatcag cagttgatga aaaaactatg catttgtaat ggcacattta gaaggatatg 1500
catcacacaa gtaaggtaca ggaaagacaa aattaaacaa tttattaatt ttccttctgt 1560
gtgttcaatt tgaaagcctc attgttaatt aaagttgtgg attatgcctc taaaaaaaaa 1620
aaaaaaaaaa aaa 1633

<210> SEQ ID NO 36
<211> LENGTH: 1665
<212> TYPE: DNA
<213> ORGANISM: Homo sapiens
<220> FEATURE:
<221> NAME/KEY: misc_feature
<223> OTHER INFORMATION: NM_001136015.2 Homo sapiens annexin A2 (ANXA2), transcript variant 4, mRNA

<400> SEQUENCE: 36
gctcagcatt tggggacgct ctcagctctc ggcgcacggc ccagggtgaa aatgtttgcc 60
attaaactca catgaagtag gaaatattta tatggataca aaaggcacct gcatgggata 120
atgtcaaatt tcatagatac tgctttgtgc ttccttcaaa atgtctactg ttcacgaaat 180
cctgtgcaag ctcagcttgg agggtgatca ctctacaccc ccaagtgcat atgggtctgt 240
caaagcctat actaactttg atgctgagcg ggatgctttg aacattgaaa cagccatcaa 300
gaccaaaggt gtggatgagg tcaccattgt caacattttg accaaccgca gcaatgcaca 360
gagacaggat attgccttcg cctaccagag aaggaccaaa aaggaacttg catcagcact 420
gaagtcagcc ttatctggcc acctggagac ggtgattttg ggcctattga agacacctgc 480
tcagtatgac gcttctgagc taaaagcttc catgaagggg ctgggaaccg acgaggactc 540
tctcattgag atcatctgct ccagaaccaa ccaggagctg caggaaatta acagagtcta 600
caaggaaatg tacaagactg atctggagaa ggacattatt tcggacacat ctggtgactt 660
ccgcaagctg atggttgccc tggcaaaggg tagaagagca gaggatggct ctgtcattga 720
ttatgaactg attgaccaag atgctcggga tctctatgac gctggagtga agaggaaagg 780
aactgatgtt cccaagtgga tcagcatcat gaccgagcgg agcgtgcccc acctccagaa 840
agtatttgat aggtacaaga gttacagccc ttatgacatg ttggaaagca tcaggaaaga 900
ggttaaagga gacctggaaa atgctttcct gaacctggtt cagtgcattc agaacaagcc 960
cctgtatttt gctgatcggc tgtatgactc catgaagggc aaggggacgc gagataaggt 1020
cctgatcaga atcatggtct cccgcagtga agtggacatg ttgaaaatta ggtctgaatt 1080
caagagaaag tacggcaagt ccctgtacta ttatatccag caagacacta agggcgacta 1140
ccagaaagcg ctgctgtacc tgtgtggtgg agatgactga agcccgacac ggcctgagcg 1200
tccagaaatg gtgctcacca tgcttccagc taacaggtct agaaaaccag cttgcgaata 1260
acagtccccg tggccatccc tgtgagggtg acgttagcat tacccccaac ctcattttag 1320
ttgcctaagc attgcctggc cttcctgtct agtctctcct gtaagccaaa gaaatgaaca 1380
ttccaaggag ttggaagtga agtctatgat gtgaaacact ttgcctcctg tgtactgtgt 1440
cataaacaga tgaataaact gaatttgtac tttagaaaca cgtactttgt ggccctgctt 1500
tcaactgaat tgtttgaaaa ttaaacgtgc ttggggttca gctggtgagg ctgtccctgt 1560
aggaagaaag ctctgggact gagctgtaca gtatggttgc cctatccaa gtgtcgctat 1620 ttaagttaaa tttaaatgaa ataaaataaa ataaaatcaa aaaaa 1665

<210> SEQ ID NO 37
<211> LENGTH: 1395
<212> TYPE: DNA
<213> ORGANISM: Mus Musculus

<400> SEQUENCE: 37
gtctgaaacc atctgagcag agtctctctt cagtccccgg gaagacaagc aaatacaaag 60
atacttctct aaaaatggca atggtatcag aattcctcaa gcaggcccgt tttcttgaaa 120
atcaagaaca ggaatatgtt caagctgtaa aatcatacaa aggtggtcct gggtcagcag 180
tgagccccta cccttccttc aatgtatcct cggatgttgc tgccttgcac aaagctatca 240
tggttaaagg tgtggatgaa gcaaccatca ttgacattct taccaagagg accaatgctc 300
agcgccagca gatcaaggcc gcgtacttac aggagaatgg aaagcccttg gatgaagtct 360
tgagaaaagc ccttacaggc cacctggagg aggttgtttt ggctatgcta aaaactccag 420
ctcagtttga tgcagatgaa ctccgtggtg ccatgaaggg acttggaaca gatgaagaca 480
ctctcattga gattttgaca acaagatcta acgaacaaat cagagagatt aatagagtct 540
acagagaaga gctgaaaaga gatctggcca aagacatcac ttcagataca tctggagact 600
ttcggaaagc cttgcttgct cttgccaagg gtgaccgttg tcaggacttg agtgtgaatc 660
aagatttggc tgatacagat gccagggctt tgtatgaagc tggagaaagg agaaagggga 720
cagacgtgaa cgtcttcacc acaattctga ccagcaggag ctttcctcat cttcgcagag 780
tgtttcagaa ttacggaaag tacagtcaac atgacatgaa caaagctctg gatctggaac 840
tgaagggtga cattgagaag tgcctcacaa ccatcgtgaa gtgtgccacc agcactccag 900
ctttctttgc cgagaagctg tacgaagcca tgaagggtgc cggaactcgc cataaggcat 960
tgatcaggat tatggtctcc cgttcggaaa ttgacatgaa tgaaatcaaa gtattttacc 1020
agaagaagta tggaatctct ctttgccaag ccatcctgga tgaaaccaaa ggagactatg 1080
aaaaaatcct ggtggctctg tgtggtggaa actagacatc ccaactattc tgcaaggttc 1140
tgaggagaat gtctcttagc tgttttcctt cgatggcatg ggcttaagta ggaaagttgc 1200
tttggcagat aagtctaatt acctgctttg aataatatag cctataaata gattttacat 1260
cattactctg tacaatagag aaatacttgt tttgttaatt atgtttatcc caaattataa 1320
agccccataa gcaagtcact ttggtaccat tcctgagaaa gaagtttaca tataataaaa 1380
taaaacaatt ttata 1395

<210> SEQ ID NO 38
<211> LENGTH: 1374
<212> TYPE: DNA
<213> ORGANISM: Mus Musculus

<400> SEQUENCE: 38
gcccagccgg gctgctccgc ttcaagggag gctctcagcg atacgtgccc ggcccagctt 60
ttttttcttt caaaatgtct actgtccacg aaatcctgtg caagctcagc ctggagggtg 120
atcattctac acccccaagt gcctacgggt cagtcaaacc ctacaccaac ttcgatgctg 180
agagggatgc tctgaacatt gagacagcag tcaagaccaa aggagtggat gaggtcacca 240
ttgtcaacat cctgacaaac cgcagcaatg tgcagaggca ggacattgcc ttcgcctatc 300
agagaaggac caaaaaggag ctcccgtcag cgctgaagtc agccttatct ggccacctgg 360
agacggtgat tttgggccta ttgaagacac ctgcccagta tgatgcttcg gaactaaaag 420
cttccatgaa gggcctgggg actgacgagg actccctcat tgagatcatc tgctcacgaa 480
ccaaccagga gctgcaagag atcaacagag tgtacaagga aatgtacaag actgatctgg 540
agaaggacat catctctgac acatctggag acttccgaaa gctgatggtc gcccttgcaa 600
agggcagacg agcagaggat ggctcagtta ttgactacga gctgattgac caggatgccc 660
gggagctcta tgatgccggg gtgaagagga aaggaaccga cgtccccaag tggatcagca 720
tcatgactga gcgcagtgtg tgccacctcc agaaagtgtt cgaaaggtac aagagctaca 780
gcccttatga catgctggag agcatcaaga aagaggtcaa aggggacctg gagaacgcct 840
tcctgaacct ggtccagtgc atccagaaca agcccctgta cttcgctgac cggctgtacg 900
actccatgaa gggcaagggg actcgagaca aggtcctgat tagaatcatg gtctctcgca 960
gtgaagtgga catgctgaaa atcagatctg aattcaagag gaaatatggc aagtccctgt 1020
actactacat ccagcaagac accaagggtg actaccagaa ggcactgctg tacctgtgtg 1080
gtggggatga ctgaagggct cagcacagtg gatcacccag aagtggctct acctgtgccc 1140
caacctggcg ttctagagac ttcgctctcc actaatggac ccctgagctc ctccctgtga 1200
ggatgatgac agggctgccg accctttccc catcttagct gcccttgcct ggctttctcc 1260
tcattctctc ctttatgcca aagaagtgaa cattccaggg agtggggcgt agcgtctgtg 1320
acatgagaca cttcctctta tgtactgtgt cgtgaataaa ccgtttttac ttta 1374

<210> SEQ ID NO 39
<211> LENGTH: 2670
<212> TYPE: DNA
<213> ORGANISM: Mus Musculus

<400> SEQUENCE: 39
gcgccacgtg tccccctcca ccgtgcgccc agcctgcgct gcggctgctg ctaggctaac 60
gggcttcgag ctgcgtctgt ccatacgccc tgatctgagg cctccctagc gcgtggtttc 120
tgctgcagaa cctgagacca tggccaaaat agcacagggt gccatgtacc gaggctctgt 180
ccacgacttc ccagagtttg acgcaaatca ggatgctgag gccttgtaca cagccatgaa 240
gggcttcggc agtgacaagg agtccatact ggagctgatc acctcccgca gcaacaagca 300
gaggcaggag atctgccaga attacaagtc cctgtatggc aaggacctca tcgaagactt 360
gaagtatgag ttgacgggga agttcgagcg gctgatagtg aacctgatga ggccacttgc 420
ctattgtgac gccaaagaga ttaaagacgc catctcgggc gttggcacag atgagaagtg 480
ccttattgaa attttggctt cccggaccaa tgagcagatg caccagctgg tggccgcata 540
caaagacgcc tatgagcgag acctggaatc tgacatcatt ggagacactt ccggccactt 600
ccagaagatg ctggtggtac tgctccaggg aacccgggag aatgacgatg ttgtgagcga 660
ggatttggtc cagcaggatg tccaggacct gtatgaggca ggggaactga aatggggaac 720
agatgaggcc cagttcatct acatcttggg aaaccgcagc aaacagcacc tacgactggt 780
gtttgatgag tatctgaaga ccacagggaa gcccatcgaa gccagtatca gaggggagct 840
gtctggagac tttgagaagc tgatgttggc cgtggtgaag tgcatccgaa gcaccccgga 900
gtattttgcg gaaaggctgt tcaaagccat gaagggccta gggacccgag acaacactct 960
gatccgcatc atggtctcca ggagcgagct ggatatgctt gacatccggg agatcttccg 1020
gaccaagtat gagaagtcac tctacagcat gatcaagaat gatacttccg gtgaatacaa 1080
gaaggctctg ctgaagctgt gtggaggaga tgatgatgcc gctggccagt tcttcccgga 1140
ggcagcacag gtggcctatc agatgtggga acttagtgca gtgtcccgag tcgagctgaa 1200
gggtactgtg tgtgcagcca atgatttcaa ccctgacgct gatgccaagg ccctgcggaa 1260
agccatgaag ggaattggaa ctgatgaagc caccatcatc gacatcgtca cccaccggag 1320
caacgcccag cggcagcaga tccggcagac cttcaaatct cactttggcc gggatttaat 1380
ggctgacctg aagtcagaga tctcgggaga cctggcaagg ctgattctgg ggctcatgat 1440
gccacctgcc cattacgatg ctaagcagct gaagaaagct atggagggag ccggcacaga 1500
tgaaaagact ctcatagaaa tcctggccac ccggaccaat gctgaaatcc gggccatcaa 1560
cgaggcctac aaggaggatt atcacaagtc cctggaggat gccttgagct cagacacatc 1620
tggccacttc agaaggattc tcatttctct ggccacagga aatcgagagg aaggaggaga 1680
aaaccgggac caggcccagg aagatgccca ggtggctgct gagatcttgg aaatagcaga 1740
cacccccagc ggagacaaaa cttccttgga gacacgcttc atgaccgtcc tgtgcacccg 1800
tagctatccc cacctgcgca gagtcttcca ggagttcatc aagaagacca actatgacat 1860
agagcatgtc atcaagaagg agatgtctgg ggatgtcaag gacgcatttg tggccatcgt 1920
tcagagtgtc aagaacaagc ctctcttctt tgctgataaa ctgtacaagt ccatgaaggg 1980
tgctggcaca gatgagaaga ccctcaccag ggtgatggtg tctcggagtg agatagatct 2040
gctcaacatc cggagggaat tcattgagaa atatgacaag tctctacacc aagccattga 2100
gggtgacacc tctggagact tcatgaaggc tttgcttgct ctgtgtggcg gagaggacta 2160
aagctcctga cctcagaggg ccccctctac caagcagtgg ccaactgcac cagctgccgc 2220
cgtgacctga ccaagccatt gctccagctt caggatctaa ggaagacgca aggggtgggg 2280
ttggactgtc catccagctg gggcactctc tagccattga gggtcccagg cggtcccttc 2340
tgttatccct cccgctcatg gctaaggggc tggtgaacca cggccatata ctgcattcaa 2400
ctctgatccc cttctaccta ctcctccgcc cgccctggtt tccatccctc cacataaccc 2460
tgcctgactt gagctttgtc acatctcaag acataccaaa cctctgtcta tgaaatgagt 2520
gatgtgtgtg ctttaaaggg cgggctgtgg tgcctggtgc caggcaagca ttctgggata 2580
atagagatga cagattaatt tgactgacgg gtgatcatcc ccggctgtca ccgtccaatc 2640
tgataaaagt accaagctag gaatttccac 2670

<210> SEQ ID NO 40
<211> LENGTH: 673
<212> TYPE: PRT
<213> ORGANISM: Homo Sapiens

<400> SEQUENCE: 40

Met Ala Lys Pro Ala Gln Gly Ala Lys Tyr Arg Gly Ser Ile His Asp
1 5 10 15

Phe Pro Gly Phe Asp Pro Asn Gln Asp Ala Glu Ala Leu Tyr Thr Ala
20 25 30

Met Lys Gly Phe Gly Ser Asp Lys Glu Ala Ile Leu Asp Ile Ile Thr
35 40 45

Ser Arg Ser Asn Arg Gln Arg Gln Glu Val Cys Gln Ser Tyr Lys Ser
50 55 60

Leu Tyr Gly Lys Asp Leu Ile Ala Asp Leu Lys Tyr Glu Leu Thr Gly
65 70 75 80

Lys Phe Glu Arg Leu Ile Val Gly Leu Met Arg Pro Pro Ala Tyr Cys
85 90 95

Asp Ala Lys Glu Ile Lys Asp Ala Ile Ser Gly Ile Gly Thr Asp Glu
100 105 110

Lys Cys Leu Ile Glu Ile Leu Ala Ser Arg Thr Asn Glu Gln Met His
115 120 125

Gln Leu Val Ala Ala Tyr Lys Asp Ala Tyr Glu Arg Asp Leu Glu Ala
130 135 140

Asp Ile Ile Gly Asp Thr Ser Gly His Phe Gln Lys Met Leu Val Val
145 150 155 160

Leu Leu Gln Gly Thr Arg Glu Glu Asp Asp Val Val Ser Glu Asp Leu
165 170 175

Val Gln Gln Asp Val Gln Asp Leu Tyr Glu Ala Gly Glu Leu Lys Trp
180 185 190

Gly Thr Asp Glu Ala Gln Phe Ile Tyr Ile Leu Gly Asn Arg Ser Lys
195 200 205

Gln His Leu Arg Leu Val Phe Asp Glu Tyr Leu Lys Thr Thr Gly Lys
210 215 220

Pro Ile Glu Ala Ser Ile Arg Gly Glu Leu Ser Gly Asp Phe Glu Lys
225 230 235 240

Leu Met Leu Ala Val Val Lys Cys Ile Arg Ser Thr Pro Glu Tyr Phe
245 250 255

Ala Glu Arg Leu Phe Lys Ala Met Lys Gly Leu Gly Thr Arg Asp Asn
260 265 270

Thr Leu Ile Arg Ile Met Val Ser Arg Ser Glu Leu Asp Met Leu Asp
275 280 285

Ile Arg Glu Ile Phe Arg Thr Lys Tyr Glu Lys Ser Leu Tyr Ser Met
    290                 295                 300

Ile Lys Asn Asp Thr Ser Gly Glu Tyr Lys Lys Thr Leu Leu Lys Leu
305                 310                 315                 320

Ser Gly Gly Asp Asp Asp Ala Ala Gly Gln Phe Phe Pro Glu Ala Ala
                325                 330                 335

Gln Val Ala Tyr Gln Met Trp Glu Leu Ser Ala Val Ala Arg Val Glu
            340                 345                 350

Leu Lys Gly Thr Val Arg Pro Ala Asn Asp Phe Asn Pro Asp Ala Asp
        355                 360                 365

Ala Lys Ala Leu Arg Lys Ala Met Lys Gly Leu Gly Thr Asp Glu Asp
    370                 375                 380

Thr Ile Ile Asp Ile Ile Thr His Arg Ser Asn Val Gln Arg Gln Gln
385                 390                 395                 400

Ile Arg Gln Thr Phe Lys Ser His Phe Gly Arg Asp Leu Met Thr Asp
                405                 410                 415

Leu Lys Ser Glu Ile Ser Gly Asp Leu Ala Arg Leu Ile Leu Gly Leu
            420                 425                 430

Met Met Pro Pro Ala His Tyr Asp Ala Lys Gln Leu Lys Lys Ala Met
        435                 440                 445

Glu Gly Ala Gly Thr Asp Glu Lys Ala Leu Ile Glu Ile Leu Ala Thr
    450                 455                 460

Arg Thr Asn Ala Glu Ile Arg Ala Ile Asn Glu Ala Tyr Lys Glu Asp
465                 470                 475                 480

Tyr His Lys Ser Leu Glu Asp Ala Leu Ser Ser Asp Thr Ser Gly His
                485                 490                 495

Phe Arg Arg Ile Leu Ile Ser Leu Ala Thr Gly His Arg Glu Glu Gly
            500                 505                 510

Gly Glu Asn Leu Asp Gln Ala Arg Glu Asp Ala Gln Val Ala Ala Glu
        515                 520                 525

Ile Leu Glu Ile Ala Asp Thr Pro Ser Gly Asp Lys Thr Ser Leu Glu
    530                 535                 540

Thr Arg Phe Met Thr Ile Leu Cys Thr Arg Ser Tyr Pro His Leu Arg
545                 550                 555                 560

Arg Val Phe Gln Glu Phe Ile Lys Met Thr Asn Tyr Asp Val Glu His
                565                 570                 575

Thr Ile Lys Lys Glu Met Ser Gly Asp Val Arg Asp Ala Phe Val Ala
            580                 585                 590

Ile Val Gln Ser Val Lys Asn Lys Pro Leu Phe Phe Ala Asp Lys Leu
        595                 600                 605

Tyr Lys Ser Met Lys Gly Ala Gly Thr Asp Glu Lys Thr Leu Thr Arg
    610                 615                 620

Ile Met Val Ser Arg Ser Glu Ile Asp Leu Leu Asn Ile Arg Arg Glu
625                 630                 635                 640

Phe Ile Glu Lys Tyr Asp Lys Ser Leu His Gln Ala Ile Glu Gly Asp
                645                 650                 655

Thr Ser Gly Asp Phe Leu Lys Ala Leu Leu Ala Leu Cys Gly Gly Glu
            660                 665                 670

Asp

<210> SEQ ID NO 41
<211> LENGTH: 673
<212> TYPE: PRT

<213> ORGANISM: Macaca mulatta

<400> SEQUENCE: 41

```
Met Ala Lys Pro Ala Gln Gly Ala Lys Tyr Arg Gly Ser Ile His Asp
1               5                   10                  15

Phe Pro Gly Phe Asp Pro Asn Gln Asp Ala Glu Ala Leu Tyr Thr Ala
            20                  25                  30

Met Lys Gly Phe Gly Ser Asp Lys Glu Ala Ile Leu Asp Ile Ile Thr
        35                  40                  45

Ser Arg Ser Asn Arg Gln Arg Gln Glu Ile Cys Gln Ser Tyr Lys Ser
    50                  55                  60

Leu Tyr Gly Lys Asp Leu Ile Ala Asp Leu Lys Tyr Glu Leu Thr Gly
65                  70                  75                  80

Lys Phe Glu Arg Leu Ile Val Gly Leu Met Arg Pro Pro Ala Tyr Cys
                85                  90                  95

Asp Ala Lys Glu Ile Lys Asp Ala Ile Ser Gly Ile Gly Thr Asp Glu
            100                 105                 110

Lys Cys Leu Ile Glu Ile Leu Ala Ser Arg Thr Asn Glu Gln Met His
        115                 120                 125

Gln Leu Val Ala Ala Tyr Lys Asp Ala Tyr Glu Arg Asp Leu Glu Ala
    130                 135                 140

Asp Ile Ile Gly Asp Thr Ser Gly His Phe Gln Lys Met Leu Val Val
145                 150                 155                 160

Leu Leu Gln Gly Thr Arg Glu Glu Asp Asp Val Val Ser Glu Asp Leu
                165                 170                 175

Val Gln Gln Asp Val Gln Asp Leu Tyr Glu Ala Gly Glu Leu Lys Trp
            180                 185                 190

Gly Thr Asp Glu Ala Gln Phe Ile Tyr Ile Leu Gly Asn Arg Ser Lys
        195                 200                 205

Gln His Leu Arg Leu Val Phe Asp Glu Tyr Leu Lys Thr Thr Gly Lys
    210                 215                 220

Pro Ile Glu Ala Ser Ile Arg Gly Glu Leu Ser Gly Asp Phe Glu Lys
225                 230                 235                 240

Leu Met Leu Ala Val Val Lys Cys Ile Arg Ser Thr Pro Glu Tyr Phe
                245                 250                 255

Ala Glu Arg Leu Phe Lys Ala Met Lys Gly Leu Gly Thr Arg Asp Asn
            260                 265                 270

Thr Leu Ile Arg Ile Met Val Ser Arg Ser Glu Leu Asp Met Leu Asp
        275                 280                 285

Ile Arg Glu Ile Phe Arg Thr Lys Tyr Glu Lys Ser Leu Tyr Ser Met
    290                 295                 300

Ile Lys Asn Asp Thr Ser Gly Glu Tyr Lys Lys Ser Leu Leu Lys Leu
305                 310                 315                 320

Cys Gly Gly Asp Asp Asp Ala Ala Gly Gln Phe Phe Pro Glu Ala Ala
                325                 330                 335

Gln Val Ala Tyr Gln Met Trp Glu Leu Ser Ala Val Ala Arg Val Glu
            340                 345                 350

Leu Lys Gly Thr Val Arg Pro Ala Asn Asp Phe Asn Pro Asp Ala Asp
        355                 360                 365

Ala Lys Ala Leu Arg Lys Ala Met Lys Gly Leu Gly Thr Asp Glu Asp
    370                 375                 380

Thr Ile Ile Asp Ile Ile Thr His Arg Ser Asn Ala Gln Arg Gln Gln
385                 390                 395                 400
```

```
Ile Arg Gln Thr Phe Lys Ser His Phe Gly Arg Asp Leu Met Ser Asp
                405                 410                 415

Leu Lys Ser Glu Ile Ser Gly Asp Leu Ala Arg Leu Ile Leu Gly Leu
            420                 425                 430

Met Met Pro Pro Ala His Tyr Asp Ala Lys Gln Leu Lys Lys Ala Met
        435                 440                 445

Glu Gly Ala Gly Thr Asp Glu Lys Ala Leu Ile Glu Ile Leu Ala Thr
    450                 455                 460

Arg Thr Asn Ala Glu Ile Arg Ala Ile Asn Glu Ala Tyr Lys Glu Asp
465                 470                 475                 480

Tyr His Lys Ser Leu Glu Asp Ala Leu Ser Ser Asp Thr Ser Gly His
                485                 490                 495

Phe Arg Arg Ile Leu Ile Ser Leu Ala Thr Gly Asn Arg Glu Glu Gly
            500                 505                 510

Gly Glu Asn Leu Asp Gln Ala Arg Glu Asp Ala Gln Val Ala Ala Glu
        515                 520                 525

Ile Leu Glu Ile Ala Asp Thr Pro Ser Gly Asp Lys Ala Ser Leu Glu
    530                 535                 540

Thr Arg Phe Met Thr Ile Leu Cys Thr Arg Ser Tyr Pro His Leu Arg
545                 550                 555                 560

Arg Val Phe Gln Glu Phe Ile Lys Met Thr Asn Tyr Asp Val Glu His
                565                 570                 575

Thr Ile Lys Lys Glu Met Ser Gly Asp Val Arg Asp Ala Phe Val Ala
            580                 585                 590

Ile Val Gln Ser Val Lys Asn Lys Pro Leu Phe Phe Ala Asp Lys Leu
        595                 600                 605

Tyr Lys Ser Met Lys Gly Ala Gly Thr Asp Glu Lys Thr Leu Thr Arg
    610                 615                 620

Ile Met Val Ser Arg Ser Glu Ile Asp Leu Leu Asn Ile Arg Arg Glu
625                 630                 635                 640

Phe Ile Glu Lys Tyr Asp Lys Ser Leu His Gln Ala Ile Glu Gly Asp
                645                 650                 655

Thr Ser Gly Asp Phe Leu Lys Ala Leu Leu Ala Leu Cys Gly Gly Glu
            660                 665                 670

Asp


<210> SEQ ID NO 42
<211> LENGTH: 672
<212> TYPE: PRT
<213> ORGANISM: Canios Lupus Familiaris

<400> SEQUENCE: 42

Met Ala Lys Pro Gln Gly Val Lys Tyr Arg Gly Ser Ile His Asp Phe
1               5                   10                  15

Pro Asn Phe Asp Pro Asn Gln Asp Ala Glu Ala Leu Tyr Thr Ala Met
            20                  25                  30

Lys Gly Phe Gly Ser Asp Lys Glu Ala Ile Leu Glu Leu Ile Thr Ser
        35                  40                  45

Arg Ser Asn Arg Gln Arg Gln Glu Ile Ser Gln Ser Tyr Lys Ser Leu
    50                  55                  60

Tyr Gly Lys Asp Leu Ile Ala Asp Leu Lys Tyr Glu Leu Thr Gly Lys
65                  70                  75                  80

Phe Glu Arg Leu Ile Val Gly Leu Met Arg Pro Leu Ala Tyr Cys Asp
                85                  90                  95
```

```
Ala Lys Glu Ile Lys Asp Ala Ile Ser Gly Ile Gly Thr Asp Glu Lys
            100                 105                 110

Cys Leu Ile Glu Ile Leu Ala Ser Arg Thr Asn Glu Gln Ile His Gln
        115                 120                 125

Leu Val Ala Ala Tyr Lys Asp Ala Tyr Glu Arg Asp Leu Glu Ala Asp
    130                 135                 140

Ile Ile Gly Asp Thr Ser Gly His Phe Gln Lys Met Leu Val Val Leu
145                 150                 155                 160

Leu Gln Gly Thr Arg Glu Gln Asp Asp Val Val Ser Glu Asp Leu Val
                165                 170                 175

Gln Gln Asp Val Gln Asp Leu Tyr Glu Ala Gly Glu Leu Lys Trp Gly
            180                 185                 190

Thr Asp Glu Ala Gln Phe Ile Tyr Ile Leu Gly Asn Arg Ser Lys Gln
        195                 200                 205

His Leu Arg Leu Val Phe Asp Glu Tyr Leu Arg Thr Thr Gly Lys Pro
    210                 215                 220

Ile Glu Ala Ser Ile Arg Gly Glu Leu Ser Gly Asp Phe Glu Lys Leu
225                 230                 235                 240

Met Leu Ala Val Val Lys Cys Ile Arg Ser Thr Pro Glu Tyr Phe Ala
                245                 250                 255

Glu Arg Leu Phe Lys Ala Met Lys Gly Leu Gly Thr Arg Asp Asn Thr
            260                 265                 270

Leu Ile Arg Ile Met Val Ser Arg Ser Glu Leu Asp Met Leu Asp Ile
        275                 280                 285

Arg Glu Ile Phe Arg Thr Lys Tyr Glu Lys Ser Leu Tyr Ser Met Ile
    290                 295                 300

Lys Asn Asp Thr Ser Gly Glu Tyr Lys Lys Ala Leu Leu Lys Leu Cys
305                 310                 315                 320

Gly Gly Asp Asp Asp Ala Ala Gly Gln Phe Phe Pro Glu Ala Ala Gln
                325                 330                 335

Val Ala Tyr Gln Met Trp Glu Leu Ser Ala Val Ala Arg Val Glu Leu
            340                 345                 350

Lys Gly Thr Val Arg Pro Val Asp Asn Phe Asn Pro Asp Ala Asp Ala
        355                 360                 365

Lys Ala Leu Arg Lys Ala Met Lys Gly Leu Gly Thr Asp Glu Asp Thr
    370                 375                 380

Ile Ile Asp Ile Ile Thr His Arg Ser Asn Ala Gln Arg Gln Gln Ile
385                 390                 395                 400

Arg Gln Thr Phe Lys Ser His Phe Gly Arg Asp Leu Met Ala Asp Leu
                405                 410                 415

Lys Ser Glu Ile Ser Gly Asp Leu Ala Arg Leu Ile Leu Gly Leu Met
            420                 425                 430

Met Pro Pro Ala His Tyr Asp Ala Lys Gln Leu Lys Lys Ala Met Glu
        435                 440                 445

Gly Ala Gly Thr Asp Glu Lys Ala Leu Ile Glu Ile Leu Ala Thr Arg
    450                 455                 460

Thr Asn Ala Glu Ile Arg Ala Ile Cys Glu Ala Tyr Lys Glu Asp Tyr
465                 470                 475                 480

His Lys Ser Leu Glu Asp Ala Leu Ser Ser Asp Thr Ser Gly His Phe
                485                 490                 495

Arg Arg Ile Leu Ile Ser Leu Ala Thr Gly Asn Arg Glu Glu Gly Gly
            500                 505                 510

Glu Asp Arg Asn Gln Ala Arg Glu Asp Ala Gln Val Ala Ala Glu Ile
```

```
        515                 520                 525

Leu Glu Ile Ala Asp Thr Pro Ser Gly Asp Lys Thr Ser Leu Glu Thr
    530                 535                 540

Arg Phe Met Thr Ile Leu Cys Thr Arg Ser Tyr Pro His Leu Arg Arg
545                 550                 555                 560

Val Phe Gln Glu Phe Val Lys Met Thr Asn Tyr Asp Val Glu His Thr
                565                 570                 575

Ile Lys Lys Glu Met Ser Gly Asp Val Arg Asp Val Phe Val Ala Ile
            580                 585                 590

Val Gln Ser Val Lys Asn Lys Pro Leu Phe Phe Ala Asp Lys Leu Tyr
        595                 600                 605

Lys Ser Met Lys Gly Ala Gly Thr Asp Asp Lys Thr Leu Thr Arg Ile
    610                 615                 620

Met Val Ser Arg Ser Glu Ile Asp Leu Leu Asn Ile Arg Arg Glu Phe
625                 630                 635                 640

Ile Glu Lys Tyr Asp Lys Ser Leu His Gln Ala Ile Glu Gly Asp Thr
                645                 650                 655

Ser Gly Asp Phe Leu Lys Ala Leu Leu Ala Ile Cys Gly Gly Glu Asp
            660                 665                 670


<210> SEQ ID NO 43
<211> LENGTH: 673
<212> TYPE: PRT
<213> ORGANISM: Rattus Norvegicus

<400> SEQUENCE: 43

Met Ala Lys Ile Ala Gln Gly Ala Met Tyr Arg Gly Ser Val His Asp
1               5                   10                  15

Phe Ala Asp Phe Asp Ala Asn Gln Asp Ala Glu Ala Leu Tyr Thr Ala
            20                  25                  30

Met Lys Gly Phe Gly Ser Asp Lys Glu Ser Ile Leu Glu Leu Ile Thr
        35                  40                  45

Ser Arg Ser Asn Lys Gln Arg Gln Glu Ile Cys Gln Ser Tyr Lys Ser
    50                  55                  60

Leu Tyr Gly Lys Asp Leu Ile Ala Asp Leu Lys Tyr Glu Leu Thr Gly
65                  70                  75                  80

Lys Phe Glu Arg Leu Ile Val Asn Leu Met Arg Pro Leu Ala Tyr Cys
                85                  90                  95

Asp Ala Lys Glu Ile Lys Asp Ala Ile Ser Gly Ile Gly Thr Asp Glu
            100                 105                 110

Lys Cys Leu Ile Glu Ile Leu Ala Ser Arg Thr Asn Glu Gln Ile His
        115                 120                 125

Gln Leu Val Ala Ala Tyr Lys Asp Ala Tyr Glu Arg Asp Leu Glu Ser
    130                 135                 140

Asp Ile Ile Gly Asp Thr Ser Gly His Phe Gln Lys Met Leu Val Val
145                 150                 155                 160

Leu Leu Gln Gly Thr Arg Glu Asn Asp Asp Val Val Ser Glu Asp Leu
                165                 170                 175

Val Gln Gln Asp Val Gln Asp Leu Tyr Glu Ala Gly Glu Leu Lys Trp
            180                 185                 190

Gly Thr Asp Glu Ala Gln Phe Ile Tyr Ile Leu Gly Asn Arg Ser Lys
        195                 200                 205

Gln His Leu Arg Leu Val Phe Asp Glu Tyr Leu Lys Thr Thr Gly Lys
    210                 215                 220
```

```
Pro Ile Glu Ala Ser Ile Arg Gly Glu Leu Ser Gly Asp Phe Glu Lys
225                 230                 235                 240

Leu Met Leu Ala Val Val Lys Cys Ile Arg Ser Thr Pro Glu Tyr Phe
                245                 250                 255

Ala Glu Arg Leu Phe Lys Ala Met Lys Gly Leu Gly Thr Arg Asp Asn
            260                 265                 270

Thr Leu Ile Arg Ile Met Val Ser Arg Ser Glu Leu Asp Met Leu Asp
        275                 280                 285

Ile Arg Glu Ile Phe Arg Thr Lys Tyr Glu Lys Ser Leu Tyr Ser Met
    290                 295                 300

Ile Lys Asn Asp Thr Ser Gly Glu Tyr Lys Lys Ala Leu Leu Lys Leu
305                 310                 315                 320

Cys Gly Gly Asp Asp Asp Ala Ala Gly Gln Phe Phe Pro Glu Ala Ala
                325                 330                 335

Gln Val Ala Tyr Gln Met Trp Glu Leu Ser Ala Val Ser Arg Val Glu
            340                 345                 350

Leu Lys Gly Thr Val Arg Ala Ala Asn Asp Phe Asn Pro Asp Ala Asp
        355                 360                 365

Ala Lys Ala Leu Arg Lys Ala Met Lys Gly Ile Gly Thr Asp Glu Ala
    370                 375                 380

Thr Ile Ile Asp Ile Ile Thr Gln Arg Ser Asn Ala Gln Arg Gln Gln
385                 390                 395                 400

Ile Arg Gln Thr Phe Lys Ser His Phe Gly Arg Asp Leu Met Ala Asp
                405                 410                 415

Leu Lys Ser Glu Ile Ser Gly Asp Leu Ala Arg Leu Ile Leu Gly Leu
            420                 425                 430

Met Met Pro Pro Ala His Tyr Asp Ala Lys Gln Leu Lys Lys Ala Met
        435                 440                 445

Glu Gly Ala Gly Thr Asp Glu Lys Ala Leu Ile Glu Ile Leu Ala Thr
    450                 455                 460

Arg Thr Asn Ala Glu Ile Arg Ala Ile Asn Glu Ala Tyr Lys Glu Asp
465                 470                 475                 480

Tyr His Lys Ser Leu Glu Asp Ala Leu Ser Ser Asp Thr Ser Gly His
                485                 490                 495

Phe Lys Arg Ile Leu Ile Ser Leu Ala Thr Gly Asn Arg Glu Glu Gly
            500                 505                 510

Gly Glu Asn Arg Asp Gln Ala Gln Glu Asp Ala Gln Val Ala Ala Glu
        515                 520                 525

Ile Leu Glu Ile Ala Asp Thr Pro Ser Gly Asp Lys Thr Ser Leu Glu
    530                 535                 540

Thr Arg Phe Met Thr Val Leu Cys Thr Arg Ser Tyr Pro His Leu Arg
545                 550                 555                 560

Arg Val Phe Gln Glu Phe Ile Lys Lys Thr Asn Tyr Asp Ile Glu His
                565                 570                 575

Val Ile Lys Lys Glu Met Ser Gly Asp Val Lys Asp Ala Phe Val Ala
            580                 585                 590

Ile Val Gln Ser Val Lys Asn Lys Pro Leu Phe Phe Ala Asp Lys Leu
        595                 600                 605

Tyr Lys Ser Met Lys Gly Ala Gly Thr Asp Glu Lys Thr Leu Thr Arg
    610                 615                 620

Val Met Val Ser Arg Ser Glu Ile Asp Leu Leu Asn Ile Arg Arg Glu
625                 630                 635                 640

Phe Ile Glu Lys Tyr Asp Lys Ser Leu His Gln Ala Ile Glu Gly Asp
```

```
                645                 650                 655

Thr Ser Gly Asp Phe Met Lys Ala Leu Leu Ala Leu Cys Gly Gly Glu
            660                 665                 670

Asp


<210> SEQ ID NO 44
<211> LENGTH: 673
<212> TYPE: PRT
<213> ORGANISM: Mus Musculus

<400> SEQUENCE: 44

Met Ala Lys Ile Ala Gln Gly Ala Met Tyr Arg Gly Ser Val His Asp
1               5                   10                  15

Phe Pro Glu Phe Asp Ala Asn Gln Asp Ala Glu Ala Leu Tyr Thr Ala
            20                  25                  30

Met Lys Gly Phe Gly Ser Asp Lys Glu Ser Ile Leu Glu Leu Ile Thr
        35                  40                  45

Ser Arg Ser Asn Lys Gln Arg Gln Glu Ile Cys Gln Asn Tyr Lys Ser
    50                  55                  60

Leu Tyr Gly Lys Asp Leu Ile Glu Asp Leu Lys Tyr Glu Leu Thr Gly
65                  70                  75                  80

Lys Phe Glu Arg Leu Ile Val Asn Leu Met Arg Pro Leu Ala Tyr Cys
                85                  90                  95

Asp Ala Lys Glu Ile Lys Asp Ala Ile Ser Gly Val Gly Thr Asp Glu
            100                 105                 110

Lys Cys Leu Ile Glu Ile Leu Ala Ser Arg Thr Asn Glu Gln Met His
        115                 120                 125

Gln Leu Val Ala Ala Tyr Lys Asp Ala Tyr Glu Arg Asp Leu Glu Ser
    130                 135                 140

Asp Ile Ile Gly Asp Thr Ser Gly His Phe Gln Lys Met Leu Val Val
145                 150                 155                 160

Leu Leu Gln Gly Thr Arg Glu Asn Asp Asp Val Val Ser Glu Asp Leu
                165                 170                 175

Val Gln Gln Asp Val Gln Asp Leu Tyr Glu Ala Gly Glu Leu Lys Trp
            180                 185                 190

Gly Thr Asp Glu Ala Gln Phe Ile Tyr Ile Leu Gly Asn Arg Ser Lys
        195                 200                 205

Gln His Leu Arg Leu Val Phe Asp Glu Tyr Leu Lys Thr Thr Gly Lys
    210                 215                 220

Pro Ile Glu Ala Ser Ile Arg Gly Glu Leu Ser Gly Asp Phe Glu Lys
225                 230                 235                 240

Leu Met Leu Ala Val Val Lys Cys Ile Arg Ser Thr Pro Glu Tyr Phe
                245                 250                 255

Ala Glu Arg Leu Phe Lys Ala Met Lys Gly Leu Gly Thr Arg Asp Asn
            260                 265                 270

Thr Leu Ile Arg Ile Met Val Ser Arg Ser Glu Leu Asp Met Leu Asp
        275                 280                 285

Ile Arg Glu Ile Phe Arg Thr Lys Tyr Glu Lys Ser Leu Tyr Ser Met
    290                 295                 300

Ile Lys Asn Asp Thr Ser Gly Glu Tyr Lys Lys Ala Leu Leu Lys Leu
305                 310                 315                 320

Cys Gly Gly Asp Asp Asp Ala Ala Gly Gln Phe Phe Pro Glu Ala Ala
                325                 330                 335

Gln Val Ala Tyr Gln Met Trp Glu Leu Ser Ala Val Ser Arg Val Glu
```

```
            340                 345                 350

Leu Lys Gly Thr Val Cys Ala Ala Asn Asp Phe Asn Pro Asp Ala Asp
        355                 360                 365

Ala Lys Ala Leu Arg Lys Ala Met Lys Gly Ile Gly Thr Asp Glu Ala
    370                 375                 380

Thr Ile Ile Asp Ile Val Thr His Arg Ser Asn Ala Gln Arg Gln Gln
385                 390                 395                 400

Ile Arg Gln Thr Phe Lys Ser His Phe Gly Arg Asp Leu Met Ala Asp
                405                 410                 415

Leu Lys Ser Glu Ile Ser Gly Asp Leu Ala Arg Leu Ile Leu Gly Leu
            420                 425                 430

Met Met Pro Pro Ala His Tyr Asp Ala Lys Gln Leu Lys Lys Ala Met
        435                 440                 445

Glu Gly Ala Gly Thr Asp Glu Lys Thr Leu Ile Glu Ile Leu Ala Thr
    450                 455                 460

Arg Thr Asn Ala Glu Ile Arg Ala Ile Asn Glu Ala Tyr Lys Glu Asp
465                 470                 475                 480

Tyr His Lys Ser Leu Glu Asp Ala Leu Ser Ser Asp Thr Ser Gly His
                485                 490                 495

Phe Arg Arg Ile Leu Ile Ser Leu Ala Thr Gly Asn Arg Glu Glu Gly
            500                 505                 510

Gly Glu Asn Arg Asp Gln Ala Gln Glu Asp Ala Gln Val Ala Ala Glu
        515                 520                 525

Ile Leu Glu Ile Ala Asp Thr Pro Ser Gly Asp Lys Thr Ser Leu Glu
    530                 535                 540

Thr Arg Phe Met Thr Val Leu Cys Thr Arg Ser Tyr Pro His Leu Arg
545                 550                 555                 560

Arg Val Phe Gln Glu Phe Ile Lys Lys Thr Asn Tyr Asp Ile Glu His
                565                 570                 575

Val Ile Lys Lys Glu Met Ser Gly Asp Val Lys Asp Ala Phe Val Ala
            580                 585                 590

Ile Val Gln Ser Val Lys Asn Lys Pro Leu Phe Phe Ala Asp Lys Leu
        595                 600                 605

Tyr Lys Ser Met Lys Gly Ala Gly Thr Asp Glu Lys Thr Leu Thr Arg
    610                 615                 620

Val Met Val Ser Arg Ser Glu Ile Asp Leu Leu Asn Ile Arg Arg Glu
625                 630                 635                 640

Phe Ile Glu Lys Tyr Asp Lys Ser Leu His Gln Ala Ile Glu Gly Asp
                645                 650                 655

Thr Ser Gly Asp Phe Met Lys Ala Leu Leu Ala Leu Cys Gly Gly Glu
            660                 665                 670

Asp
```

<210> SEQ ID NO 45
<211> LENGTH: 667
<212> TYPE: PRT
<213> ORGANISM: Homo sapiens
<220> FEATURE:
<221> NAME/KEY: MISC_FEATURE
<223> OTHER INFORMATION: NP_001350043.1 annexin A6 isoform 3

<400> SEQUENCE: 45

```
Met Ala Lys Pro Ala Gln Gly Ala Lys Tyr Arg Gly Ser Ile His Asp
1               5                   10                  15

Phe Pro Gly Phe Asp Pro Asn Gln Asp Ala Glu Ala Leu Tyr Thr Ala
```

```
            20                  25                  30

Met Lys Gly Phe Gly Ser Asp Lys Glu Ala Ile Leu Asp Ile Ile Thr
        35                  40                  45

Ser Arg Ser Asn Arg Gln Arg Gln Glu Val Cys Gln Ser Tyr Lys Ser
    50                  55                  60

Leu Tyr Gly Lys Asp Leu Ile Ala Asp Leu Lys Tyr Glu Leu Thr Gly
65                  70                  75                  80

Lys Phe Glu Arg Leu Ile Val Gly Leu Met Arg Pro Pro Ala Tyr Cys
                85                  90                  95

Asp Ala Lys Glu Ile Lys Asp Ala Ile Ser Gly Ile Gly Thr Asp Glu
            100                 105                 110

Lys Cys Leu Ile Glu Ile Leu Ala Ser Arg Thr Asn Glu Gln Met His
        115                 120                 125

Gln Leu Val Ala Ala Tyr Lys Asp Ala Tyr Glu Arg Asp Leu Glu Ala
    130                 135                 140

Asp Ile Ile Gly Asp Thr Ser Gly His Phe Gln Lys Met Leu Val Val
145                 150                 155                 160

Leu Leu Gln Gly Thr Arg Glu Glu Asp Asp Val Val Ser Glu Asp Leu
                165                 170                 175

Val Gln Gln Asp Val Gln Asp Leu Tyr Glu Ala Gly Glu Leu Lys Trp
            180                 185                 190

Gly Thr Asp Glu Ala Gln Phe Ile Tyr Ile Leu Gly Asn Arg Ser Lys
        195                 200                 205

Gln His Leu Arg Leu Val Phe Asp Glu Tyr Leu Lys Thr Thr Gly Lys
    210                 215                 220

Pro Ile Glu Ala Ser Ile Arg Gly Glu Leu Ser Gly Asp Phe Glu Lys
225                 230                 235                 240

Leu Met Leu Ala Val Val Lys Cys Ile Arg Ser Thr Pro Glu Tyr Phe
                245                 250                 255

Ala Glu Arg Leu Phe Lys Ala Met Lys Gly Leu Gly Thr Arg Asp Asn
            260                 265                 270

Thr Leu Ile Arg Ile Met Val Ser Arg Ser Glu Leu Asp Met Leu Asp
        275                 280                 285

Ile Arg Glu Ile Phe Arg Thr Lys Tyr Glu Lys Ser Leu Tyr Ser Met
    290                 295                 300

Ile Lys Asn Asp Thr Ser Gly Glu Tyr Lys Lys Thr Leu Leu Lys Leu
305                 310                 315                 320

Ser Gly Gly Asp Asp Asp Ala Ala Gly Gln Phe Phe Pro Glu Ala Ala
                325                 330                 335

Gln Val Ala Tyr Gln Met Trp Glu Leu Ser Ala Val Ala Arg Val Glu
            340                 345                 350

Leu Lys Gly Thr Val Arg Pro Ala Asn Asp Phe Asn Pro Asp Ala Asp
        355                 360                 365

Ala Lys Ala Leu Arg Lys Ala Met Lys Gly Leu Gly Thr Asp Glu Asp
    370                 375                 380

Thr Ile Ile Asp Ile Ile Thr His Arg Ser Asn Val Gln Arg Gln Gln
385                 390                 395                 400

Ile Arg Gln Thr Phe Lys Ser His Phe Gly Arg Asp Leu Met Thr Asp
                405                 410                 415

Leu Lys Ser Glu Ile Ser Gly Asp Leu Ala Arg Leu Ile Leu Gly Leu
            420                 425                 430

Met Met Pro Pro Ala His Tyr Asp Ala Lys Gln Leu Lys Lys Ala Met
        435                 440                 445
```

```
Glu Gly Ala Gly Thr Asp Glu Lys Ala Leu Ile Glu Ile Leu Ala Thr
    450                 455                 460

Arg Thr Asn Ala Glu Ile Arg Ala Ile Asn Glu Ala Tyr Lys Glu Asp
465                 470                 475                 480

Tyr His Lys Ser Leu Glu Asp Ala Leu Ser Ser Asp Thr Ser Gly His
                485                 490                 495

Phe Arg Arg Ile Leu Ile Ser Leu Ala Thr Gly His Arg Glu Glu Gly
            500                 505                 510

Gly Glu Asn Leu Asp Gln Ala Arg Glu Asp Ala Gln Glu Ile Ala Asp
        515                 520                 525

Thr Pro Ser Gly Asp Lys Thr Ser Leu Glu Thr Arg Phe Met Thr Ile
    530                 535                 540

Leu Cys Thr Arg Ser Tyr Pro His Leu Arg Arg Val Phe Gln Glu Phe
545                 550                 555                 560

Ile Lys Met Thr Asn Tyr Asp Val Glu His Thr Ile Lys Lys Glu Met
                565                 570                 575

Ser Gly Asp Val Arg Asp Ala Phe Val Ala Ile Val Gln Ser Val Lys
            580                 585                 590

Asn Lys Pro Leu Phe Phe Ala Asp Lys Leu Tyr Lys Ser Met Lys Gly
        595                 600                 605

Ala Gly Thr Asp Glu Lys Thr Leu Thr Arg Ile Met Val Ser Arg Ser
    610                 615                 620

Glu Ile Asp Leu Leu Asn Ile Arg Arg Glu Phe Ile Glu Lys Tyr Asp
625                 630                 635                 640

Lys Ser Leu His Gln Ala Ile Glu Gly Asp Thr Ser Gly Asp Phe Leu
                645                 650                 655

Lys Ala Leu Leu Ala Leu Cys Gly Gly Glu Asp
            660                 665
```

```
<210> SEQ ID NO 46
<211> LENGTH: 2871
<212> TYPE: DNA
<213> ORGANISM: Homo sapiens
<220> FEATURE:
<221> NAME/KEY: misc_feature
<223> OTHER INFORMATION: NM_001363114.2 Homo sapiens annexin A6 (ANXA6),
      transcript variant 3, mRNA

<400> SEQUENCE: 46

gcggttgctg ctgggctaac gggctccgat ccagcgagcg ctgcgtcctc gagtccctgc      60

gcccgtgcgt ccgtctgcga cccgaggcct ccgctgcgcg tggattctgc tgcgaaccgg     120

agaccatggc caaaccagca cagggtgcca agtaccgggg ctccatccat gacttcccag     180

gctttgaccc caaccaggat gccgaggctc tgtacactgc catgaagggc tttggcagtg     240

acaaggaggc catactggac ataatcacct cacggagcaa caggcagagg caggaggtct     300

gccagagcta caagtccctc tacggcaagg acctcattgc tgatttaaag tatgaattga     360

cgggcaagtt tgaacggttg attgtgggcc tgatgaggcc acctgcctat tgtgatgcca     420

aagaaattaa agatgccatc tcgggcattg gcactgatga gaagtgcctc attgagatct     480

tggcttcccg gaccaatgag cagatgcacc agctggtggc agcatacaaa gatgcctacg     540

agcgggacct ggaggctgac atcatcggcg acacctctgg ccacttccag aagatgcttg     600

tggtcctgct ccagggaacc agggaggagg atgacgtagt gagcgaggac ctggtacaac     660

aggatgtcca ggacctatac gaggcagggg aactgaaatg ggaacagat gaagcccagt     720
```

```
tcatttacat cttgggaaat cgcagcaagc agcatcttcg gttggtgttc gatgagtatc    780

tgaagaccac agggaagccg attgaagcca gcatccgagg ggagctgtct ggggactttg    840

agaagctaat gctggccgta gtgaagtgta tccggagcac cccggaatat tttgctgaaa    900

ggctcttcaa ggctatgaag ggcctgggga ctcgggacaa caccctgatc cgcatcatgg    960

tctcccgtag tgagttggac atgctcgaca ttcgggagat cttccggacc aagtatgaga   1020

agtccctcta cagcatgatc aagaatgaca cctctggcga gtacaagaag actctgctga   1080

agctgtctgg gggagatgat gatgctgctg gccagttctt cccggaggca gcgcaggtgg   1140

cctatcagat gtgggaactt agtgcagtgg cccgagtaga gctgaaggga actgtgcgcc   1200

cagccaatga cttcaaccct gacgcagatg ccaaagcgct gcggaaagcc atgaagggac   1260

tcgggactga cgaagacaca atcatcgata tcatcacgca ccgcagcaat gtccagcggc   1320

agcagatccg gcagaccttc aagtctcact ttggccggga cttaatgact gacctgaagt   1380

ctgagatctc tggagacctg gcaaggctga ttctggggct catgatgcca ccggcccatt   1440

acgatgccaa gcagttgaag aaggccatgg agggagccgg cacagatgaa aaggctctta   1500

ttgaaatcct ggccactcgg accaatgctg aaatccgggc catcaatgag gcctataagg   1560

aggactatca caagtccctg gaggatgctc tgagctcaga cacatctggc cacttcagga   1620

ggatcctcat ttctctggcc acggggcatc gtgaggaggg aggagaaaac ctggaccagg   1680

cacgggaaga tgcccaggaa atagcagaca cacctagtgg agacaaaact tccttggaga   1740

cacgtttcat gacgatcctg tgtacccgga gctatccgca cctccggaga gtcttccagg   1800

agttcatcaa gatgaccaac tatgacgtgg agcacaccat caagaaggag atgtctgggg   1860

atgtcaggga tgcatttgtg gccattgttc aaagtgtcaa gaacaagcct ctcttctttg   1920

ccgacaaact ttacaaatcc atgaagggtg ctggcacaga tgagaagact ctgaccagga   1980

tcatggtatc ccgcagtgag attgacctgc tcaacatccg gagggaattc attgagaaat   2040

atgacaagtc tctccaccaa gccattgagg gtgacacctc cggagacttc ctgaaggcct   2100

tgctggctct ctgtggtggt gaggactagg gccacagctt tggcgggcac ttctgccaag   2160

aaatggttat cagcaccagc cgccatggcc aagcctgatt gttccagctc cagagactaa   2220

ggaaggggca ggggtggggg gaggggttgg gttgggctct tatcttcagt ggagcttagg   2280

aaacgctccc actcccacgg gccatcgagg gcccagcacg gctgagcggc tgaaaaaccg   2340

tagccataga tcctgtccac ctccactccc ctctgaccct caggctttcc cagcttcctc   2400

cccttgctac agcctctgcc ctggtttggg ctatgtcaga tccaaaaaca tcctgaacct   2460

ctgtctgtaa aatgagtagt gtctgtactt tgaatgaggg ggttggtggc aggggccagt   2520

tgaatgtgct gggcggggtg gtgggaagga tagtaaatgt gctggggcaa actgacaaat   2580

cttcccatcc atttcaccac ccatctccat ccaggccgcg ctagagtact ggaccaggaa   2640

tttggatgcc tgggttcaaa tctgcatctg ccatgcactt gtttctgacc ttaggccagc   2700

ccctttccct ccctgagtct ctattttctt atctacaatg agacagttgg acaaaaaaat   2760

cttggcttcc cttctaacat taacttccta aagtatgcct ccgattcatt cccttgacac   2820

tttttatttc taaggaagaa ataaaaagag atacacaaac acataaacac a            2871
```

<210> SEQ ID NO 47
<211> LENGTH: 6
<212> TYPE: PRT
<213> ORGANISM: Homo sapiens
<220> FEATURE:
<221> NAME/KEY: MISC_FEATURE -continued

```
<223> OTHER INFORMATION: Amino acid sequence that is present in annexin
      A6 isoform 1 and annexin A6 isoform 2 but lacking in annexin A6
      isoform 3

<400> SEQUENCE: 47

Val Ala Ala Glu Ile Leu
1               5
```